US010517990B2

(12) United States Patent
Olsen et al.

(10) Patent No.: US 10,517,990 B2
(45) Date of Patent: Dec. 31, 2019

(54) THERMOREVERSIBLE HYDROGELS FROM THE ARRESTED PHASE SEPARATION OF ELASTIN-LIKE POLYPEPTIDES

(71) Applicant: Massachusetts Institute of Technology, Cambridge, MA (US)

(72) Inventors: Bradley D. Olsen, Arlington, MA (US); Matthew J. Glassman, Yorba Linda, CA (US); Reginald K. Avery, Bel Air, MD (US)

(73) Assignee: Massachusetts Institute of Technology, Cambridge, MA (US)

( * ) Notice: Subject to any disclaimer, the term of this patent is extended or adjusted under 35 U.S.C. 154(b) by 6 days.

(21) Appl. No.: 14/956,998

(22) Filed: Dec. 2, 2015

(65) Prior Publication Data
US 2017/0049923 A1   Feb. 23, 2017

Related U.S. Application Data

(60) Provisional application No. 62/086,496, filed on Dec. 2, 2014.

(51) Int. Cl.
A61L 26/00 (2006.01)
A61K 8/64 (2006.01)
A61Q 19/08 (2006.01)

(52) U.S. Cl.
CPC .............. *A61L 26/008* (2013.01); *A61K 8/64* (2013.01); *A61L 26/0047* (2013.01); *A61Q 19/08* (2013.01); *A61K 2800/91* (2013.01); *A61L 2300/252* (2013.01); *A61L 2430/02* (2013.01); *A61L 2430/06* (2013.01); *A61L 2430/34* (2013.01)

(58) Field of Classification Search
CPC . A61K 2800/91; A61K 8/64; A61L 2300/252; A61L 2430/02; A61L 2430/06; A61L 2430/34; A61L 26/0047; A61L 26/008; A61Q 19/08
See application file for complete search history.

(56) References Cited

U.S. PATENT DOCUMENTS

| 2004/0171545 A1 | 9/2004 | Chaikof et al. |
| 2010/0048473 A1 | 2/2010 | Chaikof et al. |
| 2014/0024722 A1 | 1/2014 | Olsen et al. |

FOREIGN PATENT DOCUMENTS

WO   WO-2010/048281 A1   4/2010

OTHER PUBLICATIONS

International Search Report and Written Opinion for International Application No. PCT/US2015/063382 dated Aug. 31, 2016.
Sallach, et al., "Long-term biostability of self-assembling protein polymers in the absence of covalent crosslinking," Biomaterials, 31(4): 779-791 (2010).
Amiram et al., "A highly parallel method for synthesizing DNA repeats enables the discovery of 'smart' protein polymers," Nature Mater, 10(2), 141-148 (2011).
Bessa et al., "Thermoresponsive self-assembled elastin-based nanoparticles for delivery of BMPs," J Control Release, 142(3): 312-318 (2010).

*Primary Examiner* — Rachael E Bredefeld
*Assistant Examiner* — Erinne R Dabkowski
(74) *Attorney, Agent, or Firm* — Dana M. Gordon; Foley Hoag LLP

(57) ABSTRACT

Elastin-like polypeptides (ELPs) form hydrogels upon heating. The polypeptides can comprise the generic sequence $(XPAVG)_n$ (SEQ ID NO: 4), wherein independently for each occurrence X can be any one of a number of different natural or unnatural amino acids, and n is chosen to determine the size of the protein. Hydrogels comprising the polypeptides have mechanical properties, including elastic modulus and fracture toughness, required for load-bearing applications.

16 Claims, 40 Drawing Sheets
Specification includes a Sequence Listing.

SEQUENCE LISTING

```
<160> NUMBER OF SEQ ID NOS: 88

<210> SEQ ID NO 1
<211> LENGTH: 2502
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any natural or unnatural amino acid
<220> FEATURE:
<221> NAME/KEY: MOD_RES
<222> LOCATION: (2)..(2)
<223> OTHER INFORMATION: Ile or Val
<220> FEATURE:
<221> NAME/KEY: MOD_RES
<222> LOCATION: (7)..(7)
<223> OTHER INFORMATION: Ile or Val
<220> FEATURE:
<221> NAME/KEY: MOD_RES
<222> LOCATION: (12)..(12)
<223> OTHER INFORMATION: Ile or Val
<220> FEATURE:
<221> NAME/KEY: MOD_RES
<222> LOCATION: (17)..(17)
<223> OTHER INFORMATION: Ile or Val
<220> FEATURE:
<221> NAME/KEY: MOD_RES
<222> LOCATION: (22)..(22)
<223> OTHER INFORMATION: Ile or Val
<220> FEATURE:
<221> NAME/KEY: MOD_RES
<222> LOCATION: (27)..(27)
<223> OTHER INFORMATION: Ile or Val
<220> FEATURE:
<221> NAME/KEY: MOD_RES
<222> LOCATION: (32)..(32)
<223> OTHER INFORMATION: Ile or Val
<220> FEATURE:
<221> NAME/KEY: MOD_RES
<222> LOCATION: (37)..(37)
<223> OTHER INFORMATION: Ile or Val
<220> FEATURE:
<221> NAME/KEY: MOD_RES
<222> LOCATION: (42)..(42)
<223> OTHER INFORMATION: Ile or Val
<220> FEATURE:
<221> NAME/KEY: MOD_RES
<222> LOCATION: (47)..(47)
```

```
<223> OTHER INFORMATION: Ile or Val
<220> FEATURE:
<221> NAME/KEY: MOD_RES
<222> LOCATION: (52)..(52)
<223> OTHER INFORMATION: Ile or Val
<220> FEATURE:
<221> NAME/KEY: MOD_RES
<222> LOCATION: (57)..(57)
<223> OTHER INFORMATION: Ile or Val
<220> FEATURE:
<221> NAME/KEY: MOD_RES
<222> LOCATION: (62)..(62)
<223> OTHER INFORMATION: Ile or Val
<220> FEATURE:
<221> NAME/KEY: MOD_RES
<222> LOCATION: (67)..(67)
<223> OTHER INFORMATION: Ile or Val
<220> FEATURE:
<221> NAME/KEY: MOD_RES
<222> LOCATION: (72)..(72)
<223> OTHER INFORMATION: Ile or Val
<220> FEATURE:
<221> NAME/KEY: MOD_RES
<222> LOCATION: (77)..(77)
<223> OTHER INFORMATION: Ile or Val
<220> FEATURE:
<221> NAME/KEY: MOD_RES
<222> LOCATION: (82)..(82)
<223> OTHER INFORMATION: Ile or Val
<220> FEATURE:
<221> NAME/KEY: MOD_RES
<222> LOCATION: (87)..(87)
<223> OTHER INFORMATION: Ile or Val
<220> FEATURE:
<221> NAME/KEY: MOD_RES
<222> LOCATION: (92)..(92)
<223> OTHER INFORMATION: Ile or Val
<220> FEATURE:
<221> NAME/KEY: MOD_RES
<222> LOCATION: (97)..(97)
<223> OTHER INFORMATION: Ile or Val
<220> FEATURE:
<221> NAME/KEY: MOD_RES
<222> LOCATION: (102)..(102)
<223> OTHER INFORMATION: Ile or Val
<220> FEATURE:
<221> NAME/KEY: MOD_RES
<222> LOCATION: (107)..(107)
<223> OTHER INFORMATION: Ile or Val
<220> FEATURE:
<221> NAME/KEY: MOD_RES
<222> LOCATION: (112)..(112)
<223> OTHER INFORMATION: Ile or Val
<220> FEATURE:
<221> NAME/KEY: MOD_RES
<222> LOCATION: (117)..(117)
<223> OTHER INFORMATION: Ile or Val
<220> FEATURE:
<221> NAME/KEY: MOD_RES
<222> LOCATION: (122)..(122)
<223> OTHER INFORMATION: Ile or Val
<220> FEATURE:
<221> NAME/KEY: MOD_RES
<222> LOCATION: (127)..(127)
<223> OTHER INFORMATION: Ile or Val
<220> FEATURE:
<221> NAME/KEY: MOD_RES
<222> LOCATION: (132)..(132)
<223> OTHER INFORMATION: Ile or Val
<220> FEATURE:
<221> NAME/KEY: MOD_RES
<222> LOCATION: (137)..(137)
<223> OTHER INFORMATION: Ile or Val
<220> FEATURE:
<221> NAME/KEY: MOD_RES
<222> LOCATION: (142)..(142)
<223> OTHER INFORMATION: Ile or Val
<220> FEATURE:
<221> NAME/KEY: MOD_RES
```

```
<222> LOCATION: (147)..(147)
<223> OTHER INFORMATION: Ile or Val
<220> FEATURE:
<221> NAME/KEY: MOD_RES
<222> LOCATION: (152)..(152)
<223> OTHER INFORMATION: Ile or Val
<220> FEATURE:
<221> NAME/KEY: MOD_RES
<222> LOCATION: (157)..(157)
<223> OTHER INFORMATION: Ile or Val
<220> FEATURE:
<221> NAME/KEY: MOD_RES
<222> LOCATION: (162)..(162)
<223> OTHER INFORMATION: Ile or Val
<220> FEATURE:
<221> NAME/KEY: MOD_RES
<222> LOCATION: (167)..(167)
<223> OTHER INFORMATION: Ile or Val
<220> FEATURE:
<221> NAME/KEY: MOD_RES
<222> LOCATION: (172)..(172)
<223> OTHER INFORMATION: Ile or Val
<220> FEATURE:
<221> NAME/KEY: MOD_RES
<222> LOCATION: (177)..(177)
<223> OTHER INFORMATION: Ile or Val
<220> FEATURE:
<221> NAME/KEY: MOD_RES
<222> LOCATION: (182)..(182)
<223> OTHER INFORMATION: Ile or Val
<220> FEATURE:
<221> NAME/KEY: MOD_RES
<222> LOCATION: (187)..(187)
<223> OTHER INFORMATION: Ile or Val
<220> FEATURE:
<221> NAME/KEY: MOD_RES
<222> LOCATION: (192)..(192)
<223> OTHER INFORMATION: Ile or Val
<220> FEATURE:
<221> NAME/KEY: MOD_RES
<222> LOCATION: (197)..(197)
<223> OTHER INFORMATION: Ile or Val
<220> FEATURE:
<221> NAME/KEY: MOD_RES
<222> LOCATION: (202)..(202)
<223> OTHER INFORMATION: Ile or Val
<220> FEATURE:
<221> NAME/KEY: MOD_RES
<222> LOCATION: (207)..(207)
<223> OTHER INFORMATION: Ile or Val
<220> FEATURE:
<221> NAME/KEY: MOD_RES
<222> LOCATION: (212)..(212)
<223> OTHER INFORMATION: Ile or Val
<220> FEATURE:
<221> NAME/KEY: MOD_RES
<222> LOCATION: (217)..(217)
<223> OTHER INFORMATION: Ile or Val
<220> FEATURE:
<221> NAME/KEY: MOD_RES
<222> LOCATION: (222)..(222)
<223> OTHER INFORMATION: Ile or Val
<220> FEATURE:
<221> NAME/KEY: MOD_RES
<222> LOCATION: (227)..(227)
<223> OTHER INFORMATION: Ile or Val
<220> FEATURE:
<221> NAME/KEY: MOD_RES
<222> LOCATION: (232)..(232)
<223> OTHER INFORMATION: Ile or Val
<220> FEATURE:
<221> NAME/KEY: MOD_RES
<222> LOCATION: (237)..(237)
<223> OTHER INFORMATION: Ile or Val
<220> FEATURE:
<221> NAME/KEY: MOD_RES
<222> LOCATION: (242)..(242)
<223> OTHER INFORMATION: Ile or Val
<220> FEATURE:
```

```
<221> NAME/KEY: MOD_RES
<222> LOCATION: (247)..(247)
<223> OTHER INFORMATION: Ile or Val
<220> FEATURE:
<221> NAME/KEY: MOD_RES
<222> LOCATION: (252)..(252)
<223> OTHER INFORMATION: Ile or Val
<220> FEATURE:
<221> NAME/KEY: MOD_RES
<222> LOCATION: (257)..(257)
<223> OTHER INFORMATION: Ile or Val
<220> FEATURE:
<221> NAME/KEY: MOD_RES
<222> LOCATION: (262)..(262)
<223> OTHER INFORMATION: Ile or Val
<220> FEATURE:
<221> NAME/KEY: MOD_RES
<222> LOCATION: (267)..(267)
<223> OTHER INFORMATION: Ile or Val
<220> FEATURE:
<221> NAME/KEY: MOD_RES
<222> LOCATION: (272)..(272)
<223> OTHER INFORMATION: Ile or Val
<220> FEATURE:
<221> NAME/KEY: MOD_RES
<222> LOCATION: (277)..(277)
<223> OTHER INFORMATION: Ile or Val
<220> FEATURE:
<221> NAME/KEY: MOD_RES
<222> LOCATION: (282)..(282)
<223> OTHER INFORMATION: Ile or Val
<220> FEATURE:
<221> NAME/KEY: MOD_RES
<222> LOCATION: (287)..(287)
<223> OTHER INFORMATION: Ile or Val
<220> FEATURE:
<221> NAME/KEY: MOD_RES
<222> LOCATION: (292)..(292)
<223> OTHER INFORMATION: Ile or Val
<220> FEATURE:
<221> NAME/KEY: MOD_RES
<222> LOCATION: (297)..(297)
<223> OTHER INFORMATION: Ile or Val
<220> FEATURE:
<221> NAME/KEY: MOD_RES
<222> LOCATION: (302)..(302)
<223> OTHER INFORMATION: Ile or Val
<220> FEATURE:
<221> NAME/KEY: MOD_RES
<222> LOCATION: (307)..(307)
<223> OTHER INFORMATION: Ile or Val
<220> FEATURE:
<221> NAME/KEY: MOD_RES
<222> LOCATION: (312)..(312)
<223> OTHER INFORMATION: Ile or Val
<220> FEATURE:
<221> NAME/KEY: MOD_RES
<222> LOCATION: (317)..(317)
<223> OTHER INFORMATION: Ile or Val
<220> FEATURE:
<221> NAME/KEY: MOD_RES
<222> LOCATION: (322)..(322)
<223> OTHER INFORMATION: Ile or Val
<220> FEATURE:
<221> NAME/KEY: MOD_RES
<222> LOCATION: (327)..(327)
<223> OTHER INFORMATION: Ile or Val
<220> FEATURE:
<221> NAME/KEY: MOD_RES
<222> LOCATION: (332)..(332)
<223> OTHER INFORMATION: Ile or Val
<220> FEATURE:
<221> NAME/KEY: MOD_RES
<222> LOCATION: (337)..(337)
<223> OTHER INFORMATION: Ile or Val
<220> FEATURE:
<221> NAME/KEY: MOD_RES
<222> LOCATION: (342)..(342)
<223> OTHER INFORMATION: Ile or Val
```

-continued

```
<220> FEATURE:
<221> NAME/KEY: MOD_RES
<222> LOCATION: (347)..(347)
<223> OTHER INFORMATION: Ile or Val
<220> FEATURE:
<221> NAME/KEY: MOD_RES
<222> LOCATION: (352)..(352)
<223> OTHER INFORMATION: Ile or Val
<220> FEATURE:
<221> NAME/KEY: MOD_RES
<222> LOCATION: (357)..(357)
<223> OTHER INFORMATION: Ile or Val
<220> FEATURE:
<221> NAME/KEY: MOD_RES
<222> LOCATION: (362)..(362)
<223> OTHER INFORMATION: Ile or Val
<220> FEATURE:
<221> NAME/KEY: MOD_RES
<222> LOCATION: (367)..(367)
<223> OTHER INFORMATION: Ile or Val
<220> FEATURE:
<221> NAME/KEY: MOD_RES
<222> LOCATION: (372)..(372)
<223> OTHER INFORMATION: Ile or Val
<220> FEATURE:
<221> NAME/KEY: MOD_RES
<222> LOCATION: (377)..(377)
<223> OTHER INFORMATION: Ile or Val
<220> FEATURE:
<221> NAME/KEY: MOD_RES
<222> LOCATION: (382)..(382)
<223> OTHER INFORMATION: Ile or Val
<220> FEATURE:
<221> NAME/KEY: MOD_RES
<222> LOCATION: (387)..(387)
<223> OTHER INFORMATION: Ile or Val
<220> FEATURE:
<221> NAME/KEY: MOD_RES
<222> LOCATION: (392)..(392)
<223> OTHER INFORMATION: Ile or Val
<220> FEATURE:
<221> NAME/KEY: MOD_RES
<222> LOCATION: (397)..(397)
<223> OTHER INFORMATION: Ile or Val
<220> FEATURE:
<221> NAME/KEY: MOD_RES
<222> LOCATION: (402)..(402)
<223> OTHER INFORMATION: Ile or Val
<220> FEATURE:
<221> NAME/KEY: MOD_RES
<222> LOCATION: (407)..(407)
<223> OTHER INFORMATION: Ile or Val
<220> FEATURE:
<221> NAME/KEY: MOD_RES
<222> LOCATION: (412)..(412)
<223> OTHER INFORMATION: Ile or Val
<220> FEATURE:
<221> NAME/KEY: MOD_RES
<222> LOCATION: (417)..(417)
<223> OTHER INFORMATION: Ile or Val
<220> FEATURE:
<221> NAME/KEY: MOD_RES
<222> LOCATION: (422)..(422)
<223> OTHER INFORMATION: Ile or Val
<220> FEATURE:
<221> NAME/KEY: MOD_RES
<222> LOCATION: (427)..(427)
<223> OTHER INFORMATION: Ile or Val
<220> FEATURE:
<221> NAME/KEY: MOD_RES
<222> LOCATION: (432)..(432)
<223> OTHER INFORMATION: Ile or Val
<220> FEATURE:
<221> NAME/KEY: MOD_RES
<222> LOCATION: (437)..(437)
<223> OTHER INFORMATION: Ile or Val
<220> FEATURE:
<221> NAME/KEY: MOD_RES
<222> LOCATION: (442)..(442)
```

```
<223> OTHER INFORMATION: Ile or Val
<220> FEATURE:
<221> NAME/KEY: MOD_RES
<222> LOCATION: (447)..(447)
<223> OTHER INFORMATION: Ile or Val
<220> FEATURE:
<221> NAME/KEY: MOD_RES
<222> LOCATION: (452)..(452)
<223> OTHER INFORMATION: Ile or Val
<220> FEATURE:
<221> NAME/KEY: MOD_RES
<222> LOCATION: (457)..(457)
<223> OTHER INFORMATION: Ile or Val
<220> FEATURE:
<221> NAME/KEY: MOD_RES
<222> LOCATION: (462)..(462)
<223> OTHER INFORMATION: Ile or Val
<220> FEATURE:
<221> NAME/KEY: MOD_RES
<222> LOCATION: (467)..(467)
<223> OTHER INFORMATION: Ile or Val
<220> FEATURE:
<221> NAME/KEY: MOD_RES
<222> LOCATION: (472)..(472)
<223> OTHER INFORMATION: Ile or Val
<220> FEATURE:
<221> NAME/KEY: MOD_RES
<222> LOCATION: (477)..(477)
<223> OTHER INFORMATION: Ile or Val
<220> FEATURE:
<221> NAME/KEY: MOD_RES
<222> LOCATION: (482)..(482)
<223> OTHER INFORMATION: Ile or Val
<220> FEATURE:
<221> NAME/KEY: MOD_RES
<222> LOCATION: (487)..(487)
<223> OTHER INFORMATION: Ile or Val
<220> FEATURE:
<221> NAME/KEY: MOD_RES
<222> LOCATION: (492)..(492)
<223> OTHER INFORMATION: Ile or Val
<220> FEATURE:
<221> NAME/KEY: MOD_RES
<222> LOCATION: (497)..(497)
<223> OTHER INFORMATION: Ile or Val
<220> FEATURE:
<221> NAME/KEY: MOD_RES
<222> LOCATION: (502)..(502)
<223> OTHER INFORMATION: Ile or Val
<220> FEATURE:
<221> NAME/KEY: MOD_RES
<222> LOCATION: (507)..(507)
<223> OTHER INFORMATION: Ile or Val
<220> FEATURE:
<221> NAME/KEY: MOD_RES
<222> LOCATION: (512)..(512)
<223> OTHER INFORMATION: Ile or Val
<220> FEATURE:
<221> NAME/KEY: MOD_RES
<222> LOCATION: (517)..(517)
<223> OTHER INFORMATION: Ile or Val
<220> FEATURE:
<221> NAME/KEY: MOD_RES
<222> LOCATION: (522)..(522)
<223> OTHER INFORMATION: Ile or Val
<220> FEATURE:
<221> NAME/KEY: MOD_RES
<222> LOCATION: (527)..(527)
<223> OTHER INFORMATION: Ile or Val
<220> FEATURE:
<221> NAME/KEY: MOD_RES
<222> LOCATION: (532)..(532)
<223> OTHER INFORMATION: Ile or Val
<220> FEATURE:
<221> NAME/KEY: MOD_RES
<222> LOCATION: (537)..(537)
<223> OTHER INFORMATION: Ile or Val
<220> FEATURE:
<221> NAME/KEY: MOD_RES
```

```
<222> LOCATION: (542)..(542)
<223> OTHER INFORMATION: Ile or Val
<220> FEATURE:
<221> NAME/KEY: MOD_RES
<222> LOCATION: (547)..(547)
<223> OTHER INFORMATION: Ile or Val
<220> FEATURE:
<221> NAME/KEY: MOD_RES
<222> LOCATION: (552)..(552)
<223> OTHER INFORMATION: Ile or Val
<220> FEATURE:
<221> NAME/KEY: MOD_RES
<222> LOCATION: (557)..(557)
<223> OTHER INFORMATION: Ile or Val
<220> FEATURE:
<221> NAME/KEY: MOD_RES
<222> LOCATION: (562)..(562)
<223> OTHER INFORMATION: Ile or Val
<220> FEATURE:
<221> NAME/KEY: MOD_RES
<222> LOCATION: (567)..(567)
<223> OTHER INFORMATION: Ile or Val
<220> FEATURE:
<221> NAME/KEY: MOD_RES
<222> LOCATION: (572)..(572)
<223> OTHER INFORMATION: Ile or Val
<220> FEATURE:
<221> NAME/KEY: MOD_RES
<222> LOCATION: (577)..(577)
<223> OTHER INFORMATION: Ile or Val
<220> FEATURE:
<221> NAME/KEY: MOD_RES
<222> LOCATION: (582)..(582)
<223> OTHER INFORMATION: Ile or Val
<220> FEATURE:
<221> NAME/KEY: MOD_RES
<222> LOCATION: (587)..(587)
<223> OTHER INFORMATION: Ile or Val
<220> FEATURE:
<221> NAME/KEY: MOD_RES
<222> LOCATION: (592)..(592)
<223> OTHER INFORMATION: Ile or Val
<220> FEATURE:
<221> NAME/KEY: MOD_RES
<222> LOCATION: (597)..(597)
<223> OTHER INFORMATION: Ile or Val
<220> FEATURE:
<221> NAME/KEY: MOD_RES
<222> LOCATION: (602)..(602)
<223> OTHER INFORMATION: Ile or Val
<220> FEATURE:
<221> NAME/KEY: MOD_RES
<222> LOCATION: (607)..(607)
<223> OTHER INFORMATION: Ile or Val
<220> FEATURE:
<221> NAME/KEY: MOD_RES
<222> LOCATION: (612)..(612)
<223> OTHER INFORMATION: Ile or Val
<220> FEATURE:
<221> NAME/KEY: MOD_RES
<222> LOCATION: (617)..(617)
<223> OTHER INFORMATION: Ile or Val
<220> FEATURE:
<221> NAME/KEY: MOD_RES
<222> LOCATION: (622)..(622)
<223> OTHER INFORMATION: Ile or Val
<220> FEATURE:
<221> NAME/KEY: MOD_RES
<222> LOCATION: (627)..(627)
<223> OTHER INFORMATION: Ile or Val
<220> FEATURE:
<221> NAME/KEY: MOD_RES
<222> LOCATION: (632)..(632)
<223> OTHER INFORMATION: Ile or Val
<220> FEATURE:
<221> NAME/KEY: MOD_RES
<222> LOCATION: (637)..(637)
<223> OTHER INFORMATION: Ile or Val
<220> FEATURE:
```

```
<221> NAME/KEY: MOD_RES
<222> LOCATION: (642)..(642)
<223> OTHER INFORMATION: Ile or Val
<220> FEATURE:
<221> NAME/KEY: MOD_RES
<222> LOCATION: (647)..(647)
<223> OTHER INFORMATION: Ile or Val
<220> FEATURE:
<221> NAME/KEY: MOD_RES
<222> LOCATION: (652)..(652)
<223> OTHER INFORMATION: Ile or Val
<220> FEATURE:
<221> NAME/KEY: MOD_RES
<222> LOCATION: (657)..(657)
<223> OTHER INFORMATION: Ile or Val
<220> FEATURE:
<221> NAME/KEY: MOD_RES
<222> LOCATION: (662)..(662)
<223> OTHER INFORMATION: Ile or Val
<220> FEATURE:
<221> NAME/KEY: MOD_RES
<222> LOCATION: (667)..(667)
<223> OTHER INFORMATION: Ile or Val
<220> FEATURE:
<221> NAME/KEY: MOD_RES
<222> LOCATION: (672)..(672)
<223> OTHER INFORMATION: Ile or Val
<220> FEATURE:
<221> NAME/KEY: MOD_RES
<222> LOCATION: (677)..(677)
<223> OTHER INFORMATION: Ile or Val
<220> FEATURE:
<221> NAME/KEY: MOD_RES
<222> LOCATION: (682)..(682)
<223> OTHER INFORMATION: Ile or Val
<220> FEATURE:
<221> NAME/KEY: MOD_RES
<222> LOCATION: (687)..(687)
<223> OTHER INFORMATION: Ile or Val
<220> FEATURE:
<221> NAME/KEY: MOD_RES
<222> LOCATION: (692)..(692)
<223> OTHER INFORMATION: Ile or Val
<220> FEATURE:
<221> NAME/KEY: MOD_RES
<222> LOCATION: (697)..(697)
<223> OTHER INFORMATION: Ile or Val
<220> FEATURE:
<221> NAME/KEY: MOD_RES
<222> LOCATION: (702)..(702)
<223> OTHER INFORMATION: Ile or Val
<220> FEATURE:
<221> NAME/KEY: MOD_RES
<222> LOCATION: (707)..(707)
<223> OTHER INFORMATION: Ile or Val
<220> FEATURE:
<221> NAME/KEY: MOD_RES
<222> LOCATION: (712)..(712)
<223> OTHER INFORMATION: Ile or Val
<220> FEATURE:
<221> NAME/KEY: MOD_RES
<222> LOCATION: (717)..(717)
<223> OTHER INFORMATION: Ile or Val
<220> FEATURE:
<221> NAME/KEY: MOD_RES
<222> LOCATION: (722)..(722)
<223> OTHER INFORMATION: Ile or Val
<220> FEATURE:
<221> NAME/KEY: MOD_RES
<222> LOCATION: (727)..(727)
<223> OTHER INFORMATION: Ile or Val
<220> FEATURE:
<221> NAME/KEY: MOD_RES
<222> LOCATION: (732)..(732)
<223> OTHER INFORMATION: Ile or Val
<220> FEATURE:
<221> NAME/KEY: MOD_RES
<222> LOCATION: (737)..(737)
<223> OTHER INFORMATION: Ile or Val
```

```
<220> FEATURE:
<221> NAME/KEY: MOD_RES
<222> LOCATION: (742)..(742)
<223> OTHER INFORMATION: Ile or Val
<220> FEATURE:
<221> NAME/KEY: MOD_RES
<222> LOCATION: (747)..(747)
<223> OTHER INFORMATION: Ile or Val
<220> FEATURE:
<221> NAME/KEY: MOD_RES
<222> LOCATION: (752)..(752)
<223> OTHER INFORMATION: Ile or Val
<220> FEATURE:
<221> NAME/KEY: MOD_RES
<222> LOCATION: (757)..(757)
<223> OTHER INFORMATION: Ile or Val
<220> FEATURE:
<221> NAME/KEY: MOD_RES
<222> LOCATION: (762)..(762)
<223> OTHER INFORMATION: Ile or Val
<220> FEATURE:
<221> NAME/KEY: MOD_RES
<222> LOCATION: (767)..(767)
<223> OTHER INFORMATION: Ile or Val
<220> FEATURE:
<221> NAME/KEY: MOD_RES
<222> LOCATION: (772)..(772)
<223> OTHER INFORMATION: Ile or Val
<220> FEATURE:
<221> NAME/KEY: MOD_RES
<222> LOCATION: (777)..(777)
<223> OTHER INFORMATION: Ile or Val
<220> FEATURE:
<221> NAME/KEY: MOD_RES
<222> LOCATION: (782)..(782)
<223> OTHER INFORMATION: Ile or Val
<220> FEATURE:
<221> NAME/KEY: MOD_RES
<222> LOCATION: (787)..(787)
<223> OTHER INFORMATION: Ile or Val
<220> FEATURE:
<221> NAME/KEY: MOD_RES
<222> LOCATION: (792)..(792)
<223> OTHER INFORMATION: Ile or Val
<220> FEATURE:
<221> NAME/KEY: MOD_RES
<222> LOCATION: (797)..(797)
<223> OTHER INFORMATION: Ile or Val
<220> FEATURE:
<221> NAME/KEY: MOD_RES
<222> LOCATION: (802)..(802)
<223> OTHER INFORMATION: Ile or Val
<220> FEATURE:
<221> NAME/KEY: MOD_RES
<222> LOCATION: (807)..(807)
<223> OTHER INFORMATION: Ile or Val
<220> FEATURE:
<221> NAME/KEY: MOD_RES
<222> LOCATION: (812)..(812)
<223> OTHER INFORMATION: Ile or Val
<220> FEATURE:
<221> NAME/KEY: MOD_RES
<222> LOCATION: (817)..(817)
<223> OTHER INFORMATION: Ile or Val
<220> FEATURE:
<221> NAME/KEY: MOD_RES
<222> LOCATION: (822)..(822)
<223> OTHER INFORMATION: Ile or Val
<220> FEATURE:
<221> NAME/KEY: MOD_RES
<222> LOCATION: (827)..(827)
<223> OTHER INFORMATION: Ile or Val
<220> FEATURE:
<221> NAME/KEY: MOD_RES
<222> LOCATION: (832)..(832)
<223> OTHER INFORMATION: Ile or Val
<220> FEATURE:
<221> NAME/KEY: MOD_RES
<222> LOCATION: (837)..(837)
```

```
<223> OTHER INFORMATION: Ile or Val
<220> FEATURE:
<221> NAME/KEY: MOD_RES
<222> LOCATION: (842)..(842)
<223> OTHER INFORMATION: Ile or Val
<220> FEATURE:
<221> NAME/KEY: MOD_RES
<222> LOCATION: (847)..(847)
<223> OTHER INFORMATION: Ile or Val
<220> FEATURE:
<221> NAME/KEY: MOD_RES
<222> LOCATION: (852)..(852)
<223> OTHER INFORMATION: Ile or Val
<220> FEATURE:
<221> NAME/KEY: MOD_RES
<222> LOCATION: (857)..(857)
<223> OTHER INFORMATION: Ile or Val
<220> FEATURE:
<221> NAME/KEY: MOD_RES
<222> LOCATION: (862)..(862)
<223> OTHER INFORMATION: Ile or Val
<220> FEATURE:
<221> NAME/KEY: MOD_RES
<222> LOCATION: (867)..(867)
<223> OTHER INFORMATION: Ile or Val
<220> FEATURE:
<221> NAME/KEY: MOD_RES
<222> LOCATION: (872)..(872)
<223> OTHER INFORMATION: Ile or Val
<220> FEATURE:
<221> NAME/KEY: MOD_RES
<222> LOCATION: (877)..(877)
<223> OTHER INFORMATION: Ile or Val
<220> FEATURE:
<221> NAME/KEY: MOD_RES
<222> LOCATION: (882)..(882)
<223> OTHER INFORMATION: Ile or Val
<220> FEATURE:
<221> NAME/KEY: MOD_RES
<222> LOCATION: (887)..(887)
<223> OTHER INFORMATION: Ile or Val
<220> FEATURE:
<221> NAME/KEY: MOD_RES
<222> LOCATION: (892)..(892)
<223> OTHER INFORMATION: Ile or Val
<220> FEATURE:
<221> NAME/KEY: MOD_RES
<222> LOCATION: (897)..(897)
<223> OTHER INFORMATION: Ile or Val
<220> FEATURE:
<221> NAME/KEY: MOD_RES
<222> LOCATION: (902)..(902)
<223> OTHER INFORMATION: Ile or Val
<220> FEATURE:
<221> NAME/KEY: MOD_RES
<222> LOCATION: (907)..(907)
<223> OTHER INFORMATION: Ile or Val
<220> FEATURE:
<221> NAME/KEY: MOD_RES
<222> LOCATION: (912)..(912)
<223> OTHER INFORMATION: Ile or Val
<220> FEATURE:
<221> NAME/KEY: MOD_RES
<222> LOCATION: (917)..(917)
<223> OTHER INFORMATION: Ile or Val
<220> FEATURE:
<221> NAME/KEY: MOD_RES
<222> LOCATION: (922)..(922)
<223> OTHER INFORMATION: Ile or Val
<220> FEATURE:
<221> NAME/KEY: MOD_RES
<222> LOCATION: (927)..(927)
<223> OTHER INFORMATION: Ile or Val
<220> FEATURE:
<221> NAME/KEY: MOD_RES
<222> LOCATION: (932)..(932)
<223> OTHER INFORMATION: Ile or Val
<220> FEATURE:
<221> NAME/KEY: MOD_RES
```

-continued

```
<222> LOCATION: (937)..(937)
<223> OTHER INFORMATION: Ile or Val
<220> FEATURE:
<221> NAME/KEY: MOD_RES
<222> LOCATION: (942)..(942)
<223> OTHER INFORMATION: Ile or Val
<220> FEATURE:
<221> NAME/KEY: MOD_RES
<222> LOCATION: (947)..(947)
<223> OTHER INFORMATION: Ile or Val
<220> FEATURE:
<221> NAME/KEY: MOD_RES
<222> LOCATION: (952)..(952)
<223> OTHER INFORMATION: Ile or Val
<220> FEATURE:
<221> NAME/KEY: MOD_RES
<222> LOCATION: (957)..(957)
<223> OTHER INFORMATION: Ile or Val
<220> FEATURE:
<221> NAME/KEY: MOD_RES
<222> LOCATION: (962)..(962)
<223> OTHER INFORMATION: Ile or Val
<220> FEATURE:
<221> NAME/KEY: MOD_RES
<222> LOCATION: (967)..(967)
<223> OTHER INFORMATION: Ile or Val
<220> FEATURE:
<221> NAME/KEY: MOD_RES
<222> LOCATION: (972)..(972)
<223> OTHER INFORMATION: Ile or Val
<220> FEATURE:
<221> NAME/KEY: MOD_RES
<222> LOCATION: (977)..(977)
<223> OTHER INFORMATION: Ile or Val
<220> FEATURE:
<221> NAME/KEY: MOD_RES
<222> LOCATION: (982)..(982)
<223> OTHER INFORMATION: Ile or Val
<220> FEATURE:
<221> NAME/KEY: MOD_RES
<222> LOCATION: (987)..(987)
<223> OTHER INFORMATION: Ile or Val
<220> FEATURE:
<221> NAME/KEY: MOD_RES
<222> LOCATION: (992)..(992)
<223> OTHER INFORMATION: Ile or Val
<220> FEATURE:
<221> NAME/KEY: MOD_RES
<222> LOCATION: (997)..(997)
<223> OTHER INFORMATION: Ile or Val
<220> FEATURE:
<221> NAME/KEY: MOD_RES
<222> LOCATION: (1002)..(1002)
<223> OTHER INFORMATION: Ile or Val
<220> FEATURE:
<221> NAME/KEY: MOD_RES
<222> LOCATION: (1007)..(1007)
<223> OTHER INFORMATION: Ile or Val
<220> FEATURE:
<221> NAME/KEY: MOD_RES
<222> LOCATION: (1012)..(1012)
<223> OTHER INFORMATION: Ile or Val
<220> FEATURE:
<221> NAME/KEY: MOD_RES
<222> LOCATION: (1017)..(1017)
<223> OTHER INFORMATION: Ile or Val
<220> FEATURE:
<221> NAME/KEY: MOD_RES
<222> LOCATION: (1022)..(1022)
<223> OTHER INFORMATION: Ile or Val
<220> FEATURE:
<221> NAME/KEY: MOD_RES
<222> LOCATION: (1027)..(1027)
<223> OTHER INFORMATION: Ile or Val
<220> FEATURE:
<221> NAME/KEY: MOD_RES
<222> LOCATION: (1032)..(1032)
<223> OTHER INFORMATION: Ile or Val
<220> FEATURE:
```

```
<221> NAME/KEY: MOD_RES
<222> LOCATION: (1037)..(1037)
<223> OTHER INFORMATION: Ile or Val
<220> FEATURE:
<221> NAME/KEY: MOD_RES
<222> LOCATION: (1042)..(1042)
<223> OTHER INFORMATION: Ile or Val
<220> FEATURE:
<221> NAME/KEY: MOD_RES
<222> LOCATION: (1047)..(1047)
<223> OTHER INFORMATION: Ile or Val
<220> FEATURE:
<221> NAME/KEY: MOD_RES
<222> LOCATION: (1052)..(1052)
<223> OTHER INFORMATION: Ile or Val
<220> FEATURE:
<221> NAME/KEY: MOD_RES
<222> LOCATION: (1057)..(1057)
<223> OTHER INFORMATION: Ile or Val
<220> FEATURE:
<221> NAME/KEY: MOD_RES
<222> LOCATION: (1062)..(1062)
<223> OTHER INFORMATION: Ile or Val
<220> FEATURE:
<221> NAME/KEY: MOD_RES
<222> LOCATION: (1067)..(1067)
<223> OTHER INFORMATION: Ile or Val
<220> FEATURE:
<221> NAME/KEY: MOD_RES
<222> LOCATION: (1072)..(1072)
<223> OTHER INFORMATION: Ile or Val
<220> FEATURE:
<221> NAME/KEY: MOD_RES
<222> LOCATION: (1077)..(1077)
<223> OTHER INFORMATION: Ile or Val
<220> FEATURE:
<221> NAME/KEY: MOD_RES
<222> LOCATION: (1082)..(1082)
<223> OTHER INFORMATION: Ile or Val
<220> FEATURE:
<221> NAME/KEY: MOD_RES
<222> LOCATION: (1087)..(1087)
<223> OTHER INFORMATION: Ile or Val
<220> FEATURE:
<221> NAME/KEY: MOD_RES
<222> LOCATION: (1092)..(1092)
<223> OTHER INFORMATION: Ile or Val
<220> FEATURE:
<221> NAME/KEY: MOD_RES
<222> LOCATION: (1097)..(1097)
<223> OTHER INFORMATION: Ile or Val
<220> FEATURE:
<221> NAME/KEY: MOD_RES
<222> LOCATION: (1102)..(1102)
<223> OTHER INFORMATION: Ile or Val
<220> FEATURE:
<221> NAME/KEY: MOD_RES
<222> LOCATION: (1107)..(1107)
<223> OTHER INFORMATION: Ile or Val
<220> FEATURE:
<221> NAME/KEY: MOD_RES
<222> LOCATION: (1112)..(1112)
<223> OTHER INFORMATION: Ile or Val
<220> FEATURE:
<221> NAME/KEY: MOD_RES
<222> LOCATION: (1117)..(1117)
<223> OTHER INFORMATION: Ile or Val
<220> FEATURE:
<221> NAME/KEY: MOD_RES
<222> LOCATION: (1122)..(1122)
<223> OTHER INFORMATION: Ile or Val
<220> FEATURE:
<221> NAME/KEY: MOD_RES
<222> LOCATION: (1127)..(1127)
<223> OTHER INFORMATION: Ile or Val
<220> FEATURE:
<221> NAME/KEY: MOD_RES
<222> LOCATION: (1132)..(1132)
<223> OTHER INFORMATION: Ile or Val
```

```
<220> FEATURE:
<221> NAME/KEY: MOD_RES
<222> LOCATION: (1137)..(1137)
<223> OTHER INFORMATION: Ile or Val
<220> FEATURE:
<221> NAME/KEY: MOD_RES
<222> LOCATION: (1142)..(1142)
<223> OTHER INFORMATION: Ile or Val
<220> FEATURE:
<221> NAME/KEY: MOD_RES
<222> LOCATION: (1147)..(1147)
<223> OTHER INFORMATION: Ile or Val
<220> FEATURE:
<221> NAME/KEY: MOD_RES
<222> LOCATION: (1152)..(1152)
<223> OTHER INFORMATION: Ile or Val
<220> FEATURE:
<221> NAME/KEY: MOD_RES
<222> LOCATION: (1157)..(1157)
<223> OTHER INFORMATION: Ile or Val
<220> FEATURE:
<221> NAME/KEY: MOD_RES
<222> LOCATION: (1162)..(1162)
<223> OTHER INFORMATION: Ile or Val
<220> FEATURE:
<221> NAME/KEY: MOD_RES
<222> LOCATION: (1167)..(1167)
<223> OTHER INFORMATION: Ile or Val
<220> FEATURE:
<221> NAME/KEY: MOD_RES
<222> LOCATION: (1172)..(1172)
<223> OTHER INFORMATION: Ile or Val
<220> FEATURE:
<221> NAME/KEY: MOD_RES
<222> LOCATION: (1177)..(1177)
<223> OTHER INFORMATION: Ile or Val
<220> FEATURE:
<221> NAME/KEY: MOD_RES
<222> LOCATION: (1182)..(1182)
<223> OTHER INFORMATION: Ile or Val
<220> FEATURE:
<221> NAME/KEY: MOD_RES
<222> LOCATION: (1187)..(1187)
<223> OTHER INFORMATION: Ile or Val
<220> FEATURE:
<221> NAME/KEY: MOD_RES
<222> LOCATION: (1192)..(1192)
<223> OTHER INFORMATION: Ile or Val
<220> FEATURE:
<221> NAME/KEY: MOD_RES
<222> LOCATION: (1197)..(1197)
<223> OTHER INFORMATION: Ile or Val
<220> FEATURE:
<221> NAME/KEY: MOD_RES
<222> LOCATION: (1202)..(1202)
<223> OTHER INFORMATION: Ile or Val
<220> FEATURE:
<221> NAME/KEY: MOD_RES
<222> LOCATION: (1207)..(1207)
<223> OTHER INFORMATION: Ile or Val
<220> FEATURE:
<221> NAME/KEY: MOD_RES
<222> LOCATION: (1212)..(1212)
<223> OTHER INFORMATION: Ile or Val
<220> FEATURE:
<221> NAME/KEY: MOD_RES
<222> LOCATION: (1217)..(1217)
<223> OTHER INFORMATION: Ile or Val
<220> FEATURE:
<221> NAME/KEY: MOD_RES
<222> LOCATION: (1222)..(1222)
<223> OTHER INFORMATION: Ile or Val
<220> FEATURE:
<221> NAME/KEY: MOD_RES
<222> LOCATION: (1227)..(1227)
<223> OTHER INFORMATION: Ile or Val
<220> FEATURE:
<221> NAME/KEY: MOD_RES
<222> LOCATION: (1232)..(1232)
```

```
<223> OTHER INFORMATION: Ile or Val
<220> FEATURE:
<221> NAME/KEY: MOD_RES
<222> LOCATION: (1237)..(1237)
<223> OTHER INFORMATION: Ile or Val
<220> FEATURE:
<221> NAME/KEY: MOD_RES
<222> LOCATION: (1242)..(1242)
<223> OTHER INFORMATION: Ile or Val
<220> FEATURE:
<221> NAME/KEY: MOD_RES
<222> LOCATION: (1247)..(1247)
<223> OTHER INFORMATION: Ile or Val
<220> FEATURE:
<221> NAME/KEY: MOD_RES
<222> LOCATION: (1252)..(1252)
<223> OTHER INFORMATION: Ile or Val
<220> FEATURE:
<221> NAME/KEY: MOD_RES
<222> LOCATION: (1257)..(1257)
<223> OTHER INFORMATION: Ile or Val
<220> FEATURE:
<221> NAME/KEY: MOD_RES
<222> LOCATION: (1262)..(1262)
<223> OTHER INFORMATION: Ile or Val
<220> FEATURE:
<221> NAME/KEY: MOD_RES
<222> LOCATION: (1267)..(1267)
<223> OTHER INFORMATION: Ile or Val
<220> FEATURE:
<221> NAME/KEY: MOD_RES
<222> LOCATION: (1272)..(1272)
<223> OTHER INFORMATION: Ile or Val
<220> FEATURE:
<221> NAME/KEY: MOD_RES
<222> LOCATION: (1277)..(1277)
<223> OTHER INFORMATION: Ile or Val
<220> FEATURE:
<221> NAME/KEY: MOD_RES
<222> LOCATION: (1282)..(1282)
<223> OTHER INFORMATION: Ile or Val
<220> FEATURE:
<221> NAME/KEY: MOD_RES
<222> LOCATION: (1287)..(1287)
<223> OTHER INFORMATION: Ile or Val
<220> FEATURE:
<221> NAME/KEY: MOD_RES
<222> LOCATION: (1292)..(1292)
<223> OTHER INFORMATION: Ile or Val
<220> FEATURE:
<221> NAME/KEY: MOD_RES
<222> LOCATION: (1297)..(1297)
<223> OTHER INFORMATION: Ile or Val
<220> FEATURE:
<221> NAME/KEY: MOD_RES
<222> LOCATION: (1302)..(1302)
<223> OTHER INFORMATION: Ile or Val
<220> FEATURE:
<221> NAME/KEY: MOD_RES
<222> LOCATION: (1307)..(1307)
<223> OTHER INFORMATION: Ile or Val
<220> FEATURE:
<221> NAME/KEY: MOD_RES
<222> LOCATION: (1312)..(1312)
<223> OTHER INFORMATION: Ile or Val
<220> FEATURE:
<221> NAME/KEY: MOD_RES
<222> LOCATION: (1317)..(1317)
<223> OTHER INFORMATION: Ile or Val
<220> FEATURE:
<221> NAME/KEY: MOD_RES
<222> LOCATION: (1322)..(1322)
<223> OTHER INFORMATION: Ile or Val
<220> FEATURE:
<221> NAME/KEY: MOD_RES
<222> LOCATION: (1327)..(1327)
<223> OTHER INFORMATION: Ile or Val
<220> FEATURE:
<221> NAME/KEY: MOD_RES
```

```
<222> LOCATION: (1332)..(1332)
<223> OTHER INFORMATION: Ile or Val
<220> FEATURE:
<221> NAME/KEY: MOD_RES
<222> LOCATION: (1337)..(1337)
<223> OTHER INFORMATION: Ile or Val
<220> FEATURE:
<221> NAME/KEY: MOD_RES
<222> LOCATION: (1342)..(1342)
<223> OTHER INFORMATION: Ile or Val
<220> FEATURE:
<221> NAME/KEY: MOD_RES
<222> LOCATION: (1347)..(1347)
<223> OTHER INFORMATION: Ile or Val
<220> FEATURE:
<221> NAME/KEY: MOD_RES
<222> LOCATION: (1352)..(1352)
<223> OTHER INFORMATION: Ile or Val
<220> FEATURE:
<221> NAME/KEY: MOD_RES
<222> LOCATION: (1357)..(1357)
<223> OTHER INFORMATION: Ile or Val
<220> FEATURE:
<221> NAME/KEY: MOD_RES
<222> LOCATION: (1362)..(1362)
<223> OTHER INFORMATION: Ile or Val
<220> FEATURE:
<221> NAME/KEY: MOD_RES
<222> LOCATION: (1367)..(1367)
<223> OTHER INFORMATION: Ile or Val
<220> FEATURE:
<221> NAME/KEY: MOD_RES
<222> LOCATION: (1372)..(1372)
<223> OTHER INFORMATION: Ile or Val
<220> FEATURE:
<221> NAME/KEY: MOD_RES
<222> LOCATION: (1377)..(1377)
<223> OTHER INFORMATION: Ile or Val
<220> FEATURE:
<221> NAME/KEY: MOD_RES
<222> LOCATION: (1382)..(1382)
<223> OTHER INFORMATION: Ile or Val
<220> FEATURE:
<221> NAME/KEY: MOD_RES
<222> LOCATION: (1387)..(1387)
<223> OTHER INFORMATION: Ile or Val
<220> FEATURE:
<221> NAME/KEY: MOD_RES
<222> LOCATION: (1392)..(1392)
<223> OTHER INFORMATION: Ile or Val
<220> FEATURE:
<221> NAME/KEY: MOD_RES
<222> LOCATION: (1397)..(1397)
<223> OTHER INFORMATION: Ile or Val
<220> FEATURE:
<221> NAME/KEY: MOD_RES
<222> LOCATION: (1402)..(1402)
<223> OTHER INFORMATION: Ile or Val
<220> FEATURE:
<221> NAME/KEY: MOD_RES
<222> LOCATION: (1407)..(1407)
<223> OTHER INFORMATION: Ile or Val
<220> FEATURE:
<221> NAME/KEY: MOD_RES
<222> LOCATION: (1412)..(1412)
<223> OTHER INFORMATION: Ile or Val
<220> FEATURE:
<221> NAME/KEY: MOD_RES
<222> LOCATION: (1417)..(1417)
<223> OTHER INFORMATION: Ile or Val
<220> FEATURE:
<221> NAME/KEY: MOD_RES
<222> LOCATION: (1422)..(1422)
<223> OTHER INFORMATION: Ile or Val
<220> FEATURE:
<221> NAME/KEY: MOD_RES
<222> LOCATION: (1427)..(1427)
<223> OTHER INFORMATION: Ile or Val
<220> FEATURE:
```

```
<221> NAME/KEY: MOD_RES
<222> LOCATION: (1432)..(1432)
<223> OTHER INFORMATION: Ile or Val
<220> FEATURE:
<221> NAME/KEY: MOD_RES
<222> LOCATION: (1437)..(1437)
<223> OTHER INFORMATION: Ile or Val
<220> FEATURE:
<221> NAME/KEY: MOD_RES
<222> LOCATION: (1442)..(1442)
<223> OTHER INFORMATION: Ile or Val
<220> FEATURE:
<221> NAME/KEY: MOD_RES
<222> LOCATION: (1447)..(1447)
<223> OTHER INFORMATION: Ile or Val
<220> FEATURE:
<221> NAME/KEY: MOD_RES
<222> LOCATION: (1452)..(1452)
<223> OTHER INFORMATION: Ile or Val
<220> FEATURE:
<221> NAME/KEY: MOD_RES
<222> LOCATION: (1457)..(1457)
<223> OTHER INFORMATION: Ile or Val
<220> FEATURE:
<221> NAME/KEY: MOD_RES
<222> LOCATION: (1462)..(1462)
<223> OTHER INFORMATION: Ile or Val
<220> FEATURE:
<221> NAME/KEY: MOD_RES
<222> LOCATION: (1467)..(1467)
<223> OTHER INFORMATION: Ile or Val
<220> FEATURE:
<221> NAME/KEY: MOD_RES
<222> LOCATION: (1472)..(1472)
<223> OTHER INFORMATION: Ile or Val
<220> FEATURE:
<221> NAME/KEY: MOD_RES
<222> LOCATION: (1477)..(1477)
<223> OTHER INFORMATION: Ile or Val
<220> FEATURE:
<221> NAME/KEY: MOD_RES
<222> LOCATION: (1482)..(1482)
<223> OTHER INFORMATION: Ile or Val
<220> FEATURE:
<221> NAME/KEY: MOD_RES
<222> LOCATION: (1487)..(1487)
<223> OTHER INFORMATION: Ile or Val
<220> FEATURE:
<221> NAME/KEY: MOD_RES
<222> LOCATION: (1492)..(1492)
<223> OTHER INFORMATION: Ile or Val
<220> FEATURE:
<221> NAME/KEY: MOD_RES
<222> LOCATION: (1497)..(1497)
<223> OTHER INFORMATION: Ile or Val
<220> FEATURE:
<221> NAME/KEY: MOD_RES
<222> LOCATION: (1502)..(1502)
<223> OTHER INFORMATION: Ile or Val
<220> FEATURE:
<221> NAME/KEY: MOD_RES
<222> LOCATION: (1507)..(1507)
<223> OTHER INFORMATION: Ile or Val
<220> FEATURE:
<221> NAME/KEY: MOD_RES
<222> LOCATION: (1512)..(1512)
<223> OTHER INFORMATION: Ile or Val
<220> FEATURE:
<221> NAME/KEY: MOD_RES
<222> LOCATION: (1517)..(1517)
<223> OTHER INFORMATION: Ile or Val
<220> FEATURE:
<221> NAME/KEY: MOD_RES
<222> LOCATION: (1522)..(1522)
<223> OTHER INFORMATION: Ile or Val
<220> FEATURE:
<221> NAME/KEY: MOD_RES
<222> LOCATION: (1527)..(1527)
<223> OTHER INFORMATION: Ile or Val
```

```
<220> FEATURE:
<221> NAME/KEY: MOD_RES
<222> LOCATION: (1532)..(1532)
<223> OTHER INFORMATION: Ile or Val
<220> FEATURE:
<221> NAME/KEY: MOD_RES
<222> LOCATION: (1537)..(1537)
<223> OTHER INFORMATION: Ile or Val
<220> FEATURE:
<221> NAME/KEY: MOD_RES
<222> LOCATION: (1542)..(1542)
<223> OTHER INFORMATION: Ile or Val
<220> FEATURE:
<221> NAME/KEY: MOD_RES
<222> LOCATION: (1547)..(1547)
<223> OTHER INFORMATION: Ile or Val
<220> FEATURE:
<221> NAME/KEY: MOD_RES
<222> LOCATION: (1552)..(1552)
<223> OTHER INFORMATION: Ile or Val
<220> FEATURE:
<221> NAME/KEY: MOD_RES
<222> LOCATION: (1557)..(1557)
<223> OTHER INFORMATION: Ile or Val
<220> FEATURE:
<221> NAME/KEY: MOD_RES
<222> LOCATION: (1562)..(1562)
<223> OTHER INFORMATION: Ile or Val
<220> FEATURE:
<221> NAME/KEY: MOD_RES
<222> LOCATION: (1567)..(1567)
<223> OTHER INFORMATION: Ile or Val
<220> FEATURE:
<221> NAME/KEY: MOD_RES
<222> LOCATION: (1572)..(1572)
<223> OTHER INFORMATION: Ile or Val
<220> FEATURE:
<221> NAME/KEY: MOD_RES
<222> LOCATION: (1577)..(1577)
<223> OTHER INFORMATION: Ile or Val
<220> FEATURE:
<221> NAME/KEY: MOD_RES
<222> LOCATION: (1582)..(1582)
<223> OTHER INFORMATION: Ile or Val
<220> FEATURE:
<221> NAME/KEY: MOD_RES
<222> LOCATION: (1587)..(1587)
<223> OTHER INFORMATION: Ile or Val
<220> FEATURE:
<221> NAME/KEY: MOD_RES
<222> LOCATION: (1592)..(1592)
<223> OTHER INFORMATION: Ile or Val
<220> FEATURE:
<221> NAME/KEY: MOD_RES
<222> LOCATION: (1597)..(1597)
<223> OTHER INFORMATION: Ile or Val
<220> FEATURE:
<221> NAME/KEY: MOD_RES
<222> LOCATION: (1602)..(1602)
<223> OTHER INFORMATION: Ile or Val
<220> FEATURE:
<221> NAME/KEY: MOD_RES
<222> LOCATION: (1607)..(1607)
<223> OTHER INFORMATION: Ile or Val
<220> FEATURE:
<221> NAME/KEY: MOD_RES
<222> LOCATION: (1612)..(1612)
<223> OTHER INFORMATION: Ile or Val
<220> FEATURE:
<221> NAME/KEY: MOD_RES
<222> LOCATION: (1617)..(1617)
<223> OTHER INFORMATION: Ile or Val
<220> FEATURE:
<221> NAME/KEY: MOD_RES
<222> LOCATION: (1622)..(1622)
<223> OTHER INFORMATION: Ile or Val
<220> FEATURE:
<221> NAME/KEY: MOD_RES
<222> LOCATION: (1627)..(1627)
```

```
<223> OTHER INFORMATION: Ile or Val
<220> FEATURE:
<221> NAME/KEY: MOD_RES
<222> LOCATION: (1632)..(1632)
<223> OTHER INFORMATION: Ile or Val
<220> FEATURE:
<221> NAME/KEY: MOD_RES
<222> LOCATION: (1637)..(1637)
<223> OTHER INFORMATION: Ile or Val
<220> FEATURE:
<221> NAME/KEY: MOD_RES
<222> LOCATION: (1642)..(1642)
<223> OTHER INFORMATION: Ile or Val
<220> FEATURE:
<221> NAME/KEY: MOD_RES
<222> LOCATION: (1647)..(1647)
<223> OTHER INFORMATION: Ile or Val
<220> FEATURE:
<221> NAME/KEY: MOD_RES
<222> LOCATION: (1652)..(1652)
<223> OTHER INFORMATION: Ile or Val
<220> FEATURE:
<221> NAME/KEY: MOD_RES
<222> LOCATION: (1657)..(1657)
<223> OTHER INFORMATION: Ile or Val
<220> FEATURE:
<221> NAME/KEY: MOD_RES
<222> LOCATION: (1662)..(1662)
<223> OTHER INFORMATION: Ile or Val
<220> FEATURE:
<221> NAME/KEY: MOD_RES
<222> LOCATION: (1667)..(1667)
<223> OTHER INFORMATION: Ile or Val
<220> FEATURE:
<221> NAME/KEY: MOD_RES
<222> LOCATION: (1672)..(1672)
<223> OTHER INFORMATION: Ile or Val
<220> FEATURE:
<221> NAME/KEY: MOD_RES
<222> LOCATION: (1677)..(1677)
<223> OTHER INFORMATION: Ile or Val
<220> FEATURE:
<221> NAME/KEY: MOD_RES
<222> LOCATION: (1682)..(1682)
<223> OTHER INFORMATION: Ile or Val
<220> FEATURE:
<221> NAME/KEY: MOD_RES
<222> LOCATION: (1687)..(1687)
<223> OTHER INFORMATION: Ile or Val
<220> FEATURE:
<221> NAME/KEY: MOD_RES
<222> LOCATION: (1692)..(1692)
<223> OTHER INFORMATION: Ile or Val
<220> FEATURE:
<221> NAME/KEY: MOD_RES
<222> LOCATION: (1697)..(1697)
<223> OTHER INFORMATION: Ile or Val
<220> FEATURE:
<221> NAME/KEY: MOD_RES
<222> LOCATION: (1702)..(1702)
<223> OTHER INFORMATION: Ile or Val
<220> FEATURE:
<221> NAME/KEY: MOD_RES
<222> LOCATION: (1707)..(1707)
<223> OTHER INFORMATION: Ile or Val
<220> FEATURE:
<221> NAME/KEY: MOD_RES
<222> LOCATION: (1712)..(1712)
<223> OTHER INFORMATION: Ile or Val
<220> FEATURE:
<221> NAME/KEY: MOD_RES
<222> LOCATION: (1717)..(1717)
<223> OTHER INFORMATION: Ile or Val
<220> FEATURE:
<221> NAME/KEY: MOD_RES
<222> LOCATION: (1722)..(1722)
<223> OTHER INFORMATION: Ile or Val
<220> FEATURE:
<221> NAME/KEY: MOD_RES
```

-continued

```
<222> LOCATION: (1727)..(1727)
<223> OTHER INFORMATION: Ile or Val
<220> FEATURE:
<221> NAME/KEY: MOD_RES
<222> LOCATION: (1732)..(1732)
<223> OTHER INFORMATION: Ile or Val
<220> FEATURE:
<221> NAME/KEY: MOD_RES
<222> LOCATION: (1737)..(1737)
<223> OTHER INFORMATION: Ile or Val
<220> FEATURE:
<221> NAME/KEY: MOD_RES
<222> LOCATION: (1742)..(1742)
<223> OTHER INFORMATION: Ile or Val
<220> FEATURE:
<221> NAME/KEY: MOD_RES
<222> LOCATION: (1747)..(1747)
<223> OTHER INFORMATION: Ile or Val
<220> FEATURE:
<221> NAME/KEY: MOD_RES
<222> LOCATION: (1752)..(1752)
<223> OTHER INFORMATION: Ile or Val
<220> FEATURE:
<221> NAME/KEY: MOD_RES
<222> LOCATION: (1757)..(1757)
<223> OTHER INFORMATION: Ile or Val
<220> FEATURE:
<221> NAME/KEY: MOD_RES
<222> LOCATION: (1762)..(1762)
<223> OTHER INFORMATION: Ile or Val
<220> FEATURE:
<221> NAME/KEY: MOD_RES
<222> LOCATION: (1767)..(1767)
<223> OTHER INFORMATION: Ile or Val
<220> FEATURE:
<221> NAME/KEY: MOD_RES
<222> LOCATION: (1772)..(1772)
<223> OTHER INFORMATION: Ile or Val
<220> FEATURE:
<221> NAME/KEY: MOD_RES
<222> LOCATION: (1777)..(1777)
<223> OTHER INFORMATION: Ile or Val
<220> FEATURE:
<221> NAME/KEY: MOD_RES
<222> LOCATION: (1782)..(1782)
<223> OTHER INFORMATION: Ile or Val
<220> FEATURE:
<221> NAME/KEY: MOD_RES
<222> LOCATION: (1787)..(1787)
<223> OTHER INFORMATION: Ile or Val
<220> FEATURE:
<221> NAME/KEY: MOD_RES
<222> LOCATION: (1792)..(1792)
<223> OTHER INFORMATION: Ile or Val
<220> FEATURE:
<221> NAME/KEY: MOD_RES
<222> LOCATION: (1797)..(1797)
<223> OTHER INFORMATION: Ile or Val
<220> FEATURE:
<221> NAME/KEY: MOD_RES
<222> LOCATION: (1802)..(1802)
<223> OTHER INFORMATION: Ile or Val
<220> FEATURE:
<221> NAME/KEY: MOD_RES
<222> LOCATION: (1807)..(1807)
<223> OTHER INFORMATION: Ile or Val
<220> FEATURE:
<221> NAME/KEY: MOD_RES
<222> LOCATION: (1812)..(1812)
<223> OTHER INFORMATION: Ile or Val
<220> FEATURE:
<221> NAME/KEY: MOD_RES
<222> LOCATION: (1817)..(1817)
<223> OTHER INFORMATION: Ile or Val
<220> FEATURE:
<221> NAME/KEY: MOD_RES
<222> LOCATION: (1822)..(1822)
<223> OTHER INFORMATION: Ile or Val
<220> FEATURE:
```

```
<221> NAME/KEY: MOD_RES
<222> LOCATION: (1827)..(1827)
<223> OTHER INFORMATION: Ile or Val
<220> FEATURE:
<221> NAME/KEY: MOD_RES
<222> LOCATION: (1832)..(1832)
<223> OTHER INFORMATION: Ile or Val
<220> FEATURE:
<221> NAME/KEY: MOD_RES
<222> LOCATION: (1837)..(1837)
<223> OTHER INFORMATION: Ile or Val
<220> FEATURE:
<221> NAME/KEY: MOD_RES
<222> LOCATION: (1842)..(1842)
<223> OTHER INFORMATION: Ile or Val
<220> FEATURE:
<221> NAME/KEY: MOD_RES
<222> LOCATION: (1847)..(1847)
<223> OTHER INFORMATION: Ile or Val
<220> FEATURE:
<221> NAME/KEY: MOD_RES
<222> LOCATION: (1852)..(1852)
<223> OTHER INFORMATION: Ile or Val
<220> FEATURE:
<221> NAME/KEY: MOD_RES
<222> LOCATION: (1857)..(1857)
<223> OTHER INFORMATION: Ile or Val
<220> FEATURE:
<221> NAME/KEY: MOD_RES
<222> LOCATION: (1862)..(1862)
<223> OTHER INFORMATION: Ile or Val
<220> FEATURE:
<221> NAME/KEY: MOD_RES
<222> LOCATION: (1867)..(1867)
<223> OTHER INFORMATION: Ile or Val
<220> FEATURE:
<221> NAME/KEY: MOD_RES
<222> LOCATION: (1872)..(1872)
<223> OTHER INFORMATION: Ile or Val
<220> FEATURE:
<221> NAME/KEY: MOD_RES
<222> LOCATION: (1877)..(1877)
<223> OTHER INFORMATION: Ile or Val
<220> FEATURE:
<221> NAME/KEY: MOD_RES
<222> LOCATION: (1882)..(1882)
<223> OTHER INFORMATION: Ile or Val
<220> FEATURE:
<221> NAME/KEY: MOD_RES
<222> LOCATION: (1887)..(1887)
<223> OTHER INFORMATION: Ile or Val
<220> FEATURE:
<221> NAME/KEY: MOD_RES
<222> LOCATION: (1892)..(1892)
<223> OTHER INFORMATION: Ile or Val
<220> FEATURE:
<221> NAME/KEY: MOD_RES
<222> LOCATION: (1897)..(1897)
<223> OTHER INFORMATION: Ile or Val
<220> FEATURE:
<221> NAME/KEY: MOD_RES
<222> LOCATION: (1902)..(1902)
<223> OTHER INFORMATION: Ile or Val
<220> FEATURE:
<221> NAME/KEY: MOD_RES
<222> LOCATION: (1907)..(1907)
<223> OTHER INFORMATION: Ile or Val
<220> FEATURE:
<221> NAME/KEY: MOD_RES
<222> LOCATION: (1912)..(1912)
<223> OTHER INFORMATION: Ile or Val
<220> FEATURE:
<221> NAME/KEY: MOD_RES
<222> LOCATION: (1917)..(1917)
<223> OTHER INFORMATION: Ile or Val
<220> FEATURE:
<221> NAME/KEY: MOD_RES
<222> LOCATION: (1922)..(1922)
<223> OTHER INFORMATION: Ile or Val
```

```
<220> FEATURE:
<221> NAME/KEY: MOD_RES
<222> LOCATION: (1927)..(1927)
<223> OTHER INFORMATION: Ile or Val
<220> FEATURE:
<221> NAME/KEY: MOD_RES
<222> LOCATION: (1932)..(1932)
<223> OTHER INFORMATION: Ile or Val
<220> FEATURE:
<221> NAME/KEY: MOD_RES
<222> LOCATION: (1937)..(1937)
<223> OTHER INFORMATION: Ile or Val
<220> FEATURE:
<221> NAME/KEY: MOD_RES
<222> LOCATION: (1942)..(1942)
<223> OTHER INFORMATION: Ile or Val
<220> FEATURE:
<221> NAME/KEY: MOD_RES
<222> LOCATION: (1947)..(1947)
<223> OTHER INFORMATION: Ile or Val
<220> FEATURE:
<221> NAME/KEY: MOD_RES
<222> LOCATION: (1952)..(1952)
<223> OTHER INFORMATION: Ile or Val
<220> FEATURE:
<221> NAME/KEY: MOD_RES
<222> LOCATION: (1957)..(1957)
<223> OTHER INFORMATION: Ile or Val
<220> FEATURE:
<221> NAME/KEY: MOD_RES
<222> LOCATION: (1962)..(1962)
<223> OTHER INFORMATION: Ile or Val
<220> FEATURE:
<221> NAME/KEY: MOD_RES
<222> LOCATION: (1967)..(1967)
<223> OTHER INFORMATION: Ile or Val
<220> FEATURE:
<221> NAME/KEY: MOD_RES
<222> LOCATION: (1972)..(1972)
<223> OTHER INFORMATION: Ile or Val
<220> FEATURE:
<221> NAME/KEY: MOD_RES
<222> LOCATION: (1977)..(1977)
<223> OTHER INFORMATION: Ile or Val
<220> FEATURE:
<221> NAME/KEY: MOD_RES
<222> LOCATION: (1982)..(1982)
<223> OTHER INFORMATION: Ile or Val
<220> FEATURE:
<221> NAME/KEY: MOD_RES
<222> LOCATION: (1987)..(1987)
<223> OTHER INFORMATION: Ile or Val
<220> FEATURE:
<221> NAME/KEY: MOD_RES
<222> LOCATION: (1992)..(1992)
<223> OTHER INFORMATION: Ile or Val
<220> FEATURE:
<221> NAME/KEY: MOD_RES
<222> LOCATION: (1997)..(1997)
<223> OTHER INFORMATION: Ile or Val
<220> FEATURE:
<221> NAME/KEY: MOD_RES
<222> LOCATION: (2002)..(2002)
<223> OTHER INFORMATION: Ile or Val
<220> FEATURE:
<221> NAME/KEY: MOD_RES
<222> LOCATION: (2007)..(2007)
<223> OTHER INFORMATION: Ile or Val
<220> FEATURE:
<221> NAME/KEY: MOD_RES
<222> LOCATION: (2012)..(2012)
<223> OTHER INFORMATION: Ile or Val
<220> FEATURE:
<221> NAME/KEY: MOD_RES
<222> LOCATION: (2017)..(2017)
<223> OTHER INFORMATION: Ile or Val
<220> FEATURE:
<221> NAME/KEY: MOD_RES
<222> LOCATION: (2022)..(2022)
```

```
<223> OTHER INFORMATION: Ile or Val
<220> FEATURE:
<221> NAME/KEY: MOD_RES
<222> LOCATION: (2027)..(2027)
<223> OTHER INFORMATION: Ile or Val
<220> FEATURE:
<221> NAME/KEY: MOD_RES
<222> LOCATION: (2032)..(2032)
<223> OTHER INFORMATION: Ile or Val
<220> FEATURE:
<221> NAME/KEY: MOD_RES
<222> LOCATION: (2037)..(2037)
<223> OTHER INFORMATION: Ile or Val
<220> FEATURE:
<221> NAME/KEY: MOD_RES
<222> LOCATION: (2042)..(2042)
<223> OTHER INFORMATION: Ile or Val
<220> FEATURE:
<221> NAME/KEY: MOD_RES
<222> LOCATION: (2047)..(2047)
<223> OTHER INFORMATION: Ile or Val
<220> FEATURE:
<221> NAME/KEY: MOD_RES
<222> LOCATION: (2052)..(2052)
<223> OTHER INFORMATION: Ile or Val
<220> FEATURE:
<221> NAME/KEY: MOD_RES
<222> LOCATION: (2057)..(2057)
<223> OTHER INFORMATION: Ile or Val
<220> FEATURE:
<221> NAME/KEY: MOD_RES
<222> LOCATION: (2062)..(2062)
<223> OTHER INFORMATION: Ile or Val
<220> FEATURE:
<221> NAME/KEY: MOD_RES
<222> LOCATION: (2067)..(2067)
<223> OTHER INFORMATION: Ile or Val
<220> FEATURE:
<221> NAME/KEY: MOD_RES
<222> LOCATION: (2072)..(2072)
<223> OTHER INFORMATION: Ile or Val
<220> FEATURE:
<221> NAME/KEY: MOD_RES
<222> LOCATION: (2077)..(2077)
<223> OTHER INFORMATION: Ile or Val
<220> FEATURE:
<221> NAME/KEY: MOD_RES
<222> LOCATION: (2082)..(2082)
<223> OTHER INFORMATION: Ile or Val
<220> FEATURE:
<221> NAME/KEY: MOD_RES
<222> LOCATION: (2087)..(2087)
<223> OTHER INFORMATION: Ile or Val
<220> FEATURE:
<221> NAME/KEY: MOD_RES
<222> LOCATION: (2092)..(2092)
<223> OTHER INFORMATION: Ile or Val
<220> FEATURE:
<221> NAME/KEY: MOD_RES
<222> LOCATION: (2097)..(2097)
<223> OTHER INFORMATION: Ile or Val
<220> FEATURE:
<221> NAME/KEY: MOD_RES
<222> LOCATION: (2102)..(2102)
<223> OTHER INFORMATION: Ile or Val
<220> FEATURE:
<221> NAME/KEY: MOD_RES
<222> LOCATION: (2107)..(2107)
<223> OTHER INFORMATION: Ile or Val
<220> FEATURE:
<221> NAME/KEY: MOD_RES
<222> LOCATION: (2112)..(2112)
<223> OTHER INFORMATION: Ile or Val
<220> FEATURE:
<221> NAME/KEY: MOD_RES
<222> LOCATION: (2117)..(2117)
<223> OTHER INFORMATION: Ile or Val
<220> FEATURE:
<221> NAME/KEY: MOD_RES
```

```
<222> LOCATION: (2122)..(2122)
<223> OTHER INFORMATION: Ile or Val
<220> FEATURE:
<221> NAME/KEY: MOD_RES
<222> LOCATION: (2127)..(2127)
<223> OTHER INFORMATION: Ile or Val
<220> FEATURE:
<221> NAME/KEY: MOD_RES
<222> LOCATION: (2132)..(2132)
<223> OTHER INFORMATION: Ile or Val
<220> FEATURE:
<221> NAME/KEY: MOD_RES
<222> LOCATION: (2137)..(2137)
<223> OTHER INFORMATION: Ile or Val
<220> FEATURE:
<221> NAME/KEY: MOD_RES
<222> LOCATION: (2142)..(2142)
<223> OTHER INFORMATION: Ile or Val
<220> FEATURE:
<221> NAME/KEY: MOD_RES
<222> LOCATION: (2147)..(2147)
<223> OTHER INFORMATION: Ile or Val
<220> FEATURE:
<221> NAME/KEY: MOD_RES
<222> LOCATION: (2152)..(2152)
<223> OTHER INFORMATION: Ile or Val
<220> FEATURE:
<221> NAME/KEY: MOD_RES
<222> LOCATION: (2157)..(2157)
<223> OTHER INFORMATION: Ile or Val
<220> FEATURE:
<221> NAME/KEY: MOD_RES
<222> LOCATION: (2162)..(2162)
<223> OTHER INFORMATION: Ile or Val
<220> FEATURE:
<221> NAME/KEY: MOD_RES
<222> LOCATION: (2167)..(2167)
<223> OTHER INFORMATION: Ile or Val
<220> FEATURE:
<221> NAME/KEY: MOD_RES
<222> LOCATION: (2172)..(2172)
<223> OTHER INFORMATION: Ile or Val
<220> FEATURE:
<221> NAME/KEY: MOD_RES
<222> LOCATION: (2177)..(2177)
<223> OTHER INFORMATION: Ile or Val
<220> FEATURE:
<221> NAME/KEY: MOD_RES
<222> LOCATION: (2182)..(2182)
<223> OTHER INFORMATION: Ile or Val
<220> FEATURE:
<221> NAME/KEY: MOD_RES
<222> LOCATION: (2187)..(2187)
<223> OTHER INFORMATION: Ile or Val
<220> FEATURE:
<221> NAME/KEY: MOD_RES
<222> LOCATION: (2192)..(2192)
<223> OTHER INFORMATION: Ile or Val
<220> FEATURE:
<221> NAME/KEY: MOD_RES
<222> LOCATION: (2197)..(2197)
<223> OTHER INFORMATION: Ile or Val
<220> FEATURE:
<221> NAME/KEY: MOD_RES
<222> LOCATION: (2202)..(2202)
<223> OTHER INFORMATION: Ile or Val
<220> FEATURE:
<221> NAME/KEY: MOD_RES
<222> LOCATION: (2207)..(2207)
<223> OTHER INFORMATION: Ile or Val
<220> FEATURE:
<221> NAME/KEY: MOD_RES
<222> LOCATION: (2212)..(2212)
<223> OTHER INFORMATION: Ile or Val
<220> FEATURE:
<221> NAME/KEY: MOD_RES
<222> LOCATION: (2217)..(2217)
<223> OTHER INFORMATION: Ile or Val
<220> FEATURE:
```

-continued

```
<221> NAME/KEY: MOD_RES
<222> LOCATION: (2222)..(2222)
<223> OTHER INFORMATION: Ile or Val
<220> FEATURE:
<221> NAME/KEY: MOD_RES
<222> LOCATION: (2227)..(2227)
<223> OTHER INFORMATION: Ile or Val
<220> FEATURE:
<221> NAME/KEY: MOD_RES
<222> LOCATION: (2232)..(2232)
<223> OTHER INFORMATION: Ile or Val
<220> FEATURE:
<221> NAME/KEY: MOD_RES
<222> LOCATION: (2237)..(2237)
<223> OTHER INFORMATION: Ile or Val
<220> FEATURE:
<221> NAME/KEY: MOD_RES
<222> LOCATION: (2242)..(2242)
<223> OTHER INFORMATION: Ile or Val
<220> FEATURE:
<221> NAME/KEY: MOD_RES
<222> LOCATION: (2247)..(2247)
<223> OTHER INFORMATION: Ile or Val
<220> FEATURE:
<221> NAME/KEY: MOD_RES
<222> LOCATION: (2252)..(2252)
<223> OTHER INFORMATION: Ile or Val
<220> FEATURE:
<221> NAME/KEY: MOD_RES
<222> LOCATION: (2257)..(2257)
<223> OTHER INFORMATION: Ile or Val
<220> FEATURE:
<221> NAME/KEY: MOD_RES
<222> LOCATION: (2262)..(2262)
<223> OTHER INFORMATION: Ile or Val
<220> FEATURE:
<221> NAME/KEY: MOD_RES
<222> LOCATION: (2267)..(2267)
<223> OTHER INFORMATION: Ile or Val
<220> FEATURE:
<221> NAME/KEY: MOD_RES
<222> LOCATION: (2272)..(2272)
<223> OTHER INFORMATION: Ile or Val
<220> FEATURE:
<221> NAME/KEY: MOD_RES
<222> LOCATION: (2277)..(2277)
<223> OTHER INFORMATION: Ile or Val
<220> FEATURE:
<221> NAME/KEY: MOD_RES
<222> LOCATION: (2282)..(2282)
<223> OTHER INFORMATION: Ile or Val
<220> FEATURE:
<221> NAME/KEY: MOD_RES
<222> LOCATION: (2287)..(2287)
<223> OTHER INFORMATION: Ile or Val
<220> FEATURE:
<221> NAME/KEY: MOD_RES
<222> LOCATION: (2292)..(2292)
<223> OTHER INFORMATION: Ile or Val
<220> FEATURE:
<221> NAME/KEY: MOD_RES
<222> LOCATION: (2297)..(2297)
<223> OTHER INFORMATION: Ile or Val
<220> FEATURE:
<221> NAME/KEY: MOD_RES
<222> LOCATION: (2302)..(2302)
<223> OTHER INFORMATION: Ile or Val
<220> FEATURE:
<221> NAME/KEY: MOD_RES
<222> LOCATION: (2307)..(2307)
<223> OTHER INFORMATION: Ile or Val
<220> FEATURE:
<221> NAME/KEY: MOD_RES
<222> LOCATION: (2312)..(2312)
<223> OTHER INFORMATION: Ile or Val
<220> FEATURE:
<221> NAME/KEY: MOD_RES
<222> LOCATION: (2317)..(2317)
<223> OTHER INFORMATION: Ile or Val
```

-continued

```
<220> FEATURE:
<221> NAME/KEY: MOD_RES
<222> LOCATION: (2322)..(2322)
<223> OTHER INFORMATION: Ile or Val
<220> FEATURE:
<221> NAME/KEY: MOD_RES
<222> LOCATION: (2327)..(2327)
<223> OTHER INFORMATION: Ile or Val
<220> FEATURE:
<221> NAME/KEY: MOD_RES
<222> LOCATION: (2332)..(2332)
<223> OTHER INFORMATION: Ile or Val
<220> FEATURE:
<221> NAME/KEY: MOD_RES
<222> LOCATION: (2337)..(2337)
<223> OTHER INFORMATION: Ile or Val
<220> FEATURE:
<221> NAME/KEY: MOD_RES
<222> LOCATION: (2342)..(2342)
<223> OTHER INFORMATION: Ile or Val
<220> FEATURE:
<221> NAME/KEY: MOD_RES
<222> LOCATION: (2347)..(2347)
<223> OTHER INFORMATION: Ile or Val
<220> FEATURE:
<221> NAME/KEY: MOD_RES
<222> LOCATION: (2352)..(2352)
<223> OTHER INFORMATION: Ile or Val
<220> FEATURE:
<221> NAME/KEY: MOD_RES
<222> LOCATION: (2357)..(2357)
<223> OTHER INFORMATION: Ile or Val
<220> FEATURE:
<221> NAME/KEY: MOD_RES
<222> LOCATION: (2362)..(2362)
<223> OTHER INFORMATION: Ile or Val
<220> FEATURE:
<221> NAME/KEY: MOD_RES
<222> LOCATION: (2367)..(2367)
<223> OTHER INFORMATION: Ile or Val
<220> FEATURE:
<221> NAME/KEY: MOD_RES
<222> LOCATION: (2372)..(2372)
<223> OTHER INFORMATION: Ile or Val
<220> FEATURE:
<221> NAME/KEY: MOD_RES
<222> LOCATION: (2377)..(2377)
<223> OTHER INFORMATION: Ile or Val
<220> FEATURE:
<221> NAME/KEY: MOD_RES
<222> LOCATION: (2382)..(2382)
<223> OTHER INFORMATION: Ile or Val
<220> FEATURE:
<221> NAME/KEY: MOD_RES
<222> LOCATION: (2387)..(2387)
<223> OTHER INFORMATION: Ile or Val
<220> FEATURE:
<221> NAME/KEY: MOD_RES
<222> LOCATION: (2392)..(2392)
<223> OTHER INFORMATION: Ile or Val
<220> FEATURE:
<221> NAME/KEY: MOD_RES
<222> LOCATION: (2397)..(2397)
<223> OTHER INFORMATION: Ile or Val
<220> FEATURE:
<221> NAME/KEY: MOD_RES
<222> LOCATION: (2402)..(2402)
<223> OTHER INFORMATION: Ile or Val
<220> FEATURE:
<221> NAME/KEY: MOD_RES
<222> LOCATION: (2407)..(2407)
<223> OTHER INFORMATION: Ile or Val
<220> FEATURE:
<221> NAME/KEY: MOD_RES
<222> LOCATION: (2412)..(2412)
<223> OTHER INFORMATION: Ile or Val
<220> FEATURE:
<221> NAME/KEY: MOD_RES
<222> LOCATION: (2417)..(2417)
```

```
<223> OTHER INFORMATION: Ile or Val
<220> FEATURE:
<221> NAME/KEY: MOD_RES
<222> LOCATION: (2422)..(2422)
<223> OTHER INFORMATION: Ile or Val
<220> FEATURE:
<221> NAME/KEY: MOD_RES
<222> LOCATION: (2427)..(2427)
<223> OTHER INFORMATION: Ile or Val
<220> FEATURE:
<221> NAME/KEY: MOD_RES
<222> LOCATION: (2432)..(2432)
<223> OTHER INFORMATION: Ile or Val
<220> FEATURE:
<221> NAME/KEY: MOD_RES
<222> LOCATION: (2437)..(2437)
<223> OTHER INFORMATION: Ile or Val
<220> FEATURE:
<221> NAME/KEY: MOD_RES
<222> LOCATION: (2442)..(2442)
<223> OTHER INFORMATION: Ile or Val
<220> FEATURE:
<221> NAME/KEY: MOD_RES
<222> LOCATION: (2447)..(2447)
<223> OTHER INFORMATION: Ile or Val
<220> FEATURE:
<221> NAME/KEY: MOD_RES
<222> LOCATION: (2452)..(2452)
<223> OTHER INFORMATION: Ile or Val
<220> FEATURE:
<221> NAME/KEY: MOD_RES
<222> LOCATION: (2457)..(2457)
<223> OTHER INFORMATION: Ile or Val
<220> FEATURE:
<221> NAME/KEY: MOD_RES
<222> LOCATION: (2462)..(2462)
<223> OTHER INFORMATION: Ile or Val
<220> FEATURE:
<221> NAME/KEY: MOD_RES
<222> LOCATION: (2467)..(2467)
<223> OTHER INFORMATION: Ile or Val
<220> FEATURE:
<221> NAME/KEY: MOD_RES
<222> LOCATION: (2472)..(2472)
<223> OTHER INFORMATION: Ile or Val
<220> FEATURE:
<221> NAME/KEY: MOD_RES
<222> LOCATION: (2477)..(2477)
<223> OTHER INFORMATION: Ile or Val
<220> FEATURE:
<221> NAME/KEY: MOD_RES
<222> LOCATION: (2482)..(2482)
<223> OTHER INFORMATION: Ile or Val
<220> FEATURE:
<221> NAME/KEY: MOD_RES
<222> LOCATION: (2487)..(2487)
<223> OTHER INFORMATION: Ile or Val
<220> FEATURE:
<221> NAME/KEY: MOD_RES
<222> LOCATION: (2492)..(2492)
<223> OTHER INFORMATION: Ile or Val
<220> FEATURE:
<221> NAME/KEY: MOD_RES
<222> LOCATION: (2497)..(2497)
<223> OTHER INFORMATION: Ile or Val
<220> FEATURE:
<221> NAME/KEY: MOD_RES
<222> LOCATION: (2502)..(2502)
<223> OTHER INFORMATION: Any natural or unnatural amino acid
<220> FEATURE:
<221> NAME/KEY: MISC_FEATURE
<222> LOCATION: (2)..(2501)
<223> OTHER INFORMATION: This region may encompass 5-500 "XPAVG"
      repeating units, wherein X is Ile or Val and some
      positions may be absent

<400> SEQUENCE: 1

Xaa Xaa Pro Ala Val Gly Xaa Pro Ala Val Gly Xaa Pro Ala Val Gly
```

```
1               5                   10                  15
Xaa Pro Ala Val Gly Xaa Pro Ala Val Gly Xaa Pro Ala Val Gly Xaa
                20                  25                  30
Pro Ala Val Gly Xaa Pro Ala Val Gly Xaa Pro Ala Val Gly Xaa Pro
                35                  40                  45
Ala Val Gly Xaa Pro Ala Val Gly Xaa Pro Ala Val Gly Xaa Pro Ala
                50                  55                  60
Val Gly Xaa Pro Ala Val Gly Xaa Pro Ala Val Gly Xaa Pro Ala Val
 65                 70                  75                  80
Gly Xaa Pro Ala Val Gly Xaa Pro Ala Val Gly Xaa Pro Ala Val Gly
                85                  90                  95
Xaa Pro Ala Val Gly Xaa Pro Ala Val Gly Xaa Pro Ala Val Gly Xaa
                100                 105                 110
Pro Ala Val Gly Xaa Pro Ala Val Gly Xaa Pro Ala Val Gly Xaa Pro
                115                 120                 125
Ala Val Gly Xaa Pro Ala Val Gly Xaa Pro Ala Val Gly Xaa Pro Ala
                130                 135                 140
Val Gly Xaa Pro Ala Val Gly Xaa Pro Ala Val Gly Xaa Pro Ala Val
145                 150                 155                 160
Gly Xaa Pro Ala Val Gly Xaa Pro Ala Val Gly Xaa Pro Ala Val Gly
                165                 170                 175
Xaa Pro Ala Val Gly Xaa Pro Ala Val Gly Xaa Pro Ala Val Gly Xaa
                180                 185                 190
Pro Ala Val Gly Xaa Pro Ala Val Gly Xaa Pro Ala Val Gly Xaa Pro
                195                 200                 205
Ala Val Gly Xaa Pro Ala Val Gly Xaa Pro Ala Val Gly Xaa Pro Ala
                210                 215                 220
Val Gly Xaa Pro Ala Val Gly Xaa Pro Ala Val Gly Xaa Pro Ala Val
225                 230                 235                 240
Gly Xaa Pro Ala Val Gly Xaa Pro Ala Val Gly Xaa Pro Ala Val Gly
                245                 250                 255
Xaa Pro Ala Val Gly Xaa Pro Ala Val Gly Xaa Pro Ala Val Gly Xaa
                260                 265                 270
Pro Ala Val Gly Xaa Pro Ala Val Gly Xaa Pro Ala Val Gly Xaa Pro
                275                 280                 285
Ala Val Gly Xaa Pro Ala Val Gly Xaa Pro Ala Val Gly Xaa Pro Ala
                290                 295                 300
Val Gly Xaa Pro Ala Val Gly Xaa Pro Ala Val Gly Xaa Pro Ala Val
305                 310                 315                 320
Gly Xaa Pro Ala Val Gly Xaa Pro Ala Val Gly Xaa Pro Ala Val Gly
                325                 330                 335
Xaa Pro Ala Val Gly Xaa Pro Ala Val Gly Xaa Pro Ala Val Gly Xaa
                340                 345                 350
Pro Ala Val Gly Xaa Pro Ala Val Gly Xaa Pro Ala Val Gly Xaa Pro
                355                 360                 365
Ala Val Gly Xaa Pro Ala Val Gly Xaa Pro Ala Val Gly Xaa Pro Ala
                370                 375                 380
Val Gly Xaa Pro Ala Val Gly Xaa Pro Ala Val Gly Xaa Pro Ala Val
385                 390                 395                 400
Gly Xaa Pro Ala Val Gly Xaa Pro Ala Val Gly Xaa Pro Ala Val Gly
                405                 410                 415
Xaa Pro Ala Val Gly Xaa Pro Ala Val Gly Xaa Pro Ala Val Gly Xaa
                420                 425                 430
```

```
Pro Ala Val Gly Xaa Pro Ala Val Gly Xaa Pro Ala Val Gly Xaa Pro
        435                 440                 445
Ala Val Gly Xaa Pro Ala Val Gly Xaa Pro Ala Val Gly Xaa Pro Ala
    450                 455                 460
Val Gly Xaa Pro Ala Val Gly Xaa Pro Ala Val Gly Xaa Pro Ala Val
465                 470                 475                 480
Gly Xaa Pro Ala Val Gly Xaa Pro Ala Val Gly Xaa Pro Ala Val Gly
            485                 490                 495
Xaa Pro Ala Val Gly Xaa Pro Ala Val Gly Xaa Pro Ala Val Gly Xaa
                500                 505                 510
Pro Ala Val Gly Xaa Pro Ala Val Gly Xaa Pro Ala Val Gly Xaa Pro
        515                 520                 525
Ala Val Gly Xaa Pro Ala Val Gly Xaa Pro Ala Val Gly Xaa Pro Ala
    530                 535                 540
Val Gly Xaa Pro Ala Val Gly Xaa Pro Ala Val Gly Xaa Pro Ala Val
545                 550                 555                 560
Gly Xaa Pro Ala Val Gly Xaa Pro Ala Val Gly Xaa Pro Ala Val Gly
            565                 570                 575
Xaa Pro Ala Val Gly Xaa Pro Ala Val Gly Xaa Pro Ala Val Gly Xaa
                580                 585                 590
Pro Ala Val Gly Xaa Pro Ala Val Gly Xaa Pro Ala Val Gly Xaa Pro
        595                 600                 605
Ala Val Gly Xaa Pro Ala Val Gly Xaa Pro Ala Val Gly Xaa Pro Ala
    610                 615                 620
Val Gly Xaa Pro Ala Val Gly Xaa Pro Ala Val Gly Xaa Pro Ala Val
625                 630                 635                 640
Gly Xaa Pro Ala Val Gly Xaa Pro Ala Val Gly Xaa Pro Ala Val Gly
            645                 650                 655
Xaa Pro Ala Val Gly Xaa Pro Ala Val Gly Xaa Pro Ala Val Gly Xaa
                660                 665                 670
Pro Ala Val Gly Xaa Pro Ala Val Gly Xaa Pro Ala Val Gly Xaa Pro
        675                 680                 685
Ala Val Gly Xaa Pro Ala Val Gly Xaa Pro Ala Val Gly Xaa Pro Ala
    690                 695                 700
Val Gly Xaa Pro Ala Val Gly Xaa Pro Ala Val Gly Xaa Pro Ala Val
705                 710                 715                 720
Gly Xaa Pro Ala Val Gly Xaa Pro Ala Val Gly Xaa Pro Ala Val Gly
            725                 730                 735
Xaa Pro Ala Val Gly Xaa Pro Ala Val Gly Xaa Pro Ala Val Gly Xaa
                740                 745                 750
Pro Ala Val Gly Xaa Pro Ala Val Gly Xaa Pro Ala Val Gly Xaa Pro
        755                 760                 765
Ala Val Gly Xaa Pro Ala Val Gly Xaa Pro Ala Val Gly Xaa Pro Ala
    770                 775                 780
Val Gly Xaa Pro Ala Val Gly Xaa Pro Ala Val Gly Xaa Pro Ala Val
785                 790                 795                 800
Gly Xaa Pro Ala Val Gly Xaa Pro Ala Val Gly Xaa Pro Ala Val Gly
            805                 810                 815
Xaa Pro Ala Val Gly Xaa Pro Ala Val Gly Xaa Pro Ala Val Gly Xaa
                820                 825                 830
Pro Ala Val Gly Xaa Pro Ala Val Gly Xaa Pro Ala Val Gly Xaa Pro
        835                 840                 845
```

Ala Val Gly Xaa Pro Ala Val Gly Xaa Pro Ala Val Gly Xaa Pro Ala
850                 855                 860

Val Gly Xaa Pro Ala Val Gly Xaa Pro Ala Val Gly Xaa Pro Ala Val
865                 870                 875                 880

Gly Xaa Pro Ala Val Gly Xaa Pro Ala Val Gly Xaa Pro Ala Val Gly
            885                 890                 895

Xaa Pro Ala Val Gly Xaa Pro Ala Val Gly Xaa Pro Ala Val Gly Xaa
        900                 905                 910

Pro Ala Val Gly Xaa Pro Ala Val Gly Xaa Pro Ala Val Gly Xaa Pro
    915                 920                 925

Ala Val Gly Xaa Pro Ala Val Gly Xaa Pro Ala Val Gly Xaa Pro Ala
930                 935                 940

Val Gly Xaa Pro Ala Val Gly Xaa Pro Ala Val Gly Xaa Pro Ala Val
945                 950                 955                 960

Gly Xaa Pro Ala Val Gly Xaa Pro Ala Val Gly Xaa Pro Ala Val Gly
            965                 970                 975

Xaa Pro Ala Val Gly Xaa Pro Ala Val Gly Xaa Pro Ala Val Gly Xaa
        980                 985                 990

Pro Ala Val Gly Xaa Pro Ala Val  Gly Xaa Pro Ala Val  Gly Xaa Pro
    995                 1000                1005

Ala Val  Gly Xaa Pro Ala Val  Gly Xaa Pro Ala Val  Gly Xaa Pro
1010                 1015                1020

Ala Val  Gly Xaa Pro Ala Val  Gly Xaa Pro Ala Val  Gly Xaa Pro
1025                 1030                1035

Ala Val  Gly Xaa Pro Ala Val  Gly Xaa Pro Ala Val  Gly Xaa Pro
1040                 1045                1050

Ala Val  Gly Xaa Pro Ala Val  Gly Xaa Pro Ala Val  Gly Xaa Pro
1055                 1060                1065

Ala Val  Gly Xaa Pro Ala Val  Gly Xaa Pro Ala Val  Gly Xaa Pro
1070                 1075                1080

Ala Val  Gly Xaa Pro Ala Val  Gly Xaa Pro Ala Val  Gly Xaa Pro
1085                 1090                1095

Ala Val  Gly Xaa Pro Ala Val  Gly Xaa Pro Ala Val  Gly Xaa Pro
1100                 1105                1110

Ala Val  Gly Xaa Pro Ala Val  Gly Xaa Pro Ala Val  Gly Xaa Pro
1115                 1120                1125

Ala Val  Gly Xaa Pro Ala Val  Gly Xaa Pro Ala Val  Gly Xaa Pro
1130                 1135                1140

Ala Val  Gly Xaa Pro Ala Val  Gly Xaa Pro Ala Val  Gly Xaa Pro
1145                 1150                1155

Ala Val  Gly Xaa Pro Ala Val  Gly Xaa Pro Ala Val  Gly Xaa Pro
1160                 1165                1170

Ala Val  Gly Xaa Pro Ala Val  Gly Xaa Pro Ala Val  Gly Xaa Pro
1175                 1180                1185

Ala Val  Gly Xaa Pro Ala Val  Gly Xaa Pro Ala Val  Gly Xaa Pro
1190                 1195                1200

Ala Val  Gly Xaa Pro Ala Val  Gly Xaa Pro Ala Val  Gly Xaa Pro
1205                 1210                1215

Ala Val  Gly Xaa Pro Ala Val  Gly Xaa Pro Ala Val  Gly Xaa Pro
1220                 1225                1230

Ala Val  Gly Xaa Pro Ala Val  Gly Xaa Pro Ala Val  Gly Xaa Pro
1235                 1240                1245

Ala Val  Gly Xaa Pro Ala Val  Gly Xaa Pro Ala Val  Gly Xaa Pro

-continued

Ala Val Gly Xaa Pro Ala Val Gly Xaa Pro Ala Val Gly Xaa Pro
1250                1255                1260

Ala Val Gly Xaa Pro Ala Val Gly Xaa Pro Ala Val Gly Xaa Pro
1265                1270                1275

Ala Val Gly Xaa Pro Ala Val Gly Xaa Pro Ala Val Gly Xaa Pro
1280                1285                1290

Ala Val Gly Xaa Pro Ala Val Gly Xaa Pro Ala Val Gly Xaa Pro
1295                1300                1305

Ala Val Gly Xaa Pro Ala Val Gly Xaa Pro Ala Val Gly Xaa Pro
1310                1315                1320

Ala Val Gly Xaa Pro Ala Val Gly Xaa Pro Ala Val Gly Xaa Pro
1325                1330                1335

Ala Val Gly Xaa Pro Ala Val Gly Xaa Pro Ala Val Gly Xaa Pro
1340                1345                1350

Ala Val Gly Xaa Pro Ala Val Gly Xaa Pro Ala Val Gly Xaa Pro
1355                1360                1365

Ala Val Gly Xaa Pro Ala Val Gly Xaa Pro Ala Val Gly Xaa Pro
1370                1375                1380

Ala Val Gly Xaa Pro Ala Val Gly Xaa Pro Ala Val Gly Xaa Pro
1385                1390                1395

Ala Val Gly Xaa Pro Ala Val Gly Xaa Pro Ala Val Gly Xaa Pro
1400                1405                1410

Ala Val Gly Xaa Pro Ala Val Gly Xaa Pro Ala Val Gly Xaa Pro
1415                1420                1425

Ala Val Gly Xaa Pro Ala Val Gly Xaa Pro Ala Val Gly Xaa Pro
1430                1435                1440

Ala Val Gly Xaa Pro Ala Val Gly Xaa Pro Ala Val Gly Xaa Pro
1445                1450                1455

Ala Val Gly Xaa Pro Ala Val Gly Xaa Pro Ala Val Gly Xaa Pro
1460                1465                1470

Ala Val Gly Xaa Pro Ala Val Gly Xaa Pro Ala Val Gly Xaa Pro
1475                1480                1485

Ala Val Gly Xaa Pro Ala Val Gly Xaa Pro Ala Val Gly Xaa Pro
1490                1495                1500

Ala Val Gly Xaa Pro Ala Val Gly Xaa Pro Ala Val Gly Xaa Pro
1505                1510                1515

Ala Val Gly Xaa Pro Ala Val Gly Xaa Pro Ala Val Gly Xaa Pro
1520                1525                1530

Ala Val Gly Xaa Pro Ala Val Gly Xaa Pro Ala Val Gly Xaa Pro
1535                1540                1545

Ala Val Gly Xaa Pro Ala Val Gly Xaa Pro Ala Val Gly Xaa Pro
1550                1555                1560

Ala Val Gly Xaa Pro Ala Val Gly Xaa Pro Ala Val Gly Xaa Pro
1565                1570                1575

Ala Val Gly Xaa Pro Ala Val Gly Xaa Pro Ala Val Gly Xaa Pro
1580                1585                1590

Ala Val Gly Xaa Pro Ala Val Gly Xaa Pro Ala Val Gly Xaa Pro
1595                1600                1605

Ala Val Gly Xaa Pro Ala Val Gly Xaa Pro Ala Val Gly Xaa Pro
1610                1615                1620

Ala Val Gly Xaa Pro Ala Val Gly Xaa Pro Ala Val Gly Xaa Pro
1625                1630                1635

Ala Val Gly Xaa Pro Ala Val Gly Xaa Pro Ala Val Gly Xaa Pro
1640                1645                1650

```
Ala Val Gly Xaa Pro Ala Val Gly Xaa Pro Ala Val Gly Xaa Pro
    1655                1660                1665

Ala Val Gly Xaa Pro Ala Val Gly Xaa Pro Ala Val Gly Xaa Pro
    1670                1675                1680

Ala Val Gly Xaa Pro Ala Val Gly Xaa Pro Ala Val Gly Xaa Pro
    1685                1690                1695

Ala Val Gly Xaa Pro Ala Val Gly Xaa Pro Ala Val Gly Xaa Pro
    1700                1705                1710

Ala Val Gly Xaa Pro Ala Val Gly Xaa Pro Ala Val Gly Xaa Pro
    1715                1720                1725

Ala Val Gly Xaa Pro Ala Val Gly Xaa Pro Ala Val Gly Xaa Pro
    1730                1735                1740

Ala Val Gly Xaa Pro Ala Val Gly Xaa Pro Ala Val Gly Xaa Pro
    1745                1750                1755

Ala Val Gly Xaa Pro Ala Val Gly Xaa Pro Ala Val Gly Xaa Pro
    1760                1765                1770

Ala Val Gly Xaa Pro Ala Val Gly Xaa Pro Ala Val Gly Xaa Pro
    1775                1780                1785

Ala Val Gly Xaa Pro Ala Val Gly Xaa Pro Ala Val Gly Xaa Pro
    1790                1795                1800

Ala Val Gly Xaa Pro Ala Val Gly Xaa Pro Ala Val Gly Xaa Pro
    1805                1810                1815

Ala Val Gly Xaa Pro Ala Val Gly Xaa Pro Ala Val Gly Xaa Pro
    1820                1825                1830

Ala Val Gly Xaa Pro Ala Val Gly Xaa Pro Ala Val Gly Xaa Pro
    1835                1840                1845

Ala Val Gly Xaa Pro Ala Val Gly Xaa Pro Ala Val Gly Xaa Pro
    1850                1855                1860

Ala Val Gly Xaa Pro Ala Val Gly Xaa Pro Ala Val Gly Xaa Pro
    1865                1870                1875

Ala Val Gly Xaa Pro Ala Val Gly Xaa Pro Ala Val Gly Xaa Pro
    1880                1885                1890

Ala Val Gly Xaa Pro Ala Val Gly Xaa Pro Ala Val Gly Xaa Pro
    1895                1900                1905

Ala Val Gly Xaa Pro Ala Val Gly Xaa Pro Ala Val Gly Xaa Pro
    1910                1915                1920

Ala Val Gly Xaa Pro Ala Val Gly Xaa Pro Ala Val Gly Xaa Pro
    1925                1930                1935

Ala Val Gly Xaa Pro Ala Val Gly Xaa Pro Ala Val Gly Xaa Pro
    1940                1945                1950

Ala Val Gly Xaa Pro Ala Val Gly Xaa Pro Ala Val Gly Xaa Pro
    1955                1960                1965

Ala Val Gly Xaa Pro Ala Val Gly Xaa Pro Ala Val Gly Xaa Pro
    1970                1975                1980

Ala Val Gly Xaa Pro Ala Val Gly Xaa Pro Ala Val Gly Xaa Pro
    1985                1990                1995

Ala Val Gly Xaa Pro Ala Val Gly Xaa Pro Ala Val Gly Xaa Pro
    2000                2005                2010

Ala Val Gly Xaa Pro Ala Val Gly Xaa Pro Ala Val Gly Xaa Pro
    2015                2020                2025

Ala Val Gly Xaa Pro Ala Val Gly Xaa Pro Ala Val Gly Xaa Pro
    2030                2035                2040
```

-continued

Ala Val Gly Xaa Pro Ala Val Gly Xaa Pro Ala Val Gly Xaa Pro
2045            2050            2055

Ala Val Gly Xaa Pro Ala Val Gly Xaa Pro Ala Val Gly Xaa Pro
2060            2065            2070

Ala Val Gly Xaa Pro Ala Val Gly Xaa Pro Ala Val Gly Xaa Pro
2075            2080            2085

Ala Val Gly Xaa Pro Ala Val Gly Xaa Pro Ala Val Gly Xaa Pro
2090            2095            2100

Ala Val Gly Xaa Pro Ala Val Gly Xaa Pro Ala Val Gly Xaa Pro
2105            2110            2115

Ala Val Gly Xaa Pro Ala Val Gly Xaa Pro Ala Val Gly Xaa Pro
2120            2125            2130

Ala Val Gly Xaa Pro Ala Val Gly Xaa Pro Ala Val Gly Xaa Pro
2135            2140            2145

Ala Val Gly Xaa Pro Ala Val Gly Xaa Pro Ala Val Gly Xaa Pro
2150            2155            2160

Ala Val Gly Xaa Pro Ala Val Gly Xaa Pro Ala Val Gly Xaa Pro
2165            2170            2175

Ala Val Gly Xaa Pro Ala Val Gly Xaa Pro Ala Val Gly Xaa Pro
2180            2185            2190

Ala Val Gly Xaa Pro Ala Val Gly Xaa Pro Ala Val Gly Xaa Pro
2195            2200            2205

Ala Val Gly Xaa Pro Ala Val Gly Xaa Pro Ala Val Gly Xaa Pro
2210            2215            2220

Ala Val Gly Xaa Pro Ala Val Gly Xaa Pro Ala Val Gly Xaa Pro
2225            2230            2235

Ala Val Gly Xaa Pro Ala Val Gly Xaa Pro Ala Val Gly Xaa Pro
2240            2245            2250

Ala Val Gly Xaa Pro Ala Val Gly Xaa Pro Ala Val Gly Xaa Pro
2255            2260            2265

Ala Val Gly Xaa Pro Ala Val Gly Xaa Pro Ala Val Gly Xaa Pro
2270            2275            2280

Ala Val Gly Xaa Pro Ala Val Gly Xaa Pro Ala Val Gly Xaa Pro
2285            2290            2295

Ala Val Gly Xaa Pro Ala Val Gly Xaa Pro Ala Val Gly Xaa Pro
2300            2305            2310

Ala Val Gly Xaa Pro Ala Val Gly Xaa Pro Ala Val Gly Xaa Pro
2315            2320            2325

Ala Val Gly Xaa Pro Ala Val Gly Xaa Pro Ala Val Gly Xaa Pro
2330            2335            2340

Ala Val Gly Xaa Pro Ala Val Gly Xaa Pro Ala Val Gly Xaa Pro
2345            2350            2355

Ala Val Gly Xaa Pro Ala Val Gly Xaa Pro Ala Val Gly Xaa Pro
2360            2365            2370

Ala Val Gly Xaa Pro Ala Val Gly Xaa Pro Ala Val Gly Xaa Pro
2375            2380            2385

Ala Val Gly Xaa Pro Ala Val Gly Xaa Pro Ala Val Gly Xaa Pro
2390            2395            2400

Ala Val Gly Xaa Pro Ala Val Gly Xaa Pro Ala Val Gly Xaa Pro
2405            2410            2415

Ala Val Gly Xaa Pro Ala Val Gly Xaa Pro Ala Val Gly Xaa Pro
2420            2425            2430

Ala Val Gly Xaa Pro Ala Val Gly Xaa Pro Ala Val Gly Xaa Pro

```
                2435                2440                2445

Ala Val Gly Xaa Pro Ala Val Gly Xaa Pro Ala Val Gly Xaa Pro
        2450                2455                2460

Ala Val Gly Xaa Pro Ala Val Gly Xaa Pro Ala Val Gly Xaa Pro
        2465                2470                2475

Ala Val Gly Xaa Pro Ala Val Gly Xaa Pro Ala Val Gly Xaa Pro
        2480                2485                2490

Ala Val Gly Xaa Pro Ala Val Gly Xaa
        2495                2500

<210> SEQ ID NO 2
<211> LENGTH: 84
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (23)..(23)
<223> OTHER INFORMATION: Any amino acid
<220> FEATURE:
<221> NAME/KEY: MOD_RES
<222> LOCATION: (28)..(28)
<223> OTHER INFORMATION: Any amino acid
<220> FEATURE:
<221> NAME/KEY: MOD_RES
<222> LOCATION: (33)..(33)
<223> OTHER INFORMATION: Any amino acid
<220> FEATURE:
<221> NAME/KEY: MOD_RES
<222> LOCATION: (38)..(38)
<223> OTHER INFORMATION: Any amino acid
<220> FEATURE:
<221> NAME/KEY: MOD_RES
<222> LOCATION: (43)..(43)
<223> OTHER INFORMATION: Any amino acid
<220> FEATURE:
<221> NAME/KEY: MOD_RES
<222> LOCATION: (48)..(48)
<223> OTHER INFORMATION: Any amino acid
<220> FEATURE:
<221> NAME/KEY: MOD_RES
<222> LOCATION: (53)..(53)
<223> OTHER INFORMATION: Any amino acid
<220> FEATURE:
<221> NAME/KEY: MOD_RES
<222> LOCATION: (58)..(58)
<223> OTHER INFORMATION: Any amino acid
<220> FEATURE:
<221> NAME/KEY: MOD_RES
<222> LOCATION: (63)..(63)
<223> OTHER INFORMATION: Any amino acid

<400> SEQUENCE: 2

Lys Cys Thr Ser Ala Gly Ala Gly Ala Gly Pro Glu Gly Arg Gly Asp
1               5                   10                  15

Ser Xaa Pro Ala Val Gly Xaa Pro Ala Val Gly Xaa Pro Ala Val Gly
            20                  25                  30

Xaa Pro Ala Val Gly Xaa Pro Ala Val Gly Xaa Pro Ala Val Gly Xaa
        35                  40                  45

Pro Ala Val Gly Xaa Pro Ala Val Gly Xaa Pro Ala Val Gly Xaa Pro
    50                  55                  60

Ala Val Gly Arg Gly Asp Ser Ala Gly Ala Gly Ala Gly Pro Glu Gly
65                  70                  75                  80
```

Thr Ser Cys Lys

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Pro Gly Val Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any natural or unnatural amino acid

<400> SEQUENCE: 4

Xaa Pro Ala Val Gly
1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Gly Asp Ser
1

<210> SEQ ID NO 6
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any natural or unnatural amino acid
<220> FEATURE:
<221> NAME/KEY: MOD_RES
<222> LOCATION: (252)..(252)
<223> OTHER INFORMATION: Any natural or unnatural amino acid

<400> SEQUENCE: 6

Xaa Ile Pro Ala Val Gly Val Pro Ala Val Gly Ile Pro Ala Val Gly
1               5                   10                  15

Val Pro Ala Val Gly Ile Pro Ala Val Gly Ile Pro Ala Val Gly Val
                20                  25                  30

Pro Ala Val Gly Ile Pro Ala Val Gly Val Pro Ala Val Gly Ile Pro
            35                  40                  45

Ala Val Gly Ile Pro Ala Val Gly Val Pro Ala Val Gly Ile Pro Ala
        50                  55                  60

```
Val Gly Val Pro Ala Val Gly Ile Pro Ala Val Gly Ile Pro Ala Val
 65                  70                  75                  80

Gly Val Pro Ala Val Gly Ile Pro Ala Val Gly Val Pro Ala Val Gly
                 85                  90                  95

Ile Pro Ala Val Gly Ile Pro Ala Val Gly Val Pro Ala Val Gly Ile
            100                 105                 110

Pro Ala Val Gly Val Pro Ala Val Gly Ile Pro Ala Val Gly Ile Pro
            115                 120                 125

Ala Val Gly Val Pro Ala Val Gly Ile Pro Ala Val Gly Val Pro Ala
        130                 135                 140

Val Gly Ile Pro Ala Val Gly Ile Pro Ala Val Gly Val Pro Ala Val
145                 150                 155                 160

Gly Ile Pro Ala Val Gly Val Pro Ala Val Gly Ile Pro Ala Val Gly
                165                 170                 175

Ile Pro Ala Val Gly Val Pro Ala Val Gly Ile Pro Ala Val Gly Val
            180                 185                 190

Pro Ala Val Gly Ile Pro Ala Val Gly Ile Pro Ala Val Gly Val Pro
            195                 200                 205

Ala Val Gly Ile Pro Ala Val Gly Val Pro Ala Val Gly Ile Pro Ala
        210                 215                 220

Val Gly Ile Pro Ala Val Gly Val Pro Ala Val Gly Ile Pro Ala Val
225                 230                 235                 240

Gly Val Pro Ala Val Gly Ile Pro Ala Val Gly Xaa
                245                 250

<210> SEQ ID NO 7
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Gly Trp Gly Ser Ala Ser Gly Leu Val Gly Ile Pro Ala Val Gly
1               5                   10                  15

Val Pro Ala Val Gly Ile Pro Ala Val Gly Val Pro Ala Val Gly Ile
            20                  25                  30

Pro Ala Val Gly Ile Pro Ala Val Gly Val Pro Ala Val Gly Ile Pro
        35                  40                  45

Ala Val Gly Val Pro Ala Val Gly Ile Pro Ala Val Gly Ile Pro Ala
    50                  55                  60

Val Gly Val Pro Ala Val Gly Ile Pro Ala Val Gly Val Pro Ala Val
 65                 70                  75                  80

Gly Ile Pro Ala Val Gly Ile Pro Ala Val Gly Val Pro Ala Val Gly
                 85                  90                  95

Ile Pro Ala Val Gly Val Pro Ala Val Gly Ile Pro Ala Val Gly Ile
            100                 105                 110

Pro Ala Val Gly Val Pro Ala Val Gly Ile Pro Ala Val Gly Val Pro
            115                 120                 125

Ala Val Gly Ile Pro Ala Val Gly Ile Pro Ala Val Gly Val Pro Ala
        130                 135                 140

Val Gly Ile Pro Ala Val Gly Val Pro Ala Val Gly Ile Pro Ala Val
145                 150                 155                 160

Gly Ile Pro Ala Val Gly Val Pro Ala Val Gly Ile Pro Ala Val Gly
```

-continued

```
                165                 170                 175

Val Pro Ala Val Gly Ile Pro Ala Val Gly Ile Pro Ala Val Gly Val
            180                 185                 190

Pro Ala Val Gly Ile Pro Ala Val Gly Val Pro Ala Val Gly Ile Pro
        195                 200                 205

Ala Val Gly Ile Pro Ala Val Gly Val Pro Ala Val Gly Ile Pro Ala
    210                 215                 220

Val Gly Val Pro Ala Val Gly Ile Pro Ala Val Gly Ile Pro Ala Val
225                 230                 235                 240

Gly Val Pro Ala Val Gly Ile Pro Ala Val Gly Val Pro Ala Val Gly
                245                 250                 255

Ile Pro Ala Val Gly Glu Thr Thr Ser
            260                 265

<210> SEQ ID NO 8
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any natural or unnatural amino acid
<220> FEATURE:
<221> NAME/KEY: MOD_RES
<222> LOCATION: (252)..(252)
<223> OTHER INFORMATION: Any natural or unnatural amino acid

<400> SEQUENCE: 8

Xaa Val Pro Ala Val Gly Val Pro Ala Val Gly Ile Pro Ala Val Gly
1               5                   10                  15

Val Pro Ala Val Gly Val Pro Ala Val Gly Val Pro Ala Val Gly Val
                20                  25                  30

Pro Ala Val Gly Ile Pro Ala Val Gly Val Pro Ala Val Gly Val Pro
            35                  40                  45

Ala Val Gly Val Pro Ala Val Gly Val Pro Ala Val Gly Ile Pro Ala
    50                  55                  60

Val Gly Val Pro Ala Val Gly Val Pro Ala Val Gly Val Pro Ala Val
65                  70                  75                  80

Gly Val Pro Ala Val Gly Ile Pro Ala Val Gly Val Pro Ala Val Gly
                85                  90                  95

Val Pro Ala Val Gly Val Pro Ala Val Gly Val Pro Ala Val Gly Ile
            100                 105                 110

Pro Ala Val Gly Val Pro Ala Val Gly Val Pro Ala Val Gly Val Pro
        115                 120                 125

Ala Val Gly Val Pro Ala Val Gly Ile Pro Ala Val Gly Val Pro Ala
    130                 135                 140

Val Gly Val Pro Ala Val Gly Val Pro Ala Val Gly Val Pro Ala Val
145                 150                 155                 160

Gly Ile Pro Ala Val Gly Val Pro Ala Val Gly Val Pro Ala Val Gly
                165                 170                 175

Val Pro Ala Val Gly Val Pro Ala Val Gly Ile Pro Ala Val Gly Val
            180                 185                 190

Pro Ala Val Gly Val Pro Ala Val Gly Val Pro Ala Val Gly Val Pro
        195                 200                 205

Ala Val Gly Ile Pro Ala Val Gly Val Pro Ala Val Gly Val Pro Ala
```

```
                210                 215                 220
Val Gly Val Pro Ala Val Gly Val Pro Ala Val Gly Ile Pro Ala Val
225                 230                 235                 240

Gly Val Pro Ala Val Gly Val Pro Ala Val Gly Xaa
                245                 250

<210> SEQ ID NO 9
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Gly Trp Gly Ser Ala Ser Gly Leu Val Gly Val Pro Ala Val Gly
1               5                   10                  15

Val Pro Ala Val Gly Ile Pro Ala Val Gly Val Pro Ala Val Gly Val
                20                  25                  30

Pro Ala Val Gly Val Pro Ala Val Gly Val Pro Ala Val Gly Ile Pro
            35                  40                  45

Ala Val Gly Val Pro Ala Val Gly Val Pro Ala Val Gly Val Pro Ala
        50                  55                  60

Val Gly Val Pro Ala Val Gly Ile Pro Ala Val Gly Val Pro Ala Val
65                  70                  75                  80

Gly Val Pro Ala Val Gly Val Pro Ala Val Gly Val Pro Ala Val Gly
                85                  90                  95

Ile Pro Ala Val Gly Val Pro Ala Val Gly Val Pro Ala Val Gly Val
                100                 105                 110

Pro Ala Val Gly Val Pro Ala Val Gly Ile Pro Ala Val Gly Val Pro
            115                 120                 125

Ala Val Gly Val Pro Ala Val Gly Val Pro Ala Val Gly Val Pro Ala
        130                 135                 140

Val Gly Ile Pro Ala Val Gly Val Pro Ala Val Gly Val Pro Ala Val
145                 150                 155                 160

Gly Val Pro Ala Val Gly Val Pro Ala Val Gly Ile Pro Ala Val Gly
                165                 170                 175

Val Pro Ala Val Gly Val Pro Ala Val Gly Val Pro Ala Val Gly Val
                180                 185                 190

Pro Ala Val Gly Ile Pro Ala Val Gly Val Pro Ala Val Gly Val Pro
            195                 200                 205

Ala Val Gly Val Pro Ala Val Gly Val Pro Ala Val Gly Ile Pro Ala
        210                 215                 220

Val Gly Val Pro Ala Val Gly Val Pro Ala Val Gly Val Pro Ala Val
225                 230                 235                 240

Gly Val Pro Ala Val Gly Ile Pro Ala Val Gly Val Pro Ala Val Gly
                245                 250                 255

Val Pro Ala Val Gly Glu Thr Thr Ser
                260                 265

<210> SEQ ID NO 10
<211> LENGTH: 286
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (1)..(1)
<223> OTHER INFORMATION: Any natural or unnatural amino acid
<220> FEATURE:
<221> NAME/KEY: MOD_RES
<222> LOCATION: (286)..(286)
<223> OTHER INFORMATION: Any natural or unnatural amino acid

<400> SEQUENCE: 10

Xaa Lys Cys Thr Ser Ala Gly Ala Gly Ala Gly Pro Glu Gly Arg Gly
1               5                   10                  15

Asp Ser Ile Pro Ala Val Gly Val Pro Ala Val Gly Ile Pro Ala Val
            20                  25                  30

Gly Val Pro Ala Val Gly Ile Pro Ala Val Gly Ile Pro Ala Val Gly
        35                  40                  45

Val Pro Ala Val Gly Ile Pro Ala Val Gly Val Pro Ala Val Gly Ile
    50                  55                  60

Pro Ala Val Gly Ile Pro Ala Val Gly Val Pro Ala Val Gly Ile Pro
65                  70                  75                  80

Ala Val Gly Val Pro Ala Val Gly Ile Pro Ala Val Gly Ile Pro Ala
                85                  90                  95

Val Gly Val Pro Ala Val Gly Ile Pro Ala Val Gly Val Pro Ala Val
            100                 105                 110

Gly Ile Pro Ala Val Gly Ile Pro Ala Val Gly Val Pro Ala Val Gly
        115                 120                 125

Ile Pro Ala Val Gly Val Pro Ala Val Gly Ile Pro Ala Val Gly Ile
    130                 135                 140

Pro Ala Val Gly Val Pro Ala Val Gly Ile Pro Ala Val Gly Val Pro
145                 150                 155                 160

Ala Val Gly Ile Pro Ala Val Gly Ile Pro Ala Val Gly Val Pro Ala
                165                 170                 175

Val Gly Ile Pro Ala Val Gly Val Pro Ala Val Gly Ile Pro Ala Val
            180                 185                 190

Gly Ile Pro Ala Val Gly Val Pro Ala Val Gly Ile Pro Ala Val Gly
        195                 200                 205

Val Pro Ala Val Gly Ile Pro Ala Val Gly Ile Pro Ala Val Gly Val
    210                 215                 220

Pro Ala Val Gly Ile Pro Ala Val Gly Val Pro Ala Val Gly Ile Pro
225                 230                 235                 240

Ala Val Gly Ile Pro Ala Val Gly Val Pro Ala Val Gly Ile Pro Ala
                245                 250                 255

Val Gly Val Pro Ala Val Gly Ile Pro Ala Val Gly Arg Gly Asp Ser
            260                 265                 270

Ala Gly Ala Gly Ala Gly Pro Glu Gly Thr Ser Cys Lys Xaa
        275                 280                 285

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Gly Ala Gly Ala Gly Pro Glu Gly
1               5
```

<210> SEQ ID NO 12
<211> LENGTH: 300
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

Met Gly Trp Gly Ser Lys Cys Thr Ser Ala Gly Ala Gly Ala Gly Pro
1               5                   10                  15

Glu Gly Arg Gly Asp Ser Thr Ser Gly Leu Val Gly Ile Pro Ala Val
            20                  25                  30

Gly Val Pro Ala Val Gly Ile Pro Ala Val Gly Val Pro Ala Val Gly
        35                  40                  45

Ile Pro Ala Val Gly Ile Pro Ala Val Gly Val Pro Ala Val Gly Ile
    50                  55                  60

Pro Ala Val Gly Val Pro Ala Val Gly Ile Pro Ala Val Gly Ile Pro
65                  70                  75                  80

Ala Val Gly Val Pro Ala Val Gly Ile Pro Ala Val Gly Val Pro Ala
                85                  90                  95

Val Gly Ile Pro Ala Val Gly Ile Pro Ala Val Gly Val Pro Ala Val
            100                 105                 110

Gly Ile Pro Ala Val Gly Val Pro Ala Val Gly Ile Pro Ala Val Gly
        115                 120                 125

Ile Pro Ala Val Gly Val Pro Ala Val Gly Ile Pro Ala Val Gly Val
    130                 135                 140

Pro Ala Val Gly Ile Pro Ala Val Gly Ile Pro Ala Val Gly Val Pro
145                 150                 155                 160

Ala Val Gly Ile Pro Ala Val Gly Val Pro Ala Val Gly Ile Pro Ala
                165                 170                 175

Val Gly Ile Pro Ala Val Gly Val Pro Ala Val Gly Ile Pro Ala Val
            180                 185                 190

Gly Val Pro Ala Val Gly Ile Pro Ala Val Gly Ile Pro Ala Val Gly
        195                 200                 205

Val Pro Ala Val Gly Ile Pro Ala Val Gly Val Pro Ala Val Gly Ile
    210                 215                 220

Pro Ala Val Gly Ile Pro Ala Val Gly Val Pro Ala Val Gly Ile Pro
225                 230                 235                 240

Ala Val Gly Val Pro Ala Val Gly Ile Pro Ala Val Gly Ile Pro Ala
                245                 250                 255

Val Gly Val Pro Ala Val Gly Ile Pro Ala Val Gly Val Pro Ala Val
            260                 265                 270

Gly Ile Pro Ala Val Gly Glu Thr Thr Ser Arg Gly Asp Ser Ala Gly
        275                 280                 285

Ala Gly Ala Gly Pro Glu Gly Thr Ser Cys Lys Leu
    290                 295                 300

<210> SEQ ID NO 13
<211> LENGTH: 352
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Any natural or unnatural amino acid
<220> FEATURE:
<221> NAME/KEY: MOD_RES
<222> LOCATION: (352)..(352)
<223> OTHER INFORMATION: Any natural or unnatural amino acid

<400> SEQUENCE: 13

Xaa Val Pro Ala Val Gly Val Pro Ala Val Gly Ile Pro Ala Val Gly
1               5                   10                  15

Val Pro Ala Val Gly Val Pro Ala Val Gly Val Pro Ala Val Gly Val
            20                  25                  30

Pro Ala Val Gly Ile Pro Ala Val Gly Val Pro Ala Val Gly Val Pro
        35                  40                  45

Ala Val Gly Val Pro Ala Val Gly Val Pro Ala Val Gly Ile Pro Ala
    50                  55                  60

Val Gly Val Pro Ala Val Gly Val Pro Ala Val Gly Val Pro Ala Val
65                  70                  75                  80

Gly Val Pro Ala Val Gly Ile Pro Ala Val Gly Val Pro Ala Val Gly
                85                  90                  95

Val Pro Ala Val Gly Val Pro Ala Val Gly Val Pro Ala Val Gly Ile
            100                 105                 110

Pro Ala Val Gly Val Pro Ala Val Gly Val Pro Ala Val Gly Val Pro
        115                 120                 125

Ala Val Gly Val Pro Ala Val Gly Ile Pro Ala Val Gly Val Pro Ala
    130                 135                 140

Val Gly Val Pro Ala Val Gly Val Pro Ala Val Gly Val Pro Ala Val
145                 150                 155                 160

Gly Ile Pro Ala Val Gly Val Pro Ala Val Gly Val Pro Ala Val Gly
                165                 170                 175

Val Pro Ala Val Gly Val Pro Ala Val Gly Ile Pro Ala Val Gly Val
            180                 185                 190

Pro Ala Val Gly Val Pro Ala Val Gly Val Pro Ala Val Gly Val Pro
        195                 200                 205

Ala Val Gly Ile Pro Ala Val Gly Val Pro Ala Val Gly Val Pro Ala
    210                 215                 220

Val Gly Val Pro Ala Val Gly Val Pro Ala Val Gly Ile Pro Ala Val
225                 230                 235                 240

Gly Val Pro Ala Val Gly Val Pro Ala Val Gly Val Pro Ala Val Gly
                245                 250                 255

Val Pro Ala Val Gly Ile Pro Ala Val Gly Val Pro Ala Val Gly Val
            260                 265                 270

Pro Ala Val Gly Val Pro Ala Val Gly Val Pro Ala Val Gly Ile Pro
        275                 280                 285

Ala Val Gly Val Pro Ala Val Gly Val Pro Ala Val Gly Val Pro Ala
    290                 295                 300

Val Gly Val Pro Ala Val Gly Ile Pro Ala Val Gly Val Pro Ala Val
305                 310                 315                 320

Gly Val Pro Ala Val Gly Val Pro Ala Val Gly Val Pro Ala Val Gly
                325                 330                 335

Ile Pro Ala Val Gly Val Pro Ala Val Gly Val Pro Ala Val Gly Xaa
            340                 345                 350

<210> SEQ ID NO 14
<211> LENGTH: 365
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 14

Met Gly Trp Gly Ser Ala Ser Gly Leu Val Gly Val Pro Ala Val Gly
1               5                   10                  15

Val Pro Ala Val Gly Ile Pro Ala Val Gly Val Pro Ala Val Gly Val
            20                  25                  30

Pro Ala Val Gly Val Pro Ala Val Gly Val Pro Ala Val Gly Ile Pro
        35                  40                  45

Ala Val Gly Val Pro Ala Val Gly Val Pro Ala Val Gly Val Pro Ala
    50                  55                  60

Val Gly Val Pro Ala Val Gly Ile Pro Ala Val Gly Val Pro Ala Val
65                  70                  75                  80

Gly Val Pro Ala Val Gly Val Pro Ala Val Gly Val Pro Ala Val Gly
                85                  90                  95

Ile Pro Ala Val Gly Val Pro Ala Val Gly Val Pro Ala Val Gly Val
            100                 105                 110

Pro Ala Val Gly Val Pro Ala Val Gly Ile Pro Ala Val Gly Val Pro
        115                 120                 125

Ala Val Gly Val Pro Ala Val Gly Val Pro Ala Val Gly Val Pro Ala
    130                 135                 140

Val Gly Ile Pro Ala Val Gly Val Pro Ala Val Gly Val Pro Ala Val
145                 150                 155                 160

Gly Val Pro Ala Val Gly Val Pro Ala Val Gly Ile Pro Ala Val Gly
                165                 170                 175

Val Pro Ala Val Gly Val Pro Ala Val Gly Val Pro Ala Val Gly Val
            180                 185                 190

Pro Ala Val Gly Ile Pro Ala Val Gly Val Pro Ala Val Gly Val Pro
        195                 200                 205

Ala Val Gly Val Pro Ala Val Gly Val Pro Ala Val Gly Ile Pro Ala
    210                 215                 220

Val Gly Val Pro Ala Val Gly Val Pro Ala Val Gly Val Pro Ala Val
225                 230                 235                 240

Gly Val Pro Ala Val Gly Ile Pro Ala Val Gly Val Pro Ala Val Gly
                245                 250                 255

Val Pro Ala Val Gly Val Pro Ala Val Gly Val Pro Ala Val Gly Ile
            260                 265                 270

Pro Ala Val Gly Val Pro Ala Val Gly Val Pro Ala Val Gly Val Pro
        275                 280                 285

Ala Val Gly Val Pro Ala Val Gly Ile Pro Ala Val Gly Val Pro Ala
    290                 295                 300

Val Gly Val Pro Ala Val Gly Val Pro Ala Val Gly Val Pro Ala Val
305                 310                 315                 320

Gly Ile Pro Ala Val Gly Val Pro Ala Val Gly Val Pro Ala Val Gly
                325                 330                 335

Val Pro Ala Val Gly Val Pro Ala Val Gly Ile Pro Ala Val Gly Val
            340                 345                 350

Pro Ala Val Gly Val Pro Ala Val Gly Glu Thr Thr Ser
        355                 360                 365

<210> SEQ ID NO 15
<211> LENGTH: 602
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any natural or unnatural amino acid
<220> FEATURE:
<221> NAME/KEY: MOD_RES
<222> LOCATION: (602)..(602)
<223> OTHER INFORMATION: Any natural or unnatural amino acid

<400> SEQUENCE: 15

Xaa Val Pro Ala Val Gly Val Pro Ala Val Gly Ile Pro Ala Val Gly
1               5                   10                  15

Val Pro Ala Val Gly Val Pro Ala Val Gly Val Pro Ala Val Gly Val
            20                  25                  30

Pro Ala Val Gly Ile Pro Ala Val Gly Val Pro Ala Val Gly Val Pro
        35                  40                  45

Ala Val Gly Val Pro Ala Val Gly Val Pro Ala Val Gly Ile Pro Ala
    50                  55                  60

Val Gly Val Pro Ala Val Gly Val Pro Ala Val Gly Val Pro Ala Val
65                  70                  75                  80

Gly Val Pro Ala Val Gly Ile Pro Ala Val Gly Val Pro Ala Val Gly
                85                  90                  95

Val Pro Ala Val Gly Val Pro Ala Val Gly Val Pro Ala Val Gly Ile
            100                 105                 110

Pro Ala Val Gly Val Pro Ala Val Gly Val Pro Ala Val Gly Val Pro
        115                 120                 125

Ala Val Gly Val Pro Ala Val Gly Ile Pro Ala Val Gly Val Pro Ala
    130                 135                 140

Val Gly Val Pro Ala Val Gly Val Pro Ala Val Gly Val Pro Ala Val
145                 150                 155                 160

Gly Ile Pro Ala Val Gly Val Pro Ala Val Gly Val Pro Ala Val Gly
                165                 170                 175

Val Pro Ala Val Gly Val Pro Ala Val Gly Ile Pro Ala Val Gly Val
            180                 185                 190

Pro Ala Val Gly Val Pro Ala Val Gly Val Pro Ala Val Gly Val Pro
        195                 200                 205

Ala Val Gly Ile Pro Ala Val Gly Val Pro Ala Val Gly Val Pro Ala
    210                 215                 220

Val Gly Val Pro Ala Val Gly Val Pro Ala Val Gly Ile Pro Ala Val
225                 230                 235                 240

Gly Val Pro Ala Val Gly Val Pro Ala Val Gly Val Pro Ala Val Gly
                245                 250                 255

Val Pro Ala Val Gly Ile Pro Ala Val Gly Val Pro Ala Val Gly Val
            260                 265                 270

Pro Ala Val Gly Val Pro Ala Val Gly Val Pro Ala Val Gly Ile Pro
        275                 280                 285

Ala Val Gly Val Pro Ala Val Gly Val Pro Ala Val Gly Val Pro Ala
    290                 295                 300

Val Gly Val Pro Ala Val Gly Ile Pro Ala Val Gly Val Pro Ala Val
305                 310                 315                 320

Gly Val Pro Ala Val Gly Val Pro Ala Val Gly Val Pro Ala Val Gly
                325                 330                 335

Ile Pro Ala Val Gly Val Pro Ala Val Gly Val Pro Ala Val Gly Val
            340                 345                 350
```

```
Pro Ala Val Gly Val Pro Ala Val Gly Ile Pro Ala Val Gly Val Pro
        355                 360                 365
Ala Val Gly Val Pro Ala Val Gly Val Pro Ala Val Gly Val Pro Ala
        370                 375                 380
Val Gly Ile Pro Ala Val Gly Val Pro Ala Val Gly Val Pro Ala Val
385                 390                 395                 400
Gly Val Pro Ala Val Gly Val Pro Ala Val Gly Ile Pro Ala Val Gly
                405                 410                 415
Val Pro Ala Val Gly Val Pro Ala Val Gly Val Pro Ala Val Gly Val
                420                 425                 430
Pro Ala Val Gly Ile Pro Ala Val Gly Val Pro Ala Val Gly Val Pro
        435                 440                 445
Ala Val Gly Val Pro Ala Val Gly Val Pro Ala Val Gly Ile Pro Ala
        450                 455                 460
Val Gly Val Pro Ala Val Gly Val Pro Ala Val Gly Val Pro Ala Val
465                 470                 475                 480
Gly Val Pro Ala Val Gly Ile Pro Ala Val Gly Val Pro Ala Val Gly
                485                 490                 495
Val Pro Ala Val Gly Val Pro Ala Val Gly Val Pro Ala Val Gly Ile
                500                 505                 510
Pro Ala Val Gly Val Pro Ala Val Gly Val Pro Ala Val Gly Val Pro
        515                 520                 525
Ala Val Gly Val Pro Ala Val Gly Ile Pro Ala Val Gly Val Pro Ala
        530                 535                 540
Val Gly Val Pro Ala Val Gly Val Pro Ala Val Gly Val Pro Ala Val
545                 550                 555                 560
Gly Ile Pro Ala Val Gly Val Pro Ala Val Gly Val Pro Ala Val Gly
                565                 570                 575
Val Pro Ala Val Gly Val Pro Ala Val Gly Ile Pro Ala Val Gly Val
                580                 585                 590
Pro Ala Val Gly Val Pro Ala Val Gly Xaa
        595                 600

<210> SEQ ID NO 16
<211> LENGTH: 615
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Gly Trp Gly Ser Ala Ser Gly Leu Val Gly Val Pro Ala Val Gly
1               5                   10                  15
Val Pro Ala Val Gly Ile Pro Ala Val Gly Val Pro Ala Val Gly Val
                20                  25                  30
Pro Ala Val Gly Val Pro Ala Val Gly Val Pro Ala Val Gly Ile Pro
        35                  40                  45
Ala Val Gly Val Pro Ala Val Gly Val Pro Ala Val Gly Val Pro Ala
        50                  55                  60
Val Gly Val Pro Ala Val Gly Ile Pro Ala Val Gly Val Pro Ala Val
65                  70                  75                  80
Gly Val Pro Ala Val Gly Val Pro Ala Val Gly Val Pro Ala Val Gly
                85                  90                  95
Ile Pro Ala Val Gly Val Pro Ala Val Gly Val Pro Ala Val Gly Val
```

-continued

```
                100             105             110
Pro Ala Val Gly Val Pro Ala Val Gly Ile Pro Ala Val Gly Val Pro
            115             120             125
Ala Val Gly Val Pro Ala Val Gly Val Pro Ala Val Gly Val Pro Ala
            130             135             140
Val Gly Ile Pro Ala Val Gly Val Pro Ala Val Gly Val Pro Ala Val
145             150             155             160
Gly Val Pro Ala Val Gly Val Pro Ala Val Gly Ile Pro Ala Val Gly
            165             170             175
Val Pro Ala Val Gly Val Pro Ala Val Gly Val Pro Ala Val Gly Val
            180             185             190
Pro Ala Val Gly Ile Pro Ala Val Gly Val Pro Ala Val Gly Val Pro
            195             200             205
Ala Val Gly Val Pro Ala Val Gly Val Pro Ala Val Gly Ile Pro Ala
            210             215             220
Val Gly Val Pro Ala Val Gly Val Pro Ala Val Gly Val Pro Ala Val
225             230             235             240
Gly Val Pro Ala Val Gly Ile Pro Ala Val Gly Val Pro Ala Val Gly
            245             250             255
Val Pro Ala Val Gly Val Pro Ala Val Gly Val Pro Ala Val Gly Ile
            260             265             270
Pro Ala Val Gly Val Pro Ala Val Gly Val Pro Ala Val Gly Val Pro
            275             280             285
Ala Val Gly Val Pro Ala Val Gly Ile Pro Ala Val Gly Val Pro Ala
            290             295             300
Val Gly Val Pro Ala Val Gly Val Pro Ala Val Gly Val Pro Ala Val
305             310             315             320
Gly Ile Pro Ala Val Gly Val Pro Ala Val Gly Val Pro Ala Val Gly
            325             330             335
Val Pro Ala Val Gly Val Pro Ala Val Gly Ile Pro Ala Val Gly Val
            340             345             350
Pro Ala Val Gly Val Pro Ala Val Gly Val Pro Ala Val Gly Val Pro
            355             360             365
Ala Val Gly Ile Pro Ala Val Gly Val Pro Ala Val Gly Val Pro Ala
            370             375             380
Val Gly Val Pro Ala Val Gly Val Pro Ala Val Gly Ile Pro Ala Val
385             390             395             400
Gly Val Pro Ala Val Gly Val Pro Ala Val Gly Val Pro Ala Val Gly
            405             410             415
Val Pro Ala Val Gly Ile Pro Ala Val Gly Val Pro Ala Val Gly Val
            420             425             430
Pro Ala Val Gly Val Pro Ala Val Gly Val Pro Ala Val Gly Ile Pro
            435             440             445
Ala Val Gly Val Pro Ala Val Gly Val Pro Ala Val Gly Val Pro Ala
            450             455             460
Val Gly Val Pro Ala Val Gly Ile Pro Ala Val Gly Val Pro Ala Val
465             470             475             480
Gly Val Pro Ala Val Gly Val Pro Ala Val Gly Val Pro Ala Val Gly
            485             490             495
Ile Pro Ala Val Gly Val Pro Ala Val Gly Val Pro Ala Val Gly Val
            500             505             510
Pro Ala Val Gly Val Pro Ala Val Gly Ile Pro Ala Val Gly Val Pro
            515             520             525
```

```
Ala Val Gly Val Pro Ala Val Gly Val Pro Ala Val Gly Val Pro Ala
        530                 535                 540

Val Gly Ile Pro Ala Val Gly Val Pro Ala Val Gly Val Pro Ala Val
545                 550                 555                 560

Gly Val Pro Ala Val Gly Val Pro Ala Val Gly Ile Pro Ala Val Gly
                565                 570                 575

Val Pro Ala Val Gly Val Pro Ala Val Gly Val Pro Ala Val Gly Val
                580                 585                 590

Pro Ala Val Gly Ile Pro Ala Val Gly Val Pro Ala Val Gly Val Pro
            595                 600                 605

Ala Val Gly Glu Thr Thr Ser
        610                 615

<210> SEQ ID NO 17
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Gly Trp Gly Ser Ala Ser Gly Leu Val Gly Ile Pro Ala Val Gly
1               5                   10                  15

Val Pro Ala Val Gly Ile Pro Ala Val Gly Val Pro Ala Val Gly Ile
                20                  25                  30

Pro Ala Val Gly Ile Pro Ala Val Gly Val Pro Ala Val Gly Ile Pro
            35                  40                  45

Ala Val Gly Val Pro Ala Val Gly Ile Pro Ala Val Gly Ile Pro Ala
        50                  55                  60

Val Gly Val Pro Ala Val Gly Ile Pro Ala Val Gly Val Pro Ala Val
65                  70                  75                  80

Gly Ile Pro Ala Val Gly Ile Pro Ala Val Gly Val Pro Ala Val Gly
                85                  90                  95

Ile Pro Ala Val Gly Val Pro Ala Val Gly Ile Pro Ala Val Gly Ile
                100                 105                 110

Pro Ala Val Gly Val Pro Ala Val Gly Ile Pro Ala Val Gly Val Pro
            115                 120                 125

Ala Val Gly Ile Pro Ala Val Gly Ile Pro Ala Val Gly Val Pro Ala
        130                 135                 140

Val Gly Ile Pro Ala Val Gly Val Pro Ala Val Gly Ile Pro Ala Val
145                 150                 155                 160

Gly Ile Pro Ala Val Gly Val Pro Ala Val Gly Ile Pro Ala Val Gly
                165                 170                 175

Val Pro Ala Val Gly Ile Pro Ala Val Gly Ile Pro Ala Val Gly Val
                180                 185                 190

Pro Ala Val Gly Ile Pro Ala Val Gly Val Pro Ala Val Gly Ile Pro
            195                 200                 205

Ala Val Gly Ile Pro Ala Val Gly Val Pro Ala Val Gly Ile Pro Ala
        210                 215                 220

Val Gly Val Pro Ala Val Gly Ile Pro Ala Val Gly Ile Pro Ala Val
225                 230                 235                 240

Gly Val Pro Ala Val Gly Ile Pro Ala Val Gly Val Pro Ala Val Gly
                245                 250                 255

Ile Pro Ala Val Gly Glu Thr Thr Ser
```

<210> SEQ ID NO 18
<211> LENGTH: 265
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 18

Met Gly Trp Gly Ser Ala Ser Gly Leu Val Gly Val Pro Ala Val Gly
1               5                   10                  15

Val Pro Ala Val Gly Ile Pro Ala Val Gly Val Pro Ala Val Gly Val
                20                  25                  30

Pro Ala Val Gly Val Pro Ala Val Gly Val Pro Ala Val Gly Ile Pro
            35                  40                  45

Ala Val Gly Val Pro Ala Val Gly Val Pro Ala Val Gly Val Pro Ala
        50                  55                  60

Val Gly Val Pro Ala Val Gly Ile Pro Ala Val Gly Val Pro Ala Val
65                  70                  75                  80

Gly Val Pro Ala Val Gly Val Pro Ala Val Gly Val Pro Ala Val Gly
                85                  90                  95

Ile Pro Ala Val Gly Val Pro Ala Val Gly Val Pro Ala Val Gly Val
                100                 105                 110

Pro Ala Val Gly Val Pro Ala Val Gly Ile Pro Ala Val Gly Val Pro
            115                 120                 125

Ala Val Gly Val Pro Ala Val Gly Val Pro Ala Val Gly Val Pro Ala
        130                 135                 140

Val Gly Ile Pro Ala Val Gly Val Pro Ala Val Gly Val Pro Ala Val
145                 150                 155                 160

Gly Val Pro Ala Val Gly Val Pro Ala Val Gly Ile Pro Ala Val Gly
                165                 170                 175

Val Pro Ala Val Gly Val Pro Ala Val Gly Val Pro Ala Val Gly Val
                180                 185                 190

Pro Ala Val Gly Ile Pro Ala Val Gly Val Pro Ala Val Gly Val Pro
            195                 200                 205

Ala Val Gly Val Pro Ala Val Gly Val Pro Ala Val Gly Ile Pro Ala
        210                 215                 220

Val Gly Val Pro Ala Val Gly Val Pro Ala Val Gly Val Pro Ala Val
225                 230                 235                 240

Gly Val Pro Ala Val Gly Ile Pro Ala Val Gly Val Pro Ala Val Gly
                245                 250                 255

Val Pro Ala Val Gly Glu Thr Thr Ser
            260                 265

<210> SEQ ID NO 19
<211> LENGTH: 300
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 19

Met Gly Trp Gly Ser Lys Cys Thr Ser Ala Gly Ala Gly Ala Gly Pro
1               5                   10                  15

Glu Gly Arg Gly Asp Ser Thr Ser Gly Leu Val Gly Ile Pro Ala Val 20                  25                  30
Gly Val Pro Ala Val Gly Ile Pro Ala Val Gly Val Pro Ala Val Gly
            35                  40                  45
Ile Pro Ala Val Gly Ile Pro Ala Val Gly Val Pro Ala Val Gly Ile
        50                  55                  60
Pro Ala Val Gly Val Pro Ala Val Gly Ile Pro Ala Val Gly Ile Pro
65                  70                  75                  80
Ala Val Gly Val Pro Ala Val Gly Ile Pro Ala Val Gly Val Pro Ala
                85                  90                  95
Val Gly Ile Pro Ala Val Gly Ile Pro Ala Val Gly Val Pro Ala Val
            100                 105                 110
Gly Ile Pro Ala Val Gly Val Pro Ala Val Gly Ile Pro Ala Val Gly
        115                 120                 125
Ile Pro Ala Val Gly Val Pro Ala Val Gly Ile Pro Ala Val Gly Val
        130                 135                 140
Pro Ala Val Gly Ile Pro Ala Val Gly Ile Pro Ala Val Gly Val Pro
145                 150                 155                 160
Ala Val Gly Ile Pro Ala Val Gly Val Pro Ala Val Gly Ile Pro Ala
                165                 170                 175
Val Gly Ile Pro Ala Val Gly Val Pro Ala Val Gly Ile Pro Ala Val
            180                 185                 190
Gly Val Pro Ala Val Gly Ile Pro Ala Val Gly Ile Pro Ala Val Gly
        195                 200                 205
Val Pro Ala Val Gly Ile Pro Ala Val Gly Val Pro Ala Val Gly Ile
        210                 215                 220
Pro Ala Val Gly Ile Pro Ala Val Gly Val Pro Ala Val Gly Ile Pro
225                 230                 235                 240
Ala Val Gly Val Pro Ala Val Gly Ile Pro Ala Val Gly Ile Pro Ala
                245                 250                 255
Val Gly Val Pro Ala Val Gly Ile Pro Ala Val Gly Val Pro Ala Val
            260                 265                 270
Gly Ile Pro Ala Val Gly Glu Thr Thr Ser Arg Gly Asp Ser Ala Gly
        275                 280                 285
Ala Gly Ala Gly Pro Glu Gly Thr Ser Cys Lys Leu
        290                 295                 300

<210> SEQ ID NO 20
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
ggatccgcta gcggtctcgt tggtattcct gctgttggtg tgccggctgt tggtatccca      60
gctgttggcg ttccggctgt aggtattccg gctgttggtg agaccactag ttaaatgaat     120
aagctt                                                                126

<210> SEQ ID NO 21
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 21
ggatccgcta gcggtctcgt tggtgttcct gctgtcggtg tgccggctgt tggtattcca    60
gctgttggcg tgccggctgt aggtgtcccg gctgttggcg agaccactag ttaaatgaat   120
aagctt                                                              126

<210> SEQ ID NO 22
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gatccaaatg tacctctgcc ggcgctggtg cgggcccgga aggtcgtggt gattcta       57

<210> SEQ ID NO 23
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
caaatgtacc tctgccggcg ctggtgcggg cccggaaggt cgtggtgatt ctactag       57

<210> SEQ ID NO 24
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ctagtcgtgg tgattctgcc ggcgctggtg cgggcccgga aggtacaagc tgta          54

<210> SEQ ID NO 25
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tcgtggtgat tctgccggcg ctggtgcggg cccggaaggt acaagctgta agct          54

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile or Val

<400> SEQUENCE: 26

Xaa Pro Ala Val Gly
1               5
```

```
<210> SEQ ID NO 27
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ile or Val
<220> FEATURE:
<221> NAME/KEY: MOD_RES
<222> LOCATION: (6)..(6)
<223> OTHER INFORMATION: Ile or Val
<220> FEATURE:
<221> NAME/KEY: MOD_RES
<222> LOCATION: (11)..(11)
<223> OTHER INFORMATION: Ile or Val
<220> FEATURE:
<221> NAME/KEY: MOD_RES
<222> LOCATION: (16)..(16)
<223> OTHER INFORMATION: Ile or Val
<220> FEATURE:
<221> NAME/KEY: MOD_RES
<222> LOCATION: (21)..(21)
<223> OTHER INFORMATION: Ile or Val
<220> FEATURE:
<221> NAME/KEY: MOD_RES
<222> LOCATION: (26)..(26)
<223> OTHER INFORMATION: Ile or Val
<220> FEATURE:
<221> NAME/KEY: MOD_RES
<222> LOCATION: (31)..(31)
<223> OTHER INFORMATION: Ile or Val
<220> FEATURE:
<221> NAME/KEY: MOD_RES
<222> LOCATION: (36)..(36)
<223> OTHER INFORMATION: Ile or Val
<220> FEATURE:
<221> NAME/KEY: MOD_RES
<222> LOCATION: (41)..(41)
<223> OTHER INFORMATION: Ile or Val
<220> FEATURE:
<221> NAME/KEY: MOD_RES
<222> LOCATION: (46)..(46)
<223> OTHER INFORMATION: Ile or Val

<400> SEQUENCE: 27

Xaa Pro Ala Val Gly Xaa Pro Ala Val Gly Xaa Pro Ala Val Gly Xaa
1               5                   10                  15

Pro Ala Val Gly Xaa Pro Ala Val Gly Xaa Pro Ala Val Gly Xaa Pro
            20                  25                  30

Ala Val Gly Xaa Pro Ala Val Gly Xaa Pro Ala Val Gly Xaa Pro Ala
        35                  40                  45

Val Gly
    50

<210> SEQ ID NO 28
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ile or Val
<220> FEATURE:
<221> NAME/KEY: MOD_RES
<222> LOCATION: (6)..(6)
<223> OTHER INFORMATION: Ile or Val
<220> FEATURE:
```

```
<221> NAME/KEY: MOD_RES
<222> LOCATION: (11)..(11)
<223> OTHER INFORMATION: Ile or Val
<220> FEATURE:
<221> NAME/KEY: MOD_RES
<222> LOCATION: (16)..(16)
<223> OTHER INFORMATION: Ile or Val
<220> FEATURE:
<221> NAME/KEY: MOD_RES
<222> LOCATION: (21)..(21)
<223> OTHER INFORMATION: Ile or Val
<220> FEATURE:
<221> NAME/KEY: MOD_RES
<222> LOCATION: (26)..(26)
<223> OTHER INFORMATION: Ile or Val
<220> FEATURE:
<221> NAME/KEY: MOD_RES
<222> LOCATION: (31)..(31)
<223> OTHER INFORMATION: Ile or Val
<220> FEATURE:
<221> NAME/KEY: MOD_RES
<222> LOCATION: (36)..(36)
<223> OTHER INFORMATION: Ile or Val
<220> FEATURE:
<221> NAME/KEY: MOD_RES
<222> LOCATION: (41)..(41)
<223> OTHER INFORMATION: Ile or Val
<220> FEATURE:
<221> NAME/KEY: MOD_RES
<222> LOCATION: (46)..(46)
<223> OTHER INFORMATION: Ile or Val

<400> SEQUENCE: 28

Xaa Pro Ala Val Gly Xaa Pro Ala Val Gly Xaa Pro Ala Val Gly Xaa
1               5                   10                  15

Pro Ala Val Gly Xaa Pro Ala Val Gly Xaa Pro Ala Val Gly Xaa Pro
            20                  25                  30

Ala Val Gly Xaa Pro Ala Val Gly Xaa Pro Ala Val Gly Xaa Pro Ala
        35                  40                  45

Val Gly
    50

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile or Val
<220> FEATURE:
<221> NAME/KEY: MOD_RES
<222> LOCATION: (3)..(3)
<223> OTHER INFORMATION: Ala or Gly

<400> SEQUENCE: 29

Xaa Pro Xaa Val Gly
1               5

<210> SEQ ID NO 30
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
```

```
<223> OTHER INFORMATION: Ile or Val
<220> FEATURE:
<221> NAME/KEY: MOD_RES
<222> LOCATION: (6)..(6)
<223> OTHER INFORMATION: Ile or Val
<220> FEATURE:
<221> NAME/KEY: MOD_RES
<222> LOCATION: (11)..(11)
<223> OTHER INFORMATION: Ile or Val
<220> FEATURE:
<221> NAME/KEY: MOD_RES
<222> LOCATION: (16)..(16)
<223> OTHER INFORMATION: Ile or Val
<220> FEATURE:
<221> NAME/KEY: MOD_RES
<222> LOCATION: (21)..(21)
<223> OTHER INFORMATION: Ile or Val
<220> FEATURE:
<221> NAME/KEY: MOD_RES
<222> LOCATION: (26)..(26)
<223> OTHER INFORMATION: Ile or Val
<220> FEATURE:
<221> NAME/KEY: MOD_RES
<222> LOCATION: (31)..(31)
<223> OTHER INFORMATION: Ile or Val
<220> FEATURE:
<221> NAME/KEY: MOD_RES
<222> LOCATION: (36)..(36)
<223> OTHER INFORMATION: Ile or Val
<220> FEATURE:
<221> NAME/KEY: MOD_RES
<222> LOCATION: (41)..(41)
<223> OTHER INFORMATION: Ile or Val
<220> FEATURE:
<221> NAME/KEY: MOD_RES
<222> LOCATION: (46)..(46)
<223> OTHER INFORMATION: Ile or Val
<220> FEATURE:
<221> NAME/KEY: MOD_RES
<222> LOCATION: (51)..(51)
<223> OTHER INFORMATION: Ile or Val
<220> FEATURE:
<221> NAME/KEY: MOD_RES
<222> LOCATION: (56)..(56)
<223> OTHER INFORMATION: Ile or Val
<220> FEATURE:
<221> NAME/KEY: MOD_RES
<222> LOCATION: (61)..(61)
<223> OTHER INFORMATION: Ile or Val
<220> FEATURE:
<221> NAME/KEY: MOD_RES
<222> LOCATION: (66)..(66)
<223> OTHER INFORMATION: Ile or Val
<220> FEATURE:
<221> NAME/KEY: MOD_RES
<222> LOCATION: (71)..(71)
<223> OTHER INFORMATION: Ile or Val
<220> FEATURE:
<221> NAME/KEY: MOD_RES
<222> LOCATION: (76)..(76)
<223> OTHER INFORMATION: Ile or Val
<220> FEATURE:
<221> NAME/KEY: MOD_RES
<222> LOCATION: (81)..(81)
<223> OTHER INFORMATION: Ile or Val
<220> FEATURE:
<221> NAME/KEY: MOD_RES
<222> LOCATION: (86)..(86)
<223> OTHER INFORMATION: Ile or Val
<220> FEATURE:
<221> NAME/KEY: MOD_RES
<222> LOCATION: (91)..(91)
<223> OTHER INFORMATION: Ile or Val
<220> FEATURE:
<221> NAME/KEY: MOD_RES
<222> LOCATION: (96)..(96)
<223> OTHER INFORMATION: Ile or Val
<220> FEATURE:
<221> NAME/KEY: MOD_RES
```

```
<222> LOCATION: (101)..(101)
<223> OTHER INFORMATION: Ile or Val
<220> FEATURE:
<221> NAME/KEY: MOD_RES
<222> LOCATION: (106)..(106)
<223> OTHER INFORMATION: Ile or Val
<220> FEATURE:
<221> NAME/KEY: MOD_RES
<222> LOCATION: (111)..(111)
<223> OTHER INFORMATION: Ile or Val
<220> FEATURE:
<221> NAME/KEY: MOD_RES
<222> LOCATION: (116)..(116)
<223> OTHER INFORMATION: Ile or Val
<220> FEATURE:
<221> NAME/KEY: MISC_FEATURE
<222> LOCATION: (116)..(116)
<223> OTHER INFORMATION: This sequence may encompass 10, 14 or 24
      repeating "XPAVG" repeating units, wherein X is Ile or Val
      and some positions may be absent

<400> SEQUENCE: 30

Xaa Pro Ala Val Gly Xaa Pro Ala Val Gly Xaa Pro Ala Val Gly Xaa
1               5                   10                  15

Pro Ala Val Gly Xaa Pro Ala Val Gly Xaa Pro Ala Val Gly Xaa Pro
            20                  25                  30

Ala Val Gly Xaa Pro Ala Val Gly Xaa Pro Ala Val Gly Xaa Pro Ala
        35                  40                  45

Val Gly Xaa Pro Ala Val Gly Xaa Pro Ala Val Gly Xaa Pro Ala Val
    50                  55                  60

Gly Xaa Pro Ala Val Gly Xaa Pro Ala Val Gly Xaa Pro Ala Val Gly
65                  70                  75                  80

Xaa Pro Ala Val Gly Xaa Pro Ala Val Gly Xaa Pro Ala Val Gly Xaa
                85                  90                  95

Pro Ala Val Gly Xaa Pro Ala Val Gly Xaa Pro Ala Val Gly Xaa Pro
            100                 105                 110

Ala Val Gly Xaa Pro Ala Val Gly
        115                 120

<210> SEQ ID NO 31
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ile or Val
<220> FEATURE:
<221> NAME/KEY: MOD_RES
<222> LOCATION: (6)..(6)
<223> OTHER INFORMATION: Ile or Val
<220> FEATURE:
<221> NAME/KEY: MOD_RES
<222> LOCATION: (11)..(11)
<223> OTHER INFORMATION: Ile or Val
<220> FEATURE:
<221> NAME/KEY: MOD_RES
<222> LOCATION: (16)..(16)
<223> OTHER INFORMATION: Ile or Val
<220> FEATURE:
<221> NAME/KEY: MOD_RES
<222> LOCATION: (21)..(21)
<223> OTHER INFORMATION: Ile or Val
<220> FEATURE:
<221> NAME/KEY: MOD_RES
<222> LOCATION: (26)..(26)
<223> OTHER INFORMATION: Ile or Val
```

```
<220> FEATURE:
<221> NAME/KEY: MOD_RES
<222> LOCATION: (31)..(31)
<223> OTHER INFORMATION: Ile or Val
<220> FEATURE:
<221> NAME/KEY: MOD_RES
<222> LOCATION: (36)..(36)
<223> OTHER INFORMATION: Ile or Val
<220> FEATURE:
<221> NAME/KEY: MOD_RES
<222> LOCATION: (41)..(41)
<223> OTHER INFORMATION: Ile or Val
<220> FEATURE:
<221> NAME/KEY: MOD_RES
<222> LOCATION: (46)..(46)
<223> OTHER INFORMATION: Ile or Val

<400> SEQUENCE: 31

Xaa Pro Gly Val Gly Xaa Pro Gly Val Gly Xaa Pro Gly Val Gly Xaa
1               5                   10                  15

Pro Gly Val Gly Xaa Pro Gly Val Gly Xaa Pro Gly Val Gly Xaa Pro
            20                  25                  30

Gly Val Gly Xaa Pro Gly Val Gly Xaa Pro Gly Val Gly Xaa Pro Gly
        35                  40                  45

Val Gly
    50

<210> SEQ ID NO 32
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ile or Val
<220> FEATURE:
<221> NAME/KEY: MOD_RES
<222> LOCATION: (6)..(6)
<223> OTHER INFORMATION: Ile or Val
<220> FEATURE:
<221> NAME/KEY: MOD_RES
<222> LOCATION: (11)..(11)
<223> OTHER INFORMATION: Ile or Val
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (21)..(21)
<223> OTHER INFORMATION: Ile or Val
<220> FEATURE:
<221> NAME/KEY: MOD_RES
<222> LOCATION: (26)..(26)
<223> OTHER INFORMATION: Ile or Val
<220> FEATURE:
<221> NAME/KEY: MOD_RES
<222> LOCATION: (31)..(31)
<223> OTHER INFORMATION: Ile or Val
<220> FEATURE:
<221> NAME/KEY: MOD_RES
<222> LOCATION: (36)..(36)
<223> OTHER INFORMATION: Ile or Val
<220> FEATURE:
<221> NAME/KEY: MOD_RES
<222> LOCATION: (41)..(41)
<223> OTHER INFORMATION: Ile or Val
<220> FEATURE:
<221> NAME/KEY: MOD_RES
<222> LOCATION: (46)..(46)
<223> OTHER INFORMATION: Ile or Val
```

<220> FEATURE:
<221> NAME/KEY: MOD_RES
<222> LOCATION: (51)..(51)
<223> OTHER INFORMATION: Ile or Val
<220> FEATURE:
<221> NAME/KEY: MOD_RES
<222> LOCATION: (56)..(56)
<223> OTHER INFORMATION: Ile or Val
<220> FEATURE:
<221> NAME/KEY: MOD_RES
<222> LOCATION: (61)..(61)
<223> OTHER INFORMATION: Ile or Val
<220> FEATURE:
<221> NAME/KEY: MOD_RES
<222> LOCATION: (66)..(66)
<223> OTHER INFORMATION: Ile or Val

<400> SEQUENCE: 32

```
Xaa Pro Ala Val Gly Xaa Pro Ala Val Gly Xaa Pro Ala Val Gly Xaa
1               5                  10                  15

Pro Ala Val Gly Xaa Pro Ala Val Gly Xaa Pro Ala Val Gly Xaa Pro
            20                  25                  30

Ala Val Gly Xaa Pro Ala Val Gly Xaa Pro Ala Val Gly Xaa Pro Ala
        35                  40                  45

Val Gly Xaa Pro Ala Val Gly Xaa Pro Ala Val Gly Xaa Pro Ala Val
    50                  55                  60

Gly Xaa Pro Ala Val Gly
65                  70
```

<210> SEQ ID NO 33
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ile or Val
<220> FEATURE:
<221> NAME/KEY: MOD_RES
<222> LOCATION: (6)..(6)
<223> OTHER INFORMATION: Ile or Val
<220> FEATURE:
<221> NAME/KEY: MOD_RES
<222> LOCATION: (11)..(11)
<223> OTHER INFORMATION: Ile or Val
<220> FEATURE:
<221> NAME/KEY: MOD_RES
<222> LOCATION: (16)..(16)
<223> OTHER INFORMATION: Ile or Val
<220> FEATURE:
<221> NAME/KEY: MOD_RES
<222> LOCATION: (21)..(21)
<223> OTHER INFORMATION: Ile or Val
<220> FEATURE:
<221> NAME/KEY: MOD_RES
<222> LOCATION: (26)..(26)
<223> OTHER INFORMATION: Ile or Val
<220> FEATURE:
<221> NAME/KEY: MOD_RES
<222> LOCATION: (31)..(31)
<223> OTHER INFORMATION: Ile or Val
<220> FEATURE:
<221> NAME/KEY: MOD_RES
<222> LOCATION: (36)..(36)
<223> OTHER INFORMATION: Ile or Val
<220> FEATURE:
<221> NAME/KEY: MOD_RES
<222> LOCATION: (41)..(41)
<223> OTHER INFORMATION: Ile or Val
<220> FEATURE:

```
<221> NAME/KEY: MOD_RES
<222> LOCATION: (46)..(46)
<223> OTHER INFORMATION: Ile or Val
<220> FEATURE:
<221> NAME/KEY: MOD_RES
<222> LOCATION: (51)..(51)
<223> OTHER INFORMATION: Ile or Val
<220> FEATURE:
<221> NAME/KEY: MOD_RES
<222> LOCATION: (56)..(56)
<223> OTHER INFORMATION: Ile or Val
<220> FEATURE:
<221> NAME/KEY: MOD_RES
<222> LOCATION: (61)..(61)
<223> OTHER INFORMATION: Ile or Val
<220> FEATURE:
<221> NAME/KEY: MOD_RES
<222> LOCATION: (66)..(66)
<223> OTHER INFORMATION: Ile or Val
<220> FEATURE:
<221> NAME/KEY: MOD_RES
<222> LOCATION: (71)..(71)
<223> OTHER INFORMATION: Ile or Val
<220> FEATURE:
<221> NAME/KEY: MOD_RES
<222> LOCATION: (76)..(76)
<223> OTHER INFORMATION: Ile or Val
<220> FEATURE:
<221> NAME/KEY: MOD_RES
<222> LOCATION: (81)..(81)
<223> OTHER INFORMATION: Ile or Val
<220> FEATURE:
<221> NAME/KEY: MOD_RES
<222> LOCATION: (86)..(86)
<223> OTHER INFORMATION: Ile or Val
<220> FEATURE:
<221> NAME/KEY: MOD_RES
<222> LOCATION: (91)..(91)
<223> OTHER INFORMATION: Ile or Val
<220> FEATURE:
<221> NAME/KEY: MOD_RES
<222> LOCATION: (96)..(96)
<223> OTHER INFORMATION: Ile or Val
<220> FEATURE:
<221> NAME/KEY: MOD_RES
<222> LOCATION: (101)..(101)
<223> OTHER INFORMATION: Ile or Val
<220> FEATURE:
<221> NAME/KEY: MOD_RES
<222> LOCATION: (106)..(106)
<223> OTHER INFORMATION: Ile or Val
<220> FEATURE:
<221> NAME/KEY: MOD_RES
<222> LOCATION: (111)..(111)
<223> OTHER INFORMATION: Ile or Val
<220> FEATURE:
<221> NAME/KEY: MOD_RES
<222> LOCATION: (116)..(116)
<223> OTHER INFORMATION: Ile or Val

<400> SEQUENCE: 33

Xaa Pro Ala Val Gly Xaa Pro Ala Val Gly Xaa Pro Ala Val Gly Xaa
 1               5                  10                  15

Pro Ala Val Gly Xaa Pro Ala Val Gly Xaa Pro Ala Val Gly Xaa Pro
            20                  25                  30

Ala Val Gly Xaa Pro Ala Val Gly Xaa Pro Ala Val Gly Xaa Pro Ala
        35                  40                  45

Val Gly Xaa Pro Ala Val Gly Xaa Pro Ala Val Gly Xaa Pro Ala Val
    50                  55                  60

Gly Xaa Pro Ala Val Gly Xaa Pro Ala Val Gly Xaa Pro Ala Val Gly
65                  70                  75                  80

Xaa Pro Ala Val Gly Xaa Pro Ala Val Gly Xaa Pro Ala Val Gly Xaa
                85                  90                  95
```

Pro Ala Val Gly Xaa Pro Ala Val Gly Xaa Pro Ala Val Gly Xaa Pro
                100                 105                 110

Ala Val Gly Xaa Pro Ala Val Gly
        115                 120

<210> SEQ ID NO 34
<211> LENGTH: 143
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
ccatgggcgg atccgctagc ggtctcgttg gtattcctgc tgttggtgtg ccggctgttg      60
gtatcccagc tgttggcgtt ccggctgtag gtattccggc tgttggtgag accactagtt    120
aaatgaataa gctttaactc gag                                            143

<210> SEQ ID NO 35
<211> LENGTH: 143
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
ccatgggcgg atccgctagc ggtctcgttg gtgttcctgc tgtcggtgtg ccggctgttg      60
gtattccagc tgttggcgtg ccggctgtag gtgtcccggc tgttggcgag accactagtt    120
aaatgaataa gctttaactc gag                                            143

<210> SEQ ID NO 36
<211> LENGTH: 143
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
ccatgggcgg atccgctagc ggtctcgttg gtgtacctgg tgttggcgtc ccgggtgtag      60
gtatcccagg cgttggtgta ccgggtgtag gcgttccagg cgttggcgag accactagtt    120
aaatgaataa gctttaactc gag                                            143

<210> SEQ ID NO 37
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Gly Trp Gly Ser Ala Ser Gly Leu Val Gly Val Pro Gly Val Gly
1               5                   10                  15

Val Pro Gly Val Gly Ile Pro Gly Val Gly Val Pro Gly Val Gly Val
            20                  25                  30

Pro Gly Val Gly Val Pro Gly Val Gly Val Pro Gly Val Gly Ile Pro
        35                  40                  45

Gly Val Gly Val Pro Gly Val Gly Val Pro Gly Val Gly Val Pro Gly

```
                50                  55                  60
Val Gly Val Pro Gly Val Gly Ile Pro Gly Val Gly Val Pro Gly Val
 65                  70                  75                  80

Gly Val Pro Gly Val Gly Val Pro Gly Val Gly Val Pro Gly Val Gly
                 85                  90                  95

Ile Pro Gly Val Gly Val Pro Gly Val Gly Val Pro Gly Val Gly Val
                100                 105                 110

Pro Gly Val Gly Val Pro Gly Val Gly Ile Pro Gly Val Gly Val Pro
                115                 120                 125

Gly Val Gly Val Pro Gly Val Gly Val Pro Gly Val Gly Val Pro Gly
                130                 135                 140

Val Gly Ile Pro Gly Val Gly Val Pro Gly Val Gly Val Pro Gly Val
145                 150                 155                 160

Gly Val Pro Gly Val Gly Val Pro Gly Val Gly Ile Pro Gly Val Gly
                165                 170                 175

Val Pro Gly Val Gly Val Pro Gly Val Gly Val Pro Gly Val Gly Val
                180                 185                 190

Pro Gly Val Gly Ile Pro Gly Val Gly Val Pro Gly Val Gly Val Pro
                195                 200                 205

Gly Val Gly Val Pro Gly Val Gly Val Pro Gly Val Gly Ile Pro Gly
                210                 215                 220

Val Gly Val Pro Gly Val Gly Val Pro Gly Val Gly Val Pro Gly Val
225                 230                 235                 240

Gly Val Pro Gly Val Gly Ile Pro Gly Val Gly Val Pro Gly Val Gly
                245                 250                 255

Val Pro Gly Val Gly Glu Thr Thr Ser
                260                 265

<210> SEQ ID NO 38
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Gly Trp Gly Ser Ala Ser Gly Leu Val Gly Val Pro Ala Val Gly
 1               5                  10                  15

Val Pro Ala Val Gly Ile Pro Ala Val Gly Val Pro Ala Val Gly Val
                20                  25                  30

Pro Ala Val Gly Val Pro Ala Val Gly Val Pro Ala Val Gly Ile Pro
                35                  40                  45

Ala Val Gly Val Pro Ala Val Gly Val Pro Ala Val Gly Val Pro Ala
                50                  55                  60

Val Gly Val Pro Ala Val Gly Ile Pro Ala Val Gly Val Pro Ala Val
 65                  70                  75                  80

Gly Val Pro Ala Val Gly Val Pro Ala Val Gly Val Pro Ala Val Gly
                 85                  90                  95

Ile Pro Ala Val Gly Val Pro Ala Val Gly Val Pro Ala Val Gly Val
                100                 105                 110

Pro Ala Val Gly Val Pro Ala Val Gly Ile Pro Ala Val Gly Val Pro
                115                 120                 125

Ala Val Gly Val Pro Ala Val Gly Val Pro Ala Val Gly Val Pro Ala
                130                 135                 140
```

```
Val Gly Ile Pro Ala Val Gly Val Pro Ala Val Gly Val Pro Ala Val
145                 150                 155                 160

Gly Val Pro Ala Val Gly Val Pro Ala Val Gly Ile Pro Ala Val Gly
                165                 170                 175

Val Pro Ala Val Gly Val Pro Ala Val Gly Val Pro Ala Val Gly Val
            180                 185                 190

Pro Ala Val Gly Ile Pro Ala Val Gly Val Pro Ala Val Gly Val Pro
        195                 200                 205

Ala Val Gly Val Pro Ala Val Gly Val Pro Ala Val Gly Ile Pro Ala
    210                 215                 220

Val Gly Val Pro Ala Val Gly Val Pro Ala Val Gly Val Pro Ala Val
225                 230                 235                 240

Gly Val Pro Ala Val Gly Ile Pro Ala Val Gly Val Pro Ala Val Gly
                245                 250                 255

Val Pro Ala Val Gly Glu Thr Thr Ser
            260                 265

<210> SEQ ID NO 39
<211> LENGTH: 365
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Gly Trp Gly Ser Ala Ser Gly Leu Val Gly Val Pro Ala Val Gly
1               5                   10                  15

Val Pro Ala Val Gly Ile Pro Ala Val Gly Val Pro Ala Val Gly Val
            20                  25                  30

Pro Ala Val Gly Val Pro Ala Val Gly Val Pro Ala Val Gly Ile Pro
        35                  40                  45

Ala Val Gly Val Pro Ala Val Gly Val Pro Ala Val Gly Val Pro Ala
    50                  55                  60

Val Gly Val Pro Ala Val Gly Ile Pro Ala Val Gly Val Pro Ala Val
65                  70                  75                  80

Gly Val Pro Ala Val Gly Val Pro Ala Val Gly Val Pro Ala Val Gly
                85                  90                  95

Ile Pro Ala Val Gly Val Pro Ala Val Gly Val Pro Ala Val Gly Val
                100                 105                 110

Pro Ala Val Gly Val Pro Ala Val Gly Ile Pro Ala Val Gly Val Pro
            115                 120                 125

Ala Val Gly Val Pro Ala Val Gly Val Pro Ala Val Gly Val Pro Ala
    130                 135                 140

Val Gly Ile Pro Ala Val Gly Val Pro Ala Val Gly Val Pro Ala Val
145                 150                 155                 160

Gly Val Pro Ala Val Gly Val Pro Ala Val Gly Ile Pro Ala Val Gly
                165                 170                 175

Val Pro Ala Val Gly Val Pro Ala Val Gly Val Pro Ala Val Gly Val
            180                 185                 190

Pro Ala Val Gly Ile Pro Ala Val Gly Val Pro Ala Val Gly Val Pro
        195                 200                 205

Ala Val Gly Val Pro Ala Val Gly Val Pro Ala Val Gly Ile Pro Ala
    210                 215                 220

Val Gly Val Pro Ala Val Gly Val Pro Ala Val Gly Val Pro Ala Val
225                 230                 235                 240
```

```
Gly Val Pro Ala Val Gly Ile Pro Ala Val Gly Val Pro Ala Val Gly
                245                 250                 255

Val Pro Ala Val Gly Val Pro Ala Val Gly Val Pro Ala Val Gly Ile
            260                 265                 270

Pro Ala Val Gly Val Pro Ala Val Gly Val Pro Ala Val Gly Val Pro
        275                 280                 285

Ala Val Gly Val Pro Ala Val Gly Ile Pro Ala Val Gly Val Pro Ala
    290                 295                 300

Val Gly Val Pro Ala Val Gly Val Pro Ala Val Gly Val Pro Ala Val
305                 310                 315                 320

Gly Ile Pro Ala Val Gly Val Pro Ala Val Gly Val Pro Ala Val Gly
                325                 330                 335

Val Pro Ala Val Gly Val Pro Ala Val Gly Ile Pro Ala Val Gly Val
            340                 345                 350

Pro Ala Val Gly Val Pro Ala Val Gly Glu Thr Thr Ser
        355                 360                 365

<210> SEQ ID NO 40
<211> LENGTH: 615
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Gly Trp Gly Ser Ala Ser Gly Leu Val Gly Val Pro Ala Val Gly
1               5                   10                  15

Val Pro Ala Val Gly Ile Pro Ala Val Gly Val Pro Ala Val Gly Val
            20                  25                  30

Pro Ala Val Gly Val Pro Ala Val Gly Val Pro Ala Val Gly Ile Pro
        35                  40                  45

Ala Val Gly Val Pro Ala Val Gly Val Pro Ala Val Gly Val Pro Ala
    50                  55                  60

Val Gly Val Pro Ala Val Gly Ile Pro Ala Val Gly Val Pro Ala Val
65                  70                  75                  80

Gly Val Pro Ala Val Gly Val Pro Ala Val Gly Val Pro Ala Val Gly
                85                  90                  95

Ile Pro Ala Val Gly Val Pro Ala Val Gly Val Pro Ala Val Gly Val
            100                 105                 110

Pro Ala Val Gly Val Pro Ala Val Gly Ile Pro Ala Val Gly Val Pro
        115                 120                 125

Ala Val Gly Val Pro Ala Val Gly Val Pro Ala Val Gly Val Pro Ala
    130                 135                 140

Val Gly Ile Pro Ala Val Gly Val Pro Ala Val Gly Val Pro Ala Val
145                 150                 155                 160

Gly Val Pro Ala Val Gly Val Pro Ala Val Gly Ile Pro Ala Val Gly
                165                 170                 175

Val Pro Ala Val Gly Val Pro Ala Val Gly Val Pro Ala Val Gly Val
            180                 185                 190

Pro Ala Val Gly Ile Pro Ala Val Gly Val Pro Ala Val Gly Val Pro
        195                 200                 205

Ala Val Gly Val Pro Ala Val Gly Val Pro Ala Val Gly Ile Pro Ala
    210                 215                 220

Val Gly Val Pro Ala Val Gly Val Pro Ala Val Gly Val Pro Ala Val
```

```
            225                 230                 235                 240
Gly Val Pro Ala Val Gly Ile Pro Ala Val Gly Val Pro Ala Val Gly
                245                 250                 255
Val Pro Ala Val Gly Val Pro Ala Val Gly Val Pro Ala Val Gly Ile
                260                 265                 270
Pro Ala Val Gly Val Pro Ala Val Gly Val Pro Ala Val Gly Val Pro
                275                 280                 285
Ala Val Gly Val Pro Ala Val Gly Ile Pro Ala Val Gly Val Pro Ala
            290                 295                 300
Val Gly Val Pro Ala Val Gly Val Pro Ala Val Gly Val Pro Ala Val
305                 310                 315                 320
Gly Ile Pro Ala Val Gly Val Pro Ala Val Gly Val Pro Ala Val Gly
                325                 330                 335
Val Pro Ala Val Gly Val Pro Ala Val Gly Ile Pro Ala Val Gly Val
                340                 345                 350
Pro Ala Val Gly Val Pro Ala Val Gly Val Pro Ala Val Gly Val Pro
                355                 360                 365
Ala Val Gly Ile Pro Ala Val Gly Val Pro Ala Val Gly Val Pro Ala
            370                 375                 380
Val Gly Val Pro Ala Val Gly Val Pro Ala Val Gly Ile Pro Ala Val
385                 390                 395                 400
Gly Val Pro Ala Val Gly Val Pro Ala Val Gly Val Pro Ala Val Gly
                405                 410                 415
Val Pro Ala Val Gly Ile Pro Ala Val Gly Val Pro Ala Val Gly Val
                420                 425                 430
Pro Ala Val Gly Val Pro Ala Val Gly Val Pro Ala Val Gly Ile Pro
                435                 440                 445
Ala Val Gly Val Pro Ala Val Gly Val Pro Ala Val Gly Val Pro Ala
            450                 455                 460
Val Gly Val Pro Ala Val Gly Ile Pro Ala Val Gly Val Pro Ala Val
465                 470                 475                 480
Gly Val Pro Ala Val Gly Val Pro Ala Val Gly Val Pro Ala Val Gly
                485                 490                 495
Ile Pro Ala Val Gly Val Pro Ala Val Gly Val Pro Ala Val Gly Val
                500                 505                 510
Pro Ala Val Gly Val Pro Ala Val Gly Ile Pro Ala Val Gly Val Pro
                515                 520                 525
Ala Val Gly Val Pro Ala Val Gly Val Pro Ala Val Gly Val Pro Ala
            530                 535                 540
Val Gly Ile Pro Ala Val Gly Val Pro Ala Val Gly Val Pro Ala Val
545                 550                 555                 560
Gly Val Pro Ala Val Gly Val Pro Ala Val Gly Ile Pro Ala Val Gly
                565                 570                 575
Val Pro Ala Val Gly Val Pro Ala Val Gly Val Pro Ala Val Gly Val
                580                 585                 590
Pro Ala Val Gly Ile Pro Ala Val Gly Val Pro Ala Val Gly Val Pro
            595                 600                 605
Ala Val Gly Glu Thr Thr Ser
        610                 615

<210> SEQ ID NO 41
<211> LENGTH: 265
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 41

Met Gly Trp Gly Ser Ala Ser Gly Leu Val Gly Ile Pro Ala Val Gly
1               5                   10                  15

Val Pro Ala Val Gly Ile Pro Ala Val Gly Val Pro Ala Val Gly Ile
                20                  25                  30

Pro Ala Val Gly Ile Pro Ala Val Gly Val Pro Ala Val Gly Ile Pro
            35                  40                  45

Ala Val Gly Val Pro Ala Val Gly Ile Pro Ala Val Gly Ile Pro Ala
        50                  55                  60

Val Gly Val Pro Ala Val Gly Ile Pro Ala Val Gly Val Pro Ala Val
65                  70                  75                  80

Gly Ile Pro Ala Val Gly Ile Pro Ala Val Gly Val Pro Ala Val Gly
                85                  90                  95

Ile Pro Ala Val Gly Val Pro Ala Val Gly Ile Pro Ala Val Gly Ile
                100                 105                 110

Pro Ala Val Gly Val Pro Ala Val Gly Ile Pro Ala Val Gly Val Pro
            115                 120                 125

Ala Val Gly Ile Pro Ala Val Gly Ile Pro Ala Val Gly Val Pro Ala
        130                 135                 140

Val Gly Ile Pro Ala Val Gly Val Pro Ala Val Gly Ile Pro Ala Val
145                 150                 155                 160

Gly Ile Pro Ala Val Gly Val Pro Ala Val Gly Ile Pro Ala Val Gly
                165                 170                 175

Val Pro Ala Val Gly Ile Pro Ala Val Gly Ile Pro Ala Val Gly Val
                180                 185                 190

Pro Ala Val Gly Ile Pro Ala Val Gly Val Pro Ala Val Gly Ile Pro
            195                 200                 205

Ala Val Gly Ile Pro Ala Val Gly Val Pro Ala Val Gly Ile Pro Ala
        210                 215                 220

Val Gly Val Pro Ala Val Gly Ile Pro Ala Val Gly Ile Pro Ala Val
225                 230                 235                 240

Gly Val Pro Ala Val Gly Ile Pro Ala Val Gly Val Pro Ala Val Gly
                245                 250                 255

Ile Pro Ala Val Gly Glu Thr Thr Ser
                260                 265

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid

<400> SEQUENCE: 42

Xaa Pro Gly Val Gly
1               5

<210> SEQ ID NO 43
<211> LENGTH: 250
<212> TYPE: PRT

-continued

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ile or Val
<220> FEATURE:
<221> NAME/KEY: MOD_RES
<222> LOCATION: (6)..(6)
<223> OTHER INFORMATION: Ile or Val
<220> FEATURE:
<221> NAME/KEY: MOD_RES
<222> LOCATION: (11)..(11)
<223> OTHER INFORMATION: Ile or Val
<220> FEATURE:
<221> NAME/KEY: MOD_RES
<222> LOCATION: (16)..(16)
<223> OTHER INFORMATION: Ile or Val
<220> FEATURE:
<221> NAME/KEY: MOD_RES
<222> LOCATION: (21)..(21)
<223> OTHER INFORMATION: Ile or Val
<220> FEATURE:
<221> NAME/KEY: MOD_RES
<222> LOCATION: (26)..(26)
<223> OTHER INFORMATION: Ile or Val
<220> FEATURE:
<221> NAME/KEY: MOD_RES
<222> LOCATION: (31)..(31)
<223> OTHER INFORMATION: Ile or Val
<220> FEATURE:
<221> NAME/KEY: MOD_RES
<222> LOCATION: (36)..(36)
<223> OTHER INFORMATION: Ile or Val
<220> FEATURE:
<221> NAME/KEY: MOD_RES
<222> LOCATION: (41)..(41)
<223> OTHER INFORMATION: Ile or Val
<220> FEATURE:
<221> NAME/KEY: MOD_RES
<222> LOCATION: (46)..(46)
<223> OTHER INFORMATION: Ile or Val
<220> FEATURE:
<221> NAME/KEY: MOD_RES
<222> LOCATION: (51)..(51)
<223> OTHER INFORMATION: Ile or Val
<220> FEATURE:
<221> NAME/KEY: MOD_RES
<222> LOCATION: (56)..(56)
<223> OTHER INFORMATION: Ile or Val
<220> FEATURE:
<221> NAME/KEY: MOD_RES
<222> LOCATION: (61)..(61)
<223> OTHER INFORMATION: Ile or Val
<220> FEATURE:
<221> NAME/KEY: MOD_RES
<222> LOCATION: (66)..(66)
<223> OTHER INFORMATION: Ile or Val
<220> FEATURE:
<221> NAME/KEY: MOD_RES
<222> LOCATION: (71)..(71)
<223> OTHER INFORMATION: Ile or Val
<220> FEATURE:
<221> NAME/KEY: MOD_RES
<222> LOCATION: (76)..(76)
<223> OTHER INFORMATION: Ile or Val
<220> FEATURE:
<221> NAME/KEY: MOD_RES
<222> LOCATION: (81)..(81)
<223> OTHER INFORMATION: Ile or Val
<220> FEATURE:
<221> NAME/KEY: MOD_RES
<222> LOCATION: (86)..(86)
<223> OTHER INFORMATION: Ile or Val
<220> FEATURE:
<221> NAME/KEY: MOD_RES
<222> LOCATION: (91)..(91)
```

```
<223> OTHER INFORMATION: Ile or Val
<220> FEATURE:
<221> NAME/KEY: MOD_RES
<222> LOCATION: (96)..(96)
<223> OTHER INFORMATION: Ile or Val
<220> FEATURE:
<221> NAME/KEY: MOD_RES
<222> LOCATION: (101)..(101)
<223> OTHER INFORMATION: Ile or Val
<220> FEATURE:
<221> NAME/KEY: MOD_RES
<222> LOCATION: (106)..(106)
<223> OTHER INFORMATION: Ile or Val
<220> FEATURE:
<221> NAME/KEY: MOD_RES
<222> LOCATION: (111)..(111)
<223> OTHER INFORMATION: Ile or Val
<220> FEATURE:
<221> NAME/KEY: MOD_RES
<222> LOCATION: (116)..(116)
<223> OTHER INFORMATION: Ile or Val
<220> FEATURE:
<221> NAME/KEY: MOD_RES
<222> LOCATION: (121)..(121)
<223> OTHER INFORMATION: Ile or Val
<220> FEATURE:
<221> NAME/KEY: MOD_RES
<222> LOCATION: (126)..(126)
<223> OTHER INFORMATION: Ile or Val
<220> FEATURE:
<221> NAME/KEY: MOD_RES
<222> LOCATION: (131)..(131)
<223> OTHER INFORMATION: Ile or Val
<220> FEATURE:
<221> NAME/KEY: MOD_RES
<222> LOCATION: (136)..(136)
<223> OTHER INFORMATION: Ile or Val
<220> FEATURE:
<221> NAME/KEY: MOD_RES
<222> LOCATION: (141)..(141)
<223> OTHER INFORMATION: Ile or Val
<220> FEATURE:
<221> NAME/KEY: MOD_RES
<222> LOCATION: (146)..(146)
<223> OTHER INFORMATION: Ile or Val
<220> FEATURE:
<221> NAME/KEY: MOD_RES
<222> LOCATION: (151)..(151)
<223> OTHER INFORMATION: Ile or Val
<220> FEATURE:
<221> NAME/KEY: MOD_RES
<222> LOCATION: (156)..(156)
<223> OTHER INFORMATION: Ile or Val
<220> FEATURE:
<221> NAME/KEY: MOD_RES
<222> LOCATION: (161)..(161)
<223> OTHER INFORMATION: Ile or Val
<220> FEATURE:
<221> NAME/KEY: MOD_RES
<222> LOCATION: (166)..(166)
<223> OTHER INFORMATION: Ile or Val
<220> FEATURE:
<221> NAME/KEY: MOD_RES
<222> LOCATION: (171)..(171)
<223> OTHER INFORMATION: Ile or Val
<220> FEATURE:
<221> NAME/KEY: MOD_RES
<222> LOCATION: (176)..(176)
<223> OTHER INFORMATION: Ile or Val
<220> FEATURE:
<221> NAME/KEY: MOD_RES
<222> LOCATION: (181)..(181)
<223> OTHER INFORMATION: Ile or Val
<220> FEATURE:
<221> NAME/KEY: MOD_RES
<222> LOCATION: (186)..(186)
<223> OTHER INFORMATION: Ile or Val
<220> FEATURE:
<221> NAME/KEY: MOD_RES
```

```
<222> LOCATION: (191)..(191)
<223> OTHER INFORMATION: Ile or Val
<220> FEATURE:
<221> NAME/KEY: MOD_RES
<222> LOCATION: (196)..(196)
<223> OTHER INFORMATION: Ile or Val
<220> FEATURE:
<221> NAME/KEY: MOD_RES
<222> LOCATION: (201)..(201)
<223> OTHER INFORMATION: Ile or Val
<220> FEATURE:
<221> NAME/KEY: MOD_RES
<222> LOCATION: (206)..(206)
<223> OTHER INFORMATION: Ile or Val
<220> FEATURE:
<221> NAME/KEY: MOD_RES
<222> LOCATION: (211)..(211)
<223> OTHER INFORMATION: Ile or Val
<220> FEATURE:
<221> NAME/KEY: MOD_RES
<222> LOCATION: (216)..(216)
<223> OTHER INFORMATION: Ile or Val
<220> FEATURE:
<221> NAME/KEY: MOD_RES
<222> LOCATION: (221)..(221)
<223> OTHER INFORMATION: Ile or Val
<220> FEATURE:
<221> NAME/KEY: MOD_RES
<222> LOCATION: (226)..(226)
<223> OTHER INFORMATION: Ile or Val
<220> FEATURE:
<221> NAME/KEY: MOD_RES
<222> LOCATION: (231)..(231)
<223> OTHER INFORMATION: Ile or Val
<220> FEATURE:
<221> NAME/KEY: MOD_RES
<222> LOCATION: (236)..(236)
<223> OTHER INFORMATION: Ile or Val
<220> FEATURE:
<221> NAME/KEY: MOD_RES
<222> LOCATION: (241)..(241)
<223> OTHER INFORMATION: Ile or Val
<220> FEATURE:
<221> NAME/KEY: MOD_RES
<222> LOCATION: (246)..(246)
<223> OTHER INFORMATION: Ile or Val

<400> SEQUENCE: 43

Xaa Pro Ala Val Gly Xaa Pro Ala Val Gly Xaa Pro Ala Val Gly Xaa
1               5                   10                  15

Pro Ala Val Gly Xaa Pro Ala Val Gly Xaa Pro Ala Val Gly Xaa Pro
            20                  25                  30

Ala Val Gly Xaa Pro Ala Val Gly Xaa Pro Ala Val Gly Xaa Pro Ala
        35                  40                  45

Val Gly Xaa Pro Ala Val Gly Xaa Pro Ala Val Gly Xaa Pro Ala Val
    50                  55                  60

Gly Xaa Pro Ala Val Gly Xaa Pro Ala Val Gly Xaa Pro Ala Val Gly
65                  70                  75                  80

Xaa Pro Ala Val Gly Xaa Pro Ala Val Gly Xaa Pro Ala Val Gly Xaa
                85                  90                  95

Pro Ala Val Gly Xaa Pro Ala Val Gly Xaa Pro Ala Val Gly Xaa Pro
            100                 105                 110

Ala Val Gly Xaa Pro Ala Val Gly Xaa Pro Ala Val Gly Xaa Pro Ala
        115                 120                 125

Val Gly Xaa Pro Ala Val Gly Xaa Pro Ala Val Gly Xaa Pro Ala Val
    130                 135                 140

Gly Xaa Pro Ala Val Gly Xaa Pro Ala Val Gly Xaa Pro Ala Val Gly
145                 150                 155                 160
```

Xaa Pro Ala Val Gly Xaa Pro Ala Val Gly Xaa Pro Ala Val Gly Xaa
                165                 170                 175

Pro Ala Val Gly Xaa Pro Ala Val Gly Xaa Pro Ala Val Gly Xaa Pro
            180                 185                 190

Ala Val Gly Xaa Pro Ala Val Gly Xaa Pro Ala Val Gly Xaa Pro Ala
        195                 200                 205

Val Gly Xaa Pro Ala Val Gly Xaa Pro Ala Val Gly Xaa Pro Ala Val
    210                 215                 220

Gly Xaa Pro Ala Val Gly Xaa Pro Ala Val Gly Xaa Pro Ala Val Gly
225                 230                 235                 240

Xaa Pro Ala Val Gly Xaa Pro Ala Val Gly
                245                 250

<210> SEQ ID NO 44
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gatccaaatg tacctctgcc ggcgctggtg cgggcccgga aggtcgtggt gattcta        57

<210> SEQ ID NO 45
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ctagtagaat caccacgacc ttccgggccc gcaccagcgc cggcagaggt acatttg        57

<210> SEQ ID NO 46
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ctagtcgtgg tgattctgcc ggcgctggtg cgggcccgga aggtacaagc tgta           54

<210> SEQ ID NO 47
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
agcttacagc ttgtaccttc cgggcccgca ccagcgccgg cagaatcacc acga           54

<210> SEQ ID NO 48
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 48

Met Gly Trp Gly Ser Ala Ser Gly Leu Val Gly Ile Pro Ala Val Gly
1               5                   10                  15

Val Pro Ala Val Gly Ile Pro Ala Val Gly Val Pro Ala Val Gly Ile
                20                  25                  30

Pro Ala Val Gly Ile Pro Ala Val Gly Val Pro Ala Val Gly Ile Pro
            35                  40                  45

Ala Val Gly Val Pro Ala Val Gly Ile Pro Ala Val Gly Ile Pro Ala
        50                  55                  60

Val Gly Val Pro Ala Val Gly Ile Pro Ala Val Gly Val Pro Ala Val
65                  70                  75                  80

Gly Ile Pro Ala Val Gly Ile Pro Ala Val Gly Val Pro Ala Val Gly
                85                  90                  95

Ile Pro Ala Val Gly Val Pro Ala Val Gly Ile Pro Ala Val Gly Ile
                100                 105                 110

Pro Ala Val Gly Val Pro Ala Val Gly Ile Pro Ala Val Gly Val Pro
            115                 120                 125

Ala Val Gly Ile Pro Ala Val Gly Ile Pro Ala Val Gly Val Pro Ala
        130                 135                 140

Val Gly Ile Pro Ala Val Gly Val Pro Ala Val Gly Ile Pro Ala Val
145                 150                 155                 160

Gly Ile Pro Ala Val Gly Val Pro Ala Val Gly Ile Pro Ala Val Gly
                165                 170                 175

Val Pro Ala Val Gly Ile Pro Ala Val Gly Ile Pro Ala Val Gly Val
                180                 185                 190

Pro Ala Val Gly Ile Pro Ala Val Gly Val Pro Ala Val Gly Ile Pro
            195                 200                 205

Ala Val Gly Ile Pro Ala Val Gly Val Pro Ala Val Gly Ile Pro Ala
        210                 215                 220

Val Gly Val Pro Ala Val Gly Ile Pro Ala Val Gly Ile Pro Ala Val
225                 230                 235                 240

Gly Val Pro Ala Val Gly Ile Pro Ala Val Gly Val Pro Ala Val Gly
                245                 250                 255

Ile Pro Ala Val Gly Glu Thr Thr Ser
                260                 265

<210> SEQ ID NO 49
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Gly Trp Gly Ser Lys Cys Thr Ser Ala Gly Ala Gly Ala Gly Pro
1               5                   10                  15

Glu Gly Arg Gly Asp Ser Thr Ser Gly Leu Val Gly Ile Pro Ala Val
                20                  25                  30

Gly Val Pro Ala Val Gly Ile Pro Ala Val Gly Val Pro Ala Val Gly
            35                  40                  45

Ile Pro Ala Val Gly Ile Pro Ala Val Gly Val Pro Ala Val Gly Ile
        50                  55                  60

Pro Ala Val Gly Val Pro Ala Val Gly Ile Pro Ala Val Gly Ile Pro
65                  70                  75                  80

-continued

Ala Val Gly Val Pro Ala Val Gly Ile Pro Ala Val Gly Val Pro Ala
                85                  90                  95
Val Gly Ile Pro Ala Val Gly Ile Pro Ala Val Gly Val Pro Ala Val
            100                 105                 110
Gly Ile Pro Ala Val Gly Val Pro Ala Val Gly Ile Pro Ala Val Gly
        115                 120                 125
Ile Pro Ala Val Gly Val Pro Ala Val Gly Ile Pro Ala Val Gly Val
    130                 135                 140
Pro Ala Val Gly Ile Pro Ala Val Gly Ile Pro Ala Val Gly Val Pro
145                 150                 155                 160
Ala Val Gly Ile Pro Ala Val Gly Val Pro Ala Val Gly Ile Pro Ala
                165                 170                 175
Val Gly Ile Pro Ala Val Gly Val Pro Ala Val Gly Ile Pro Ala Val
            180                 185                 190
Gly Val Pro Ala Val Gly Ile Pro Ala Val Gly Ile Pro Ala Val Gly
        195                 200                 205
Val Pro Ala Val Gly Ile Pro Ala Val Gly Val Pro Ala Val Gly Ile
    210                 215                 220
Pro Ala Val Gly Ile Pro Ala Val Gly Val Pro Ala Val Gly Ile Pro
225                 230                 235                 240
Ala Val Gly Val Pro Ala Val Gly Ile Pro Ala Val Gly Ile Pro Ala
                245                 250                 255
Val Gly Val Pro Ala Val Gly Ile Pro Ala Val Gly Val Pro Ala Val
            260                 265                 270
Gly Ile Pro Ala Val Gly Glu Thr Thr Ser Arg Gly Asp Ser Ala Gly
        275                 280                 285
Ala Gly Ala Gly Pro Glu Gly Thr Ser Cys Lys Leu
    290                 295                 300

<210> SEQ ID NO 50
<211> LENGTH: 600
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:

```
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (41)..(41)
<223> OTHER INFORMATION: Any amino acid
<220> FEATURE:
<221> NAME/KEY: MOD_RES
<222> LOCATION: (46)..(46)
<223> OTHER INFORMATION: Any amino acid
<220> FEATURE:
<221> NAME/KEY: MOD_RES
<222> LOCATION: (51)..(51)
<223> OTHER INFORMATION: Any amino acid
<220> FEATURE:
<221> NAME/KEY: MOD_RES
<222> LOCATION: (56)..(56)
<223> OTHER INFORMATION: Any amino acid
<220> FEATURE:
<221> NAME/KEY: MOD_RES
<222> LOCATION: (61)..(61)
<223> OTHER INFORMATION: Any amino acid
<220> FEATURE:
<221> NAME/KEY: MOD_RES
<222> LOCATION: (66)..(66)
<223> OTHER INFORMATION: Any amino acid
<220> FEATURE:
<221> NAME/KEY: MOD_RES
<222> LOCATION: (71)..(71)
<223> OTHER INFORMATION: Any amino acid
<220> FEATURE:
<221> NAME/KEY: MOD_RES
<222> LOCATION: (76)..(76)
<223> OTHER INFORMATION: Any amino acid
<220> FEATURE:
<221> NAME/KEY: MOD_RES
<222> LOCATION: (81)..(81)
<223> OTHER INFORMATION: Any amino acid
<220> FEATURE:
<221> NAME/KEY: MOD_RES
<222> LOCATION: (86)..(86)
<223> OTHER INFORMATION: Any amino acid
<220> FEATURE:
<221> NAME/KEY: MOD_RES
<222> LOCATION: (91)..(91)
<223> OTHER INFORMATION: Any amino acid
<220> FEATURE:
<221> NAME/KEY: MOD_RES
<222> LOCATION: (96)..(96)
<223> OTHER INFORMATION: Any amino acid
<220> FEATURE:
<221> NAME/KEY: MOD_RES
<222> LOCATION: (101)..(101)
<223> OTHER INFORMATION: Any amino acid
<220> FEATURE:
<221> NAME/KEY: MOD_RES
<222> LOCATION: (106)..(106)
<223> OTHER INFORMATION: Any amino acid
<220> FEATURE:
<221> NAME/KEY: MOD_RES
<222> LOCATION: (111)..(111)
<223> OTHER INFORMATION: Any amino acid
<220> FEATURE:
<221> NAME/KEY: MOD_RES
<222> LOCATION: (116)..(116)
<223> OTHER INFORMATION: Any amino acid
<220> FEATURE:
<221> NAME/KEY: MOD_RES
<222> LOCATION: (121)..(121)
<223> OTHER INFORMATION: Any amino acid
<220> FEATURE:
<221> NAME/KEY: MOD_RES
<222> LOCATION: (126)..(126)
<223> OTHER INFORMATION: Any amino acid
<220> FEATURE:
<221> NAME/KEY: MOD_RES
<222> LOCATION: (131)..(131)
<223> OTHER INFORMATION: Any amino acid
```

```
-continued

<220> FEATURE:
<221> NAME/KEY: MOD_RES
<222> LOCATION: (136)..(136)
<223> OTHER INFORMATION: Any amino acid
<220> FEATURE:
<221> NAME/KEY: MOD_RES
<222> LOCATION: (141)..(141)
<223> OTHER INFORMATION: Any amino acid
<220> FEATURE:
<221> NAME/KEY: MOD_RES
<222> LOCATION: (146)..(146)
<223> OTHER INFORMATION: Any amino acid
<220> FEATURE:
<221> NAME/KEY: MOD_RES
<222> LOCATION: (151)..(151)
<223> OTHER INFORMATION: Any amino acid
<220> FEATURE:
<221> NAME/KEY: MOD_RES
<222> LOCATION: (156)..(156)
<223> OTHER INFORMATION: Any amino acid
<220> FEATURE:
<221> NAME/KEY: MOD_RES
<222> LOCATION: (161)..(161)
<223> OTHER INFORMATION: Any amino acid
<220> FEATURE:
<221> NAME/KEY: MOD_RES
<222> LOCATION: (166)..(166)
<223> OTHER INFORMATION: Any amino acid
<220> FEATURE:
<221> NAME/KEY: MOD_RES
<222> LOCATION: (171)..(171)
<223> OTHER INFORMATION: Any amino acid
<220> FEATURE:
<221> NAME/KEY: MOD_RES
<222> LOCATION: (176)..(176)
<223> OTHER INFORMATION: Any amino acid
<220> FEATURE:
<221> NAME/KEY: MOD_RES
<222> LOCATION: (181)..(181)
<223> OTHER INFORMATION: Any amino acid
<220> FEATURE:
<221> NAME/KEY: MOD_RES
<222> LOCATION: (186)..(186)
<223> OTHER INFORMATION: Any amino acid
<220> FEATURE:
<221> NAME/KEY: MOD_RES
<222> LOCATION: (191)..(191)
<223> OTHER INFORMATION: Any amino acid
<220> FEATURE:
<221> NAME/KEY: MOD_RES
<222> LOCATION: (196)..(196)
<223> OTHER INFORMATION: Any amino acid
<220> FEATURE:
<221> NAME/KEY: MOD_RES
<222> LOCATION: (201)..(201)
<223> OTHER INFORMATION: Any amino acid
<220> FEATURE:
<221> NAME/KEY: MOD_RES
<222> LOCATION: (206)..(206)
<223> OTHER INFORMATION: Any amino acid
<220> FEATURE:
<221> NAME/KEY: MOD_RES
<222> LOCATION: (211)..(211)
<223> OTHER INFORMATION: Any amino acid
<220> FEATURE:
<221> NAME/KEY: MOD_RES
<222> LOCATION: (216)..(216)
<223> OTHER INFORMATION: Any amino acid
<220> FEATURE:
<221> NAME/KEY: MOD_RES
<222> LOCATION: (221)..(221)
<223> OTHER INFORMATION: Any amino acid
<220> FEATURE:
<221> NAME/KEY: MOD_RES
<222> LOCATION: (226)..(226)
<223> OTHER INFORMATION: Any amino acid
<220> FEATURE:
<221> NAME/KEY: MOD_RES
<222> LOCATION: (231)..(231)
```

```
<223> OTHER INFORMATION: Any amino acid
<220> FEATURE:
<221> NAME/KEY: MOD_RES
<222> LOCATION: (236)..(236)
<223> OTHER INFORMATION: Any amino acid
<220> FEATURE:
<221> NAME/KEY: MOD_RES
<222> LOCATION: (241)..(241)
<223> OTHER INFORMATION: Any amino acid
<220> FEATURE:
<221> NAME/KEY: MOD_RES
<222> LOCATION: (246)..(246)
<223> OTHER INFORMATION: Any amino acid
<220> FEATURE:
<221> NAME/KEY: MOD_RES
<222> LOCATION: (251)..(251)
<223> OTHER INFORMATION: Any amino acid
<220> FEATURE:
<221> NAME/KEY: MOD_RES
<222> LOCATION: (256)..(256)
<223> OTHER INFORMATION: Any amino acid
<220> FEATURE:
<221> NAME/KEY: MOD_RES
<222> LOCATION: (261)..(261)
<223> OTHER INFORMATION: Any amino acid
<220> FEATURE:
<221> NAME/KEY: MOD_RES
<222> LOCATION: (266)..(266)
<223> OTHER INFORMATION: Any amino acid
<220> FEATURE:
<221> NAME/KEY: MOD_RES
<222> LOCATION: (271)..(271)
<223> OTHER INFORMATION: Any amino acid
<220> FEATURE:
<221> NAME/KEY: MOD_RES
<222> LOCATION: (276)..(276)
<223> OTHER INFORMATION: Any amino acid
<220> FEATURE:
<221> NAME/KEY: MOD_RES
<222> LOCATION: (281)..(281)
<223> OTHER INFORMATION: Any amino acid
<220> FEATURE:
<221> NAME/KEY: MOD_RES
<222> LOCATION: (286)..(286)
<223> OTHER INFORMATION: Any amino acid
<220> FEATURE:
<221> NAME/KEY: MOD_RES
<222> LOCATION: (291)..(291)
<223> OTHER INFORMATION: Any amino acid
<220> FEATURE:
<221> NAME/KEY: MOD_RES
<222> LOCATION: (296)..(296)
<223> OTHER INFORMATION: Any amino acid
<220> FEATURE:
<221> NAME/KEY: MOD_RES
<222> LOCATION: (301)..(301)
<223> OTHER INFORMATION: Any amino acid
<220> FEATURE:
<221> NAME/KEY: MOD_RES
<222> LOCATION: (306)..(306)
<223> OTHER INFORMATION: Any amino acid
<220> FEATURE:
<221> NAME/KEY: MOD_RES
<222> LOCATION: (311)..(311)
<223> OTHER INFORMATION: Any amino acid
<220> FEATURE:
<221> NAME/KEY: MOD_RES
<222> LOCATION: (316)..(316)
<223> OTHER INFORMATION: Any amino acid
<220> FEATURE:
<221> NAME/KEY: MOD_RES
<222> LOCATION: (321)..(321)
<223> OTHER INFORMATION: Any amino acid
<220> FEATURE:
<221> NAME/KEY: MOD_RES
<222> LOCATION: (326)..(326)
<223> OTHER INFORMATION: Any amino acid
<220> FEATURE:
<221> NAME/KEY: MOD_RES
```

```
<222> LOCATION: (331)..(331)
<223> OTHER INFORMATION: Any amino acid
<220> FEATURE:
<221> NAME/KEY: MOD_RES
<222> LOCATION: (336)..(336)
<223> OTHER INFORMATION: Any amino acid
<220> FEATURE:
<221> NAME/KEY: MOD_RES
<222> LOCATION: (341)..(341)
<223> OTHER INFORMATION: Any amino acid
<220> FEATURE:
<221> NAME/KEY: MOD_RES
<222> LOCATION: (346)..(346)
<223> OTHER INFORMATION: Any amino acid
<220> FEATURE:
<221> NAME/KEY: MOD_RES
<222> LOCATION: (351)..(351)
<223> OTHER INFORMATION: Any amino acid
<220> FEATURE:
<221> NAME/KEY: MOD_RES
<222> LOCATION: (356)..(356)
<223> OTHER INFORMATION: Any amino acid
<220> FEATURE:
<221> NAME/KEY: MOD_RES
<222> LOCATION: (361)..(361)
<223> OTHER INFORMATION: Any amino acid
<220> FEATURE:
<221> NAME/KEY: MOD_RES
<222> LOCATION: (366)..(366)
<223> OTHER INFORMATION: Any amino acid
<220> FEATURE:
<221> NAME/KEY: MOD_RES
<222> LOCATION: (371)..(371)
<223> OTHER INFORMATION: Any amino acid
<220> FEATURE:
<221> NAME/KEY: MOD_RES
<222> LOCATION: (376)..(376)
<223> OTHER INFORMATION: Any amino acid
<220> FEATURE:
<221> NAME/KEY: MOD_RES
<222> LOCATION: (381)..(381)
<223> OTHER INFORMATION: Any amino acid
<220> FEATURE:
<221> NAME/KEY: MOD_RES
<222> LOCATION: (386)..(386)
<223> OTHER INFORMATION: Any amino acid
<220> FEATURE:
<221> NAME/KEY: MOD_RES
<222> LOCATION: (391)..(391)
<223> OTHER INFORMATION: Any amino acid
<220> FEATURE:
<221> NAME/KEY: MOD_RES
<222> LOCATION: (396)..(396)
<223> OTHER INFORMATION: Any amino acid
<220> FEATURE:
<221> NAME/KEY: MOD_RES
<222> LOCATION: (401)..(401)
<223> OTHER INFORMATION: Any amino acid
<220> FEATURE:
<221> NAME/KEY: MOD_RES
<222> LOCATION: (406)..(406)
<223> OTHER INFORMATION: Any amino acid
<220> FEATURE:
<221> NAME/KEY: MOD_RES
<222> LOCATION: (411)..(411)
<223> OTHER INFORMATION: Any amino acid
<220> FEATURE:
<221> NAME/KEY: MOD_RES
<222> LOCATION: (416)..(416)
<223> OTHER INFORMATION: Any amino acid
<220> FEATURE:
<221> NAME/KEY: MOD_RES
<222> LOCATION: (421)..(421)
<223> OTHER INFORMATION: Any amino acid
<220> FEATURE:
<221> NAME/KEY: MOD_RES
<222> LOCATION: (426)..(426)
<223> OTHER INFORMATION: Any amino acid
<220> FEATURE:
```

```
<221> NAME/KEY: MOD_RES
<222> LOCATION: (431)..(431)
<223> OTHER INFORMATION: Any amino acid
<220> FEATURE:
<221> NAME/KEY: MOD_RES
<222> LOCATION: (436)..(436)
<223> OTHER INFORMATION: Any amino acid
<220> FEATURE:
<221> NAME/KEY: MOD_RES
<222> LOCATION: (441)..(441)
<223> OTHER INFORMATION: Any amino acid
<220> FEATURE:
<221> NAME/KEY: MOD_RES
<222> LOCATION: (446)..(446)
<223> OTHER INFORMATION: Any amino acid
<220> FEATURE:
<221> NAME/KEY: MOD_RES
<222> LOCATION: (451)..(451)
<223> OTHER INFORMATION: Any amino acid
<220> FEATURE:
<221> NAME/KEY: MOD_RES
<222> LOCATION: (456)..(456)
<223> OTHER INFORMATION: Any amino acid
<220> FEATURE:
<221> NAME/KEY: MOD_RES
<222> LOCATION: (461)..(461)
<223> OTHER INFORMATION: Any amino acid
<220> FEATURE:
<221> NAME/KEY: MOD_RES
<222> LOCATION: (466)..(466)
<223> OTHER INFORMATION: Any amino acid
<220> FEATURE:
<221> NAME/KEY: MOD_RES
<222> LOCATION: (471)..(471)
<223> OTHER INFORMATION: Any amino acid
<220> FEATURE:
<221> NAME/KEY: MOD_RES
<222> LOCATION: (476)..(476)
<223> OTHER INFORMATION: Any amino acid
<220> FEATURE:
<221> NAME/KEY: MOD_RES
<222> LOCATION: (481)..(481)
<223> OTHER INFORMATION: Any amino acid
<220> FEATURE:
<221> NAME/KEY: MOD_RES
<222> LOCATION: (486)..(486)
<223> OTHER INFORMATION: Any amino acid
<220> FEATURE:
<221> NAME/KEY: MOD_RES
<222> LOCATION: (491)..(491)
<223> OTHER INFORMATION: Any amino acid
<220> FEATURE:
<221> NAME/KEY: MOD_RES
<222> LOCATION: (496)..(496)
<223> OTHER INFORMATION: Any amino acid
<220> FEATURE:
<221> NAME/KEY: MOD_RES
<222> LOCATION: (501)..(501)
<223> OTHER INFORMATION: Any amino acid
<220> FEATURE:
<221> NAME/KEY: MOD_RES
<222> LOCATION: (506)..(506)
<223> OTHER INFORMATION: Any amino acid
<220> FEATURE:
<221> NAME/KEY: MOD_RES
<222> LOCATION: (511)..(511)
<223> OTHER INFORMATION: Any amino acid
<220> FEATURE:
<221> NAME/KEY: MOD_RES
<222> LOCATION: (516)..(516)
<223> OTHER INFORMATION: Any amino acid
<220> FEATURE:
<221> NAME/KEY: MOD_RES
<222> LOCATION: (521)..(521)
<223> OTHER INFORMATION: Any amino acid
<220> FEATURE:
<221> NAME/KEY: MOD_RES
<222> LOCATION: (526)..(526)
<223> OTHER INFORMATION: Any amino acid
```

```
<220> FEATURE:
<221> NAME/KEY: MOD_RES
<222> LOCATION: (531)..(531)
<223> OTHER INFORMATION: Any amino acid
<220> FEATURE:
<221> NAME/KEY: MOD_RES
<222> LOCATION: (536)..(536)
<223> OTHER INFORMATION: Any amino acid
<220> FEATURE:
<221> NAME/KEY: MOD_RES
<222> LOCATION: (541)..(541)
<223> OTHER INFORMATION: Any amino acid
<220> FEATURE:
<221> NAME/KEY: MOD_RES
<222> LOCATION: (546)..(546)
<223> OTHER INFORMATION: Any amino acid
<220> FEATURE:
<221> NAME/KEY: MOD_RES
<222> LOCATION: (551)..(551)
<223> OTHER INFORMATION: Any amino acid
<220> FEATURE:
<221> NAME/KEY: MOD_RES
<222> LOCATION: (556)..(556)
<223> OTHER INFORMATION: Any amino acid
<220> FEATURE:
<221> NAME/KEY: MOD_RES
<222> LOCATION: (561)..(561)
<223> OTHER INFORMATION: Any amino acid
<220> FEATURE:
<221> NAME/KEY: MOD_RES
<222> LOCATION: (566)..(566)
<223> OTHER INFORMATION: Any amino acid
<220> FEATURE:
<221> NAME/KEY: MOD_RES
<222> LOCATION: (571)..(571)
<223> OTHER INFORMATION: Any amino acid
<220> FEATURE:
<221> NAME/KEY: MOD_RES
<222> LOCATION: (576)..(576)
<223> OTHER INFORMATION: Any amino acid
<220> FEATURE:
<221> NAME/KEY: MOD_RES
<222> LOCATION: (581)..(581)
<223> OTHER INFORMATION: Any amino acid
<220> FEATURE:
<221> NAME/KEY: MOD_RES
<222> LOCATION: (586)..(586)
<223> OTHER INFORMATION: Any amino acid
<220> FEATURE:
<221> NAME/KEY: MOD_RES
<222> LOCATION: (591)..(591)
<223> OTHER INFORMATION: Any amino acid
<220> FEATURE:
<221> NAME/KEY: MOD_RES
<222> LOCATION: (596)..(596)
<223> OTHER INFORMATION: Any amino acid

<400> SEQUENCE: 50

Xaa Pro Ala Val Gly Xaa Pro Ala Val Gly Xaa Pro Ala Val Gly Xaa
1               5                   10                  15

Pro Ala Val Gly Xaa Pro Ala Val Gly Xaa Pro Ala Val Gly Xaa Pro
            20                  25                  30

Ala Val Gly Xaa Pro Ala Val Gly Xaa Pro Ala Val Gly Xaa Pro Ala
        35                  40                  45

Val Gly Xaa Pro Ala Val Gly Xaa Pro Ala Val Gly Xaa Pro Ala Val
    50                  55                  60

Gly Xaa Pro Ala Val Gly Xaa Pro Ala Val Gly Xaa Pro Ala Val Gly
65                  70                  75                  80

Xaa Pro Ala Val Gly Xaa Pro Ala Val Gly Xaa Pro Ala Val Gly Xaa
                85                  90                  95

Pro Ala Val Gly Xaa Pro Ala Val Gly Xaa Pro Ala Val Gly Xaa Pro
            100                 105                 110
```

```
Ala Val Gly Xaa Pro Ala Val Gly Xaa Pro Ala Val Gly Xaa Pro Ala
        115                 120                 125
Val Gly Xaa Pro Ala Val Gly Xaa Pro Ala Val Gly Xaa Pro Ala Val
        130                 135                 140
Gly Xaa Pro Ala Val Gly Xaa Pro Ala Val Gly Xaa Pro Ala Val Gly
145                 150                 155                 160
Xaa Pro Ala Val Gly Xaa Pro Ala Val Gly Xaa Pro Ala Val Gly Xaa
                165                 170                 175
Pro Ala Val Gly Xaa Pro Ala Val Gly Xaa Pro Ala Val Gly Xaa Pro
            180                 185                 190
Ala Val Gly Xaa Pro Ala Val Gly Xaa Pro Ala Val Gly Xaa Pro Ala
        195                 200                 205
Val Gly Xaa Pro Ala Val Gly Xaa Pro Ala Val Gly Xaa Pro Ala Val
        210                 215                 220
Gly Xaa Pro Ala Val Gly Xaa Pro Ala Val Gly Xaa Pro Ala Val Gly
225                 230                 235                 240
Xaa Pro Ala Val Gly Xaa Pro Ala Val Gly Xaa Pro Ala Val Gly Xaa
                245                 250                 255
Pro Ala Val Gly Xaa Pro Ala Val Gly Xaa Pro Ala Val Gly Xaa Pro
            260                 265                 270
Ala Val Gly Xaa Pro Ala Val Gly Xaa Pro Ala Val Gly Xaa Pro Ala
        275                 280                 285
Val Gly Xaa Pro Ala Val Gly Xaa Pro Ala Val Gly Xaa Pro Ala Val
        290                 295                 300
Gly Xaa Pro Ala Val Gly Xaa Pro Ala Val Gly Xaa Pro Ala Val Gly
305                 310                 315                 320
Xaa Pro Ala Val Gly Xaa Pro Ala Val Gly Xaa Pro Ala Val Gly Xaa
                325                 330                 335
Pro Ala Val Gly Xaa Pro Ala Val Gly Xaa Pro Ala Val Gly Xaa Pro
            340                 345                 350
Ala Val Gly Xaa Pro Ala Val Gly Xaa Pro Ala Val Gly Xaa Pro Ala
        355                 360                 365
Val Gly Xaa Pro Ala Val Gly Xaa Pro Ala Val Gly Xaa Pro Ala Val
        370                 375                 380
Gly Xaa Pro Ala Val Gly Xaa Pro Ala Val Gly Xaa Pro Ala Val Gly
385                 390                 395                 400
Xaa Pro Ala Val Gly Xaa Pro Ala Val Gly Xaa Pro Ala Val Gly Xaa
                405                 410                 415
Pro Ala Val Gly Xaa Pro Ala Val Gly Xaa Pro Ala Val Gly Xaa Pro
            420                 425                 430
Ala Val Gly Xaa Pro Ala Val Gly Xaa Pro Ala Val Gly Xaa Pro Ala
        435                 440                 445
Val Gly Xaa Pro Ala Val Gly Xaa Pro Ala Val Gly Xaa Pro Ala Val
        450                 455                 460
Gly Xaa Pro Ala Val Gly Xaa Pro Ala Val Gly Xaa Pro Ala Val Gly
465                 470                 475                 480
Xaa Pro Ala Val Gly Xaa Pro Ala Val Gly Xaa Pro Ala Val Gly Xaa
                485                 490                 495
Pro Ala Val Gly Xaa Pro Ala Val Gly Xaa Pro Ala Val Gly Xaa Pro
            500                 505                 510
Ala Val Gly Xaa Pro Ala Val Gly Xaa Pro Ala Val Gly Xaa Pro Ala
        515                 520                 525
```

```
Val Gly Xaa Pro Ala Val Gly Xaa Pro Ala Val Gly Xaa Pro Ala Val
        530                 535                 540

Gly Xaa Pro Ala Val Gly Xaa Pro Ala Val Gly Xaa Pro Ala Val Gly
545                 550                 555                 560

Xaa Pro Ala Val Gly Xaa Pro Ala Val Gly Xaa Pro Ala Val Gly Xaa
                565                 570                 575

Pro Ala Val Gly Xaa Pro Ala Val Gly Xaa Pro Ala Val Gly Xaa Pro
            580                 585                 590

Ala Val Gly Xaa Pro Ala Val Gly
            595                 600

<210> SEQ ID NO 51
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (41)..(41)
<223> OTHER INFORMATION: Any amino acid
<220> FEATURE:
<221> NAME/KEY: MOD_RES
<222> LOCATION: (46)..(46)
<223> OTHER INFORMATION: Any amino acid
<220> FEATURE:
<221> NAME/KEY: MOD_RES
<222> LOCATION: (51)..(51)
<223> OTHER INFORMATION: Any amino acid
<220> FEATURE:
<221> NAME/KEY: MOD_RES
<222> LOCATION: (56)..(56)
<223> OTHER INFORMATION: Any amino acid
<220> FEATURE:
<221> NAME/KEY: MOD_RES
<222> LOCATION: (61)..(61)
<223> OTHER INFORMATION: Any amino acid
<220> FEATURE:
<221> NAME/KEY: MOD_RES
<222> LOCATION: (66)..(66)
<223> OTHER INFORMATION: Any amino acid
```

-continued

```
<220> FEATURE:
<221> NAME/KEY: MOD_RES
<222> LOCATION: (71)..(71)
<223> OTHER INFORMATION: Any amino acid
<220> FEATURE:
<221> NAME/KEY: MOD_RES
<222> LOCATION: (76)..(76)
<223> OTHER INFORMATION: Any amino acid
<220> FEATURE:
<221> NAME/KEY: MOD_RES
<222> LOCATION: (81)..(81)
<223> OTHER INFORMATION: Any amino acid
<220> FEATURE:
<221> NAME/KEY: MOD_RES
<222> LOCATION: (86)..(86)
<223> OTHER INFORMATION: Any amino acid
<220> FEATURE:
<221> NAME/KEY: MOD_RES
<222> LOCATION: (91)..(91)
<223> OTHER INFORMATION: Any amino acid
<220> FEATURE:
<221> NAME/KEY: MOD_RES
<222> LOCATION: (96)..(96)
<223> OTHER INFORMATION: Any amino acid
<220> FEATURE:
<221> NAME/KEY: MOD_RES
<222> LOCATION: (101)..(101)
<223> OTHER INFORMATION: Any amino acid
<220> FEATURE:
<221> NAME/KEY: MOD_RES
<222> LOCATION: (106)..(106)
<223> OTHER INFORMATION: Any amino acid
<220> FEATURE:
<221> NAME/KEY: MOD_RES
<222> LOCATION: (111)..(111)
<223> OTHER INFORMATION: Any amino acid
<220> FEATURE:
<221> NAME/KEY: MOD_RES
<222> LOCATION: (116)..(116)
<223> OTHER INFORMATION: Any amino acid
<220> FEATURE:
<221> NAME/KEY: MOD_RES
<222> LOCATION: (121)..(121)
<223> OTHER INFORMATION: Any amino acid
<220> FEATURE:
<221> NAME/KEY: MOD_RES
<222> LOCATION: (126)..(126)
<223> OTHER INFORMATION: Any amino acid
<220> FEATURE:
<221> NAME/KEY: MOD_RES
<222> LOCATION: (131)..(131)
<223> OTHER INFORMATION: Any amino acid
<220> FEATURE:
<221> NAME/KEY: MOD_RES
<222> LOCATION: (136)..(136)
<223> OTHER INFORMATION: Any amino acid
<220> FEATURE:
<221> NAME/KEY: MOD_RES
<222> LOCATION: (141)..(141)
<223> OTHER INFORMATION: Any amino acid
<220> FEATURE:
<221> NAME/KEY: MOD_RES
<222> LOCATION: (146)..(146)
<223> OTHER INFORMATION: Any amino acid
<220> FEATURE:
<221> NAME/KEY: MOD_RES
<222> LOCATION: (151)..(151)
<223> OTHER INFORMATION: Any amino acid
<220> FEATURE:
<221> NAME/KEY: MOD_RES
<222> LOCATION: (156)..(156)
<223> OTHER INFORMATION: Any amino acid
<220> FEATURE:
<221> NAME/KEY: MOD_RES
<222> LOCATION: (161)..(161)
<223> OTHER INFORMATION: Any amino acid
<220> FEATURE:
<221> NAME/KEY: MOD_RES
<222> LOCATION: (166)..(166)
```

```
<223> OTHER INFORMATION: Any amino acid
<220> FEATURE:
<221> NAME/KEY: MOD_RES
<222> LOCATION: (171)..(171)
<223> OTHER INFORMATION: Any amino acid
<220> FEATURE:
<221> NAME/KEY: MOD_RES
<222> LOCATION: (176)..(176)
<223> OTHER INFORMATION: Any amino acid
<220> FEATURE:
<221> NAME/KEY: MOD_RES
<222> LOCATION: (181)..(181)
<223> OTHER INFORMATION: Any amino acid
<220> FEATURE:
<221> NAME/KEY: MOD_RES
<222> LOCATION: (186)..(186)
<223> OTHER INFORMATION: Any amino acid
<220> FEATURE:
<221> NAME/KEY: MOD_RES
<222> LOCATION: (191)..(191)
<223> OTHER INFORMATION: Any amino acid
<220> FEATURE:
<221> NAME/KEY: MOD_RES
<222> LOCATION: (196)..(196)
<223> OTHER INFORMATION: Any amino acid
<220> FEATURE:
<221> NAME/KEY: MOD_RES
<222> LOCATION: (201)..(201)
<223> OTHER INFORMATION: Any amino acid
<220> FEATURE:
<221> NAME/KEY: MOD_RES
<222> LOCATION: (206)..(206)
<223> OTHER INFORMATION: Any amino acid
<220> FEATURE:
<221> NAME/KEY: MOD_RES
<222> LOCATION: (211)..(211)
<223> OTHER INFORMATION: Any amino acid
<220> FEATURE:
<221> NAME/KEY: MOD_RES
<222> LOCATION: (216)..(216)
<223> OTHER INFORMATION: Any amino acid
<220> FEATURE:
<221> NAME/KEY: MOD_RES
<222> LOCATION: (221)..(221)
<223> OTHER INFORMATION: Any amino acid
<220> FEATURE:
<221> NAME/KEY: MOD_RES
<222> LOCATION: (226)..(226)
<223> OTHER INFORMATION: Any amino acid
<220> FEATURE:
<221> NAME/KEY: MOD_RES
<222> LOCATION: (231)..(231)
<223> OTHER INFORMATION: Any amino acid
<220> FEATURE:
<221> NAME/KEY: MOD_RES
<222> LOCATION: (236)..(236)
<223> OTHER INFORMATION: Any amino acid
<220> FEATURE:
<221> NAME/KEY: MOD_RES
<222> LOCATION: (241)..(241)
<223> OTHER INFORMATION: Any amino acid
<220> FEATURE:
<221> NAME/KEY: MOD_RES
<222> LOCATION: (246)..(246)
<223> OTHER INFORMATION: Any amino acid

<400> SEQUENCE: 51

Xaa Pro Ala Val Gly Xaa Pro Ala Val Gly Xaa Pro Ala Val Gly Xaa
1               5                   10                  15

Pro Ala Val Gly Xaa Pro Ala Val Gly Xaa Pro Ala Val Gly Xaa Pro
            20                  25                  30

Ala Val Gly Xaa Pro Ala Val Gly Xaa Pro Ala Val Gly Xaa Pro Ala
        35                  40                  45

Val Gly Xaa Pro Ala Val Gly Xaa Pro Ala Val Gly Xaa Pro Ala Val
    50                  55                  60
```

-continued

```
Gly Xaa Pro Ala Val Gly Xaa Pro Ala Val Gly Xaa Pro Ala Val Gly
 65                  70                  75                  80

Xaa Pro Ala Val Gly Xaa Pro Ala Val Gly Xaa Pro Ala Val Gly Xaa
                 85                  90                  95

Pro Ala Val Gly Xaa Pro Ala Val Gly Xaa Pro Ala Val Gly Xaa Pro
            100                 105                 110

Ala Val Gly Xaa Pro Ala Val Gly Xaa Pro Ala Val Gly Xaa Pro Ala
        115                 120                 125

Val Gly Xaa Pro Ala Val Gly Xaa Pro Ala Val Gly Xaa Pro Ala Val
    130                 135                 140

Gly Xaa Pro Ala Val Gly Xaa Pro Ala Val Gly Xaa Pro Ala Val Gly
145                 150                 155                 160

Xaa Pro Ala Val Gly Xaa Pro Ala Val Gly Xaa Pro Ala Val Gly Xaa
                165                 170                 175

Pro Ala Val Gly Xaa Pro Ala Val Gly Xaa Pro Ala Val Gly Xaa Pro
            180                 185                 190

Ala Val Gly Xaa Pro Ala Val Gly Xaa Pro Ala Val Gly Xaa Pro Ala
        195                 200                 205

Val Gly Xaa Pro Ala Val Gly Xaa Pro Ala Val Gly Xaa Pro Ala Val
    210                 215                 220

Gly Xaa Pro Ala Val Gly Xaa Pro Ala Val Gly Xaa Pro Ala Val Gly
225                 230                 235                 240

Xaa Pro Ala Val Gly Xaa Pro Ala Val Gly
                245                 250

<210> SEQ ID NO 52
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
```

```
<222> LOCATION: (41)..(41)
<223> OTHER INFORMATION: Any amino acid
<220> FEATURE:
<221> NAME/KEY: MOD_RES
<222> LOCATION: (46)..(46)
<223> OTHER INFORMATION: Any amino acid
<220> FEATURE:
<221> NAME/KEY: MOD_RES
<222> LOCATION: (51)..(51)
<223> OTHER INFORMATION: Any amino acid
<220> FEATURE:
<221> NAME/KEY: MOD_RES
<222> LOCATION: (56)..(56)
<223> OTHER INFORMATION: Any amino acid
<220> FEATURE:
<221> NAME/KEY: MOD_RES
<222> LOCATION: (61)..(61)
<223> OTHER INFORMATION: Any amino acid
<220> FEATURE:
<221> NAME/KEY: MOD_RES
<222> LOCATION: (66)..(66)
<223> OTHER INFORMATION: Any amino acid
<220> FEATURE:
<221> NAME/KEY: MOD_RES
<222> LOCATION: (71)..(71)
<223> OTHER INFORMATION: Any amino acid
<220> FEATURE:
<221> NAME/KEY: MOD_RES
<222> LOCATION: (76)..(76)
<223> OTHER INFORMATION: Any amino acid
<220> FEATURE:
<221> NAME/KEY: MOD_RES
<222> LOCATION: (81)..(81)
<223> OTHER INFORMATION: Any amino acid
<220> FEATURE:
<221> NAME/KEY: MOD_RES
<222> LOCATION: (86)..(86)
<223> OTHER INFORMATION: Any amino acid
<220> FEATURE:
<221> NAME/KEY: MOD_RES
<222> LOCATION: (91)..(91)
<223> OTHER INFORMATION: Any amino acid
<220> FEATURE:
<221> NAME/KEY: MOD_RES
<222> LOCATION: (96)..(96)
<223> OTHER INFORMATION: Any amino acid
<220> FEATURE:
<221> NAME/KEY: MOD_RES
<222> LOCATION: (101)..(101)
<223> OTHER INFORMATION: Any amino acid
<220> FEATURE:
<221> NAME/KEY: MOD_RES
<222> LOCATION: (106)..(106)
<223> OTHER INFORMATION: Any amino acid
<220> FEATURE:
<221> NAME/KEY: MOD_RES
<222> LOCATION: (111)..(111)
<223> OTHER INFORMATION: Any amino acid
<220> FEATURE:
<221> NAME/KEY: MOD_RES
<222> LOCATION: (116)..(116)
<223> OTHER INFORMATION: Any amino acid
<220> FEATURE:
<221> NAME/KEY: MOD_RES
<222> LOCATION: (121)..(121)
<223> OTHER INFORMATION: Any amino acid
<220> FEATURE:
<221> NAME/KEY: MOD_RES
<222> LOCATION: (126)..(126)
<223> OTHER INFORMATION: Any amino acid
<220> FEATURE:
<221> NAME/KEY: MOD_RES
<222> LOCATION: (131)..(131)
<223> OTHER INFORMATION: Any amino acid
<220> FEATURE:
<221> NAME/KEY: MOD_RES
<222> LOCATION: (136)..(136)
<223> OTHER INFORMATION: Any amino acid
<220> FEATURE:
```

```
<221> NAME/KEY: MOD_RES
<222> LOCATION: (141)..(141)
<223> OTHER INFORMATION: Any amino acid
<220> FEATURE:
<221> NAME/KEY: MOD_RES
<222> LOCATION: (146)..(146)
<223> OTHER INFORMATION: Any amino acid
<220> FEATURE:
<221> NAME/KEY: MOD_RES
<222> LOCATION: (151)..(151)
<223> OTHER INFORMATION: Any amino acid
<220> FEATURE:
<221> NAME/KEY: MOD_RES
<222> LOCATION: (156)..(156)
<223> OTHER INFORMATION: Any amino acid
<220> FEATURE:
<221> NAME/KEY: MOD_RES
<222> LOCATION: (161)..(161)
<223> OTHER INFORMATION: Any amino acid
<220> FEATURE:
<221> NAME/KEY: MOD_RES
<222> LOCATION: (166)..(166)
<223> OTHER INFORMATION: Any amino acid
<220> FEATURE:
<221> NAME/KEY: MOD_RES
<222> LOCATION: (171)..(171)
<223> OTHER INFORMATION: Any amino acid
<220> FEATURE:
<221> NAME/KEY: MOD_RES
<222> LOCATION: (176)..(176)
<223> OTHER INFORMATION: Any amino acid
<220> FEATURE:
<221> NAME/KEY: MOD_RES
<222> LOCATION: (181)..(181)
<223> OTHER INFORMATION: Any amino acid
<220> FEATURE:
<221> NAME/KEY: MOD_RES
<222> LOCATION: (186)..(186)
<223> OTHER INFORMATION: Any amino acid
<220> FEATURE:
<221> NAME/KEY: MOD_RES
<222> LOCATION: (191)..(191)
<223> OTHER INFORMATION: Any amino acid
<220> FEATURE:
<221> NAME/KEY: MOD_RES
<222> LOCATION: (196)..(196)
<223> OTHER INFORMATION: Any amino acid
<220> FEATURE:
<221> NAME/KEY: MOD_RES
<222> LOCATION: (201)..(201)
<223> OTHER INFORMATION: Any amino acid
<220> FEATURE:
<221> NAME/KEY: MOD_RES
<222> LOCATION: (206)..(206)
<223> OTHER INFORMATION: Any amino acid
<220> FEATURE:
<221> NAME/KEY: MOD_RES
<222> LOCATION: (211)..(211)
<223> OTHER INFORMATION: Any amino acid
<220> FEATURE:
<221> NAME/KEY: MOD_RES
<222> LOCATION: (216)..(216)
<223> OTHER INFORMATION: Any amino acid
<220> FEATURE:
<221> NAME/KEY: MOD_RES
<222> LOCATION: (221)..(221)
<223> OTHER INFORMATION: Any amino acid
<220> FEATURE:
<221> NAME/KEY: MOD_RES
<222> LOCATION: (226)..(226)
<223> OTHER INFORMATION: Any amino acid
<220> FEATURE:
<221> NAME/KEY: MOD_RES
<222> LOCATION: (231)..(231)
<223> OTHER INFORMATION: Any amino acid
<220> FEATURE:
<221> NAME/KEY: MOD_RES
<222> LOCATION: (236)..(236)
<223> OTHER INFORMATION: Any amino acid
```

<220> FEATURE:
<221> NAME/KEY: MOD_RES
<222> LOCATION: (241)..(241)
<223> OTHER INFORMATION: Any amino acid
<220> FEATURE:
<221> NAME/KEY: MOD_RES
<222> LOCATION: (246)..(246)
<223> OTHER INFORMATION: Any amino acid

<400> SEQUENCE: 52

```
Xaa Pro Gly Val Gly Xaa Pro Gly Val Gly Xaa Pro Gly Val Gly Xaa
1               5                   10                  15

Pro Gly Val Gly Xaa Pro Gly Val Gly Xaa Pro Gly Val Gly Xaa Pro
            20                  25                  30

Gly Val Gly Xaa Pro Gly Val Gly Xaa Pro Gly Val Gly Xaa Pro Gly
        35                  40                  45

Val Gly Xaa Pro Gly Val Gly Xaa Pro Gly Val Gly Xaa Pro Gly Val
    50                  55                  60

Gly Xaa Pro Gly Val Gly Xaa Pro Gly Val Gly Xaa Pro Gly Val Gly
65                  70                  75                  80

Xaa Pro Gly Val Gly Xaa Pro Gly Val Gly Xaa Pro Gly Val Gly Xaa
                85                  90                  95

Pro Gly Val Gly Xaa Pro Gly Val Gly Xaa Pro Gly Val Gly Xaa Pro
            100                 105                 110

Gly Val Gly Xaa Pro Gly Val Gly Xaa Pro Gly Val Gly Xaa Pro Gly
        115                 120                 125

Val Gly Xaa Pro Gly Val Gly Xaa Pro Gly Val Gly Xaa Pro Gly Val
    130                 135                 140

Gly Xaa Pro Gly Val Gly Xaa Pro Gly Val Gly Xaa Pro Gly Val Gly
145                 150                 155                 160

Xaa Pro Gly Val Gly Xaa Pro Gly Val Gly Xaa Pro Gly Val Gly Xaa
                165                 170                 175

Pro Gly Val Gly Xaa Pro Gly Val Gly Xaa Pro Gly Val Gly Xaa Pro
            180                 185                 190

Gly Val Gly Xaa Pro Gly Val Gly Xaa Pro Gly Val Gly Xaa Pro Gly
        195                 200                 205

Val Gly Xaa Pro Gly Val Gly Xaa Pro Gly Val Gly Xaa Pro Gly Val
    210                 215                 220

Gly Xaa Pro Gly Val Gly Xaa Pro Gly Val Gly Xaa Pro Gly Val Gly
225                 230                 235                 240

Xaa Pro Gly Val Gly Xaa Pro Gly Val Gly
                245                 250
```

<210> SEQ ID NO 53
<211> LENGTH: 250
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (11)..(11)
<223> OTHER INFORMATION: Any amino acid -continued

```
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (41)..(41)
<223> OTHER INFORMATION: Any amino acid
<220> FEATURE:
<221> NAME/KEY: MOD_RES
<222> LOCATION: (46)..(46)
<223> OTHER INFORMATION: Any amino acid
<220> FEATURE:
<221> NAME/KEY: MOD_RES
<222> LOCATION: (51)..(51)
<223> OTHER INFORMATION: Any amino acid
<220> FEATURE:
<221> NAME/KEY: MOD_RES
<222> LOCATION: (56)..(56)
<223> OTHER INFORMATION: Any amino acid
<220> FEATURE:
<221> NAME/KEY: MOD_RES
<222> LOCATION: (61)..(61)
<223> OTHER INFORMATION: Any amino acid
<220> FEATURE:
<221> NAME/KEY: MOD_RES
<222> LOCATION: (66)..(66)
<223> OTHER INFORMATION: Any amino acid
<220> FEATURE:
<221> NAME/KEY: MOD_RES
<222> LOCATION: (71)..(71)
<223> OTHER INFORMATION: Any amino acid
<220> FEATURE:
<221> NAME/KEY: MOD_RES
<222> LOCATION: (76)..(76)
<223> OTHER INFORMATION: Any amino acid
<220> FEATURE:
<221> NAME/KEY: MOD_RES
<222> LOCATION: (81)..(81)
<223> OTHER INFORMATION: Any amino acid
<220> FEATURE:
<221> NAME/KEY: MOD_RES
<222> LOCATION: (86)..(86)
<223> OTHER INFORMATION: Any amino acid
<220> FEATURE:
<221> NAME/KEY: MOD_RES
<222> LOCATION: (91)..(91)
<223> OTHER INFORMATION: Any amino acid
<220> FEATURE:
<221> NAME/KEY: MOD_RES
<222> LOCATION: (96)..(96)
<223> OTHER INFORMATION: Any amino acid
<220> FEATURE:
<221> NAME/KEY: MOD_RES
<222> LOCATION: (101)..(101)
<223> OTHER INFORMATION: Any amino acid
<220> FEATURE:
<221> NAME/KEY: MOD_RES
<222> LOCATION: (106)..(106)
<223> OTHER INFORMATION: Any amino acid
<220> FEATURE:
<221> NAME/KEY: MOD_RES
<222> LOCATION: (111)..(111)
```

```
<223> OTHER INFORMATION: Any amino acid
<220> FEATURE:
<221> NAME/KEY: MOD_RES
<222> LOCATION: (116)..(116)
<223> OTHER INFORMATION: Any amino acid
<220> FEATURE:
<221> NAME/KEY: MOD_RES
<222> LOCATION: (121)..(121)
<223> OTHER INFORMATION: Any amino acid
<220> FEATURE:
<221> NAME/KEY: MOD_RES
<222> LOCATION: (126)..(126)
<223> OTHER INFORMATION: Any amino acid
<220> FEATURE:
<221> NAME/KEY: MOD_RES
<222> LOCATION: (131)..(131)
<223> OTHER INFORMATION: Any amino acid
<220> FEATURE:
<221> NAME/KEY: MOD_RES
<222> LOCATION: (136)..(136)
<223> OTHER INFORMATION: Any amino acid
<220> FEATURE:
<221> NAME/KEY: MOD_RES
<222> LOCATION: (141)..(141)
<223> OTHER INFORMATION: Any amino acid
<220> FEATURE:
<221> NAME/KEY: MOD_RES
<222> LOCATION: (146)..(146)
<223> OTHER INFORMATION: Any amino acid
<220> FEATURE:
<221> NAME/KEY: MOD_RES
<222> LOCATION: (151)..(151)
<223> OTHER INFORMATION: Any amino acid
<220> FEATURE:
<221> NAME/KEY: MOD_RES
<222> LOCATION: (156)..(156)
<223> OTHER INFORMATION: Any amino acid
<220> FEATURE:
<221> NAME/KEY: MOD_RES
<222> LOCATION: (161)..(161)
<223> OTHER INFORMATION: Any amino acid
<220> FEATURE:
<221> NAME/KEY: MOD_RES
<222> LOCATION: (166)..(166)
<223> OTHER INFORMATION: Any amino acid
<220> FEATURE:
<221> NAME/KEY: MOD_RES
<222> LOCATION: (171)..(171)
<223> OTHER INFORMATION: Any amino acid
<220> FEATURE:
<221> NAME/KEY: MOD_RES
<222> LOCATION: (176)..(176)
<223> OTHER INFORMATION: Any amino acid
<220> FEATURE:
<221> NAME/KEY: MOD_RES
<222> LOCATION: (181)..(181)
<223> OTHER INFORMATION: Any amino acid
<220> FEATURE:
<221> NAME/KEY: MOD_RES
<222> LOCATION: (186)..(186)
<223> OTHER INFORMATION: Any amino acid
<220> FEATURE:
<221> NAME/KEY: MOD_RES
<222> LOCATION: (191)..(191)
<223> OTHER INFORMATION: Any amino acid
<220> FEATURE:
<221> NAME/KEY: MOD_RES
<222> LOCATION: (196)..(196)
<223> OTHER INFORMATION: Any amino acid
<220> FEATURE:
<221> NAME/KEY: MOD_RES
<222> LOCATION: (201)..(201)
<223> OTHER INFORMATION: Any amino acid
<220> FEATURE:
<221> NAME/KEY: MOD_RES
<222> LOCATION: (206)..(206)
<223> OTHER INFORMATION: Any amino acid
<220> FEATURE:
<221> NAME/KEY: MOD_RES
```

```
<222> LOCATION: (211)..(211)
<223> OTHER INFORMATION: Any amino acid
<220> FEATURE:
<221> NAME/KEY: MOD_RES
<222> LOCATION: (216)..(216)
<223> OTHER INFORMATION: Any amino acid
<220> FEATURE:
<221> NAME/KEY: MOD_RES
<222> LOCATION: (221)..(221)
<223> OTHER INFORMATION: Any amino acid
<220> FEATURE:
<221> NAME/KEY: MOD_RES
<222> LOCATION: (226)..(226)
<223> OTHER INFORMATION: Any amino acid
<220> FEATURE:
<221> NAME/KEY: MOD_RES
<222> LOCATION: (231)..(231)
<223> OTHER INFORMATION: Any amino acid
<220> FEATURE:
<221> NAME/KEY: MOD_RES
<222> LOCATION: (236)..(236)
<223> OTHER INFORMATION: Any amino acid
<220> FEATURE:
<221> NAME/KEY: MOD_RES
<222> LOCATION: (241)..(241)
<223> OTHER INFORMATION: Any amino acid
<220> FEATURE:
<221> NAME/KEY: MOD_RES
<222> LOCATION: (246)..(246)
<223> OTHER INFORMATION: Any amino acid

<400> SEQUENCE: 53

Xaa Pro Ala Val Gly Xaa Pro Ala Val Gly Xaa Pro Ala Val Gly Xaa
1               5                   10                  15

Pro Ala Val Gly Xaa Pro Ala Val Gly Xaa Pro Ala Val Gly Xaa Pro
            20                  25                  30

Ala Val Gly Xaa Pro Ala Val Gly Xaa Pro Ala Val Gly Xaa Pro Ala
        35                  40                  45

Val Gly Xaa Pro Ala Val Gly Xaa Pro Ala Val Gly Xaa Pro Ala Val
    50                  55                  60

Gly Xaa Pro Ala Val Gly Xaa Pro Ala Val Gly Xaa Pro Ala Val Gly
65                  70                  75                  80

Xaa Pro Ala Val Gly Xaa Pro Ala Val Gly Xaa Pro Ala Val Gly Xaa
                85                  90                  95

Pro Ala Val Gly Xaa Pro Ala Val Gly Xaa Pro Ala Val Gly Xaa Pro
            100                 105                 110

Ala Val Gly Xaa Pro Ala Val Gly Xaa Pro Ala Val Gly Xaa Pro Ala
        115                 120                 125

Val Gly Xaa Pro Ala Val Gly Xaa Pro Ala Val Gly Xaa Pro Ala Val
    130                 135                 140

Gly Xaa Pro Ala Val Gly Xaa Pro Ala Val Gly Xaa Pro Ala Val Gly
145                 150                 155                 160

Xaa Pro Ala Val Gly Xaa Pro Ala Val Gly Xaa Pro Ala Val Gly Xaa
                165                 170                 175

Pro Ala Val Gly Xaa Pro Ala Val Gly Xaa Pro Ala Val Gly Xaa Pro
            180                 185                 190

Ala Val Gly Xaa Pro Ala Val Gly Xaa Pro Ala Val Gly Xaa Pro Ala
        195                 200                 205

Val Gly Xaa Pro Ala Val Gly Xaa Pro Ala Val Gly Xaa Pro Ala Val
    210                 215                 220

Gly Xaa Pro Ala Val Gly Xaa Pro Ala Val Gly Xaa Pro Ala Val Gly
225                 230                 235                 240

Xaa Pro Ala Val Gly Xaa Pro Ala Val Gly
```

<210> SEQ ID NO 54
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (41)..(41)
<223> OTHER INFORMATION: Any amino acid
<220> FEATURE:
<221> NAME/KEY: MOD_RES
<222> LOCATION: (46)..(46)
<223> OTHER INFORMATION: Any amino acid
<220> FEATURE:
<221> NAME/KEY: MOD_RES
<222> LOCATION: (51)..(51)
<223> OTHER INFORMATION: Any amino acid
<220> FEATURE:
<221> NAME/KEY: MOD_RES
<222> LOCATION: (56)..(56)
<223> OTHER INFORMATION: Any amino acid
<220> FEATURE:
<221> NAME/KEY: MOD_RES
<222> LOCATION: (61)..(61)
<223> OTHER INFORMATION: Any amino acid
<220> FEATURE:
<221> NAME/KEY: MOD_RES
<222> LOCATION: (66)..(66)
<223> OTHER INFORMATION: Any amino acid
<220> FEATURE:
<221> NAME/KEY: MOD_RES
<222> LOCATION: (71)..(71)
<223> OTHER INFORMATION: Any amino acid
<220> FEATURE:
<221> NAME/KEY: MOD_RES
<222> LOCATION: (76)..(76)
<223> OTHER INFORMATION: Any amino acid
<220> FEATURE:
<221> NAME/KEY: MOD_RES
<222> LOCATION: (81)..(81)
<223> OTHER INFORMATION: Any amino acid
<220> FEATURE:

```
<221> NAME/KEY: MOD_RES
<222> LOCATION: (86)..(86)
<223> OTHER INFORMATION: Any amino acid
<220> FEATURE:
<221> NAME/KEY: MOD_RES
<222> LOCATION: (91)..(91)
<223> OTHER INFORMATION: Any amino acid
<220> FEATURE:
<221> NAME/KEY: MOD_RES
<222> LOCATION: (96)..(96)
<223> OTHER INFORMATION: Any amino acid
<220> FEATURE:
<221> NAME/KEY: MOD_RES
<222> LOCATION: (101)..(101)
<223> OTHER INFORMATION: Any amino acid
<220> FEATURE:
<221> NAME/KEY: MOD_RES
<222> LOCATION: (106)..(106)
<223> OTHER INFORMATION: Any amino acid
<220> FEATURE:
<221> NAME/KEY: MOD_RES
<222> LOCATION: (111)..(111)
<223> OTHER INFORMATION: Any amino acid
<220> FEATURE:
<221> NAME/KEY: MOD_RES
<222> LOCATION: (116)..(116)
<223> OTHER INFORMATION: Any amino acid
<220> FEATURE:
<221> NAME/KEY: MOD_RES
<222> LOCATION: (121)..(121)
<223> OTHER INFORMATION: Any amino acid
<220> FEATURE:
<221> NAME/KEY: MOD_RES
<222> LOCATION: (126)..(126)
<223> OTHER INFORMATION: Any amino acid
<220> FEATURE:
<221> NAME/KEY: MOD_RES
<222> LOCATION: (131)..(131)
<223> OTHER INFORMATION: Any amino acid
<220> FEATURE:
<221> NAME/KEY: MOD_RES
<222> LOCATION: (136)..(136)
<223> OTHER INFORMATION: Any amino acid
<220> FEATURE:
<221> NAME/KEY: MOD_RES
<222> LOCATION: (141)..(141)
<223> OTHER INFORMATION: Any amino acid
<220> FEATURE:
<221> NAME/KEY: MOD_RES
<222> LOCATION: (146)..(146)
<223> OTHER INFORMATION: Any amino acid
<220> FEATURE:
<221> NAME/KEY: MOD_RES
<222> LOCATION: (151)..(151)
<223> OTHER INFORMATION: Any amino acid
<220> FEATURE:
<221> NAME/KEY: MOD_RES
<222> LOCATION: (156)..(156)
<223> OTHER INFORMATION: Any amino acid
<220> FEATURE:
<221> NAME/KEY: MOD_RES
<222> LOCATION: (161)..(161)
<223> OTHER INFORMATION: Any amino acid
<220> FEATURE:
<221> NAME/KEY: MOD_RES
<222> LOCATION: (166)..(166)
<223> OTHER INFORMATION: Any amino acid
<220> FEATURE:
<221> NAME/KEY: MOD_RES
<222> LOCATION: (171)..(171)
<223> OTHER INFORMATION: Any amino acid
<220> FEATURE:
<221> NAME/KEY: MOD_RES
<222> LOCATION: (176)..(176)
<223> OTHER INFORMATION: Any amino acid
<220> FEATURE:
<221> NAME/KEY: MOD_RES
<222> LOCATION: (181)..(181)
<223> OTHER INFORMATION: Any amino acid
```

```
<220> FEATURE:
<221> NAME/KEY: MOD_RES
<222> LOCATION: (186)..(186)
<223> OTHER INFORMATION: Any amino acid
<220> FEATURE:
<221> NAME/KEY: MOD_RES
<222> LOCATION: (191)..(191)
<223> OTHER INFORMATION: Any amino acid
<220> FEATURE:
<221> NAME/KEY: MOD_RES
<222> LOCATION: (196)..(196)
<223> OTHER INFORMATION: Any amino acid
<220> FEATURE:
<221> NAME/KEY: MOD_RES
<222> LOCATION: (201)..(201)
<223> OTHER INFORMATION: Any amino acid
<220> FEATURE:
<221> NAME/KEY: MOD_RES
<222> LOCATION: (206)..(206)
<223> OTHER INFORMATION: Any amino acid
<220> FEATURE:
<221> NAME/KEY: MOD_RES
<222> LOCATION: (211)..(211)
<223> OTHER INFORMATION: Any amino acid
<220> FEATURE:
<221> NAME/KEY: MOD_RES
<222> LOCATION: (216)..(216)
<223> OTHER INFORMATION: Any amino acid
<220> FEATURE:
<221> NAME/KEY: MOD_RES
<222> LOCATION: (221)..(221)
<223> OTHER INFORMATION: Any amino acid
<220> FEATURE:
<221> NAME/KEY: MOD_RES
<222> LOCATION: (226)..(226)
<223> OTHER INFORMATION: Any amino acid
<220> FEATURE:
<221> NAME/KEY: MOD_RES
<222> LOCATION: (231)..(231)
<223> OTHER INFORMATION: Any amino acid
<220> FEATURE:
<221> NAME/KEY: MOD_RES
<222> LOCATION: (236)..(236)
<223> OTHER INFORMATION: Any amino acid
<220> FEATURE:
<221> NAME/KEY: MOD_RES
<222> LOCATION: (241)..(241)
<223> OTHER INFORMATION: Any amino acid
<220> FEATURE:
<221> NAME/KEY: MOD_RES
<222> LOCATION: (246)..(246)
<223> OTHER INFORMATION: Any amino acid
<220> FEATURE:
<221> NAME/KEY: MOD_RES
<222> LOCATION: (251)..(251)
<223> OTHER INFORMATION: Any amino acid
<220> FEATURE:
<221> NAME/KEY: MOD_RES
<222> LOCATION: (256)..(256)
<223> OTHER INFORMATION: Any amino acid
<220> FEATURE:
<221> NAME/KEY: MOD_RES
<222> LOCATION: (261)..(261)
<223> OTHER INFORMATION: Any amino acid
<220> FEATURE:
<221> NAME/KEY: MOD_RES
<222> LOCATION: (266)..(266)
<223> OTHER INFORMATION: Any amino acid
<220> FEATURE:
<221> NAME/KEY: MOD_RES
<222> LOCATION: (271)..(271)
<223> OTHER INFORMATION: Any amino acid
<220> FEATURE:
<221> NAME/KEY: MOD_RES
<222> LOCATION: (276)..(276)
<223> OTHER INFORMATION: Any amino acid
<220> FEATURE:
<221> NAME/KEY: MOD_RES
<222> LOCATION: (281)..(281)
```

```
<223> OTHER INFORMATION: Any amino acid
<220> FEATURE:
<221> NAME/KEY: MOD_RES
<222> LOCATION: (286)..(286)
<223> OTHER INFORMATION: Any amino acid
<220> FEATURE:
<221> NAME/KEY: MOD_RES
<222> LOCATION: (291)..(291)
<223> OTHER INFORMATION: Any amino acid
<220> FEATURE:
<221> NAME/KEY: MOD_RES
<222> LOCATION: (296)..(296)
<223> OTHER INFORMATION: Any amino acid
<220> FEATURE:
<221> NAME/KEY: MOD_RES
<222> LOCATION: (301)..(301)
<223> OTHER INFORMATION: Any amino acid
<220> FEATURE:
<221> NAME/KEY: MOD_RES
<222> LOCATION: (306)..(306)
<223> OTHER INFORMATION: Any amino acid
<220> FEATURE:
<221> NAME/KEY: MOD_RES
<222> LOCATION: (311)..(311)
<223> OTHER INFORMATION: Any amino acid
<220> FEATURE:
<221> NAME/KEY: MOD_RES
<222> LOCATION: (316)..(316)
<223> OTHER INFORMATION: Any amino acid
<220> FEATURE:
<221> NAME/KEY: MOD_RES
<222> LOCATION: (321)..(321)
<223> OTHER INFORMATION: Any amino acid
<220> FEATURE:
<221> NAME/KEY: MOD_RES
<222> LOCATION: (326)..(326)
<223> OTHER INFORMATION: Any amino acid
<220> FEATURE:
<221> NAME/KEY: MOD_RES
<222> LOCATION: (331)..(331)
<223> OTHER INFORMATION: Any amino acid
<220> FEATURE:
<221> NAME/KEY: MOD_RES
<222> LOCATION: (336)..(336)
<223> OTHER INFORMATION: Any amino acid
<220> FEATURE:
<221> NAME/KEY: MOD_RES
<222> LOCATION: (341)..(341)
<223> OTHER INFORMATION: Any amino acid
<220> FEATURE:
<221> NAME/KEY: MOD_RES
<222> LOCATION: (346)..(346)
<223> OTHER INFORMATION: Any amino acid

<400> SEQUENCE: 54

Xaa Pro Ala Val Gly Xaa Pro Ala Val Gly Xaa Pro Ala Val Gly Xaa
1               5                   10                  15

Pro Ala Val Gly Xaa Pro Ala Val Gly Xaa Pro Ala Val Gly Xaa Pro
            20                  25                  30

Ala Val Gly Xaa Pro Ala Val Gly Xaa Pro Ala Val Gly Xaa Pro Ala
        35                  40                  45

Val Gly Xaa Pro Ala Val Gly Xaa Pro Ala Val Gly Xaa Pro Ala Val
    50                  55                  60

Gly Xaa Pro Ala Val Gly Xaa Pro Ala Val Gly Xaa Pro Ala Val Gly
65                  70                  75                  80

Xaa Pro Ala Val Gly Xaa Pro Ala Val Gly Xaa Pro Ala Val Gly Xaa
                85                  90                  95

Pro Ala Val Gly Xaa Pro Ala Val Gly Xaa Pro Ala Val Gly Xaa Pro
            100                 105                 110

Ala Val Gly Xaa Pro Ala Val Gly Xaa Pro Ala Val Gly Xaa Pro Ala
        115                 120                 125
```

```
Val Gly Xaa Pro Ala Val Gly Xaa Pro Ala Val Gly Xaa Pro Ala Val
        130                 135                 140

Gly Xaa Pro Ala Val Gly Xaa Pro Ala Val Gly Xaa Pro Ala Val Gly
145                 150                 155                 160

Xaa Pro Ala Val Gly Xaa Pro Ala Val Gly Xaa Pro Ala Val Gly Xaa
                165                 170                 175

Pro Ala Val Gly Xaa Pro Ala Val Gly Xaa Pro Ala Val Gly Xaa Pro
            180                 185                 190

Ala Val Gly Xaa Pro Ala Val Gly Xaa Pro Ala Val Gly Xaa Pro Ala
        195                 200                 205

Val Gly Xaa Pro Ala Val Gly Xaa Pro Ala Val Gly Xaa Pro Ala Val
        210                 215                 220

Gly Xaa Pro Ala Val Gly Xaa Pro Ala Val Gly Xaa Pro Ala Val Gly
225                 230                 235                 240

Xaa Pro Ala Val Gly Xaa Pro Ala Val Gly Xaa Pro Ala Val Gly Xaa
                245                 250                 255

Pro Ala Val Gly Xaa Pro Ala Val Gly Xaa Pro Ala Val Gly Xaa Pro
            260                 265                 270

Ala Val Gly Xaa Pro Ala Val Gly Xaa Pro Ala Val Gly Xaa Pro Ala
        275                 280                 285

Val Gly Xaa Pro Ala Val Gly Xaa Pro Ala Val Gly Xaa Pro Ala Val
        290                 295                 300

Gly Xaa Pro Ala Val Gly Xaa Pro Ala Val Gly Xaa Pro Ala Val Gly
305                 310                 315                 320

Xaa Pro Ala Val Gly Xaa Pro Ala Val Gly Xaa Pro Ala Val Gly Xaa
                325                 330                 335

Pro Ala Val Gly Xaa Pro Ala Val Gly Xaa Pro Ala Val Gly
            340                 345                 350

<210> SEQ ID NO 55
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Ile Pro Ala Val Gly Val Pro Ala Val Gly Ile Pro Ala Val Gly Val
1               5                   10                  15

Pro Ala Val Gly Ile Pro Ala Val Gly Ile Pro Ala Val Gly Val Pro
            20                  25                  30

Ala Val Gly Ile Pro Ala Val Gly Val Pro Ala Val Gly Ile Pro Ala
        35                  40                  45

Val Gly Ile Pro Ala Val Gly Val Pro Ala Val Gly Ile Pro Ala Val
    50                  55                  60

Gly Val Pro Ala Val Gly Ile Pro Ala Val Gly Ile Pro Ala Val Gly
65                  70                  75                  80

Val Pro Ala Val Gly Ile Pro Ala Val Gly Val Pro Ala Val Gly Ile
                85                  90                  95

Pro Ala Val Gly Ile Pro Ala Val Gly Val Pro Ala Val Gly Ile Pro
            100                 105                 110

Ala Val Gly Val Pro Ala Val Gly Ile Pro Ala Val Gly Ile Pro Ala
        115                 120                 125

Val Gly Val Pro Ala Val Gly Ile Pro Ala Val Gly Val Pro Ala Val
```

```
                   130                 135                 140

Gly Ile Pro Ala Val Gly Ile Pro Ala Val Gly Val Pro Ala Val Gly
145                 150                 155                 160

Ile Pro Ala Val Gly Val Pro Ala Val Gly Ile Pro Ala Val Gly Ile
                165                 170                 175

Pro Ala Val Gly Val Pro Ala Val Gly Ile Pro Ala Val Gly Val Pro
            180                 185                 190

Ala Val Gly Ile Pro Ala Val Gly Ile Pro Ala Val Gly Val Pro Ala
        195                 200                 205

Val Gly Ile Pro Ala Val Gly Val Pro Ala Val Gly Ile Pro Ala Val
    210                 215                 220

Gly Ile Pro Ala Val Gly Val Pro Ala Val Gly Ile Pro Ala Val Gly
225                 230                 235                 240

Val Pro Ala Val Gly Ile Pro Ala Val Gly Cys Arg Gly Asp
                245                 250

<210> SEQ ID NO 56
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (29)..(29)
<223> OTHER INFORMATION: Ile or Val

<400> SEQUENCE: 56

Met Gly Trp Gly Ser Lys Cys Thr Ser Ala Gly Ala Gly Ala Gly Pro
1               5                   10                  15

Glu Gly Arg Gly Asp Ser Thr Ser Gly Leu Val Gly Xaa Pro Ala Val
            20                  25                  30

Gly Glu Thr Thr Ser Arg Gly Asp Ser Ala Gly Ala Gly Ala Gly Pro
        35                  40                  45

Glu Gly Thr Ser Cys Lys Leu
    50                  55

<210> SEQ ID NO 57
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ile or Val
<220> FEATURE:
<221> NAME/KEY: MOD_RES
<222> LOCATION: (6)..(6)
<223> OTHER INFORMATION: Ile or Val
<220> FEATURE:
<221> NAME/KEY: MOD_RES
<222> LOCATION: (11)..(11)
<223> OTHER INFORMATION: Ile or Val
<220> FEATURE:
<221> NAME/KEY: MOD_RES
<222> LOCATION: (16)..(16)
<223> OTHER INFORMATION: Ile or Val
<220> FEATURE:
<221> NAME/KEY: MOD_RES
<222> LOCATION: (21)..(21)
<223> OTHER INFORMATION: Ile or Val
<220> FEATURE:
```

```
<221> NAME/KEY: MOD_RES
<222> LOCATION: (26)..(26)
<223> OTHER INFORMATION: Ile or Val
<220> FEATURE:
<221> NAME/KEY: MOD_RES
<222> LOCATION: (31)..(31)
<223> OTHER INFORMATION: Ile or Val
<220> FEATURE:
<221> NAME/KEY: MOD_RES
<222> LOCATION: (36)..(36)
<223> OTHER INFORMATION: Ile or Val
<220> FEATURE:
<221> NAME/KEY: MOD_RES
<222> LOCATION: (41)..(41)
<223> OTHER INFORMATION: Ile or Val
<220> FEATURE:
<221> NAME/KEY: MOD_RES
<222> LOCATION: (46)..(46)
<223> OTHER INFORMATION: Ile or Val
<220> FEATURE:
<221> NAME/KEY: MOD_RES
<222> LOCATION: (51)..(51)
<223> OTHER INFORMATION: Ile or Val
<220> FEATURE:
<221> NAME/KEY: MOD_RES
<222> LOCATION: (56)..(56)
<223> OTHER INFORMATION: Ile or Val
<220> FEATURE:
<221> NAME/KEY: MOD_RES
<222> LOCATION: (61)..(61)
<223> OTHER INFORMATION: Ile or Val
<220> FEATURE:
<221> NAME/KEY: MOD_RES
<222> LOCATION: (66)..(66)
<223> OTHER INFORMATION: Ile or Val
<220> FEATURE:
<221> NAME/KEY: MOD_RES
<222> LOCATION: (71)..(71)
<223> OTHER INFORMATION: Ile or Val
<220> FEATURE:
<221> NAME/KEY: MOD_RES
<222> LOCATION: (76)..(76)
<223> OTHER INFORMATION: Ile or Val
<220> FEATURE:
<221> NAME/KEY: MOD_RES
<222> LOCATION: (81)..(81)
<223> OTHER INFORMATION: Ile or Val
<220> FEATURE:
<221> NAME/KEY: MOD_RES
<222> LOCATION: (86)..(86)
<223> OTHER INFORMATION: Ile or Val
<220> FEATURE:
<221> NAME/KEY: MOD_RES
<222> LOCATION: (91)..(91)
<223> OTHER INFORMATION: Ile or Val
<220> FEATURE:
<221> NAME/KEY: MOD_RES
<222> LOCATION: (96)..(96)
<223> OTHER INFORMATION: Ile or Val
<220> FEATURE:
<221> NAME/KEY: MOD_RES
<222> LOCATION: (101)..(101)
<223> OTHER INFORMATION: Ile or Val
<220> FEATURE:
<221> NAME/KEY: MOD_RES
<222> LOCATION: (106)..(106)
<223> OTHER INFORMATION: Ile or Val
<220> FEATURE:
<221> NAME/KEY: MOD_RES
<222> LOCATION: (111)..(111)
<223> OTHER INFORMATION: Ile or Val
<220> FEATURE:
<221> NAME/KEY: MOD_RES
<222> LOCATION: (116)..(116)
<223> OTHER INFORMATION: Ile or Val
<220> FEATURE:
<221> NAME/KEY: MOD_RES
<222> LOCATION: (121)..(121)
<223> OTHER INFORMATION: Ile or Val
```

```
<220> FEATURE:
<221> NAME/KEY: MOD_RES
<222> LOCATION: (126)..(126)
<223> OTHER INFORMATION: Ile or Val
<220> FEATURE:
<221> NAME/KEY: MOD_RES
<222> LOCATION: (131)..(131)
<223> OTHER INFORMATION: Ile or Val
<220> FEATURE:
<221> NAME/KEY: MOD_RES
<222> LOCATION: (136)..(136)
<223> OTHER INFORMATION: Ile or Val
<220> FEATURE:
<221> NAME/KEY: MOD_RES
<222> LOCATION: (141)..(141)
<223> OTHER INFORMATION: Ile or Val
<220> FEATURE:
<221> NAME/KEY: MOD_RES
<222> LOCATION: (146)..(146)
<223> OTHER INFORMATION: Ile or Val
<220> FEATURE:
<221> NAME/KEY: MOD_RES
<222> LOCATION: (151)..(151)
<223> OTHER INFORMATION: Ile or Val
<220> FEATURE:
<221> NAME/KEY: MOD_RES
<222> LOCATION: (156)..(156)
<223> OTHER INFORMATION: Ile or Val
<220> FEATURE:
<221> NAME/KEY: MOD_RES
<222> LOCATION: (161)..(161)
<223> OTHER INFORMATION: Ile or Val
<220> FEATURE:
<221> NAME/KEY: MOD_RES
<222> LOCATION: (166)..(166)
<223> OTHER INFORMATION: Ile or Val
<220> FEATURE:
<221> NAME/KEY: MOD_RES
<222> LOCATION: (171)..(171)
<223> OTHER INFORMATION: Ile or Val
<220> FEATURE:
<221> NAME/KEY: MOD_RES
<222> LOCATION: (176)..(176)
<223> OTHER INFORMATION: Ile or Val
<220> FEATURE:
<221> NAME/KEY: MOD_RES
<222> LOCATION: (181)..(181)
<223> OTHER INFORMATION: Ile or Val
<220> FEATURE:
<221> NAME/KEY: MOD_RES
<222> LOCATION: (186)..(186)
<223> OTHER INFORMATION: Ile or Val
<220> FEATURE:
<221> NAME/KEY: MOD_RES
<222> LOCATION: (191)..(191)
<223> OTHER INFORMATION: Ile or Val
<220> FEATURE:
<221> NAME/KEY: MOD_RES
<222> LOCATION: (196)..(196)
<223> OTHER INFORMATION: Ile or Val
<220> FEATURE:
<221> NAME/KEY: MOD_RES
<222> LOCATION: (201)..(201)
<223> OTHER INFORMATION: Ile or Val
<220> FEATURE:
<221> NAME/KEY: MOD_RES
<222> LOCATION: (206)..(206)
<223> OTHER INFORMATION: Ile or Val
<220> FEATURE:
<221> NAME/KEY: MOD_RES
<222> LOCATION: (211)..(211)
<223> OTHER INFORMATION: Ile or Val
<220> FEATURE:
<221> NAME/KEY: MOD_RES
<222> LOCATION: (216)..(216)
<223> OTHER INFORMATION: Ile or Val
<220> FEATURE:
<221> NAME/KEY: MOD_RES
<222> LOCATION: (221)..(221)
```

<223> OTHER INFORMATION: Ile or Val
<220> FEATURE:
<221> NAME/KEY: MOD_RES
<222> LOCATION: (226)..(226)
<223> OTHER INFORMATION: Ile or Val
<220> FEATURE:
<221> NAME/KEY: MOD_RES
<222> LOCATION: (231)..(231)
<223> OTHER INFORMATION: Ile or Val
<220> FEATURE:
<221> NAME/KEY: MOD_RES
<222> LOCATION: (236)..(236)
<223> OTHER INFORMATION: Ile or Val
<220> FEATURE:
<221> NAME/KEY: MOD_RES
<222> LOCATION: (241)..(241)
<223> OTHER INFORMATION: Ile or Val
<220> FEATURE:
<221> NAME/KEY: MOD_RES
<222> LOCATION: (246)..(246)
<223> OTHER INFORMATION: Ile or Val

<400> SEQUENCE: 57

Xaa Pro Ala Val Gly Xaa Pro Ala Val Gly Xaa Pro Ala Val Gly Xaa
1               5                   10                  15

Pro Ala Val Gly Xaa Pro Ala Val Gly Xaa Pro Ala Val Gly Xaa Pro
            20                  25                  30

Ala Val Gly Xaa Pro Ala Val Gly Xaa Pro Ala Val Gly Xaa Pro Ala
        35                  40                  45

Val Gly Xaa Pro Ala Val Gly Xaa Pro Ala Val Gly Xaa Pro Ala Val
    50                  55                  60

Gly Xaa Pro Ala Val Gly Xaa Pro Ala Val Gly Xaa Pro Ala Val Gly
65                  70                  75                  80

Xaa Pro Ala Val Gly Xaa Pro Ala Val Gly Xaa Pro Ala Val Gly Xaa
                85                  90                  95

Pro Ala Val Gly Xaa Pro Ala Val Gly Xaa Pro Ala Val Gly Xaa Pro
            100                 105                 110

Ala Val Gly Xaa Pro Ala Val Gly Xaa Pro Ala Val Gly Xaa Pro Ala
        115                 120                 125

Val Gly Xaa Pro Ala Val Gly Xaa Pro Ala Val Gly Xaa Pro Ala Val
    130                 135                 140

Gly Xaa Pro Ala Val Gly Xaa Pro Ala Val Gly Xaa Pro Ala Val Gly
145                 150                 155                 160

Xaa Pro Ala Val Gly Xaa Pro Ala Val Gly Xaa Pro Ala Val Gly Xaa
                165                 170                 175

Pro Ala Val Gly Xaa Pro Ala Val Gly Xaa Pro Ala Val Gly Xaa Pro
            180                 185                 190

Ala Val Gly Xaa Pro Ala Val Gly Xaa Pro Ala Val Gly Xaa Pro Ala
        195                 200                 205

Val Gly Xaa Pro Ala Val Gly Xaa Pro Ala Val Gly Xaa Pro Ala Val
    210                 215                 220

Gly Xaa Pro Ala Val Gly Xaa Pro Ala Val Gly Xaa Pro Ala Val Gly
225                 230                 235                 240

Xaa Pro Ala Val Gly Xaa Pro Ala Val Gly
                245                 250

<210> SEQ ID NO 58
<211> LENGTH: 300
<212> TYPE: PRT
<213> ORGANISM: Artificial Sequence
<220> FEATURE:
<223> OTHER INFORMATION: Description of Artificial Sequence: Synthetic

```
        polypeptide
<220> FEATURE:
<221> NAME/KEY: MOD_RES
<222> LOCATION: (29)..(29)
<223> OTHER INFORMATION: Ile or Val
<220> FEATURE:
<221> NAME/KEY: MOD_RES
<222> LOCATION: (34)..(34)
<223> OTHER INFORMATION: Ile or Val
<220> FEATURE:
<221> NAME/KEY: MOD_RES
<222> LOCATION: (39)..(39)
<223> OTHER INFORMATION: Ile or Val
<220> FEATURE:
<221> NAME/KEY: MOD_RES
<222> LOCATION: (44)..(44)
<223> OTHER INFORMATION: Ile or Val
<220> FEATURE:
<221> NAME/KEY: MOD_RES
<222> LOCATION: (49)..(49)
<223> OTHER INFORMATION: Ile or Val
<220> FEATURE:
<221> NAME/KEY: MOD_RES
<222> LOCATION: (54)..(54)
<223> OTHER INFORMATION: Ile or Val
<220> FEATURE:
<221> NAME/KEY: MOD_RES
<222> LOCATION: (59)..(59)
<223> OTHER INFORMATION: Ile or Val
<220> FEATURE:
<221> NAME/KEY: MOD_RES
<222> LOCATION: (64)..(64)
<223> OTHER INFORMATION: Ile or Val
<220> FEATURE:
<221> NAME/KEY: MOD_RES
<222> LOCATION: (69)..(69)
<223> OTHER INFORMATION: Ile or Val
<220> FEATURE:
<221> NAME/KEY: MOD_RES
<222> LOCATION: (74)..(74)
<223> OTHER INFORMATION: Ile or Val
<220> FEATURE:
<221> NAME/KEY: MOD_RES
<222> LOCATION: (79)..(79)
<223> OTHER INFORMATION: Ile or Val
<220> FEATURE:
<221> NAME/KEY: MOD_RES
<222> LOCATION: (84)..(84)
<223> OTHER INFORMATION: Ile or Val
<220> FEATURE:
<221> NAME/KEY: MOD_RES
<222> LOCATION: (89)..(89)
<223> OTHER INFORMATION: Ile or Val
<220> FEATURE:
<221> NAME/KEY: MOD_RES
<222> LOCATION: (94)..(94)
<223> OTHER INFORMATION: Ile or Val
<220> FEATURE:
<221> NAME/KEY: MOD_RES
<222> LOCATION: (99)..(99)
<223> OTHER INFORMATION: Ile or Val
<220> FEATURE:
<221> NAME/KEY: MOD_RES
<222> LOCATION: (104)..(104)
<223> OTHER INFORMATION: Ile or Val
<220> FEATURE:
<221> NAME/KEY: MOD_RES
<222> LOCATION: (109)..(109)
<223> OTHER INFORMATION: Ile or Val
<220> FEATURE:
<221> NAME/KEY: MOD_RES
<222> LOCATION: (114)..(114)
<223> OTHER INFORMATION: Ile or Val
<220> FEATURE:
<221> NAME/KEY: MOD_RES
<222> LOCATION: (119)..(119)
<223> OTHER INFORMATION: Ile or Val
<220> FEATURE:
<221> NAME/KEY: MOD_RES
```

```
<222> LOCATION: (124)..(124)
<223> OTHER INFORMATION: Ile or Val
<220> FEATURE:
<221> NAME/KEY: MOD_RES
<222> LOCATION: (129)..(129)
<223> OTHER INFORMATION: Ile or Val
<220> FEATURE:
<221> NAME/KEY: MOD_RES
<222> LOCATION: (134)..(134)
<223> OTHER INFORMATION: Ile or Val
<220> FEATURE:
<221> NAME/KEY: MOD_RES
<222> LOCATION: (139)..(139)
<223> OTHER INFORMATION: Ile or Val
<220> FEATURE:
<221> NAME/KEY: MOD_RES
<222> LOCATION: (144)..(144)
<223> OTHER INFORMATION: Ile or Val
<220> FEATURE:
<221> NAME/KEY: MOD_RES
<222> LOCATION: (149)..(149)
<223> OTHER INFORMATION: Ile or Val
<220> FEATURE:
<221> NAME/KEY: MOD_RES
<222> LOCATION: (154)..(154)
<223> OTHER INFORMATION: Ile or Val
<220> FEATURE:
<221> NAME/KEY: MOD_RES
<222> LOCATION: (159)..(159)
<223> OTHER INFORMATION: Ile or Val
<220> FEATURE:
<221> NAME/KEY: MOD_RES
<222> LOCATION: (164)..(164)
<223> OTHER INFORMATION: Ile or Val
<220> FEATURE:
<221> NAME/KEY: MOD_RES
<222> LOCATION: (169)..(169)
<223> OTHER INFORMATION: Ile or Val
<220> FEATURE:
<221> NAME/KEY: MOD_RES
<222> LOCATION: (174)..(174)
<223> OTHER INFORMATION: Ile or Val
<220> FEATURE:
<221> NAME/KEY: MOD_RES
<222> LOCATION: (179)..(179)
<223> OTHER INFORMATION: Ile or Val
<220> FEATURE:
<221> NAME/KEY: MOD_RES
<222> LOCATION: (184)..(184)
<223> OTHER INFORMATION: Ile or Val
<220> FEATURE:
<221> NAME/KEY: MOD_RES
<222> LOCATION: (189)..(189)
<223> OTHER INFORMATION: Ile or Val
<220> FEATURE:
<221> NAME/KEY: MOD_RES
<222> LOCATION: (194)..(194)
<223> OTHER INFORMATION: Ile or Val
<220> FEATURE:
<221> NAME/KEY: MOD_RES
<222> LOCATION: (199)..(199)
<223> OTHER INFORMATION: Ile or Val
<220> FEATURE:
<221> NAME/KEY: MOD_RES
<222> LOCATION: (204)..(204)
<223> OTHER INFORMATION: Ile or Val
<220> FEATURE:
<221> NAME/KEY: MOD_RES
<222> LOCATION: (209)..(209)
<223> OTHER INFORMATION: Ile or Val
<220> FEATURE:
<221> NAME/KEY: MOD_RES
<222> LOCATION: (214)..(214)
<223> OTHER INFORMATION: Ile or Val
<220> FEATURE:
<221> NAME/KEY: MOD_RES
<222> LOCATION: (219)..(219)
<223> OTHER INFORMATION: Ile or Val
<220> FEATURE:
```

```
<221> NAME/KEY: MOD_RES
<222> LOCATION: (224)..(224)
<223> OTHER INFORMATION: Ile or Val
<220> FEATURE:
<221> NAME/KEY: MOD_RES
<222> LOCATION: (229)..(229)
<223> OTHER INFORMATION: Ile or Val
<220> FEATURE:
<221> NAME/KEY: MOD_RES
<222> LOCATION: (234)..(234)
<223> OTHER INFORMATION: Ile or Val
<220> FEATURE:
<221> NAME/KEY: MOD_RES
<222> LOCATION: (239)..(239)
<223> OTHER INFORMATION: Ile or Val
<220> FEATURE:
<221> NAME/KEY: MOD_RES
<222> LOCATION: (244)..(244)
<223> OTHER INFORMATION: Ile or Val
<220> FEATURE:
<221> NAME/KEY: MOD_RES
<222> LOCATION: (249)..(249)
<223> OTHER INFORMATION: Ile or Val
<220> FEATURE:
<221> NAME/KEY: MOD_RES
<222> LOCATION: (254)..(254)
<223> OTHER INFORMATION: Ile or Val
<220> FEATURE:
<221> NAME/KEY: MOD_RES
<222> LOCATION: (259)..(259)
<223> OTHER INFORMATION: Ile or Val
<220> FEATURE:
<221> NAME/KEY: MOD_RES
<222> LOCATION: (264)..(264)
<223> OTHER INFORMATION: Ile or Val
<220> FEATURE:
<221> NAME/KEY: MOD_RES
<222> LOCATION: (269)..(269)
<223> OTHER INFORMATION: Ile or Val
<220> FEATURE:
<221> NAME/KEY: MOD_RES
<222> LOCATION: (274)..(274)
<223> OTHER INFORMATION: Ile or Val

<400> SEQUENCE: 58

Met Gly Trp Gly Ser Lys Cys Thr Ser Ala Gly Ala Gly Ala Gly Pro
1               5                   10                  15

Glu Gly Arg Gly Asp Ser Thr Ser Gly Leu Val Gly Xaa Pro Ala Val
            20                  25                  30

Gly Xaa Pro Ala Val Gly Xaa Pro Ala Val Gly Xaa Pro Ala Val Gly
        35                  40                  45

Xaa Pro Ala Val Gly Xaa Pro Ala Val Gly Xaa Pro Ala Val Gly Xaa
    50                  55                  60

Pro Ala Val Gly Xaa Pro Ala Val Gly Xaa Pro Ala Val Gly Xaa Pro
65                  70                  75                  80

Ala Val Gly Xaa Pro Ala Val Gly Xaa Pro Ala Val Gly Xaa Pro Ala
                85                  90                  95

Val Gly Xaa Pro Ala Val Gly Xaa Pro Ala Val Gly Xaa Pro Ala Val
            100                 105                 110

Gly Xaa Pro Ala Val Gly Xaa Pro Ala Val Gly Xaa Pro Ala Val Gly
        115                 120                 125

Xaa Pro Ala Val Gly Xaa Pro Ala Val Gly Xaa Pro Ala Val Gly Xaa
    130                 135                 140

Pro Ala Val Gly Xaa Pro Ala Val Gly Xaa Pro Ala Val Gly Xaa Pro
145                 150                 155                 160

Ala Val Gly Xaa Pro Ala Val Gly Xaa Pro Ala Val Gly Xaa Pro Ala
                165                 170                 175
```

Val Gly Xaa Pro Ala Val Gly Xaa Pro Ala Val Gly Xaa Pro Ala Val
            180                 185                 190

Gly Xaa Pro Ala Val Gly Xaa Pro Ala Val Gly Xaa Pro Ala Val Gly
        195                 200                 205

Xaa Pro Ala Val Gly Xaa Pro Ala Val Gly Xaa Pro Ala Val Gly Xaa
    210                 215                 220

Pro Ala Val Gly Xaa Pro Ala Val Gly Xaa Pro Ala Val Gly Xaa Pro
225                 230                 235                 240

Ala Val Gly Xaa Pro Ala Val Gly Xaa Pro Ala Val Gly Xaa Pro Ala
            245                 250                 255

Val Gly Xaa Pro Ala Val Gly Xaa Pro Ala Val Gly Xaa Pro Ala Val
            260                 265                 270

Gly Xaa Pro Ala Val Gly Glu Thr Thr Ser Arg Gly Asp Ser Ala Gly
        275                 280                 285

Ala Gly Ala Gly Pro Glu Gly Thr Ser Cys Lys Leu
            290                 295                 300

<210> SEQ ID NO 59
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (29)..(29)
<223> OTHER INFORMATION: Any amino acid
<220> FEATURE:
<221> NAME/KEY: MOD_RES
<222> LOCATION: (34)..(34)
<223> OTHER INFORMATION: Any amino acid
<220> FEATURE:
<221> NAME/KEY: MOD_RES
<222> LOCATION: (39)..(39)
<223> OTHER INFORMATION: Any amino acid
<220> FEATURE:
<221> NAME/KEY: MOD_RES
<222> LOCATION: (44)..(44)
<223> OTHER INFORMATION: Any amino acid
<220> FEATURE:
<221> NAME/KEY: MOD_RES
<222> LOCATION: (49)..(49)
<223> OTHER INFORMATION: Any amino acid
<220> FEATURE:
<221> NAME/KEY: MOD_RES
<222> LOCATION: (54)..(54)
<223> OTHER INFORMATION: Any amino acid
<220> FEATURE:
<221> NAME/KEY: MOD_RES
<222> LOCATION: (59)..(59)
<223> OTHER INFORMATION: Any amino acid
<220> FEATURE:
<221> NAME/KEY: MOD_RES
<222> LOCATION: (64)..(64)
<223> OTHER INFORMATION: Any amino acid
<220> FEATURE:
<221> NAME/KEY: MOD_RES
<222> LOCATION: (69)..(69)
<223> OTHER INFORMATION: Any amino acid
<220> FEATURE:
<221> NAME/KEY: MOD_RES
<222> LOCATION: (74)..(74)
<223> OTHER INFORMATION: Any amino acid
<220> FEATURE:
<221> NAME/KEY: MOD_RES
<222> LOCATION: (79)..(79)
<223> OTHER INFORMATION: Any amino acid
<220> FEATURE:
<221> NAME/KEY: MOD_RES
<222> LOCATION: (84)..(84)

```
<223> OTHER INFORMATION: Any amino acid
<220> FEATURE:
<221> NAME/KEY: MOD_RES
<222> LOCATION: (89)..(89)
<223> OTHER INFORMATION: Any amino acid
<220> FEATURE:
<221> NAME/KEY: MOD_RES
<222> LOCATION: (94)..(94)
<223> OTHER INFORMATION: Any amino acid
<220> FEATURE:
<221> NAME/KEY: MOD_RES
<222> LOCATION: (99)..(99)
<223> OTHER INFORMATION: Any amino acid
<220> FEATURE:
<221> NAME/KEY: MOD_RES
<222> LOCATION: (104)..(104)
<223> OTHER INFORMATION: Any amino acid
<220> FEATURE:
<221> NAME/KEY: MOD_RES
<222> LOCATION: (109)..(109)
<223> OTHER INFORMATION: Any amino acid
<220> FEATURE:
<221> NAME/KEY: MOD_RES
<222> LOCATION: (114)..(114)
<223> OTHER INFORMATION: Any amino acid
<220> FEATURE:
<221> NAME/KEY: MOD_RES
<222> LOCATION: (119)..(119)
<223> OTHER INFORMATION: Any amino acid
<220> FEATURE:
<221> NAME/KEY: MOD_RES
<222> LOCATION: (124)..(124)
<223> OTHER INFORMATION: Any amino acid
<220> FEATURE:
<221> NAME/KEY: MOD_RES
<222> LOCATION: (129)..(129)
<223> OTHER INFORMATION: Any amino acid
<220> FEATURE:
<221> NAME/KEY: MOD_RES
<222> LOCATION: (134)..(134)
<223> OTHER INFORMATION: Any amino acid
<220> FEATURE:
<221> NAME/KEY: MOD_RES
<222> LOCATION: (139)..(139)
<223> OTHER INFORMATION: Any amino acid
<220> FEATURE:
<221> NAME/KEY: MOD_RES
<222> LOCATION: (144)..(144)
<223> OTHER INFORMATION: Any amino acid
<220> FEATURE:
<221> NAME/KEY: MOD_RES
<222> LOCATION: (149)..(149)
<223> OTHER INFORMATION: Any amino acid
<220> FEATURE:
<221> NAME/KEY: MOD_RES
<222> LOCATION: (154)..(154)
<223> OTHER INFORMATION: Any amino acid
<220> FEATURE:
<221> NAME/KEY: MOD_RES
<222> LOCATION: (159)..(159)
<223> OTHER INFORMATION: Any amino acid
<220> FEATURE:
<221> NAME/KEY: MOD_RES
<222> LOCATION: (164)..(164)
<223> OTHER INFORMATION: Any amino acid
<220> FEATURE:
<221> NAME/KEY: MOD_RES
<222> LOCATION: (169)..(169)
<223> OTHER INFORMATION: Any amino acid
<220> FEATURE:
<221> NAME/KEY: MOD_RES
<222> LOCATION: (174)..(174)
<223> OTHER INFORMATION: Any amino acid
<220> FEATURE:
<221> NAME/KEY: MOD_RES
<222> LOCATION: (179)..(179)
<223> OTHER INFORMATION: Any amino acid
<220> FEATURE:
<221> NAME/KEY: MOD_RES
```

<222> LOCATION: (184)..(184)
<223> OTHER INFORMATION: Any amino acid
<220> FEATURE:
<221> NAME/KEY: MOD_RES
<222> LOCATION: (189)..(189)
<223> OTHER INFORMATION: Any amino acid
<220> FEATURE:
<221> NAME/KEY: MOD_RES
<222> LOCATION: (194)..(194)
<223> OTHER INFORMATION: Any amino acid
<220> FEATURE:
<221> NAME/KEY: MOD_RES
<222> LOCATION: (199)..(199)
<223> OTHER INFORMATION: Any amino acid
<220> FEATURE:
<221> NAME/KEY: MOD_RES
<222> LOCATION: (204)..(204)
<223> OTHER INFORMATION: Any amino acid
<220> FEATURE:
<221> NAME/KEY: MOD_RES
<222> LOCATION: (209)..(209)
<223> OTHER INFORMATION: Any amino acid
<220> FEATURE:
<221> NAME/KEY: MOD_RES
<222> LOCATION: (214)..(214)
<223> OTHER INFORMATION: Any amino acid
<220> FEATURE:
<221> NAME/KEY: MOD_RES
<222> LOCATION: (219)..(219)
<223> OTHER INFORMATION: Any amino acid
<220> FEATURE:
<221> NAME/KEY: MOD_RES
<222> LOCATION: (224)..(224)
<223> OTHER INFORMATION: Any amino acid
<220> FEATURE:
<221> NAME/KEY: MOD_RES
<222> LOCATION: (229)..(229)
<223> OTHER INFORMATION: Any amino acid
<220> FEATURE:
<221> NAME/KEY: MOD_RES
<222> LOCATION: (234)..(234)
<223> OTHER INFORMATION: Any amino acid
<220> FEATURE:
<221> NAME/KEY: MOD_RES
<222> LOCATION: (239)..(239)
<223> OTHER INFORMATION: Any amino acid
<220> FEATURE:
<221> NAME/KEY: MOD_RES
<222> LOCATION: (244)..(244)
<223> OTHER INFORMATION: Any amino acid
<220> FEATURE:
<221> NAME/KEY: MOD_RES
<222> LOCATION: (249)..(249)
<223> OTHER INFORMATION: Any amino acid
<220> FEATURE:
<221> NAME/KEY: MOD_RES
<222> LOCATION: (254)..(254)
<223> OTHER INFORMATION: Any amino acid
<220> FEATURE:
<221> NAME/KEY: MOD_RES
<222> LOCATION: (259)..(259)
<223> OTHER INFORMATION: Any amino acid
<220> FEATURE:
<221> NAME/KEY: MOD_RES
<222> LOCATION: (264)..(264)
<223> OTHER INFORMATION: Any amino acid
<220> FEATURE:
<221> NAME/KEY: MOD_RES
<222> LOCATION: (269)..(269)
<223> OTHER INFORMATION: Any amino acid
<220> FEATURE:
<221> NAME/KEY: MOD_RES
<222> LOCATION: (274)..(274)
<223> OTHER INFORMATION: Any amino acid

<400> SEQUENCE: 59

Met Gly Trp Gly Ser Lys Cys Thr Ser Ala Gly Ala Gly Ala Gly Pro
1               5                   10                  15

Glu Gly Arg Gly Asp Ser Thr Ser Gly Leu Val Gly Xaa Pro Ala Val
            20                  25                  30

Gly Xaa Pro Ala Val Gly Xaa Pro Ala Val Gly Xaa Pro Ala Val Gly
        35                  40                  45

Xaa Pro Ala Val Gly Xaa Pro Ala Val Gly Xaa Pro Ala Val Gly Xaa
 50                  55                  60

Pro Ala Val Gly Xaa Pro Ala Val Gly Xaa Pro Ala Val Gly Xaa Pro
 65                  70                  75                  80

Ala Val Gly Xaa Pro Ala Val Gly Xaa Pro Ala Val Gly Xaa Pro Ala
            85                  90                  95

Val Gly Xaa Pro Ala Val Gly Xaa Pro Ala Val Gly Xaa Pro Ala Val
        100                 105                 110

Gly Xaa Pro Ala Val Gly Xaa Pro Ala Val Gly Xaa Pro Ala Val Gly
    115                 120                 125

Xaa Pro Ala Val Gly Xaa Pro Ala Val Gly Xaa Pro Ala Val Gly Xaa
130                 135                 140

Pro Ala Val Gly Xaa Pro Ala Val Gly Xaa Pro Ala Val Gly Xaa Pro
145                 150                 155                 160

Ala Val Gly Xaa Pro Ala Val Gly Xaa Pro Ala Val Gly Xaa Pro Ala
            165                 170                 175

Val Gly Xaa Pro Ala Val Gly Xaa Pro Ala Val Gly Xaa Pro Ala Val
        180                 185                 190

Gly Xaa Pro Ala Val Gly Xaa Pro Ala Val Gly Xaa Pro Ala Val Gly
    195                 200                 205

Xaa Pro Ala Val Gly Xaa Pro Ala Val Gly Xaa Pro Ala Val Gly Xaa
210                 215                 220

Pro Ala Val Gly Xaa Pro Ala Val Gly Xaa Pro Ala Val Gly Xaa Pro
225                 230                 235                 240

Ala Val Gly Xaa Pro Ala Val Gly Xaa Pro Ala Val Gly Xaa Pro Ala
            245                 250                 255

Val Gly Xaa Pro Ala Val Gly Xaa Pro Ala Val Gly Xaa Pro Ala Val
        260                 265                 270

Gly Xaa Pro Ala Val Gly Glu Thr Thr Ser Arg Gly Asp Ser Ala Gly
    275                 280                 285

Ala Gly Ala Gly Pro Glu Gly Thr Ser Cys Lys Leu
    290                 295                 300

<210> SEQ ID NO 60
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Ile Pro Ala Val Gly Val Pro Ala Val Gly Ile Pro Ala Val Gly Val
 1               5                  10                  15

Pro Ala Val Gly Ile Pro Ala Val Gly Ile Pro Ala Val Gly Val Pro
            20                  25                  30

Ala Val Gly Ile Pro Ala Val Gly Val Pro Ala Val Gly Ile Pro Ala
        35                  40                  45

Val Gly Ile Pro Ala Val Gly Val Pro Ala Val Gly Ile Pro Ala Val
 50                  55                  60

Gly Val Pro Ala Val Gly Ile Pro Ala Val Gly Ile Pro Ala Val Gly

```
                65                  70                  75                  80
Val Pro Ala Val Gly Ile Pro Ala Val Gly Val Pro Ala Val Gly Ile
                    85                  90                  95

Pro Ala Val Gly Ile Pro Ala Val Gly Val Pro Ala Val Gly Ile Pro
                100                 105                 110

Ala Val Gly Val Pro Ala Val Gly Ile Pro Ala Val Gly Ile Pro Ala
            115                 120                 125

Val Gly Val Pro Ala Val Gly Ile Pro Ala Val Gly Val Pro Ala Val
        130                 135                 140

Gly Ile Pro Ala Val Gly Ile Pro Ala Val Gly Val Pro Ala Val Gly
145                 150                 155                 160

Ile Pro Ala Val Gly Val Pro Ala Val Gly Ile Pro Ala Val Gly Ile
                165                 170                 175

Pro Ala Val Gly Val Pro Ala Val Gly Ile Pro Ala Val Gly Val Pro
                180                 185                 190

Ala Val Gly Ile Pro Ala Val Gly Ile Pro Ala Val Gly Val Pro Ala
            195                 200                 205

Val Gly Ile Pro Ala Val Gly Val Pro Ala Val Gly Ile Pro Ala Val
        210                 215                 220

Gly Ile Pro Ala Val Gly Val Pro Ala Val Gly Ile Pro Ala Val Gly
225                 230                 235                 240

Val Pro Ala Val Gly Ile Pro Ala Val Gly
                245                 250

<210> SEQ ID NO 61
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Val Pro Ala Val Gly Val Pro Ala Val Gly Ile Pro Ala Val Gly Val
1               5                   10                  15

Pro Ala Val Gly Val Pro Ala Val Gly Val Pro Ala Val Gly Val Pro
            20                  25                  30

Ala Val Gly Ile Pro Ala Val Gly Val Pro Ala Val Gly Val Pro Ala
        35                  40                  45

Val Gly Val Pro Ala Val Gly Val Pro Ala Val Gly Ile Pro Ala Val
    50                  55                  60

Gly Val Pro Ala Val Gly Val Pro Ala Val Gly Val Pro Ala Val Gly
65                  70                  75                  80

Val Pro Ala Val Gly Ile Pro Ala Val Gly Val Pro Ala Val Gly Val
                85                  90                  95

Pro Ala Val Gly Val Pro Ala Val Gly Val Pro Ala Val Gly Ile Pro
                100                 105                 110

Ala Val Gly Val Pro Ala Val Gly Val Pro Ala Val Gly Val Pro Ala
            115                 120                 125

Val Gly Val Pro Ala Val Gly Ile Pro Ala Val Gly Val Pro Ala Val
        130                 135                 140

Gly Val Pro Ala Val Gly Val Pro Ala Val Gly Val Pro Ala Val Gly
145                 150                 155                 160

Ile Pro Ala Val Gly Val Pro Ala Val Gly Val Pro Ala Val Gly Val
                165                 170                 175
```

```
Pro Ala Val Gly Val Pro Ala Val Gly Ile Pro Ala Val Gly Val Pro
            180                 185                 190

Ala Val Gly Val Pro Ala Val Gly Val Pro Ala Val Gly Val Pro Ala
        195                 200                 205

Val Gly Ile Pro Ala Val Gly Val Pro Ala Val Gly Val Pro Ala Val
    210                 215                 220

Gly Val Pro Ala Val Gly Val Pro Ala Val Gly Ile Pro Ala Val Gly
225                 230                 235                 240

Val Pro Ala Val Gly Val Pro Ala Val Gly
            245                 250

<210> SEQ ID NO 62
<211> LENGTH: 308
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Gly Trp Gly Ser Lys Cys Thr Ser Ala Gly Ala Gly Ala Gly Pro
1               5                   10                  15

Glu Gly Arg Gly Asp Ser Thr Ser Gly Leu Val Gly Arg Gly Asp Ser
            20                  25                  30

Ile Pro Ala Val Gly Val Pro Ala Val Gly Ile Pro Ala Val Gly Val
        35                  40                  45

Pro Ala Val Gly Ile Pro Ala Val Gly Ile Pro Ala Val Gly Val Pro
    50                  55                  60

Ala Val Gly Ile Pro Ala Val Gly Val Pro Ala Val Gly Ile Pro Ala
65                  70                  75                  80

Val Gly Ile Pro Ala Val Gly Val Pro Ala Val Gly Ile Pro Ala Val
                85                  90                  95

Gly Val Pro Ala Val Gly Ile Pro Ala Val Gly Ile Pro Ala Val Gly
            100                 105                 110

Val Pro Ala Val Gly Ile Pro Ala Val Gly Val Pro Ala Val Gly Ile
        115                 120                 125

Pro Ala Val Gly Ile Pro Ala Val Gly Val Pro Ala Val Gly Ile Pro
    130                 135                 140

Ala Val Gly Val Pro Ala Val Gly Ile Pro Ala Val Gly Ile Pro Ala
145                 150                 155                 160

Val Gly Val Pro Ala Val Gly Ile Pro Ala Val Gly Val Pro Ala Val
                165                 170                 175

Gly Ile Pro Ala Val Gly Ile Pro Ala Val Gly Val Pro Ala Val Gly
            180                 185                 190

Ile Pro Ala Val Gly Val Pro Ala Val Gly Ile Pro Ala Val Gly Ile
        195                 200                 205

Pro Ala Val Gly Val Pro Ala Val Gly Ile Pro Ala Val Gly Val Pro
    210                 215                 220

Ala Val Gly Ile Pro Ala Val Gly Ile Pro Ala Val Gly Val Pro Ala
225                 230                 235                 240

Val Gly Ile Pro Ala Val Gly Val Pro Ala Val Gly Ile Pro Ala Val
                245                 250                 255

Gly Ile Pro Ala Val Gly Val Pro Ala Val Gly Ile Pro Ala Val Gly
            260                 265                 270

Val Pro Ala Val Gly Ile Pro Ala Val Gly Arg Gly Asp Ser Glu Thr
        275                 280                 285
```

Thr Ser Arg Gly Asp Ser Ala Gly Ala Gly Pro Glu Gly Thr
            290                 295                 300

Ser Cys Lys Leu
305

<210> SEQ ID NO 63
<211> LENGTH: 284
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Lys Cys Thr Ser Ala Gly Ala Gly Ala Gly Pro Glu Gly Arg Gly Asp
1               5                  10                  15

Ser Ile Pro Ala Val Gly Val Pro Ala Val Gly Ile Pro Ala Val Gly
            20                  25                  30

Val Pro Ala Val Gly Ile Pro Ala Val Gly Ile Pro Ala Val Gly Val
        35                  40                  45

Pro Ala Val Gly Ile Pro Ala Val Gly Val Pro Ala Val Gly Ile Pro
    50                  55                  60

Ala Val Gly Ile Pro Ala Val Gly Val Pro Ala Val Gly Ile Pro Ala
65                  70                  75                  80

Val Gly Val Pro Ala Val Gly Ile Pro Ala Val Gly Ile Pro Ala Val
                85                  90                  95

Gly Val Pro Ala Val Gly Ile Pro Ala Val Gly Val Pro Ala Val Gly
            100                 105                 110

Ile Pro Ala Val Gly Ile Pro Ala Val Gly Val Pro Ala Val Gly Ile
        115                 120                 125

Pro Ala Val Gly Val Pro Ala Val Gly Ile Pro Ala Val Gly Ile Pro
    130                 135                 140

Ala Val Gly Val Pro Ala Val Gly Ile Pro Ala Val Gly Val Pro Ala
145                 150                 155                 160

Val Gly Ile Pro Ala Val Gly Ile Pro Ala Val Gly Val Pro Ala Val
                165                 170                 175

Gly Ile Pro Ala Val Gly Val Pro Ala Val Gly Ile Pro Ala Val Gly
            180                 185                 190

Ile Pro Ala Val Gly Val Pro Ala Val Gly Ile Pro Ala Val Gly Val
        195                 200                 205

Pro Ala Val Gly Ile Pro Ala Val Gly Ile Pro Ala Val Gly Val Pro
    210                 215                 220

Ala Val Gly Ile Pro Ala Val Gly Val Pro Ala Val Gly Ile Pro Ala
225                 230                 235                 240

Val Gly Ile Pro Ala Val Gly Val Pro Ala Val Gly Ile Pro Ala Val
                245                 250                 255

Gly Val Pro Ala Val Gly Ile Pro Ala Val Gly Arg Gly Asp Ser Ala
            260                 265                 270

Gly Ala Gly Ala Gly Pro Glu Gly Thr Ser Cys Lys
        275                 280

<210> SEQ ID NO 64
<211> LENGTH: 106
<212> TYPE: PRT
<213> ORGANISM: Artificial Sequence
<220> FEATURE:
<223> OTHER INFORMATION: Description of Artificial Sequence: Synthetic

```
                            polypeptide
<220> FEATURE:
<221> NAME/KEY: MOD_RES
<222> LOCATION: (32)..(32)
<223> OTHER INFORMATION: Ile or Val
<220> FEATURE:
<221> NAME/KEY: MOD_RES
<222> LOCATION: (37)..(37)
<223> OTHER INFORMATION: Ile or Val
<220> FEATURE:
<221> NAME/KEY: MOD_RES
<222> LOCATION: (42)..(42)
<223> OTHER INFORMATION: Ile or Val
<220> FEATURE:
<221> NAME/KEY: MOD_RES
<222> LOCATION: (47)..(47)
<223> OTHER INFORMATION: Ile or Val
<220> FEATURE:
<221> NAME/KEY: MOD_RES
<222> LOCATION: (52)..(52)
<223> OTHER INFORMATION: Ile or Val
<220> FEATURE:
<221> NAME/KEY: MOD_RES
<222> LOCATION: (57)..(57)
<223> OTHER INFORMATION: Ile or Val
<220> FEATURE:
<221> NAME/KEY: MOD_RES
<222> LOCATION: (62)..(62)
<223> OTHER INFORMATION: Ile or Val
<220> FEATURE:
<221> NAME/KEY: MOD_RES
<222> LOCATION: (67)..(67)
<223> OTHER INFORMATION: Ile or Val
<220> FEATURE:
<221> NAME/KEY: MOD_RES
<222> LOCATION: (72)..(72)
<223> OTHER INFORMATION: Ile or Val
<220> FEATURE:
<221> NAME/KEY: MOD_RES
<222> LOCATION: (77)..(77)
<223> OTHER INFORMATION: Ile or Val

<400> SEQUENCE: 64

Met Gly Trp Gly Ser Lys Cys Thr Ser Ala Gly Ala Gly Ala Gly Pro
1               5                   10                  15

Glu Gly Arg Gly Asp Ser Thr Ser Gly Leu Val Gly Arg Gly Asp Xaa
            20                  25                  30

Pro Ala Val Gly Xaa Pro Ala Val Gly Xaa Pro Ala Val Gly Xaa Pro
        35                  40                  45

Ala Val Gly Xaa Pro Ala Val Gly Xaa Pro Ala Val Gly Xaa Pro Ala
    50                  55                  60

Val Gly Xaa Pro Ala Val Gly Xaa Pro Ala Val Gly Xaa Pro Ala Val
65                  70                  75                  80

Gly Arg Gly Asp Glu Thr Thr Ser Arg Gly Asp Ser Ala Gly Ala Gly
                85                  90                  95

Ala Gly Pro Glu Gly Thr Ser Cys Lys Leu
            100                 105

<210> SEQ ID NO 65
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Val Pro Gly Val Gly Val Pro Gly Val Gly Ile Pro Gly Val Gly Val
1               5                   10                  15
```

Pro Gly Val Gly Val Pro Gly Val Gly Val Pro Gly Val Gly Val Pro
            20                  25                  30

Gly Val Gly Ile Pro Gly Val Gly Val Pro Gly Val Gly Val Pro Gly
            35                  40                  45

Val Gly Val Pro Gly Val Gly Val Pro Gly Val Gly Ile Pro Gly Val
        50                  55                  60

Gly Val Pro Gly Val Gly Val Pro Gly Val Gly Val Pro Gly Val Gly
65                  70                  75                  80

Val Pro Gly Val Gly Ile Pro Gly Val Gly Val Pro Gly Val Gly Val
            85                  90                  95

Pro Gly Val Gly Val Pro Gly Val Gly Val Pro Gly Val Gly Ile Pro
            100                 105                 110

Gly Val Gly Val Pro Gly Val Gly Val Pro Gly Val Gly Val Pro Gly
            115                 120                 125

Val Gly Val Pro Gly Val Gly Ile Pro Gly Val Gly Val Pro Gly Val
        130                 135                 140

Gly Val Pro Gly Val Gly Val Pro Gly Val Gly Val Pro Gly Val Gly
145                 150                 155                 160

Ile Pro Gly Val Gly Val Pro Gly Val Gly Val Pro Gly Val Gly Val
            165                 170                 175

Pro Gly Val Gly Val Pro Gly Val Gly Ile Pro Gly Val Gly Val Pro
            180                 185                 190

Gly Val Gly Val Pro Gly Val Gly Val Pro Gly Val Gly Val Pro Gly
            195                 200                 205

Val Gly Ile Pro Gly Val Gly Val Pro Gly Val Gly Val Pro Gly Val
        210                 215                 220

Gly Val Pro Gly Val Gly Val Pro Gly Val Gly Ile Pro Gly Val Gly
225                 230                 235                 240

Val Pro Gly Val Gly Val Pro Gly Val Gly
            245                 250

<210> SEQ ID NO 66
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Val Pro Ala Val Gly Val Pro Ala Val Gly Ile Pro Ala Val Gly Val
1               5                   10                  15

Pro Ala Val Gly Val Pro Ala Val Gly Val Pro Ala Val Gly Val Pro
            20                  25                  30

Ala Val Gly Ile Pro Ala Val Gly Val Pro Ala Val Gly Val Pro Ala
            35                  40                  45

Val Gly Val Pro Ala Val Gly Val Pro Ala Val Gly Ile Pro Ala Val
        50                  55                  60

Gly Val Pro Ala Val Gly Val Pro Ala Val Gly Val Pro Ala Val Gly
65                  70                  75                  80

Val Pro Ala Val Gly Ile Pro Ala Val Gly Val Pro Ala Val Gly Val
            85                  90                  95

Pro Ala Val Gly Val Pro Ala Val Gly Val Pro Ala Val Gly Ile Pro
            100                 105                 110

Ala Val Gly Val Pro Ala Val Gly Val Pro Ala Val Gly Val Pro Ala
            115                 120                 125

Val Gly Val Pro Ala Val Gly Ile Pro Ala Val Gly Val Pro Ala Val
            130                 135                 140

Gly Val Pro Ala Val Gly Val Pro Ala Val Gly Val Pro Ala Val Gly
145                 150                 155                 160

Ile Pro Ala Val Gly Val Pro Ala Val Gly Val Pro Ala Val Gly Val
                165                 170                 175

Pro Ala Val Gly Val Pro Ala Val Gly Ile Pro Ala Val Gly Val Pro
            180                 185                 190

Ala Val Gly Val Pro Ala Val Gly Val Pro Ala Val Gly Val Pro Ala
        195                 200                 205

Val Gly Ile Pro Ala Val Gly Val Pro Ala Val Gly Val Pro Ala Val
    210                 215                 220

Gly Val Pro Ala Val Gly Val Pro Ala Val Gly Ile Pro Ala Val Gly
225                 230                 235                 240

Val Pro Ala Val Gly Val Pro Ala Val Gly
            245                 250

<210> SEQ ID NO 67
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Val Pro Ala Val Gly Val Pro Ala Val Gly Ile Pro Ala Val Gly Val
1               5                   10                  15

Pro Ala Val Gly Val Pro Ala Val Gly Val Pro Ala Val Gly Val Pro
            20                  25                  30

Ala Val Gly Ile Pro Ala Val Gly Val Pro Ala Val Gly Val Pro Ala
        35                  40                  45

Val Gly Val Pro Ala Val Gly Val Pro Ala Val Gly Ile Pro Ala Val
    50                  55                  60

Gly Val Pro Ala Val Gly Val Pro Ala Val Gly Val Pro Ala Val Gly
65                  70                  75                  80

Val Pro Ala Val Gly Ile Pro Ala Val Gly Val Pro Ala Val Gly Val
                85                  90                  95

Pro Ala Val Gly Val Pro Ala Val Gly Val Pro Ala Val Gly Ile Pro
            100                 105                 110

Ala Val Gly Val Pro Ala Val Gly Val Pro Ala Val Gly Val Pro Ala
        115                 120                 125

Val Gly Val Pro Ala Val Gly Ile Pro Ala Val Gly Val Pro Ala Val
    130                 135                 140

Gly Val Pro Ala Val Gly Val Pro Ala Val Gly Val Pro Ala Val Gly
145                 150                 155                 160

Ile Pro Ala Val Gly Val Pro Ala Val Gly Val Pro Ala Val Gly Val
                165                 170                 175

Pro Ala Val Gly Val Pro Ala Val Gly Ile Pro Ala Val Gly Val Pro
            180                 185                 190

Ala Val Gly Val Pro Ala Val Gly Val Pro Ala Val Gly Val Pro Ala
        195                 200                 205

Val Gly Ile Pro Ala Val Gly Val Pro Ala Val Gly Val Pro Ala Val
    210                 215                 220

Gly Val Pro Ala Val Gly Val Pro Ala Val Gly Ile Pro Ala Val Gly

```
              225                 230                 235                 240
Val Pro Ala Val Gly Val Pro Ala Val Gly Val Pro Ala Val Gly Val
                245                 250                 255

Pro Ala Val Gly Ile Pro Ala Val Gly Val Pro Ala Val Gly Val Pro
            260                 265                 270

Ala Val Gly Val Pro Ala Val Gly Val Pro Ala Val Gly Ile Pro Ala
        275                 280                 285

Val Gly Val Pro Ala Val Gly Val Pro Ala Val Gly Val Pro Ala Val
    290                 295                 300

Gly Val Pro Ala Val Gly Ile Pro Ala Val Gly Val Pro Ala Val Gly
305                 310                 315                 320

Val Pro Ala Val Gly Val Pro Ala Val Gly Val Pro Ala Val Gly Ile
                325                 330                 335

Pro Ala Val Gly Val Pro Ala Val Gly Val Pro Ala Val Gly
            340                 345                 350

<210> SEQ ID NO 68
<211> LENGTH: 600
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Val Pro Ala Val Gly Val Pro Ala Val Gly Ile Pro Ala Val Gly Val
1               5                   10                  15

Pro Ala Val Gly Val Pro Ala Val Gly Val Pro Ala Val Gly Val Pro
            20                  25                  30

Ala Val Gly Ile Pro Ala Val Gly Val Pro Ala Val Gly Val Pro Ala
        35                  40                  45

Val Gly Val Pro Ala Val Gly Val Pro Ala Val Gly Ile Pro Ala Val
    50                  55                  60

Gly Val Pro Ala Val Gly Val Pro Ala Val Gly Val Pro Ala Val Gly
65                  70                  75                  80

Val Pro Ala Val Gly Ile Pro Ala Val Gly Val Pro Ala Val Gly Val
                85                  90                  95

Pro Ala Val Gly Val Pro Ala Val Gly Val Pro Ala Val Gly Ile Pro
            100                 105                 110

Ala Val Gly Val Pro Ala Val Gly Val Pro Ala Val Gly Val Pro Ala
        115                 120                 125

Val Gly Val Pro Ala Val Gly Ile Pro Ala Val Gly Val Pro Ala Val
    130                 135                 140

Gly Val Pro Ala Val Gly Val Pro Ala Val Gly Val Pro Ala Val Gly
145                 150                 155                 160

Ile Pro Ala Val Gly Val Pro Ala Val Gly Val Pro Ala Val Gly Val
                165                 170                 175

Pro Ala Val Gly Val Pro Ala Val Gly Ile Pro Ala Val Gly Val Pro
            180                 185                 190

Ala Val Gly Val Pro Ala Val Gly Val Pro Ala Val Gly Val Pro Ala
        195                 200                 205

Val Gly Ile Pro Ala Val Gly Val Pro Ala Val Gly Val Pro Ala Val
    210                 215                 220

Gly Val Pro Ala Val Gly Val Pro Ala Val Gly Ile Pro Ala Val Gly
225                 230                 235                 240
```

Val Pro Ala Val Gly Val Pro Ala Val Gly Val Pro Ala Val Gly Val
            245                 250                 255

Pro Ala Val Gly Ile Pro Ala Val Gly Val Pro Ala Val Gly Val Pro
        260                 265                 270

Ala Val Gly Val Pro Ala Val Gly Val Pro Ala Val Gly Ile Pro Ala
    275                 280                 285

Val Gly Val Pro Ala Val Gly Val Pro Ala Val Gly Val Pro Ala Val
290                 295                 300

Gly Val Pro Ala Val Gly Ile Pro Ala Val Gly Val Pro Ala Val Gly
305                 310                 315                 320

Val Pro Ala Val Gly Val Pro Ala Val Gly Val Pro Ala Val Gly Ile
            325                 330                 335

Pro Ala Val Gly Val Pro Ala Val Gly Val Pro Ala Val Gly Val Pro
        340                 345                 350

Ala Val Gly Val Pro Ala Val Gly Ile Pro Ala Val Gly Val Pro Ala
    355                 360                 365

Val Gly Val Pro Ala Val Gly Val Pro Ala Val Gly Val Pro Ala Val
370                 375                 380

Gly Ile Pro Ala Val Gly Val Pro Ala Val Gly Val Pro Ala Val Gly
385                 390                 395                 400

Val Pro Ala Val Gly Val Pro Ala Val Gly Ile Pro Ala Val Gly Val
            405                 410                 415

Pro Ala Val Gly Val Pro Ala Val Gly Val Pro Ala Val Gly Val Pro
        420                 425                 430

Ala Val Gly Ile Pro Ala Val Gly Val Pro Ala Val Gly Val Pro Ala
    435                 440                 445

Val Gly Val Pro Ala Val Gly Val Pro Ala Val Gly Ile Pro Ala Val
450                 455                 460

Gly Val Pro Ala Val Gly Val Pro Ala Val Gly Val Pro Ala Val Gly
465                 470                 475                 480

Val Pro Ala Val Gly Ile Pro Ala Val Gly Val Pro Ala Val Gly Val
            485                 490                 495

Pro Ala Val Gly Val Pro Ala Val Gly Val Pro Ala Val Gly Ile Pro
        500                 505                 510

Ala Val Gly Val Pro Ala Val Gly Val Pro Ala Val Gly Val Pro Ala
    515                 520                 525

Val Gly Val Pro Ala Val Gly Ile Pro Ala Val Gly Val Pro Ala Val
530                 535                 540

Gly Val Pro Ala Val Gly Val Pro Ala Val Gly Val Pro Ala Val Gly
545                 550                 555                 560

Ile Pro Ala Val Gly Val Pro Ala Val Gly Val Pro Ala Val Gly Val
            565                 570                 575

Pro Ala Val Gly Val Pro Ala Val Gly Ile Pro Ala Val Gly Val Pro
        580                 585                 590

Ala Val Gly Val Pro Ala Val Gly
    595                 600

<210> SEQ ID NO 69
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

```
Ile Pro Ala Val Gly Val Pro Ala Val Gly Ile Pro Ala Val Gly Val
1               5                   10                  15

Pro Ala Val Gly Ile Pro Ala Val Gly Ile Pro Ala Val Gly Val Pro
                20                  25                  30

Ala Val Gly Ile Pro Ala Val Gly Val Pro Ala Val Gly Ile Pro Ala
            35                  40                  45

Val Gly Ile Pro Ala Val Gly Val Pro Ala Val Gly Ile Pro Ala Val
        50                  55                  60

Gly Val Pro Ala Val Gly Ile Pro Ala Val Gly Ile Pro Ala Val Gly
65                  70                  75                  80

Val Pro Ala Val Gly Ile Pro Ala Val Gly Val Pro Ala Val Gly Ile
                85                  90                  95

Pro Ala Val Gly Ile Pro Ala Val Gly Val Pro Ala Val Gly Ile Pro
                100                 105                 110

Ala Val Gly Val Pro Ala Val Gly Ile Pro Ala Val Gly Ile Pro Ala
            115                 120                 125

Val Gly Val Pro Ala Val Gly Ile Pro Ala Val Gly Val Pro Ala Val
        130                 135                 140

Gly Ile Pro Ala Val Gly Ile Pro Ala Val Gly Val Pro Ala Val Gly
145                 150                 155                 160

Ile Pro Ala Val Gly Val Pro Ala Val Gly Ile Pro Ala Val Gly Ile
                165                 170                 175

Pro Ala Val Gly Val Pro Ala Val Gly Ile Pro Ala Val Gly Val Pro
                180                 185                 190

Ala Val Gly Ile Pro Ala Val Gly Ile Pro Ala Val Gly Val Pro Ala
            195                 200                 205

Val Gly Ile Pro Ala Val Gly Val Pro Ala Val Gly Ile Pro Ala Val
        210                 215                 220

Gly Ile Pro Ala Val Gly Val Pro Ala Val Gly Ile Pro Ala Val Gly
225                 230                 235                 240

Val Pro Ala Val Gly Ile Pro Ala Val Gly
                245                 250

<210> SEQ ID NO 70
<211> LENGTH: 600
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
```

```
<222> LOCATION: (26)..(26)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (41)..(41)
<223> OTHER INFORMATION: Any amino acid
<220> FEATURE:
<221> NAME/KEY: MOD_RES
<222> LOCATION: (46)..(46)
<223> OTHER INFORMATION: Any amino acid
<220> FEATURE:
<221> NAME/KEY: MOD_RES
<222> LOCATION: (51)..(51)
<223> OTHER INFORMATION: Any amino acid
<220> FEATURE:
<221> NAME/KEY: MOD_RES
<222> LOCATION: (56)..(56)
<223> OTHER INFORMATION: Any amino acid
<220> FEATURE:
<221> NAME/KEY: MOD_RES
<222> LOCATION: (61)..(61)
<223> OTHER INFORMATION: Any amino acid
<220> FEATURE:
<221> NAME/KEY: MOD_RES
<222> LOCATION: (66)..(66)
<223> OTHER INFORMATION: Any amino acid
<220> FEATURE:
<221> NAME/KEY: MOD_RES
<222> LOCATION: (71)..(71)
<223> OTHER INFORMATION: Any amino acid
<220> FEATURE:
<221> NAME/KEY: MOD_RES
<222> LOCATION: (76)..(76)
<223> OTHER INFORMATION: Any amino acid
<220> FEATURE:
<221> NAME/KEY: MOD_RES
<222> LOCATION: (81)..(81)
<223> OTHER INFORMATION: Any amino acid
<220> FEATURE:
<221> NAME/KEY: MOD_RES
<222> LOCATION: (86)..(86)
<223> OTHER INFORMATION: Any amino acid
<220> FEATURE:
<221> NAME/KEY: MOD_RES
<222> LOCATION: (91)..(91)
<223> OTHER INFORMATION: Any amino acid
<220> FEATURE:
<221> NAME/KEY: MOD_RES
<222> LOCATION: (96)..(96)
<223> OTHER INFORMATION: Any amino acid
<220> FEATURE:
<221> NAME/KEY: MOD_RES
<222> LOCATION: (101)..(101)
<223> OTHER INFORMATION: Any amino acid
<220> FEATURE:
<221> NAME/KEY: MOD_RES
<222> LOCATION: (106)..(106)
<223> OTHER INFORMATION: Any amino acid
<220> FEATURE:
<221> NAME/KEY: MOD_RES
<222> LOCATION: (111)..(111)
<223> OTHER INFORMATION: Any amino acid
<220> FEATURE:
<221> NAME/KEY: MOD_RES
<222> LOCATION: (116)..(116)
<223> OTHER INFORMATION: Any amino acid
<220> FEATURE:
<221> NAME/KEY: MOD_RES
<222> LOCATION: (121)..(121)
<223> OTHER INFORMATION: Any amino acid
<220> FEATURE:
```

-continued

```
<221> NAME/KEY: MOD_RES
<222> LOCATION: (126)..(126)
<223> OTHER INFORMATION: Any amino acid
<220> FEATURE:
<221> NAME/KEY: MOD_RES
<222> LOCATION: (131)..(131)
<223> OTHER INFORMATION: Any amino acid
<220> FEATURE:
<221> NAME/KEY: MOD_RES
<222> LOCATION: (136)..(136)
<223> OTHER INFORMATION: Any amino acid
<220> FEATURE:
<221> NAME/KEY: MOD_RES
<222> LOCATION: (141)..(141)
<223> OTHER INFORMATION: Any amino acid
<220> FEATURE:
<221> NAME/KEY: MOD_RES
<222> LOCATION: (146)..(146)
<223> OTHER INFORMATION: Any amino acid
<220> FEATURE:
<221> NAME/KEY: MOD_RES
<222> LOCATION: (151)..(151)
<223> OTHER INFORMATION: Any amino acid
<220> FEATURE:
<221> NAME/KEY: MOD_RES
<222> LOCATION: (156)..(156)
<223> OTHER INFORMATION: Any amino acid
<220> FEATURE:
<221> NAME/KEY: MOD_RES
<222> LOCATION: (161)..(161)
<223> OTHER INFORMATION: Any amino acid
<220> FEATURE:
<221> NAME/KEY: MOD_RES
<222> LOCATION: (166)..(166)
<223> OTHER INFORMATION: Any amino acid
<220> FEATURE:
<221> NAME/KEY: MOD_RES
<222> LOCATION: (171)..(171)
<223> OTHER INFORMATION: Any amino acid
<220> FEATURE:
<221> NAME/KEY: MOD_RES
<222> LOCATION: (176)..(176)
<223> OTHER INFORMATION: Any amino acid
<220> FEATURE:
<221> NAME/KEY: MOD_RES
<222> LOCATION: (181)..(181)
<223> OTHER INFORMATION: Any amino acid
<220> FEATURE:
<221> NAME/KEY: MOD_RES
<222> LOCATION: (186)..(186)
<223> OTHER INFORMATION: Any amino acid
<220> FEATURE:
<221> NAME/KEY: MOD_RES
<222> LOCATION: (191)..(191)
<223> OTHER INFORMATION: Any amino acid
<220> FEATURE:
<221> NAME/KEY: MOD_RES
<222> LOCATION: (196)..(196)
<223> OTHER INFORMATION: Any amino acid
<220> FEATURE:
<221> NAME/KEY: MOD_RES
<222> LOCATION: (201)..(201)
<223> OTHER INFORMATION: Any amino acid
<220> FEATURE:
<221> NAME/KEY: MOD_RES
<222> LOCATION: (206)..(206)
<223> OTHER INFORMATION: Any amino acid
<220> FEATURE:
<221> NAME/KEY: MOD_RES
<222> LOCATION: (211)..(211)
<223> OTHER INFORMATION: Any amino acid
<220> FEATURE:
<221> NAME/KEY: MOD_RES
<222> LOCATION: (216)..(216)
<223> OTHER INFORMATION: Any amino acid
<220> FEATURE:
<221> NAME/KEY: MOD_RES
<222> LOCATION: (221)..(221)
<223> OTHER INFORMATION: Any amino acid
```

```
<220> FEATURE:
<221> NAME/KEY: MOD_RES
<222> LOCATION: (226)..(226)
<223> OTHER INFORMATION: Any amino acid
<220> FEATURE:
<221> NAME/KEY: MOD_RES
<222> LOCATION: (231)..(231)
<223> OTHER INFORMATION: Any amino acid
<220> FEATURE:
<221> NAME/KEY: MOD_RES
<222> LOCATION: (236)..(236)
<223> OTHER INFORMATION: Any amino acid
<220> FEATURE:
<221> NAME/KEY: MOD_RES
<222> LOCATION: (241)..(241)
<223> OTHER INFORMATION: Any amino acid
<220> FEATURE:
<221> NAME/KEY: MOD_RES
<222> LOCATION: (246)..(246)
<223> OTHER INFORMATION: Any amino acid
<220> FEATURE:
<221> NAME/KEY: MOD_RES
<222> LOCATION: (251)..(251)
<223> OTHER INFORMATION: Any amino acid
<220> FEATURE:
<221> NAME/KEY: MOD_RES
<222> LOCATION: (256)..(256)
<223> OTHER INFORMATION: Any amino acid
<220> FEATURE:
<221> NAME/KEY: MOD_RES
<222> LOCATION: (261)..(261)
<223> OTHER INFORMATION: Any amino acid
<220> FEATURE:
<221> NAME/KEY: MOD_RES
<222> LOCATION: (266)..(266)
<223> OTHER INFORMATION: Any amino acid
<220> FEATURE:
<221> NAME/KEY: MOD_RES
<222> LOCATION: (271)..(271)
<223> OTHER INFORMATION: Any amino acid
<220> FEATURE:
<221> NAME/KEY: MOD_RES
<222> LOCATION: (276)..(276)
<223> OTHER INFORMATION: Any amino acid
<220> FEATURE:
<221> NAME/KEY: MOD_RES
<222> LOCATION: (281)..(281)
<223> OTHER INFORMATION: Any amino acid
<220> FEATURE:
<221> NAME/KEY: MOD_RES
<222> LOCATION: (286)..(286)
<223> OTHER INFORMATION: Any amino acid
<220> FEATURE:
<221> NAME/KEY: MOD_RES
<222> LOCATION: (291)..(291)
<223> OTHER INFORMATION: Any amino acid
<220> FEATURE:
<221> NAME/KEY: MOD_RES
<222> LOCATION: (296)..(296)
<223> OTHER INFORMATION: Any amino acid
<220> FEATURE:
<221> NAME/KEY: MOD_RES
<222> LOCATION: (301)..(301)
<223> OTHER INFORMATION: Any amino acid
<220> FEATURE:
<221> NAME/KEY: MOD_RES
<222> LOCATION: (306)..(306)
<223> OTHER INFORMATION: Any amino acid
<220> FEATURE:
<221> NAME/KEY: MOD_RES
<222> LOCATION: (311)..(311)
<223> OTHER INFORMATION: Any amino acid
<220> FEATURE:
<221> NAME/KEY: MOD_RES
<222> LOCATION: (316)..(316)
<223> OTHER INFORMATION: Any amino acid
<220> FEATURE:
<221> NAME/KEY: MOD_RES
<222> LOCATION: (321)..(321)
```

-continued

```
<223> OTHER INFORMATION: Any amino acid
<220> FEATURE:
<221> NAME/KEY: MOD_RES
<222> LOCATION: (326)..(326)
<223> OTHER INFORMATION: Any amino acid
<220> FEATURE:
<221> NAME/KEY: MOD_RES
<222> LOCATION: (331)..(331)
<223> OTHER INFORMATION: Any amino acid
<220> FEATURE:
<221> NAME/KEY: MOD_RES
<222> LOCATION: (336)..(336)
<223> OTHER INFORMATION: Any amino acid
<220> FEATURE:
<221> NAME/KEY: MOD_RES
<222> LOCATION: (341)..(341)
<223> OTHER INFORMATION: Any amino acid
<220> FEATURE:
<221> NAME/KEY: MOD_RES
<222> LOCATION: (346)..(346)
<223> OTHER INFORMATION: Any amino acid
<220> FEATURE:
<221> NAME/KEY: MOD_RES
<222> LOCATION: (351)..(351)
<223> OTHER INFORMATION: Any amino acid
<220> FEATURE:
<221> NAME/KEY: MOD_RES
<222> LOCATION: (356)..(356)
<223> OTHER INFORMATION: Any amino acid
<220> FEATURE:
<221> NAME/KEY: MOD_RES
<222> LOCATION: (361)..(361)
<223> OTHER INFORMATION: Any amino acid
<220> FEATURE:
<221> NAME/KEY: MOD_RES
<222> LOCATION: (366)..(366)
<223> OTHER INFORMATION: Any amino acid
<220> FEATURE:
<221> NAME/KEY: MOD_RES
<222> LOCATION: (371)..(371)
<223> OTHER INFORMATION: Any amino acid
<220> FEATURE:
<221> NAME/KEY: MOD_RES
<222> LOCATION: (376)..(376)
<223> OTHER INFORMATION: Any amino acid
<220> FEATURE:
<221> NAME/KEY: MOD_RES
<222> LOCATION: (381)..(381)
<223> OTHER INFORMATION: Any amino acid
<220> FEATURE:
<221> NAME/KEY: MOD_RES
<222> LOCATION: (386)..(386)
<223> OTHER INFORMATION: Any amino acid
<220> FEATURE:
<221> NAME/KEY: MOD_RES
<222> LOCATION: (391)..(391)
<223> OTHER INFORMATION: Any amino acid
<220> FEATURE:
<221> NAME/KEY: MOD_RES
<222> LOCATION: (396)..(396)
<223> OTHER INFORMATION: Any amino acid
<220> FEATURE:
<221> NAME/KEY: MOD_RES
<222> LOCATION: (401)..(401)
<223> OTHER INFORMATION: Any amino acid
<220> FEATURE:
<221> NAME/KEY: MOD_RES
<222> LOCATION: (406)..(406)
<223> OTHER INFORMATION: Any amino acid
<220> FEATURE:
<221> NAME/KEY: MOD_RES
<222> LOCATION: (411)..(411)
<223> OTHER INFORMATION: Any amino acid
<220> FEATURE:
<221> NAME/KEY: MOD_RES
<222> LOCATION: (416)..(416)
<223> OTHER INFORMATION: Any amino acid
<220> FEATURE:
<221> NAME/KEY: MOD_RES
```

```
<222> LOCATION: (421)..(421)
<223> OTHER INFORMATION: Any amino acid
<220> FEATURE:
<221> NAME/KEY: MOD_RES
<222> LOCATION: (426)..(426)
<223> OTHER INFORMATION: Any amino acid
<220> FEATURE:
<221> NAME/KEY: MOD_RES
<222> LOCATION: (431)..(431)
<223> OTHER INFORMATION: Any amino acid
<220> FEATURE:
<221> NAME/KEY: MOD_RES
<222> LOCATION: (436)..(436)
<223> OTHER INFORMATION: Any amino acid
<220> FEATURE:
<221> NAME/KEY: MOD_RES
<222> LOCATION: (441)..(441)
<223> OTHER INFORMATION: Any amino acid
<220> FEATURE:
<221> NAME/KEY: MOD_RES
<222> LOCATION: (446)..(446)
<223> OTHER INFORMATION: Any amino acid
<220> FEATURE:
<221> NAME/KEY: MOD_RES
<222> LOCATION: (451)..(451)
<223> OTHER INFORMATION: Any amino acid
<220> FEATURE:
<221> NAME/KEY: MOD_RES
<222> LOCATION: (456)..(456)
<223> OTHER INFORMATION: Any amino acid
<220> FEATURE:
<221> NAME/KEY: MOD_RES
<222> LOCATION: (461)..(461)
<223> OTHER INFORMATION: Any amino acid
<220> FEATURE:
<221> NAME/KEY: MOD_RES
<222> LOCATION: (466)..(466)
<223> OTHER INFORMATION: Any amino acid
<220> FEATURE:
<221> NAME/KEY: MOD_RES
<222> LOCATION: (471)..(471)
<223> OTHER INFORMATION: Any amino acid
<220> FEATURE:
<221> NAME/KEY: MOD_RES
<222> LOCATION: (476)..(476)
<223> OTHER INFORMATION: Any amino acid
<220> FEATURE:
<221> NAME/KEY: MOD_RES
<222> LOCATION: (481)..(481)
<223> OTHER INFORMATION: Any amino acid
<220> FEATURE:
<221> NAME/KEY: MOD_RES
<222> LOCATION: (486)..(486)
<223> OTHER INFORMATION: Any amino acid
<220> FEATURE:
<221> NAME/KEY: MOD_RES
<222> LOCATION: (491)..(491)
<223> OTHER INFORMATION: Any amino acid
<220> FEATURE:
<221> NAME/KEY: MOD_RES
<222> LOCATION: (496)..(496)
<223> OTHER INFORMATION: Any amino acid
<220> FEATURE:
<221> NAME/KEY: MOD_RES
<222> LOCATION: (501)..(501)
<223> OTHER INFORMATION: Any amino acid
<220> FEATURE:
<221> NAME/KEY: MOD_RES
<222> LOCATION: (506)..(506)
<223> OTHER INFORMATION: Any amino acid
<220> FEATURE:
<221> NAME/KEY: MOD_RES
<222> LOCATION: (511)..(511)
<223> OTHER INFORMATION: Any amino acid
<220> FEATURE:
<221> NAME/KEY: MOD_RES
<222> LOCATION: (516)..(516)
<223> OTHER INFORMATION: Any amino acid
<220> FEATURE:
```

```
<221> NAME/KEY: MOD_RES
<222> LOCATION: (521)..(521)
<223> OTHER INFORMATION: Any amino acid
<220> FEATURE:
<221> NAME/KEY: MOD_RES
<222> LOCATION: (526)..(526)
<223> OTHER INFORMATION: Any amino acid
<220> FEATURE:
<221> NAME/KEY: MOD_RES
<222> LOCATION: (531)..(531)
<223> OTHER INFORMATION: Any amino acid
<220> FEATURE:
<221> NAME/KEY: MOD_RES
<222> LOCATION: (536)..(536)
<223> OTHER INFORMATION: Any amino acid
<220> FEATURE:
<221> NAME/KEY: MOD_RES
<222> LOCATION: (541)..(541)
<223> OTHER INFORMATION: Any amino acid
<220> FEATURE:
<221> NAME/KEY: MOD_RES
<222> LOCATION: (546)..(546)
<223> OTHER INFORMATION: Any amino acid
<220> FEATURE:
<221> NAME/KEY: MOD_RES
<222> LOCATION: (551)..(551)
<223> OTHER INFORMATION: Any amino acid
<220> FEATURE:
<221> NAME/KEY: MOD_RES
<222> LOCATION: (556)..(556)
<223> OTHER INFORMATION: Any amino acid
<220> FEATURE:
<221> NAME/KEY: MOD_RES
<222> LOCATION: (561)..(561)
<223> OTHER INFORMATION: Any amino acid
<220> FEATURE:
<221> NAME/KEY: MOD_RES
<222> LOCATION: (566)..(566)
<223> OTHER INFORMATION: Any amino acid
<220> FEATURE:
<221> NAME/KEY: MOD_RES
<222> LOCATION: (571)..(571)
<223> OTHER INFORMATION: Any amino acid
<220> FEATURE:
<221> NAME/KEY: MOD_RES
<222> LOCATION: (576)..(576)
<223> OTHER INFORMATION: Any amino acid
<220> FEATURE:
<221> NAME/KEY: MOD_RES
<222> LOCATION: (581)..(581)
<223> OTHER INFORMATION: Any amino acid
<220> FEATURE:
<221> NAME/KEY: MOD_RES
<222> LOCATION: (586)..(586)
<223> OTHER INFORMATION: Any amino acid
<220> FEATURE:
<221> NAME/KEY: MOD_RES
<222> LOCATION: (591)..(591)
<223> OTHER INFORMATION: Any amino acid
<220> FEATURE:
<221> NAME/KEY: MOD_RES
<222> LOCATION: (596)..(596)
<223> OTHER INFORMATION: Any amino acid

<400> SEQUENCE: 70

Xaa Pro Gly Val Gly Xaa Pro Gly Val Gly Xaa Pro Gly Val Gly Xaa
1               5                   10                  15

Pro Gly Val Gly Xaa Pro Gly Val Gly Xaa Pro Gly Val Gly Xaa Pro
            20                  25                  30

Gly Val Gly Xaa Pro Gly Val Gly Xaa Pro Gly Val Gly Xaa Pro Gly
        35                  40                  45

Val Gly Xaa Pro Gly Val Gly Xaa Pro Gly Val Gly Xaa Pro Gly Val
    50                  55                  60

Gly Xaa Pro Gly Val Gly Xaa Pro Gly Val Gly Xaa Pro Gly Val Gly
```

-continued

```
                65                  70                  75                  80
Xaa Pro Gly Val Gly Xaa Pro Gly Val Gly Xaa Pro Gly Val Gly Xaa
                    85                  90                  95
Pro Gly Val Gly Xaa Pro Gly Val Gly Xaa Pro Gly Val Gly Xaa Pro
                    100                 105                 110
Gly Val Gly Xaa Pro Gly Val Gly Xaa Pro Gly Val Gly Xaa Pro Gly
                    115                 120                 125
Val Gly Xaa Pro Gly Val Gly Xaa Pro Gly Val Gly Xaa Pro Gly Val
            130                 135                 140
Gly Xaa Pro Gly Val Gly Xaa Pro Gly Val Gly Xaa Pro Gly Val Gly
145                 150                 155                 160
Xaa Pro Gly Val Gly Xaa Pro Gly Val Gly Xaa Pro Gly Val Gly Xaa
                    165                 170                 175
Pro Gly Val Gly Xaa Pro Gly Val Gly Xaa Pro Gly Val Gly Xaa Pro
                    180                 185                 190
Gly Val Gly Xaa Pro Gly Val Gly Xaa Pro Gly Val Gly Xaa Pro Gly
                    195                 200                 205
Val Gly Xaa Pro Gly Val Gly Xaa Pro Gly Val Gly Xaa Pro Gly Val
            210                 215                 220
Gly Xaa Pro Gly Val Gly Xaa Pro Gly Val Gly Xaa Pro Gly Val Gly
225                 230                 235                 240
Xaa Pro Gly Val Gly Xaa Pro Gly Val Gly Xaa Pro Gly Val Gly Xaa
                    245                 250                 255
Pro Gly Val Gly Xaa Pro Gly Val Gly Xaa Pro Gly Val Gly Xaa Pro
                    260                 265                 270
Gly Val Gly Xaa Pro Gly Val Gly Xaa Pro Gly Val Gly Xaa Pro Gly
                    275                 280                 285
Val Gly Xaa Pro Gly Val Gly Xaa Pro Gly Val Gly Xaa Pro Gly Val
            290                 295                 300
Gly Xaa Pro Gly Val Gly Xaa Pro Gly Val Gly Xaa Pro Gly Val Gly
305                 310                 315                 320
Xaa Pro Gly Val Gly Xaa Pro Gly Val Gly Xaa Pro Gly Val Gly Xaa
                    325                 330                 335
Pro Gly Val Gly Xaa Pro Gly Val Gly Xaa Pro Gly Val Gly Xaa Pro
                    340                 345                 350
Gly Val Gly Xaa Pro Gly Val Gly Xaa Pro Gly Val Gly Xaa Pro Gly
            355                 360                 365
Val Gly Xaa Pro Gly Val Gly Xaa Pro Gly Val Gly Xaa Pro Gly Val
    370                 375                 380
Gly Xaa Pro Gly Val Gly Xaa Pro Gly Val Gly Xaa Pro Gly Val Gly
385                 390                 395                 400
Xaa Pro Gly Val Gly Xaa Pro Gly Val Gly Xaa Pro Gly Val Gly Xaa
                    405                 410                 415
Pro Gly Val Gly Xaa Pro Gly Val Gly Xaa Pro Gly Val Gly Xaa Pro
                    420                 425                 430
Gly Val Gly Xaa Pro Gly Val Gly Xaa Pro Gly Val Gly Xaa Pro Gly
            435                 440                 445
Val Gly Xaa Pro Gly Val Gly Xaa Pro Gly Val Gly Xaa Pro Gly Val
    450                 455                 460
Gly Xaa Pro Gly Val Gly Xaa Pro Gly Val Gly Xaa Pro Gly Val Gly
465                 470                 475                 480
Xaa Pro Gly Val Gly Xaa Pro Gly Val Gly Xaa Pro Gly Val Gly Xaa
                    485                 490                 495
```

Pro Gly Val Gly Xaa Pro Gly Val Gly Xaa Pro Gly Val Gly Xaa Pro
                500                 505                 510

Gly Val Gly Xaa Pro Gly Val Gly Xaa Pro Gly Val Gly Xaa Pro Gly
        515                 520                 525

Val Gly Xaa Pro Gly Val Gly Xaa Pro Gly Val Gly Xaa Pro Gly Val
    530                 535                 540

Gly Xaa Pro Gly Val Gly Xaa Pro Gly Val Gly Xaa Pro Gly Val Gly
545                 550                 555                 560

Xaa Pro Gly Val Gly Xaa Pro Gly Val Gly Xaa Pro Gly Val Gly Xaa
            565                 570                 575

Pro Gly Val Gly Xaa Pro Gly Val Gly Xaa Pro Gly Val Gly Xaa Pro
        580                 585                 590

Gly Val Gly Xaa Pro Gly Val Gly
        595                 600

<210> SEQ ID NO 71
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (41)..(41)
<223> OTHER INFORMATION: Any amino acid
<220> FEATURE:
<221> NAME/KEY: MOD_RES
<222> LOCATION: (46)..(46)
<223> OTHER INFORMATION: Any amino acid
<220> FEATURE:
<221> NAME/KEY: MOD_RES
<222> LOCATION: (51)..(51)
<223> OTHER INFORMATION: Any amino acid
<220> FEATURE:
<221> NAME/KEY: MOD_RES
<222> LOCATION: (56)..(56)
<223> OTHER INFORMATION: Any amino acid
<220> FEATURE:

```
<221> NAME/KEY: MOD_RES
<222> LOCATION: (61)..(61)
<223> OTHER INFORMATION: Any amino acid
<220> FEATURE:
<221> NAME/KEY: MOD_RES
<222> LOCATION: (66)..(66)
<223> OTHER INFORMATION: Any amino acid
<220> FEATURE:
<221> NAME/KEY: MOD_RES
<222> LOCATION: (71)..(71)
<223> OTHER INFORMATION: Any amino acid
<220> FEATURE:
<221> NAME/KEY: MOD_RES
<222> LOCATION: (76)..(76)
<223> OTHER INFORMATION: Any amino acid
<220> FEATURE:
<221> NAME/KEY: MOD_RES
<222> LOCATION: (81)..(81)
<223> OTHER INFORMATION: Any amino acid
<220> FEATURE:
<221> NAME/KEY: MOD_RES
<222> LOCATION: (86)..(86)
<223> OTHER INFORMATION: Any amino acid
<220> FEATURE:
<221> NAME/KEY: MOD_RES
<222> LOCATION: (91)..(91)
<223> OTHER INFORMATION: Any amino acid
<220> FEATURE:
<221> NAME/KEY: MOD_RES
<222> LOCATION: (96)..(96)
<223> OTHER INFORMATION: Any amino acid
<220> FEATURE:
<221> NAME/KEY: MOD_RES
<222> LOCATION: (101)..(101)
<223> OTHER INFORMATION: Any amino acid
<220> FEATURE:
<221> NAME/KEY: MOD_RES
<222> LOCATION: (106)..(106)
<223> OTHER INFORMATION: Any amino acid
<220> FEATURE:
<221> NAME/KEY: MOD_RES
<222> LOCATION: (111)..(111)
<223> OTHER INFORMATION: Any amino acid
<220> FEATURE:
<221> NAME/KEY: MOD_RES
<222> LOCATION: (116)..(116)
<223> OTHER INFORMATION: Any amino acid
<220> FEATURE:
<221> NAME/KEY: MOD_RES
<222> LOCATION: (121)..(121)
<223> OTHER INFORMATION: Any amino acid
<220> FEATURE:
<221> NAME/KEY: MOD_RES
<222> LOCATION: (126)..(126)
<223> OTHER INFORMATION: Any amino acid
<220> FEATURE:
<221> NAME/KEY: MOD_RES
<222> LOCATION: (131)..(131)
<223> OTHER INFORMATION: Any amino acid
<220> FEATURE:
<221> NAME/KEY: MOD_RES
<222> LOCATION: (136)..(136)
<223> OTHER INFORMATION: Any amino acid
<220> FEATURE:
<221> NAME/KEY: MOD_RES
<222> LOCATION: (141)..(141)
<223> OTHER INFORMATION: Any amino acid
<220> FEATURE:
<221> NAME/KEY: MOD_RES
<222> LOCATION: (146)..(146)
<223> OTHER INFORMATION: Any amino acid
<220> FEATURE:
<221> NAME/KEY: MOD_RES
<222> LOCATION: (151)..(151)
<223> OTHER INFORMATION: Any amino acid
<220> FEATURE:
<221> NAME/KEY: MOD_RES
<222> LOCATION: (156)..(156)
<223> OTHER INFORMATION: Any amino acid
```

```
<220> FEATURE:
<221> NAME/KEY: MOD_RES
<222> LOCATION: (161)..(161)
<223> OTHER INFORMATION: Any amino acid
<220> FEATURE:
<221> NAME/KEY: MOD_RES
<222> LOCATION: (166)..(166)
<223> OTHER INFORMATION: Any amino acid
<220> FEATURE:
<221> NAME/KEY: MOD_RES
<222> LOCATION: (171)..(171)
<223> OTHER INFORMATION: Any amino acid
<220> FEATURE:
<221> NAME/KEY: MOD_RES
<222> LOCATION: (176)..(176)
<223> OTHER INFORMATION: Any amino acid
<220> FEATURE:
<221> NAME/KEY: MOD_RES
<222> LOCATION: (181)..(181)
<223> OTHER INFORMATION: Any amino acid
<220> FEATURE:
<221> NAME/KEY: MOD_RES
<222> LOCATION: (186)..(186)
<223> OTHER INFORMATION: Any amino acid
<220> FEATURE:
<221> NAME/KEY: MOD_RES
<222> LOCATION: (191)..(191)
<223> OTHER INFORMATION: Any amino acid
<220> FEATURE:
<221> NAME/KEY: MOD_RES
<222> LOCATION: (196)..(196)
<223> OTHER INFORMATION: Any amino acid
<220> FEATURE:
<221> NAME/KEY: MOD_RES
<222> LOCATION: (201)..(201)
<223> OTHER INFORMATION: Any amino acid
<220> FEATURE:
<221> NAME/KEY: MOD_RES
<222> LOCATION: (206)..(206)
<223> OTHER INFORMATION: Any amino acid
<220> FEATURE:
<221> NAME/KEY: MOD_RES
<222> LOCATION: (211)..(211)
<223> OTHER INFORMATION: Any amino acid
<220> FEATURE:
<221> NAME/KEY: MOD_RES
<222> LOCATION: (216)..(216)
<223> OTHER INFORMATION: Any amino acid
<220> FEATURE:
<221> NAME/KEY: MOD_RES
<222> LOCATION: (221)..(221)
<223> OTHER INFORMATION: Any amino acid
<220> FEATURE:
<221> NAME/KEY: MOD_RES
<222> LOCATION: (226)..(226)
<223> OTHER INFORMATION: Any amino acid
<220> FEATURE:
<221> NAME/KEY: MOD_RES
<222> LOCATION: (231)..(231)
<223> OTHER INFORMATION: Any amino acid
<220> FEATURE:
<221> NAME/KEY: MOD_RES
<222> LOCATION: (236)..(236)
<223> OTHER INFORMATION: Any amino acid
<220> FEATURE:
<221> NAME/KEY: MOD_RES
<222> LOCATION: (241)..(241)
<223> OTHER INFORMATION: Any amino acid
<220> FEATURE:
<221> NAME/KEY: MOD_RES
<222> LOCATION: (246)..(246)
<223> OTHER INFORMATION: Any amino acid

<400> SEQUENCE: 71

Xaa Pro Gly Val Gly Xaa Pro Gly Val Gly Xaa Pro Gly Val Gly Xaa
1               5                   10                  15

Pro Gly Val Gly Xaa Pro Gly Val Gly Xaa Pro Gly Val Gly Xaa Pro
```

```
            20                  25                  30
Gly Val Gly Xaa Pro Gly Val Gly Xaa Pro Gly Val Gly Xaa Pro Gly
            35                  40                  45
Val Gly Xaa Pro Gly Val Gly Xaa Pro Gly Val Gly Xaa Pro Gly Val
            50                  55                  60
Gly Xaa Pro Gly Val Gly Xaa Pro Gly Val Gly Xaa Pro Gly Val Gly
65                  70                  75                  80
Xaa Pro Gly Val Gly Xaa Pro Gly Val Gly Xaa Pro Gly Val Gly Xaa
                85                  90                  95
Pro Gly Val Gly Xaa Pro Gly Val Gly Xaa Pro Gly Val Gly Xaa Pro
            100                 105                 110
Gly Val Gly Xaa Pro Gly Val Gly Xaa Pro Gly Val Gly Xaa Pro Gly
            115                 120                 125
Val Gly Xaa Pro Gly Val Gly Xaa Pro Gly Val Gly Xaa Pro Gly Val
            130                 135                 140
Gly Xaa Pro Gly Val Gly Xaa Pro Gly Val Gly Xaa Pro Gly Val Gly
145                 150                 155                 160
Xaa Pro Gly Val Gly Xaa Pro Gly Val Gly Xaa Pro Gly Val Gly Xaa
                165                 170                 175
Pro Gly Val Gly Xaa Pro Gly Val Gly Xaa Pro Gly Val Gly Xaa Pro
            180                 185                 190
Gly Val Gly Xaa Pro Gly Val Gly Xaa Pro Gly Val Gly Xaa Pro Gly
            195                 200                 205
Val Gly Xaa Pro Gly Val Gly Xaa Pro Gly Val Gly Xaa Pro Gly Val
            210                 215                 220
Gly Xaa Pro Gly Val Gly Xaa Pro Gly Val Gly Xaa Pro Gly Val Gly
225                 230                 235                 240
Xaa Pro Gly Val Gly Xaa Pro Gly Val Gly
                245                 250

<210> SEQ ID NO 72
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Met Gly Trp Gly Ser Ala Ser Gly Leu Val Gly Ile Pro Ala Val Gly
1               5                   10                  15
Val Pro Ala Val Gly Ile Pro Ala Val Gly Val Pro Ala Val Gly Ile
            20                  25                  30
Pro Ala Val Gly Ile Pro Ala Val Gly Val Pro Ala Val Gly Ile Pro
            35                  40                  45
Ala Val Gly Val Pro Ala Val Gly Ile Pro Ala Val Gly Ile Pro Ala
            50                  55                  60
Val Gly Val Pro Ala Val Gly Ile Pro Ala Val Gly Val Pro Ala Val
65                  70                  75                  80
Gly Ile Pro Ala Val Gly Ile Pro Ala Val Gly Val Pro Ala Val Gly
                85                  90                  95
Ile Pro Ala Val Gly Val Pro Ala Val Gly Ile Pro Ala Val Gly Ile
            100                 105                 110
Pro Ala Val Gly Val Pro Ala Val Gly Ile Pro Ala Val Gly Val Pro
            115                 120                 125
```

```
Ala Val Gly Ile Pro Ala Val Gly Ile Pro Ala Val Gly Val Pro Ala
        130                 135                 140

Val Gly Ile Pro Ala Val Gly Val Pro Ala Val Gly Ile Pro Ala Val
145                 150                 155                 160

Gly Ile Pro Ala Val Gly Val Pro Ala Val Gly Ile Pro Ala Val Gly
            165                 170                 175

Val Pro Ala Val Gly Ile Pro Ala Val Gly Ile Pro Ala Val Gly Val
            180                 185                 190

Pro Ala Val Gly Ile Pro Ala Val Gly Val Pro Ala Val Gly Ile Pro
            195                 200                 205

Ala Val Gly Ile Pro Ala Val Gly Val Pro Ala Val Gly Ile Pro Ala
        210                 215                 220

Val Gly Val Pro Ala Val Gly Ile Pro Ala Val Gly Ile Pro Ala Val
225                 230                 235                 240

Gly Val Pro Ala Val Gly Ile Pro Ala Val Gly Val Pro Ala Val Gly
            245                 250                 255

Ile Pro Ala Val Gly Glu Thr Thr Ser
        260                 265

<210> SEQ ID NO 73
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met Gly Trp Gly Ser Lys Cys Thr Ser Ala Gly Ala Gly Ala Gly Pro
1               5                   10                  15

Glu Gly Arg Gly Asp Ser Thr Ser Gly Leu Val Gly Ile Pro Ala Val
            20                  25                  30

Gly Val Pro Ala Val Gly Ile Pro Ala Val Gly Val Pro Ala Val Gly
        35                  40                  45

Ile Pro Ala Val Gly Ile Pro Ala Val Gly Val Pro Ala Val Gly Ile
    50                  55                  60

Pro Ala Val Gly Val Pro Ala Val Gly Ile Pro Ala Val Gly Ile Pro
65                  70                  75                  80

Ala Val Gly Val Pro Ala Val Gly Ile Pro Ala Val Gly Val Pro Ala
                85                  90                  95

Val Gly Ile Pro Ala Val Gly Ile Pro Ala Val Gly Val Pro Ala Val
            100                 105                 110

Gly Ile Pro Ala Val Gly Val Pro Ala Val Gly Ile Pro Ala Val Gly
        115                 120                 125

Ile Pro Ala Val Gly Val Pro Ala Val Gly Ile Pro Ala Val Gly Val
    130                 135                 140

Pro Ala Val Gly Ile Pro Ala Val Gly Ile Pro Ala Val Gly Val Pro
145                 150                 155                 160

Ala Val Gly Ile Pro Ala Val Gly Val Pro Ala Val Gly Ile Pro Ala
                165                 170                 175

Val Gly Ile Pro Ala Val Gly Val Pro Ala Val Gly Ile Pro Ala Val
            180                 185                 190

Gly Val Pro Ala Val Gly Ile Pro Ala Val Gly Ile Pro Ala Val Gly
        195                 200                 205

Val Pro Ala Val Gly Ile Pro Ala Val Gly Val Pro Ala Val Gly Ile
    210                 215                 220
```

-continued

```
Pro Ala Val Gly Ile Pro Ala Val Gly Val Pro Ala Val Gly Ile Pro
225                 230                 235                 240

Ala Val Gly Val Pro Ala Val Gly Ile Pro Ala Val Gly Ile Pro Ala
                245                 250                 255

Val Gly Val Pro Ala Val Gly Ile Pro Ala Val Gly Val Pro Ala Val
            260                 265                 270

Gly Ile Pro Ala Val Gly Glu Thr Thr Ser Arg Gly Asp Ser Ala Gly
        275                 280                 285

Ala Gly Ala Gly Pro Glu Gly Thr Ser Cys Lys Leu
    290                 295                 300

<210> SEQ ID NO 74
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (29)..(29)
<223> OTHER INFORMATION: Ile or Val
<220> FEATURE:
<221> NAME/KEY: MOD_RES
<222> LOCATION: (34)..(34)
<223> OTHER INFORMATION: Ile or Val
<220> FEATURE:
<221> NAME/KEY: MOD_RES
<222> LOCATION: (39)..(39)
<223> OTHER INFORMATION: Ile or Val
<220> FEATURE:
<221> NAME/KEY: MOD_RES
<222> LOCATION: (44)..(44)
<223> OTHER INFORMATION: Ile or Val
<220> FEATURE:
<221> NAME/KEY: MOD_RES
<222> LOCATION: (49)..(49)
<223> OTHER INFORMATION: Ile or Val
<220> FEATURE:
<221> NAME/KEY: MOD_RES
<222> LOCATION: (54)..(54)
<223> OTHER INFORMATION: Ile or Val
<220> FEATURE:
<221> NAME/KEY: MOD_RES
<222> LOCATION: (59)..(59)
<223> OTHER INFORMATION: Ile or Val
<220> FEATURE:
<221> NAME/KEY: MOD_RES
<222> LOCATION: (64)..(64)
<223> OTHER INFORMATION: Ile or Val
<220> FEATURE:
<221> NAME/KEY: MOD_RES
<222> LOCATION: (69)..(69)
<223> OTHER INFORMATION: Ile or Val
<220> FEATURE:
<221> NAME/KEY: MOD_RES
<222> LOCATION: (74)..(74)
<223> OTHER INFORMATION: Ile or Val

<400> SEQUENCE: 74

Met Gly Trp Gly Ser Lys Cys Thr Ser Ala Gly Ala Gly Ala Gly Pro
1               5                   10                  15

Glu Gly Arg Gly Asp Ser Thr Ser Gly Leu Val Gly Xaa Pro Ala Val
            20                  25                  30

Gly Xaa Pro Ala Val Gly Xaa Pro Ala Val Gly Xaa Pro Ala Val Gly
        35                  40                  45

Xaa Pro Ala Val Gly Xaa Pro Ala Val Gly Xaa Pro Ala Val Gly Xaa
    50                  55                  60
```

```
Pro Ala Val Gly Xaa Pro Ala Val Gly Xaa Pro Ala Val Gly Glu Thr
 65                  70                  75                  80

Thr Ser Arg Gly Asp Ser Ala Gly Ala Gly Pro Glu Gly Thr
                 85                  90                  95

Ser Cys Lys Leu
            100

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Met Gly Trp Gly Ser Ala Ser Gly Leu Val Gly
1               5                   10

<210> SEQ ID NO 76
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Lys Cys Thr Ser Ala Gly Ala Gly Ala Gly Pro Glu Gly Arg Gly Asp
1               5                   10                  15

Ser

<210> SEQ ID NO 77
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Met Gly Trp Gly Ser Lys Cys Thr Ser Ala Gly Ala Gly Ala Gly Pro
1               5                   10                  15

Glu Gly Arg Gly Asp Ser Thr Ser Gly Leu Val Gly
            20                  25

<210> SEQ ID NO 78
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Met Gly Trp Gly Ser Lys Cys Thr Ser Ala Gly Ala Gly Ala Gly Pro
1               5                   10                  15

Glu Gly Arg Gly Asp Ser Thr Ser Gly Leu Val Gly Arg Gly Asp
            20                  25                  30

<210> SEQ ID NO 79
<211> LENGTH: 32
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 79

Met Gly Trp Gly Ser Lys Cys Thr Ser Ala Gly Ala Gly Ala Gly Pro
1               5                   10                  15

Glu Gly Arg Gly Asp Ser Thr Ser Gly Leu Val Gly Arg Gly Asp Ser
            20                  25                  30

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Glu Thr Thr Ser
1

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Cys Arg Gly Asp
1

<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Gly Asp Ser Ala Gly Ala Gly Ala Gly Pro Glu Gly Thr Ser Cys
1               5                   10                  15

Lys

<210> SEQ ID NO 83
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Arg Gly Asp Ser Glu Thr Thr Ser Arg Gly Asp Ser Ala Gly Ala Gly
1               5                   10                  15

Ala Gly Pro Glu Gly Thr Ser Cys Lys Leu
            20                  25

<210> SEQ ID NO 84
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

Glu Thr Thr Ser Arg Gly Asp Ser Ala Gly Ala Gly Ala Gly Pro Glu
1               5                   10                  15

Gly Thr Ser Cys Lys Leu
            20

<210> SEQ ID NO 85
<211> LENGTH: 2558
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(32)
<223> OTHER INFORMATION: This region may encompass "MGWGSASGLVG",
      "KCTSAGAGAGPEGRGDS", "MGWGSKCTSAGAGAGPEGRGDSTSGLVG",
      "MGWGSKCTSAGAGAGPEGRGDS TSGLVGRGD", or
      "MGWGSKCTSAGAGAGPEGRGDSTSGLVGRGDS", wherein some positions may be
      absent
<220> FEATURE:
<221> NAME/KEY: MOD_RES
<222> LOCATION: (33)..(33)
<223> OTHER INFORMATION: Ile or Val
<220> FEATURE:
<221> NAME/KEY: MOD_RES
<222> LOCATION: (38)..(38)
<223> OTHER INFORMATION: Ile or Val
<220> FEATURE:
<221> NAME/KEY: MOD_RES
<222> LOCATION: (43)..(43)
<223> OTHER INFORMATION: Ile or Val
<220> FEATURE:
<221> NAME/KEY: MOD_RES
<222> LOCATION: (48)..(48)
<223> OTHER INFORMATION: Ile or Val
<220> FEATURE:
<221> NAME/KEY: MOD_RES
<222> LOCATION: (53)..(53)
<223> OTHER INFORMATION: Ile or Val
<220> FEATURE:
<221> NAME/KEY: MOD_RES
<222> LOCATION: (58)..(58)
<223> OTHER INFORMATION: Ile or Val
<220> FEATURE:
<221> NAME/KEY: MOD_RES
<222> LOCATION: (63)..(63)
<223> OTHER INFORMATION: Ile or Val
<220> FEATURE:
<221> NAME/KEY: MOD_RES
<222> LOCATION: (68)..(68)
<223> OTHER INFORMATION: Ile or Val
<220> FEATURE:
<221> NAME/KEY: MOD_RES
<222> LOCATION: (73)..(73)
<223> OTHER INFORMATION: Ile or Val
<220> FEATURE:
<221> NAME/KEY: MOD_RES
<222> LOCATION: (78)..(78)
<223> OTHER INFORMATION: Ile or Val
<220> FEATURE:
<221> NAME/KEY: MOD_RES
<222> LOCATION: (83)..(83)
<223> OTHER INFORMATION: Ile or Val
<220> FEATURE:
<221> NAME/KEY: MOD_RES
<222> LOCATION: (88)..(88)
<223> OTHER INFORMATION: Ile or Val
<220> FEATURE:
<221> NAME/KEY: MOD_RES
<222> LOCATION: (93)..(93)
<223> OTHER INFORMATION: Ile or Val
<220> FEATURE:

```
<221> NAME/KEY: MOD_RES
<222> LOCATION: (98)..(98)
<223> OTHER INFORMATION: Ile or Val
<220> FEATURE:
<221> NAME/KEY: MOD_RES
<222> LOCATION: (103)..(103)
<223> OTHER INFORMATION: Ile or Val
<220> FEATURE:
<221> NAME/KEY: MOD_RES
<222> LOCATION: (108)..(108)
<223> OTHER INFORMATION: Ile or Val
<220> FEATURE:
<221> NAME/KEY: MOD_RES
<222> LOCATION: (113)..(113)
<223> OTHER INFORMATION: Ile or Val
<220> FEATURE:
<221> NAME/KEY: MOD_RES
<222> LOCATION: (118)..(118)
<223> OTHER INFORMATION: Ile or Val
<220> FEATURE:
<221> NAME/KEY: MOD_RES
<222> LOCATION: (123)..(123)
<223> OTHER INFORMATION: Ile or Val
<220> FEATURE:
<221> NAME/KEY: MOD_RES
<222> LOCATION: (128)..(128)
<223> OTHER INFORMATION: Ile or Val
<220> FEATURE:
<221> NAME/KEY: MOD_RES
<222> LOCATION: (133)..(133)
<223> OTHER INFORMATION: Ile or Val
<220> FEATURE:
<221> NAME/KEY: MOD_RES
<222> LOCATION: (138)..(138)
<223> OTHER INFORMATION: Ile or Val
<220> FEATURE:
<221> NAME/KEY: MOD_RES
<222> LOCATION: (143)..(143)
<223> OTHER INFORMATION: Ile or Val
<220> FEATURE:
<221> NAME/KEY: MOD_RES
<222> LOCATION: (148)..(148)
<223> OTHER INFORMATION: Ile or Val
<220> FEATURE:
<221> NAME/KEY: MOD_RES
<222> LOCATION: (153)..(153)
<223> OTHER INFORMATION: Ile or Val
<220> FEATURE:
<221> NAME/KEY: MOD_RES
<222> LOCATION: (158)..(158)
<223> OTHER INFORMATION: Ile or Val
<220> FEATURE:
<221> NAME/KEY: MOD_RES
<222> LOCATION: (163)..(163)
<223> OTHER INFORMATION: Ile or Val
<220> FEATURE:
<221> NAME/KEY: MOD_RES
<222> LOCATION: (168)..(168)
<223> OTHER INFORMATION: Ile or Val
<220> FEATURE:
<221> NAME/KEY: MOD_RES
<222> LOCATION: (173)..(173)
<223> OTHER INFORMATION: Ile or Val
<220> FEATURE:
<221> NAME/KEY: MOD_RES
<222> LOCATION: (178)..(178)
<223> OTHER INFORMATION: Ile or Val
<220> FEATURE:
<221> NAME/KEY: MOD_RES
<222> LOCATION: (183)..(183)
<223> OTHER INFORMATION: Ile or Val
<220> FEATURE:
<221> NAME/KEY: MOD_RES
<222> LOCATION: (188)..(188)
<223> OTHER INFORMATION: Ile or Val
<220> FEATURE:
<221> NAME/KEY: MOD_RES
<222> LOCATION: (193)..(193)
<223> OTHER INFORMATION: Ile or Val
```

```
<220> FEATURE:
<221> NAME/KEY: MOD_RES
<222> LOCATION: (198)..(198)
<223> OTHER INFORMATION: Ile or Val
<220> FEATURE:
<221> NAME/KEY: MOD_RES
<222> LOCATION: (203)..(203)
<223> OTHER INFORMATION: Ile or Val
<220> FEATURE:
<221> NAME/KEY: MOD_RES
<222> LOCATION: (208)..(208)
<223> OTHER INFORMATION: Ile or Val
<220> FEATURE:
<221> NAME/KEY: MOD_RES
<222> LOCATION: (213)..(213)
<223> OTHER INFORMATION: Ile or Val
<220> FEATURE:
<221> NAME/KEY: MOD_RES
<222> LOCATION: (218)..(218)
<223> OTHER INFORMATION: Ile or Val
<220> FEATURE:
<221> NAME/KEY: MOD_RES
<222> LOCATION: (223)..(223)
<223> OTHER INFORMATION: Ile or Val
<220> FEATURE:
<221> NAME/KEY: MOD_RES
<222> LOCATION: (228)..(228)
<223> OTHER INFORMATION: Ile or Val
<220> FEATURE:
<221> NAME/KEY: MOD_RES
<222> LOCATION: (233)..(233)
<223> OTHER INFORMATION: Ile or Val
<220> FEATURE:
<221> NAME/KEY: MOD_RES
<222> LOCATION: (238)..(238)
<223> OTHER INFORMATION: Ile or Val
<220> FEATURE:
<221> NAME/KEY: MOD_RES
<222> LOCATION: (243)..(243)
<223> OTHER INFORMATION: Ile or Val
<220> FEATURE:
<221> NAME/KEY: MOD_RES
<222> LOCATION: (248)..(248)
<223> OTHER INFORMATION: Ile or Val
<220> FEATURE:
<221> NAME/KEY: MOD_RES
<222> LOCATION: (253)..(253)
<223> OTHER INFORMATION: Ile or Val
<220> FEATURE:
<221> NAME/KEY: MOD_RES
<222> LOCATION: (258)..(258)
<223> OTHER INFORMATION: Ile or Val
<220> FEATURE:
<221> NAME/KEY: MOD_RES
<222> LOCATION: (263)..(263)
<223> OTHER INFORMATION: Ile or Val
<220> FEATURE:
<221> NAME/KEY: MOD_RES
<222> LOCATION: (268)..(268)
<223> OTHER INFORMATION: Ile or Val
<220> FEATURE:
<221> NAME/KEY: MOD_RES
<222> LOCATION: (273)..(273)
<223> OTHER INFORMATION: Ile or Val
<220> FEATURE:
<221> NAME/KEY: MOD_RES
<222> LOCATION: (278)..(278)
<223> OTHER INFORMATION: Ile or Val
<220> FEATURE:
<221> NAME/KEY: MOD_RES
<222> LOCATION: (283)..(283)
<223> OTHER INFORMATION: Ile or Val
<220> FEATURE:
<221> NAME/KEY: MOD_RES
<222> LOCATION: (288)..(288)
<223> OTHER INFORMATION: Ile or Val
<220> FEATURE:
<221> NAME/KEY: MOD_RES
<222> LOCATION: (293)..(293)
```

```
<223> OTHER INFORMATION: Ile or Val
<220> FEATURE:
<221> NAME/KEY: MOD_RES
<222> LOCATION: (298)..(298)
<223> OTHER INFORMATION: Ile or Val
<220> FEATURE:
<221> NAME/KEY: MOD_RES
<222> LOCATION: (303)..(303)
<223> OTHER INFORMATION: Ile or Val
<220> FEATURE:
<221> NAME/KEY: MOD_RES
<222> LOCATION: (308)..(308)
<223> OTHER INFORMATION: Ile or Val
<220> FEATURE:
<221> NAME/KEY: MOD_RES
<222> LOCATION: (313)..(313)
<223> OTHER INFORMATION: Ile or Val
<220> FEATURE:
<221> NAME/KEY: MOD_RES
<222> LOCATION: (318)..(318)
<223> OTHER INFORMATION: Ile or Val
<220> FEATURE:
<221> NAME/KEY: MOD_RES
<222> LOCATION: (323)..(323)
<223> OTHER INFORMATION: Ile or Val
<220> FEATURE:
<221> NAME/KEY: MOD_RES
<222> LOCATION: (328)..(328)
<223> OTHER INFORMATION: Ile or Val
<220> FEATURE:
<221> NAME/KEY: MOD_RES
<222> LOCATION: (333)..(333)
<223> OTHER INFORMATION: Ile or Val
<220> FEATURE:
<221> NAME/KEY: MOD_RES
<222> LOCATION: (338)..(338)
<223> OTHER INFORMATION: Ile or Val
<220> FEATURE:
<221> NAME/KEY: MOD_RES
<222> LOCATION: (343)..(343)
<223> OTHER INFORMATION: Ile or Val
<220> FEATURE:
<221> NAME/KEY: MOD_RES
<222> LOCATION: (348)..(348)
<223> OTHER INFORMATION: Ile or Val
<220> FEATURE:
<221> NAME/KEY: MOD_RES
<222> LOCATION: (353)..(353)
<223> OTHER INFORMATION: Ile or Val
<220> FEATURE:
<221> NAME/KEY: MOD_RES
<222> LOCATION: (358)..(358)
<223> OTHER INFORMATION: Ile or Val
<220> FEATURE:
<221> NAME/KEY: MOD_RES
<222> LOCATION: (363)..(363)
<223> OTHER INFORMATION: Ile or Val
<220> FEATURE:
<221> NAME/KEY: MOD_RES
<222> LOCATION: (368)..(368)
<223> OTHER INFORMATION: Ile or Val
<220> FEATURE:
<221> NAME/KEY: MOD_RES
<222> LOCATION: (373)..(373)
<223> OTHER INFORMATION: Ile or Val
<220> FEATURE:
<221> NAME/KEY: MOD_RES
<222> LOCATION: (378)..(378)
<223> OTHER INFORMATION: Ile or Val
<220> FEATURE:
<221> NAME/KEY: MOD_RES
<222> LOCATION: (383)..(383)
<223> OTHER INFORMATION: Ile or Val
<220> FEATURE:
<221> NAME/KEY: MOD_RES
<222> LOCATION: (388)..(388)
<223> OTHER INFORMATION: Ile or Val
<220> FEATURE:
<221> NAME/KEY: MOD_RES
```

```
<222> LOCATION: (393)..(393)
<223> OTHER INFORMATION: Ile or Val
<220> FEATURE:
<221> NAME/KEY: MOD_RES
<222> LOCATION: (398)..(398)
<223> OTHER INFORMATION: Ile or Val
<220> FEATURE:
<221> NAME/KEY: MOD_RES
<222> LOCATION: (403)..(403)
<223> OTHER INFORMATION: Ile or Val
<220> FEATURE:
<221> NAME/KEY: MOD_RES
<222> LOCATION: (408)..(408)
<223> OTHER INFORMATION: Ile or Val
<220> FEATURE:
<221> NAME/KEY: MOD_RES
<222> LOCATION: (413)..(413)
<223> OTHER INFORMATION: Ile or Val
<220> FEATURE:
<221> NAME/KEY: MOD_RES
<222> LOCATION: (418)..(418)
<223> OTHER INFORMATION: Ile or Val
<220> FEATURE:
<221> NAME/KEY: MOD_RES
<222> LOCATION: (423)..(423)
<223> OTHER INFORMATION: Ile or Val
<220> FEATURE:
<221> NAME/KEY: MOD_RES
<222> LOCATION: (428)..(428)
<223> OTHER INFORMATION: Ile or Val
<220> FEATURE:
<221> NAME/KEY: MOD_RES
<222> LOCATION: (433)..(433)
<223> OTHER INFORMATION: Ile or Val
<220> FEATURE:
<221> NAME/KEY: MOD_RES
<222> LOCATION: (438)..(438)
<223> OTHER INFORMATION: Ile or Val
<220> FEATURE:
<221> NAME/KEY: MOD_RES
<222> LOCATION: (443)..(443)
<223> OTHER INFORMATION: Ile or Val
<220> FEATURE:
<221> NAME/KEY: MOD_RES
<222> LOCATION: (448)..(448)
<223> OTHER INFORMATION: Ile or Val
<220> FEATURE:
<221> NAME/KEY: MOD_RES
<222> LOCATION: (453)..(453)
<223> OTHER INFORMATION: Ile or Val
<220> FEATURE:
<221> NAME/KEY: MOD_RES
<222> LOCATION: (458)..(458)
<223> OTHER INFORMATION: Ile or Val
<220> FEATURE:
<221> NAME/KEY: MOD_RES
<222> LOCATION: (463)..(463)
<223> OTHER INFORMATION: Ile or Val
<220> FEATURE:
<221> NAME/KEY: MOD_RES
<222> LOCATION: (468)..(468)
<223> OTHER INFORMATION: Ile or Val
<220> FEATURE:
<221> NAME/KEY: MOD_RES
<222> LOCATION: (473)..(473)
<223> OTHER INFORMATION: Ile or Val
<220> FEATURE:
<221> NAME/KEY: MOD_RES
<222> LOCATION: (478)..(478)
<223> OTHER INFORMATION: Ile or Val
<220> FEATURE:
<221> NAME/KEY: MOD_RES
<222> LOCATION: (483)..(483)
<223> OTHER INFORMATION: Ile or Val
<220> FEATURE:
<221> NAME/KEY: MOD_RES
<222> LOCATION: (488)..(488)
<223> OTHER INFORMATION: Ile or Val
<220> FEATURE:
```

```
<221> NAME/KEY: MOD_RES
<222> LOCATION: (493)..(493)
<223> OTHER INFORMATION: Ile or Val
<220> FEATURE:
<221> NAME/KEY: MOD_RES
<222> LOCATION: (498)..(498)
<223> OTHER INFORMATION: Ile or Val
<220> FEATURE:
<221> NAME/KEY: MOD_RES
<222> LOCATION: (503)..(503)
<223> OTHER INFORMATION: Ile or Val
<220> FEATURE:
<221> NAME/KEY: MOD_RES
<222> LOCATION: (508)..(508)
<223> OTHER INFORMATION: Ile or Val
<220> FEATURE:
<221> NAME/KEY: MOD_RES
<222> LOCATION: (513)..(513)
<223> OTHER INFORMATION: Ile or Val
<220> FEATURE:
<221> NAME/KEY: MOD_RES
<222> LOCATION: (518)..(518)
<223> OTHER INFORMATION: Ile or Val
<220> FEATURE:
<221> NAME/KEY: MOD_RES
<222> LOCATION: (523)..(523)
<223> OTHER INFORMATION: Ile or Val
<220> FEATURE:
<221> NAME/KEY: MOD_RES
<222> LOCATION: (528)..(528)
<223> OTHER INFORMATION: Ile or Val
<220> FEATURE:
<221> NAME/KEY: MOD_RES
<222> LOCATION: (533)..(533)
<223> OTHER INFORMATION: Ile or Val
<220> FEATURE:
<221> NAME/KEY: MOD_RES
<222> LOCATION: (538)..(538)
<223> OTHER INFORMATION: Ile or Val
<220> FEATURE:
<221> NAME/KEY: MOD_RES
<222> LOCATION: (543)..(543)
<223> OTHER INFORMATION: Ile or Val
<220> FEATURE:
<221> NAME/KEY: MOD_RES
<222> LOCATION: (548)..(548)
<223> OTHER INFORMATION: Ile or Val
<220> FEATURE:
<221> NAME/KEY: MOD_RES
<222> LOCATION: (553)..(553)
<223> OTHER INFORMATION: Ile or Val
<220> FEATURE:
<221> NAME/KEY: MOD_RES
<222> LOCATION: (558)..(558)
<223> OTHER INFORMATION: Ile or Val
<220> FEATURE:
<221> NAME/KEY: MOD_RES
<222> LOCATION: (563)..(563)
<223> OTHER INFORMATION: Ile or Val
<220> FEATURE:
<221> NAME/KEY: MOD_RES
<222> LOCATION: (568)..(568)
<223> OTHER INFORMATION: Ile or Val
<220> FEATURE:
<221> NAME/KEY: MOD_RES
<222> LOCATION: (573)..(573)
<223> OTHER INFORMATION: Ile or Val
<220> FEATURE:
<221> NAME/KEY: MOD_RES
<222> LOCATION: (578)..(578)
<223> OTHER INFORMATION: Ile or Val
<220> FEATURE:
<221> NAME/KEY: MOD_RES
<222> LOCATION: (583)..(583)
<223> OTHER INFORMATION: Ile or Val
<220> FEATURE:
<221> NAME/KEY: MOD_RES
<222> LOCATION: (588)..(588)
<223> OTHER INFORMATION: Ile or Val
```

```
<220> FEATURE:
<221> NAME/KEY: MOD_RES
<222> LOCATION: (593)..(593)
<223> OTHER INFORMATION: Ile or Val
<220> FEATURE:
<221> NAME/KEY: MOD_RES
<222> LOCATION: (598)..(598)
<223> OTHER INFORMATION: Ile or Val
<220> FEATURE:
<221> NAME/KEY: MOD_RES
<222> LOCATION: (603)..(603)
<223> OTHER INFORMATION: Ile or Val
<220> FEATURE:
<221> NAME/KEY: MOD_RES
<222> LOCATION: (608)..(608)
<223> OTHER INFORMATION: Ile or Val
<220> FEATURE:
<221> NAME/KEY: MOD_RES
<222> LOCATION: (613)..(613)
<223> OTHER INFORMATION: Ile or Val
<220> FEATURE:
<221> NAME/KEY: MOD_RES
<222> LOCATION: (618)..(618)
<223> OTHER INFORMATION: Ile or Val
<220> FEATURE:
<221> NAME/KEY: MOD_RES
<222> LOCATION: (623)..(623)
<223> OTHER INFORMATION: Ile or Val
<220> FEATURE:
<221> NAME/KEY: MOD_RES
<222> LOCATION: (628)..(628)
<223> OTHER INFORMATION: Ile or Val
<220> FEATURE:
<221> NAME/KEY: MOD_RES
<222> LOCATION: (633)..(633)
<223> OTHER INFORMATION: Ile or Val
<220> FEATURE:
<221> NAME/KEY: MOD_RES
<222> LOCATION: (638)..(638)
<223> OTHER INFORMATION: Ile or Val
<220> FEATURE:
<221> NAME/KEY: MOD_RES
<222> LOCATION: (643)..(643)
<223> OTHER INFORMATION: Ile or Val
<220> FEATURE:
<221> NAME/KEY: MOD_RES
<222> LOCATION: (648)..(648)
<223> OTHER INFORMATION: Ile or Val
<220> FEATURE:
<221> NAME/KEY: MOD_RES
<222> LOCATION: (653)..(653)
<223> OTHER INFORMATION: Ile or Val
<220> FEATURE:
<221> NAME/KEY: MOD_RES
<222> LOCATION: (658)..(658)
<223> OTHER INFORMATION: Ile or Val
<220> FEATURE:
<221> NAME/KEY: MOD_RES
<222> LOCATION: (663)..(663)
<223> OTHER INFORMATION: Ile or Val
<220> FEATURE:
<221> NAME/KEY: MOD_RES
<222> LOCATION: (668)..(668)
<223> OTHER INFORMATION: Ile or Val
<220> FEATURE:
<221> NAME/KEY: MOD_RES
<222> LOCATION: (673)..(673)
<223> OTHER INFORMATION: Ile or Val
<220> FEATURE:
<221> NAME/KEY: MOD_RES
<222> LOCATION: (678)..(678)
<223> OTHER INFORMATION: Ile or Val
<220> FEATURE:
<221> NAME/KEY: MOD_RES
<222> LOCATION: (683)..(683)
<223> OTHER INFORMATION: Ile or Val
<220> FEATURE:
<221> NAME/KEY: MOD_RES
<222> LOCATION: (688)..(688)
```

```
<223> OTHER INFORMATION: Ile or Val
<220> FEATURE:
<221> NAME/KEY: MOD_RES
<222> LOCATION: (693)..(693)
<223> OTHER INFORMATION: Ile or Val
<220> FEATURE:
<221> NAME/KEY: MOD_RES
<222> LOCATION: (698)..(698)
<223> OTHER INFORMATION: Ile or Val
<220> FEATURE:
<221> NAME/KEY: MOD_RES
<222> LOCATION: (703)..(703)
<223> OTHER INFORMATION: Ile or Val
<220> FEATURE:
<221> NAME/KEY: MOD_RES
<222> LOCATION: (708)..(708)
<223> OTHER INFORMATION: Ile or Val
<220> FEATURE:
<221> NAME/KEY: MOD_RES
<222> LOCATION: (713)..(713)
<223> OTHER INFORMATION: Ile or Val
<220> FEATURE:
<221> NAME/KEY: MOD_RES
<222> LOCATION: (718)..(718)
<223> OTHER INFORMATION: Ile or Val
<220> FEATURE:
<221> NAME/KEY: MOD_RES
<222> LOCATION: (723)..(723)
<223> OTHER INFORMATION: Ile or Val
<220> FEATURE:
<221> NAME/KEY: MOD_RES
<222> LOCATION: (728)..(728)
<223> OTHER INFORMATION: Ile or Val
<220> FEATURE:
<221> NAME/KEY: MOD_RES
<222> LOCATION: (733)..(733)
<223> OTHER INFORMATION: Ile or Val
<220> FEATURE:
<221> NAME/KEY: MOD_RES
<222> LOCATION: (738)..(738)
<223> OTHER INFORMATION: Ile or Val
<220> FEATURE:
<221> NAME/KEY: MOD_RES
<222> LOCATION: (743)..(743)
<223> OTHER INFORMATION: Ile or Val
<220> FEATURE:
<221> NAME/KEY: MOD_RES
<222> LOCATION: (748)..(748)
<223> OTHER INFORMATION: Ile or Val
<220> FEATURE:
<221> NAME/KEY: MOD_RES
<222> LOCATION: (753)..(753)
<223> OTHER INFORMATION: Ile or Val
<220> FEATURE:
<221> NAME/KEY: MOD_RES
<222> LOCATION: (758)..(758)
<223> OTHER INFORMATION: Ile or Val
<220> FEATURE:
<221> NAME/KEY: MOD_RES
<222> LOCATION: (763)..(763)
<223> OTHER INFORMATION: Ile or Val
<220> FEATURE:
<221> NAME/KEY: MOD_RES
<222> LOCATION: (768)..(768)
<223> OTHER INFORMATION: Ile or Val
<220> FEATURE:
<221> NAME/KEY: MOD_RES
<222> LOCATION: (773)..(773)
<223> OTHER INFORMATION: Ile or Val
<220> FEATURE:
<221> NAME/KEY: MOD_RES
<222> LOCATION: (778)..(778)
<223> OTHER INFORMATION: Ile or Val
<220> FEATURE:
<221> NAME/KEY: MOD_RES
<222> LOCATION: (783)..(783)
<223> OTHER INFORMATION: Ile or Val
<220> FEATURE:
<221> NAME/KEY: MOD_RES
```

```
<222> LOCATION: (788)..(788)
<223> OTHER INFORMATION: Ile or Val
<220> FEATURE:
<221> NAME/KEY: MOD_RES
<222> LOCATION: (793)..(793)
<223> OTHER INFORMATION: Ile or Val
<220> FEATURE:
<221> NAME/KEY: MOD_RES
<222> LOCATION: (798)..(798)
<223> OTHER INFORMATION: Ile or Val
<220> FEATURE:
<221> NAME/KEY: MOD_RES
<222> LOCATION: (803)..(803)
<223> OTHER INFORMATION: Ile or Val
<220> FEATURE:
<221> NAME/KEY: MOD_RES
<222> LOCATION: (808)..(808)
<223> OTHER INFORMATION: Ile or Val
<220> FEATURE:
<221> NAME/KEY: MOD_RES
<222> LOCATION: (813)..(813)
<223> OTHER INFORMATION: Ile or Val
<220> FEATURE:
<221> NAME/KEY: MOD_RES
<222> LOCATION: (818)..(818)
<223> OTHER INFORMATION: Ile or Val
<220> FEATURE:
<221> NAME/KEY: MOD_RES
<222> LOCATION: (823)..(823)
<223> OTHER INFORMATION: Ile or Val
<220> FEATURE:
<221> NAME/KEY: MOD_RES
<222> LOCATION: (828)..(828)
<223> OTHER INFORMATION: Ile or Val
<220> FEATURE:
<221> NAME/KEY: MOD_RES
<222> LOCATION: (833)..(833)
<223> OTHER INFORMATION: Ile or Val
<220> FEATURE:
<221> NAME/KEY: MOD_RES
<222> LOCATION: (838)..(838)
<223> OTHER INFORMATION: Ile or Val
<220> FEATURE:
<221> NAME/KEY: MOD_RES
<222> LOCATION: (843)..(843)
<223> OTHER INFORMATION: Ile or Val
<220> FEATURE:
<221> NAME/KEY: MOD_RES
<222> LOCATION: (848)..(848)
<223> OTHER INFORMATION: Ile or Val
<220> FEATURE:
<221> NAME/KEY: MOD_RES
<222> LOCATION: (853)..(853)
<223> OTHER INFORMATION: Ile or Val
<220> FEATURE:
<221> NAME/KEY: MOD_RES
<222> LOCATION: (858)..(858)
<223> OTHER INFORMATION: Ile or Val
<220> FEATURE:
<221> NAME/KEY: MOD_RES
<222> LOCATION: (863)..(863)
<223> OTHER INFORMATION: Ile or Val
<220> FEATURE:
<221> NAME/KEY: MOD_RES
<222> LOCATION: (868)..(868)
<223> OTHER INFORMATION: Ile or Val
<220> FEATURE:
<221> NAME/KEY: MOD_RES
<222> LOCATION: (873)..(873)
<223> OTHER INFORMATION: Ile or Val
<220> FEATURE:
<221> NAME/KEY: MOD_RES
<222> LOCATION: (878)..(878)
<223> OTHER INFORMATION: Ile or Val
<220> FEATURE:
<221> NAME/KEY: MOD_RES
<222> LOCATION: (883)..(883)
<223> OTHER INFORMATION: Ile or Val
<220> FEATURE:
```

-continued

```
<221> NAME/KEY: MOD_RES
<222> LOCATION: (888)..(888)
<223> OTHER INFORMATION: Ile or Val
<220> FEATURE:
<221> NAME/KEY: MOD_RES
<222> LOCATION: (893)..(893)
<223> OTHER INFORMATION: Ile or Val
<220> FEATURE:
<221> NAME/KEY: MOD_RES
<222> LOCATION: (898)..(898)
<223> OTHER INFORMATION: Ile or Val
<220> FEATURE:
<221> NAME/KEY: MOD_RES
<222> LOCATION: (903)..(903)
<223> OTHER INFORMATION: Ile or Val
<220> FEATURE:
<221> NAME/KEY: MOD_RES
<222> LOCATION: (908)..(908)
<223> OTHER INFORMATION: Ile or Val
<220> FEATURE:
<221> NAME/KEY: MOD_RES
<222> LOCATION: (913)..(913)
<223> OTHER INFORMATION: Ile or Val
<220> FEATURE:
<221> NAME/KEY: MOD_RES
<222> LOCATION: (918)..(918)
<223> OTHER INFORMATION: Ile or Val
<220> FEATURE:
<221> NAME/KEY: MOD_RES
<222> LOCATION: (923)..(923)
<223> OTHER INFORMATION: Ile or Val
<220> FEATURE:
<221> NAME/KEY: MOD_RES
<222> LOCATION: (928)..(928)
<223> OTHER INFORMATION: Ile or Val
<220> FEATURE:
<221> NAME/KEY: MOD_RES
<222> LOCATION: (933)..(933)
<223> OTHER INFORMATION: Ile or Val
<220> FEATURE:
<221> NAME/KEY: MOD_RES
<222> LOCATION: (938)..(938)
<223> OTHER INFORMATION: Ile or Val
<220> FEATURE:
<221> NAME/KEY: MOD_RES
<222> LOCATION: (943)..(943)
<223> OTHER INFORMATION: Ile or Val
<220> FEATURE:
<221> NAME/KEY: MOD_RES
<222> LOCATION: (948)..(948)
<223> OTHER INFORMATION: Ile or Val
<220> FEATURE:
<221> NAME/KEY: MOD_RES
<222> LOCATION: (953)..(953)
<223> OTHER INFORMATION: Ile or Val
<220> FEATURE:
<221> NAME/KEY: MOD_RES
<222> LOCATION: (958)..(958)
<223> OTHER INFORMATION: Ile or Val
<220> FEATURE:
<221> NAME/KEY: MOD_RES
<222> LOCATION: (963)..(963)
<223> OTHER INFORMATION: Ile or Val
<220> FEATURE:
<221> NAME/KEY: MOD_RES
<222> LOCATION: (968)..(968)
<223> OTHER INFORMATION: Ile or Val
<220> FEATURE:
<221> NAME/KEY: MOD_RES
<222> LOCATION: (973)..(973)
<223> OTHER INFORMATION: Ile or Val
<220> FEATURE:
<221> NAME/KEY: MOD_RES
<222> LOCATION: (978)..(978)
<223> OTHER INFORMATION: Ile or Val
<220> FEATURE:
<221> NAME/KEY: MOD_RES
<222> LOCATION: (983)..(983)
<223> OTHER INFORMATION: Ile or Val
```

```
<220> FEATURE:
<221> NAME/KEY: MOD_RES
<222> LOCATION: (988)..(988)
<223> OTHER INFORMATION: Ile or Val
<220> FEATURE:
<221> NAME/KEY: MOD_RES
<222> LOCATION: (993)..(993)
<223> OTHER INFORMATION: Ile or Val
<220> FEATURE:
<221> NAME/KEY: MOD_RES
<222> LOCATION: (998)..(998)
<223> OTHER INFORMATION: Ile or Val
<220> FEATURE:
<221> NAME/KEY: MOD_RES
<222> LOCATION: (1003)..(1003)
<223> OTHER INFORMATION: Ile or Val
<220> FEATURE:
<221> NAME/KEY: MOD_RES
<222> LOCATION: (1008)..(1008)
<223> OTHER INFORMATION: Ile or Val
<220> FEATURE:
<221> NAME/KEY: MOD_RES
<222> LOCATION: (1013)..(1013)
<223> OTHER INFORMATION: Ile or Val
<220> FEATURE:
<221> NAME/KEY: MOD_RES
<222> LOCATION: (1018)..(1018)
<223> OTHER INFORMATION: Ile or Val
<220> FEATURE:
<221> NAME/KEY: MOD_RES
<222> LOCATION: (1023)..(1023)
<223> OTHER INFORMATION: Ile or Val
<220> FEATURE:
<221> NAME/KEY: MOD_RES
<222> LOCATION: (1028)..(1028)
<223> OTHER INFORMATION: Ile or Val
<220> FEATURE:
<221> NAME/KEY: MOD_RES
<222> LOCATION: (1033)..(1033)
<223> OTHER INFORMATION: Ile or Val
<220> FEATURE:
<221> NAME/KEY: MOD_RES
<222> LOCATION: (1038)..(1038)
<223> OTHER INFORMATION: Ile or Val
<220> FEATURE:
<221> NAME/KEY: MOD_RES
<222> LOCATION: (1043)..(1043)
<223> OTHER INFORMATION: Ile or Val
<220> FEATURE:
<221> NAME/KEY: MOD_RES
<222> LOCATION: (1048)..(1048)
<223> OTHER INFORMATION: Ile or Val
<220> FEATURE:
<221> NAME/KEY: MOD_RES
<222> LOCATION: (1053)..(1053)
<223> OTHER INFORMATION: Ile or Val
<220> FEATURE:
<221> NAME/KEY: MOD_RES
<222> LOCATION: (1058)..(1058)
<223> OTHER INFORMATION: Ile or Val
<220> FEATURE:
<221> NAME/KEY: MOD_RES
<222> LOCATION: (1063)..(1063)
<223> OTHER INFORMATION: Ile or Val
<220> FEATURE:
<221> NAME/KEY: MOD_RES
<222> LOCATION: (1068)..(1068)
<223> OTHER INFORMATION: Ile or Val
<220> FEATURE:
<221> NAME/KEY: MOD_RES
<222> LOCATION: (1073)..(1073)
<223> OTHER INFORMATION: Ile or Val
<220> FEATURE:
<221> NAME/KEY: MOD_RES
<222> LOCATION: (1078)..(1078)
<223> OTHER INFORMATION: Ile or Val
<220> FEATURE:
<221> NAME/KEY: MOD_RES
<222> LOCATION: (1083)..(1083)
```

```
<223> OTHER INFORMATION: Ile or Val
<220> FEATURE:
<221> NAME/KEY: MOD_RES
<222> LOCATION: (1088)..(1088)
<223> OTHER INFORMATION: Ile or Val
<220> FEATURE:
<221> NAME/KEY: MOD_RES
<222> LOCATION: (1093)..(1093)
<223> OTHER INFORMATION: Ile or Val
<220> FEATURE:
<221> NAME/KEY: MOD_RES
<222> LOCATION: (1098)..(1098)
<223> OTHER INFORMATION: Ile or Val
<220> FEATURE:
<221> NAME/KEY: MOD_RES
<222> LOCATION: (1103)..(1103)
<223> OTHER INFORMATION: Ile or Val
<220> FEATURE:
<221> NAME/KEY: MOD_RES
<222> LOCATION: (1108)..(1108)
<223> OTHER INFORMATION: Ile or Val
<220> FEATURE:
<221> NAME/KEY: MOD_RES
<222> LOCATION: (1113)..(1113)
<223> OTHER INFORMATION: Ile or Val
<220> FEATURE:
<221> NAME/KEY: MOD_RES
<222> LOCATION: (1118)..(1118)
<223> OTHER INFORMATION: Ile or Val
<220> FEATURE:
<221> NAME/KEY: MOD_RES
<222> LOCATION: (1123)..(1123)
<223> OTHER INFORMATION: Ile or Val
<220> FEATURE:
<221> NAME/KEY: MOD_RES
<222> LOCATION: (1128)..(1128)
<223> OTHER INFORMATION: Ile or Val
<220> FEATURE:
<221> NAME/KEY: MOD_RES
<222> LOCATION: (1133)..(1133)
<223> OTHER INFORMATION: Ile or Val
<220> FEATURE:
<221> NAME/KEY: MOD_RES
<222> LOCATION: (1138)..(1138)
<223> OTHER INFORMATION: Ile or Val
<220> FEATURE:
<221> NAME/KEY: MOD_RES
<222> LOCATION: (1143)..(1143)
<223> OTHER INFORMATION: Ile or Val
<220> FEATURE:
<221> NAME/KEY: MOD_RES
<222> LOCATION: (1148)..(1148)
<223> OTHER INFORMATION: Ile or Val
<220> FEATURE:
<221> NAME/KEY: MOD_RES
<222> LOCATION: (1153)..(1153)
<223> OTHER INFORMATION: Ile or Val
<220> FEATURE:
<221> NAME/KEY: MOD_RES
<222> LOCATION: (1158)..(1158)
<223> OTHER INFORMATION: Ile or Val
<220> FEATURE:
<221> NAME/KEY: MOD_RES
<222> LOCATION: (1163)..(1163)
<223> OTHER INFORMATION: Ile or Val
<220> FEATURE:
<221> NAME/KEY: MOD_RES
<222> LOCATION: (1168)..(1168)
<223> OTHER INFORMATION: Ile or Val
<220> FEATURE:
<221> NAME/KEY: MOD_RES
<222> LOCATION: (1173)..(1173)
<223> OTHER INFORMATION: Ile or Val
<220> FEATURE:
<221> NAME/KEY: MOD_RES
<222> LOCATION: (1178)..(1178)
<223> OTHER INFORMATION: Ile or Val
<220> FEATURE:
<221> NAME/KEY: MOD_RES
```

-continued

```
<222> LOCATION: (1183)..(1183)
<223> OTHER INFORMATION: Ile or Val
<220> FEATURE:
<221> NAME/KEY: MOD_RES
<222> LOCATION: (1188)..(1188)
<223> OTHER INFORMATION: Ile or Val
<220> FEATURE:
<221> NAME/KEY: MOD_RES
<222> LOCATION: (1193)..(1193)
<223> OTHER INFORMATION: Ile or Val
<220> FEATURE:
<221> NAME/KEY: MOD_RES
<222> LOCATION: (1198)..(1198)
<223> OTHER INFORMATION: Ile or Val
<220> FEATURE:
<221> NAME/KEY: MOD_RES
<222> LOCATION: (1203)..(1203)
<223> OTHER INFORMATION: Ile or Val
<220> FEATURE:
<221> NAME/KEY: MOD_RES
<222> LOCATION: (1208)..(1208)
<223> OTHER INFORMATION: Ile or Val
<220> FEATURE:
<221> NAME/KEY: MOD_RES
<222> LOCATION: (1213)..(1213)
<223> OTHER INFORMATION: Ile or Val
<220> FEATURE:
<221> NAME/KEY: MOD_RES
<222> LOCATION: (1218)..(1218)
<223> OTHER INFORMATION: Ile or Val
<220> FEATURE:
<221> NAME/KEY: MOD_RES
<222> LOCATION: (1223)..(1223)
<223> OTHER INFORMATION: Ile or Val
<220> FEATURE:
<221> NAME/KEY: MOD_RES
<222> LOCATION: (1228)..(1228)
<223> OTHER INFORMATION: Ile or Val
<220> FEATURE:
<221> NAME/KEY: MOD_RES
<222> LOCATION: (1233)..(1233)
<223> OTHER INFORMATION: Ile or Val
<220> FEATURE:
<221> NAME/KEY: MOD_RES
<222> LOCATION: (1238)..(1238)
<223> OTHER INFORMATION: Ile or Val
<220> FEATURE:
<221> NAME/KEY: MOD_RES
<222> LOCATION: (1243)..(1243)
<223> OTHER INFORMATION: Ile or Val
<220> FEATURE:
<221> NAME/KEY: MOD_RES
<222> LOCATION: (1248)..(1248)
<223> OTHER INFORMATION: Ile or Val
<220> FEATURE:
<221> NAME/KEY: MOD_RES
<222> LOCATION: (1253)..(1253)
<223> OTHER INFORMATION: Ile or Val
<220> FEATURE:
<221> NAME/KEY: MOD_RES
<222> LOCATION: (1258)..(1258)
<223> OTHER INFORMATION: Ile or Val
<220> FEATURE:
<221> NAME/KEY: MOD_RES
<222> LOCATION: (1263)..(1263)
<223> OTHER INFORMATION: Ile or Val
<220> FEATURE:
<221> NAME/KEY: MOD_RES
<222> LOCATION: (1268)..(1268)
<223> OTHER INFORMATION: Ile or Val
<220> FEATURE:
<221> NAME/KEY: MOD_RES
<222> LOCATION: (1273)..(1273)
<223> OTHER INFORMATION: Ile or Val
<220> FEATURE:
<221> NAME/KEY: MOD_RES
<222> LOCATION: (1278)..(1278)
<223> OTHER INFORMATION: Ile or Val
<220> FEATURE:
```

```
<221> NAME/KEY: MOD_RES
<222> LOCATION: (1283)..(1283)
<223> OTHER INFORMATION: Ile or Val
<220> FEATURE:
<221> NAME/KEY: MOD_RES
<222> LOCATION: (1288)..(1288)
<223> OTHER INFORMATION: Ile or Val
<220> FEATURE:
<221> NAME/KEY: MOD_RES
<222> LOCATION: (1293)..(1293)
<223> OTHER INFORMATION: Ile or Val
<220> FEATURE:
<221> NAME/KEY: MOD_RES
<222> LOCATION: (1298)..(1298)
<223> OTHER INFORMATION: Ile or Val
<220> FEATURE:
<221> NAME/KEY: MOD_RES
<222> LOCATION: (1303)..(1303)
<223> OTHER INFORMATION: Ile or Val
<220> FEATURE:
<221> NAME/KEY: MOD_RES
<222> LOCATION: (1308)..(1308)
<223> OTHER INFORMATION: Ile or Val
<220> FEATURE:
<221> NAME/KEY: MOD_RES
<222> LOCATION: (1313)..(1313)
<223> OTHER INFORMATION: Ile or Val
<220> FEATURE:
<221> NAME/KEY: MOD_RES
<222> LOCATION: (1318)..(1318)
<223> OTHER INFORMATION: Ile or Val
<220> FEATURE:
<221> NAME/KEY: MOD_RES
<222> LOCATION: (1323)..(1323)
<223> OTHER INFORMATION: Ile or Val
<220> FEATURE:
<221> NAME/KEY: MOD_RES
<222> LOCATION: (1328)..(1328)
<223> OTHER INFORMATION: Ile or Val
<220> FEATURE:
<221> NAME/KEY: MOD_RES
<222> LOCATION: (1333)..(1333)
<223> OTHER INFORMATION: Ile or Val
<220> FEATURE:
<221> NAME/KEY: MOD_RES
<222> LOCATION: (1338)..(1338)
<223> OTHER INFORMATION: Ile or Val
<220> FEATURE:
<221> NAME/KEY: MOD_RES
<222> LOCATION: (1343)..(1343)
<223> OTHER INFORMATION: Ile or Val
<220> FEATURE:
<221> NAME/KEY: MOD_RES
<222> LOCATION: (1348)..(1348)
<223> OTHER INFORMATION: Ile or Val
<220> FEATURE:
<221> NAME/KEY: MOD_RES
<222> LOCATION: (1353)..(1353)
<223> OTHER INFORMATION: Ile or Val
<220> FEATURE:
<221> NAME/KEY: MOD_RES
<222> LOCATION: (1358)..(1358)
<223> OTHER INFORMATION: Ile or Val
<220> FEATURE:
<221> NAME/KEY: MOD_RES
<222> LOCATION: (1363)..(1363)
<223> OTHER INFORMATION: Ile or Val
<220> FEATURE:
<221> NAME/KEY: MOD_RES
<222> LOCATION: (1368)..(1368)
<223> OTHER INFORMATION: Ile or Val
<220> FEATURE:
<221> NAME/KEY: MOD_RES
<222> LOCATION: (1373)..(1373)
<223> OTHER INFORMATION: Ile or Val
<220> FEATURE:
<221> NAME/KEY: MOD_RES
<222> LOCATION: (1378)..(1378)
<223> OTHER INFORMATION: Ile or Val
```

```
-continued

<220> FEATURE:
<221> NAME/KEY: MOD_RES
<222> LOCATION: (1383)..(1383)
<223> OTHER INFORMATION: Ile or Val
<220> FEATURE:
<221> NAME/KEY: MOD_RES
<222> LOCATION: (1388)..(1388)
<223> OTHER INFORMATION: Ile or Val
<220> FEATURE:
<221> NAME/KEY: MOD_RES
<222> LOCATION: (1393)..(1393)
<223> OTHER INFORMATION: Ile or Val
<220> FEATURE:
<221> NAME/KEY: MOD_RES
<222> LOCATION: (1398)..(1398)
<223> OTHER INFORMATION: Ile or Val
<220> FEATURE:
<221> NAME/KEY: MOD_RES
<222> LOCATION: (1403)..(1403)
<223> OTHER INFORMATION: Ile or Val
<220> FEATURE:
<221> NAME/KEY: MOD_RES
<222> LOCATION: (1408)..(1408)
<223> OTHER INFORMATION: Ile or Val
<220> FEATURE:
<221> NAME/KEY: MOD_RES
<222> LOCATION: (1413)..(1413)
<223> OTHER INFORMATION: Ile or Val
<220> FEATURE:
<221> NAME/KEY: MOD_RES
<222> LOCATION: (1418)..(1418)
<223> OTHER INFORMATION: Ile or Val
<220> FEATURE:
<221> NAME/KEY: MOD_RES
<222> LOCATION: (1423)..(1423)
<223> OTHER INFORMATION: Ile or Val
<220> FEATURE:
<221> NAME/KEY: MOD_RES
<222> LOCATION: (1428)..(1428)
<223> OTHER INFORMATION: Ile or Val
<220> FEATURE:
<221> NAME/KEY: MOD_RES
<222> LOCATION: (1433)..(1433)
<223> OTHER INFORMATION: Ile or Val
<220> FEATURE:
<221> NAME/KEY: MOD_RES
<222> LOCATION: (1438)..(1438)
<223> OTHER INFORMATION: Ile or Val
<220> FEATURE:
<221> NAME/KEY: MOD_RES
<222> LOCATION: (1443)..(1443)
<223> OTHER INFORMATION: Ile or Val
<220> FEATURE:
<221> NAME/KEY: MOD_RES
<222> LOCATION: (1448)..(1448)
<223> OTHER INFORMATION: Ile or Val
<220> FEATURE:
<221> NAME/KEY: MOD_RES
<222> LOCATION: (1453)..(1453)
<223> OTHER INFORMATION: Ile or Val
<220> FEATURE:
<221> NAME/KEY: MOD_RES
<222> LOCATION: (1458)..(1458)
<223> OTHER INFORMATION: Ile or Val
<220> FEATURE:
<221> NAME/KEY: MOD_RES
<222> LOCATION: (1463)..(1463)
<223> OTHER INFORMATION: Ile or Val
<220> FEATURE:
<221> NAME/KEY: MOD_RES
<222> LOCATION: (1468)..(1468)
<223> OTHER INFORMATION: Ile or Val
<220> FEATURE:
<221> NAME/KEY: MOD_RES
<222> LOCATION: (1473)..(1473)
<223> OTHER INFORMATION: Ile or Val
<220> FEATURE:
<221> NAME/KEY: MOD_RES
<222> LOCATION: (1478)..(1478)
```

```
<223> OTHER INFORMATION: Ile or Val
<220> FEATURE:
<221> NAME/KEY: MOD_RES
<222> LOCATION: (1483)..(1483)
<223> OTHER INFORMATION: Ile or Val
<220> FEATURE:
<221> NAME/KEY: MOD_RES
<222> LOCATION: (1488)..(1488)
<223> OTHER INFORMATION: Ile or Val
<220> FEATURE:
<221> NAME/KEY: MOD_RES
<222> LOCATION: (1493)..(1493)
<223> OTHER INFORMATION: Ile or Val
<220> FEATURE:
<221> NAME/KEY: MOD_RES
<222> LOCATION: (1498)..(1498)
<223> OTHER INFORMATION: Ile or Val
<220> FEATURE:
<221> NAME/KEY: MOD_RES
<222> LOCATION: (1503)..(1503)
<223> OTHER INFORMATION: Ile or Val
<220> FEATURE:
<221> NAME/KEY: MOD_RES
<222> LOCATION: (1508)..(1508)
<223> OTHER INFORMATION: Ile or Val
<220> FEATURE:
<221> NAME/KEY: MOD_RES
<222> LOCATION: (1513)..(1513)
<223> OTHER INFORMATION: Ile or Val
<220> FEATURE:
<221> NAME/KEY: MOD_RES
<222> LOCATION: (1518)..(1518)
<223> OTHER INFORMATION: Ile or Val
<220> FEATURE:
<221> NAME/KEY: MOD_RES
<222> LOCATION: (1523)..(1523)
<223> OTHER INFORMATION: Ile or Val
<220> FEATURE:
<221> NAME/KEY: MOD_RES
<222> LOCATION: (1528)..(1528)
<223> OTHER INFORMATION: Ile or Val
<220> FEATURE:
<221> NAME/KEY: MOD_RES
<222> LOCATION: (1533)..(1533)
<223> OTHER INFORMATION: Ile or Val
<220> FEATURE:
<221> NAME/KEY: MOD_RES
<222> LOCATION: (1538)..(1538)
<223> OTHER INFORMATION: Ile or Val
<220> FEATURE:
<221> NAME/KEY: MOD_RES
<222> LOCATION: (1543)..(1543)
<223> OTHER INFORMATION: Ile or Val
<220> FEATURE:
<221> NAME/KEY: MOD_RES
<222> LOCATION: (1548)..(1548)
<223> OTHER INFORMATION: Ile or Val
<220> FEATURE:
<221> NAME/KEY: MOD_RES
<222> LOCATION: (1553)..(1553)
<223> OTHER INFORMATION: Ile or Val
<220> FEATURE:
<221> NAME/KEY: MOD_RES
<222> LOCATION: (1558)..(1558)
<223> OTHER INFORMATION: Ile or Val
<220> FEATURE:
<221> NAME/KEY: MOD_RES
<222> LOCATION: (1563)..(1563)
<223> OTHER INFORMATION: Ile or Val
<220> FEATURE:
<221> NAME/KEY: MOD_RES
<222> LOCATION: (1568)..(1568)
<223> OTHER INFORMATION: Ile or Val
<220> FEATURE:
<221> NAME/KEY: MOD_RES
<222> LOCATION: (1573)..(1573)
<223> OTHER INFORMATION: Ile or Val
<220> FEATURE:
<221> NAME/KEY: MOD_RES
```

```
<222> LOCATION: (1578)..(1578)
<223> OTHER INFORMATION: Ile or Val
<220> FEATURE:
<221> NAME/KEY: MOD_RES
<222> LOCATION: (1583)..(1583)
<223> OTHER INFORMATION: Ile or Val
<220> FEATURE:
<221> NAME/KEY: MOD_RES
<222> LOCATION: (1588)..(1588)
<223> OTHER INFORMATION: Ile or Val
<220> FEATURE:
<221> NAME/KEY: MOD_RES
<222> LOCATION: (1593)..(1593)
<223> OTHER INFORMATION: Ile or Val
<220> FEATURE:
<221> NAME/KEY: MOD_RES
<222> LOCATION: (1598)..(1598)
<223> OTHER INFORMATION: Ile or Val
<220> FEATURE:
<221> NAME/KEY: MOD_RES
<222> LOCATION: (1603)..(1603)
<223> OTHER INFORMATION: Ile or Val
<220> FEATURE:
<221> NAME/KEY: MOD_RES
<222> LOCATION: (1608)..(1608)
<223> OTHER INFORMATION: Ile or Val
<220> FEATURE:
<221> NAME/KEY: MOD_RES
<222> LOCATION: (1613)..(1613)
<223> OTHER INFORMATION: Ile or Val
<220> FEATURE:
<221> NAME/KEY: MOD_RES
<222> LOCATION: (1618)..(1618)
<223> OTHER INFORMATION: Ile or Val
<220> FEATURE:
<221> NAME/KEY: MOD_RES
<222> LOCATION: (1623)..(1623)
<223> OTHER INFORMATION: Ile or Val
<220> FEATURE:
<221> NAME/KEY: MOD_RES
<222> LOCATION: (1628)..(1628)
<223> OTHER INFORMATION: Ile or Val
<220> FEATURE:
<221> NAME/KEY: MOD_RES
<222> LOCATION: (1633)..(1633)
<223> OTHER INFORMATION: Ile or Val
<220> FEATURE:
<221> NAME/KEY: MOD_RES
<222> LOCATION: (1638)..(1638)
<223> OTHER INFORMATION: Ile or Val
<220> FEATURE:
<221> NAME/KEY: MOD_RES
<222> LOCATION: (1643)..(1643)
<223> OTHER INFORMATION: Ile or Val
<220> FEATURE:
<221> NAME/KEY: MOD_RES
<222> LOCATION: (1648)..(1648)
<223> OTHER INFORMATION: Ile or Val
<220> FEATURE:
<221> NAME/KEY: MOD_RES
<222> LOCATION: (1653)..(1653)
<223> OTHER INFORMATION: Ile or Val
<220> FEATURE:
<221> NAME/KEY: MOD_RES
<222> LOCATION: (1658)..(1658)
<223> OTHER INFORMATION: Ile or Val
<220> FEATURE:
<221> NAME/KEY: MOD_RES
<222> LOCATION: (1663)..(1663)
<223> OTHER INFORMATION: Ile or Val
<220> FEATURE:
<221> NAME/KEY: MOD_RES
<222> LOCATION: (1668)..(1668)
<223> OTHER INFORMATION: Ile or Val
<220> FEATURE:
<221> NAME/KEY: MOD_RES
<222> LOCATION: (1673)..(1673)
<223> OTHER INFORMATION: Ile or Val
<220> FEATURE:
```

```
<221> NAME/KEY: MOD_RES
<222> LOCATION: (1678)..(1678)
<223> OTHER INFORMATION: Ile or Val
<220> FEATURE:
<221> NAME/KEY: MOD_RES
<222> LOCATION: (1683)..(1683)
<223> OTHER INFORMATION: Ile or Val
<220> FEATURE:
<221> NAME/KEY: MOD_RES
<222> LOCATION: (1688)..(1688)
<223> OTHER INFORMATION: Ile or Val
<220> FEATURE:
<221> NAME/KEY: MOD_RES
<222> LOCATION: (1693)..(1693)
<223> OTHER INFORMATION: Ile or Val
<220> FEATURE:
<221> NAME/KEY: MOD_RES
<222> LOCATION: (1698)..(1698)
<223> OTHER INFORMATION: Ile or Val
<220> FEATURE:
<221> NAME/KEY: MOD_RES
<222> LOCATION: (1703)..(1703)
<223> OTHER INFORMATION: Ile or Val
<220> FEATURE:
<221> NAME/KEY: MOD_RES
<222> LOCATION: (1708)..(1708)
<223> OTHER INFORMATION: Ile or Val
<220> FEATURE:
<221> NAME/KEY: MOD_RES
<222> LOCATION: (1713)..(1713)
<223> OTHER INFORMATION: Ile or Val
<220> FEATURE:
<221> NAME/KEY: MOD_RES
<222> LOCATION: (1718)..(1718)
<223> OTHER INFORMATION: Ile or Val
<220> FEATURE:
<221> NAME/KEY: MOD_RES
<222> LOCATION: (1723)..(1723)
<223> OTHER INFORMATION: Ile or Val
<220> FEATURE:
<221> NAME/KEY: MOD_RES
<222> LOCATION: (1728)..(1728)
<223> OTHER INFORMATION: Ile or Val
<220> FEATURE:
<221> NAME/KEY: MOD_RES
<222> LOCATION: (1733)..(1733)
<223> OTHER INFORMATION: Ile or Val
<220> FEATURE:
<221> NAME/KEY: MOD_RES
<222> LOCATION: (1738)..(1738)
<223> OTHER INFORMATION: Ile or Val
<220> FEATURE:
<221> NAME/KEY: MOD_RES
<222> LOCATION: (1743)..(1743)
<223> OTHER INFORMATION: Ile or Val
<220> FEATURE:
<221> NAME/KEY: MOD_RES
<222> LOCATION: (1748)..(1748)
<223> OTHER INFORMATION: Ile or Val
<220> FEATURE:
<221> NAME/KEY: MOD_RES
<222> LOCATION: (1753)..(1753)
<223> OTHER INFORMATION: Ile or Val
<220> FEATURE:
<221> NAME/KEY: MOD_RES
<222> LOCATION: (1758)..(1758)
<223> OTHER INFORMATION: Ile or Val
<220> FEATURE:
<221> NAME/KEY: MOD_RES
<222> LOCATION: (1763)..(1763)
<223> OTHER INFORMATION: Ile or Val
<220> FEATURE:
<221> NAME/KEY: MOD_RES
<222> LOCATION: (1768)..(1768)
<223> OTHER INFORMATION: Ile or Val
<220> FEATURE:
<221> NAME/KEY: MOD_RES
<222> LOCATION: (1773)..(1773)
<223> OTHER INFORMATION: Ile or Val
```

```
<220> FEATURE:
<221> NAME/KEY: MOD_RES
<222> LOCATION: (1778)..(1778)
<223> OTHER INFORMATION: Ile or Val
<220> FEATURE:
<221> NAME/KEY: MOD_RES
<222> LOCATION: (1783)..(1783)
<223> OTHER INFORMATION: Ile or Val
<220> FEATURE:
<221> NAME/KEY: MOD_RES
<222> LOCATION: (1788)..(1788)
<223> OTHER INFORMATION: Ile or Val
<220> FEATURE:
<221> NAME/KEY: MOD_RES
<222> LOCATION: (1793)..(1793)
<223> OTHER INFORMATION: Ile or Val
<220> FEATURE:
<221> NAME/KEY: MOD_RES
<222> LOCATION: (1798)..(1798)
<223> OTHER INFORMATION: Ile or Val
<220> FEATURE:
<221> NAME/KEY: MOD_RES
<222> LOCATION: (1803)..(1803)
<223> OTHER INFORMATION: Ile or Val
<220> FEATURE:
<221> NAME/KEY: MOD_RES
<222> LOCATION: (1808)..(1808)
<223> OTHER INFORMATION: Ile or Val
<220> FEATURE:
<221> NAME/KEY: MOD_RES
<222> LOCATION: (1813)..(1813)
<223> OTHER INFORMATION: Ile or Val
<220> FEATURE:
<221> NAME/KEY: MOD_RES
<222> LOCATION: (1818)..(1818)
<223> OTHER INFORMATION: Ile or Val
<220> FEATURE:
<221> NAME/KEY: MOD_RES
<222> LOCATION: (1823)..(1823)
<223> OTHER INFORMATION: Ile or Val
<220> FEATURE:
<221> NAME/KEY: MOD_RES
<222> LOCATION: (1828)..(1828)
<223> OTHER INFORMATION: Ile or Val
<220> FEATURE:
<221> NAME/KEY: MOD_RES
<222> LOCATION: (1833)..(1833)
<223> OTHER INFORMATION: Ile or Val
<220> FEATURE:
<221> NAME/KEY: MOD_RES
<222> LOCATION: (1838)..(1838)
<223> OTHER INFORMATION: Ile or Val
<220> FEATURE:
<221> NAME/KEY: MOD_RES
<222> LOCATION: (1843)..(1843)
<223> OTHER INFORMATION: Ile or Val
<220> FEATURE:
<221> NAME/KEY: MOD_RES
<222> LOCATION: (1848)..(1848)
<223> OTHER INFORMATION: Ile or Val
<220> FEATURE:
<221> NAME/KEY: MOD_RES
<222> LOCATION: (1853)..(1853)
<223> OTHER INFORMATION: Ile or Val
<220> FEATURE:
<221> NAME/KEY: MOD_RES
<222> LOCATION: (1858)..(1858)
<223> OTHER INFORMATION: Ile or Val
<220> FEATURE:
<221> NAME/KEY: MOD_RES
<222> LOCATION: (1863)..(1863)
<223> OTHER INFORMATION: Ile or Val
<220> FEATURE:
<221> NAME/KEY: MOD_RES
<222> LOCATION: (1868)..(1868)
<223> OTHER INFORMATION: Ile or Val
<220> FEATURE:
<221> NAME/KEY: MOD_RES
<222> LOCATION: (1873)..(1873)
```

-continued

```
<223> OTHER INFORMATION: Ile or Val
<220> FEATURE:
<221> NAME/KEY: MOD_RES
<222> LOCATION: (1878)..(1878)
<223> OTHER INFORMATION: Ile or Val
<220> FEATURE:
<221> NAME/KEY: MOD_RES
<222> LOCATION: (1883)..(1883)
<223> OTHER INFORMATION: Ile or Val
<220> FEATURE:
<221> NAME/KEY: MOD_RES
<222> LOCATION: (1888)..(1888)
<223> OTHER INFORMATION: Ile or Val
<220> FEATURE:
<221> NAME/KEY: MOD_RES
<222> LOCATION: (1893)..(1893)
<223> OTHER INFORMATION: Ile or Val
<220> FEATURE:
<221> NAME/KEY: MOD_RES
<222> LOCATION: (1898)..(1898)
<223> OTHER INFORMATION: Ile or Val
<220> FEATURE:
<221> NAME/KEY: MOD_RES
<222> LOCATION: (1903)..(1903)
<223> OTHER INFORMATION: Ile or Val
<220> FEATURE:
<221> NAME/KEY: MOD_RES
<222> LOCATION: (1908)..(1908)
<223> OTHER INFORMATION: Ile or Val
<220> FEATURE:
<221> NAME/KEY: MOD_RES
<222> LOCATION: (1913)..(1913)
<223> OTHER INFORMATION: Ile or Val
<220> FEATURE:
<221> NAME/KEY: MOD_RES
<222> LOCATION: (1918)..(1918)
<223> OTHER INFORMATION: Ile or Val
<220> FEATURE:
<221> NAME/KEY: MOD_RES
<222> LOCATION: (1923)..(1923)
<223> OTHER INFORMATION: Ile or Val
<220> FEATURE:
<221> NAME/KEY: MOD_RES
<222> LOCATION: (1928)..(1928)
<223> OTHER INFORMATION: Ile or Val
<220> FEATURE:
<221> NAME/KEY: MOD_RES
<222> LOCATION: (1933)..(1933)
<223> OTHER INFORMATION: Ile or Val
<220> FEATURE:
<221> NAME/KEY: MOD_RES
<222> LOCATION: (1938)..(1938)
<223> OTHER INFORMATION: Ile or Val
<220> FEATURE:
<221> NAME/KEY: MOD_RES
<222> LOCATION: (1943)..(1943)
<223> OTHER INFORMATION: Ile or Val
<220> FEATURE:
<221> NAME/KEY: MOD_RES
<222> LOCATION: (1948)..(1948)
<223> OTHER INFORMATION: Ile or Val
<220> FEATURE:
<221> NAME/KEY: MOD_RES
<222> LOCATION: (1953)..(1953)
<223> OTHER INFORMATION: Ile or Val
<220> FEATURE:
<221> NAME/KEY: MOD_RES
<222> LOCATION: (1958)..(1958)
<223> OTHER INFORMATION: Ile or Val
<220> FEATURE:
<221> NAME/KEY: MOD_RES
<222> LOCATION: (1963)..(1963)
<223> OTHER INFORMATION: Ile or Val
<220> FEATURE:
<221> NAME/KEY: MOD_RES
<222> LOCATION: (1968)..(1968)
<223> OTHER INFORMATION: Ile or Val
<220> FEATURE:
<221> NAME/KEY: MOD_RES
```

```
<222> LOCATION: (1973)..(1973)
<223> OTHER INFORMATION: Ile or Val
<220> FEATURE:
<221> NAME/KEY: MOD_RES
<222> LOCATION: (1978)..(1978)
<223> OTHER INFORMATION: Ile or Val
<220> FEATURE:
<221> NAME/KEY: MOD_RES
<222> LOCATION: (1983)..(1983)
<223> OTHER INFORMATION: Ile or Val
<220> FEATURE:
<221> NAME/KEY: MOD_RES
<222> LOCATION: (1988)..(1988)
<223> OTHER INFORMATION: Ile or Val
<220> FEATURE:
<221> NAME/KEY: MOD_RES
<222> LOCATION: (1993)..(1993)
<223> OTHER INFORMATION: Ile or Val
<220> FEATURE:
<221> NAME/KEY: MOD_RES
<222> LOCATION: (1998)..(1998)
<223> OTHER INFORMATION: Ile or Val
<220> FEATURE:
<221> NAME/KEY: MOD_RES
<222> LOCATION: (2003)..(2003)
<223> OTHER INFORMATION: Ile or Val
<220> FEATURE:
<221> NAME/KEY: MOD_RES
<222> LOCATION: (2008)..(2008)
<223> OTHER INFORMATION: Ile or Val
<220> FEATURE:
<221> NAME/KEY: MOD_RES
<222> LOCATION: (2013)..(2013)
<223> OTHER INFORMATION: Ile or Val
<220> FEATURE:
<221> NAME/KEY: MOD_RES
<222> LOCATION: (2018)..(2018)
<223> OTHER INFORMATION: Ile or Val
<220> FEATURE:
<221> NAME/KEY: MOD_RES
<222> LOCATION: (2023)..(2023)
<223> OTHER INFORMATION: Ile or Val
<220> FEATURE:
<221> NAME/KEY: MOD_RES
<222> LOCATION: (2028)..(2028)
<223> OTHER INFORMATION: Ile or Val
<220> FEATURE:
<221> NAME/KEY: MOD_RES
<222> LOCATION: (2033)..(2033)
<223> OTHER INFORMATION: Ile or Val
<220> FEATURE:
<221> NAME/KEY: MOD_RES
<222> LOCATION: (2038)..(2038)
<223> OTHER INFORMATION: Ile or Val
<220> FEATURE:
<221> NAME/KEY: MOD_RES
<222> LOCATION: (2043)..(2043)
<223> OTHER INFORMATION: Ile or Val
<220> FEATURE:
<221> NAME/KEY: MOD_RES
<222> LOCATION: (2048)..(2048)
<223> OTHER INFORMATION: Ile or Val
<220> FEATURE:
<221> NAME/KEY: MOD_RES
<222> LOCATION: (2053)..(2053)
<223> OTHER INFORMATION: Ile or Val
<220> FEATURE:
<221> NAME/KEY: MOD_RES
<222> LOCATION: (2058)..(2058)
<223> OTHER INFORMATION: Ile or Val
<220> FEATURE:
<221> NAME/KEY: MOD_RES
<222> LOCATION: (2063)..(2063)
<223> OTHER INFORMATION: Ile or Val
<220> FEATURE:
<221> NAME/KEY: MOD_RES
<222> LOCATION: (2068)..(2068)
<223> OTHER INFORMATION: Ile or Val
<220> FEATURE:
```

```
<221> NAME/KEY: MOD_RES
<222> LOCATION: (2073)..(2073)
<223> OTHER INFORMATION: Ile or Val
<220> FEATURE:
<221> NAME/KEY: MOD_RES
<222> LOCATION: (2078)..(2078)
<223> OTHER INFORMATION: Ile or Val
<220> FEATURE:
<221> NAME/KEY: MOD_RES
<222> LOCATION: (2083)..(2083)
<223> OTHER INFORMATION: Ile or Val
<220> FEATURE:
<221> NAME/KEY: MOD_RES
<222> LOCATION: (2088)..(2088)
<223> OTHER INFORMATION: Ile or Val
<220> FEATURE:
<221> NAME/KEY: MOD_RES
<222> LOCATION: (2093)..(2093)
<223> OTHER INFORMATION: Ile or Val
<220> FEATURE:
<221> NAME/KEY: MOD_RES
<222> LOCATION: (2098)..(2098)
<223> OTHER INFORMATION: Ile or Val
<220> FEATURE:
<221> NAME/KEY: MOD_RES
<222> LOCATION: (2103)..(2103)
<223> OTHER INFORMATION: Ile or Val
<220> FEATURE:
<221> NAME/KEY: MOD_RES
<222> LOCATION: (2108)..(2108)
<223> OTHER INFORMATION: Ile or Val
<220> FEATURE:
<221> NAME/KEY: MOD_RES
<222> LOCATION: (2113)..(2113)
<223> OTHER INFORMATION: Ile or Val
<220> FEATURE:
<221> NAME/KEY: MOD_RES
<222> LOCATION: (2118)..(2118)
<223> OTHER INFORMATION: Ile or Val
<220> FEATURE:
<221> NAME/KEY: MOD_RES
<222> LOCATION: (2123)..(2123)
<223> OTHER INFORMATION: Ile or Val
<220> FEATURE:
<221> NAME/KEY: MOD_RES
<222> LOCATION: (2128)..(2128)
<223> OTHER INFORMATION: Ile or Val
<220> FEATURE:
<221> NAME/KEY: MOD_RES
<222> LOCATION: (2133)..(2133)
<223> OTHER INFORMATION: Ile or Val
<220> FEATURE:
<221> NAME/KEY: MOD_RES
<222> LOCATION: (2138)..(2138)
<223> OTHER INFORMATION: Ile or Val
<220> FEATURE:
<221> NAME/KEY: MOD_RES
<222> LOCATION: (2143)..(2143)
<223> OTHER INFORMATION: Ile or Val
<220> FEATURE:
<221> NAME/KEY: MOD_RES
<222> LOCATION: (2148)..(2148)
<223> OTHER INFORMATION: Ile or Val
<220> FEATURE:
<221> NAME/KEY: MOD_RES
<222> LOCATION: (2153)..(2153)
<223> OTHER INFORMATION: Ile or Val
<220> FEATURE:
<221> NAME/KEY: MOD_RES
<222> LOCATION: (2158)..(2158)
<223> OTHER INFORMATION: Ile or Val
<220> FEATURE:
<221> NAME/KEY: MOD_RES
<222> LOCATION: (2163)..(2163)
<223> OTHER INFORMATION: Ile or Val
<220> FEATURE:
<221> NAME/KEY: MOD_RES
<222> LOCATION: (2168)..(2168)
<223> OTHER INFORMATION: Ile or Val
```

```
-continued

<220> FEATURE:
<221> NAME/KEY: MOD_RES
<222> LOCATION: (2173)..(2173)
<223> OTHER INFORMATION: Ile or Val
<220> FEATURE:
<221> NAME/KEY: MOD_RES
<222> LOCATION: (2178)..(2178)
<223> OTHER INFORMATION: Ile or Val
<220> FEATURE:
<221> NAME/KEY: MOD_RES
<222> LOCATION: (2183)..(2183)
<223> OTHER INFORMATION: Ile or Val
<220> FEATURE:
<221> NAME/KEY: MOD_RES
<222> LOCATION: (2188)..(2188)
<223> OTHER INFORMATION: Ile or Val
<220> FEATURE:
<221> NAME/KEY: MOD_RES
<222> LOCATION: (2193)..(2193)
<223> OTHER INFORMATION: Ile or Val
<220> FEATURE:
<221> NAME/KEY: MOD_RES
<222> LOCATION: (2198)..(2198)
<223> OTHER INFORMATION: Ile or Val
<220> FEATURE:
<221> NAME/KEY: MOD_RES
<222> LOCATION: (2203)..(2203)
<223> OTHER INFORMATION: Ile or Val
<220> FEATURE:
<221> NAME/KEY: MOD_RES
<222> LOCATION: (2208)..(2208)
<223> OTHER INFORMATION: Ile or Val
<220> FEATURE:
<221> NAME/KEY: MOD_RES
<222> LOCATION: (2213)..(2213)
<223> OTHER INFORMATION: Ile or Val
<220> FEATURE:
<221> NAME/KEY: MOD_RES
<222> LOCATION: (2218)..(2218)
<223> OTHER INFORMATION: Ile or Val
<220> FEATURE:
<221> NAME/KEY: MOD_RES
<222> LOCATION: (2223)..(2223)
<223> OTHER INFORMATION: Ile or Val
<220> FEATURE:
<221> NAME/KEY: MOD_RES
<222> LOCATION: (2228)..(2228)
<223> OTHER INFORMATION: Ile or Val
<220> FEATURE:
<221> NAME/KEY: MOD_RES
<222> LOCATION: (2233)..(2233)
<223> OTHER INFORMATION: Ile or Val
<220> FEATURE:
<221> NAME/KEY: MOD_RES
<222> LOCATION: (2238)..(2238)
<223> OTHER INFORMATION: Ile or Val
<220> FEATURE:
<221> NAME/KEY: MOD_RES
<222> LOCATION: (2243)..(2243)
<223> OTHER INFORMATION: Ile or Val
<220> FEATURE:
<221> NAME/KEY: MOD_RES
<222> LOCATION: (2248)..(2248)
<223> OTHER INFORMATION: Ile or Val
<220> FEATURE:
<221> NAME/KEY: MOD_RES
<222> LOCATION: (2253)..(2253)
<223> OTHER INFORMATION: Ile or Val
<220> FEATURE:
<221> NAME/KEY: MOD_RES
<222> LOCATION: (2258)..(2258)
<223> OTHER INFORMATION: Ile or Val
<220> FEATURE:
<221> NAME/KEY: MOD_RES
<222> LOCATION: (2263)..(2263)
<223> OTHER INFORMATION: Ile or Val
<220> FEATURE:
<221> NAME/KEY: MOD_RES
<222> LOCATION: (2268)..(2268)
```

```
<223> OTHER INFORMATION: Ile or Val
<220> FEATURE:
<221> NAME/KEY: MOD_RES
<222> LOCATION: (2273)..(2273)
<223> OTHER INFORMATION: Ile or Val
<220> FEATURE:
<221> NAME/KEY: MOD_RES
<222> LOCATION: (2278)..(2278)
<223> OTHER INFORMATION: Ile or Val
<220> FEATURE:
<221> NAME/KEY: MOD_RES
<222> LOCATION: (2283)..(2283)
<223> OTHER INFORMATION: Ile or Val
<220> FEATURE:
<221> NAME/KEY: MOD_RES
<222> LOCATION: (2288)..(2288)
<223> OTHER INFORMATION: Ile or Val
<220> FEATURE:
<221> NAME/KEY: MOD_RES
<222> LOCATION: (2293)..(2293)
<223> OTHER INFORMATION: Ile or Val
<220> FEATURE:
<221> NAME/KEY: MOD_RES
<222> LOCATION: (2298)..(2298)
<223> OTHER INFORMATION: Ile or Val
<220> FEATURE:
<221> NAME/KEY: MOD_RES
<222> LOCATION: (2303)..(2303)
<223> OTHER INFORMATION: Ile or Val
<220> FEATURE:
<221> NAME/KEY: MOD_RES
<222> LOCATION: (2308)..(2308)
<223> OTHER INFORMATION: Ile or Val
<220> FEATURE:
<221> NAME/KEY: MOD_RES
<222> LOCATION: (2313)..(2313)
<223> OTHER INFORMATION: Ile or Val
<220> FEATURE:
<221> NAME/KEY: MOD_RES
<222> LOCATION: (2318)..(2318)
<223> OTHER INFORMATION: Ile or Val
<220> FEATURE:
<221> NAME/KEY: MOD_RES
<222> LOCATION: (2323)..(2323)
<223> OTHER INFORMATION: Ile or Val
<220> FEATURE:
<221> NAME/KEY: MOD_RES
<222> LOCATION: (2328)..(2328)
<223> OTHER INFORMATION: Ile or Val
<220> FEATURE:
<221> NAME/KEY: MOD_RES
<222> LOCATION: (2333)..(2333)
<223> OTHER INFORMATION: Ile or Val
<220> FEATURE:
<221> NAME/KEY: MOD_RES
<222> LOCATION: (2338)..(2338)
<223> OTHER INFORMATION: Ile or Val
<220> FEATURE:
<221> NAME/KEY: MOD_RES
<222> LOCATION: (2343)..(2343)
<223> OTHER INFORMATION: Ile or Val
<220> FEATURE:
<221> NAME/KEY: MOD_RES
<222> LOCATION: (2348)..(2348)
<223> OTHER INFORMATION: Ile or Val
<220> FEATURE:
<221> NAME/KEY: MOD_RES
<222> LOCATION: (2353)..(2353)
<223> OTHER INFORMATION: Ile or Val
<220> FEATURE:
<221> NAME/KEY: MOD_RES
<222> LOCATION: (2358)..(2358)
<223> OTHER INFORMATION: Ile or Val
<220> FEATURE:
<221> NAME/KEY: MOD_RES
<222> LOCATION: (2363)..(2363)
<223> OTHER INFORMATION: Ile or Val
<220> FEATURE:
<221> NAME/KEY: MOD_RES
```

```
<222> LOCATION: (2368)..(2368)
<223> OTHER INFORMATION: Ile or Val
<220> FEATURE:
<221> NAME/KEY: MOD_RES
<222> LOCATION: (2373)..(2373)
<223> OTHER INFORMATION: Ile or Val
<220> FEATURE:
<221> NAME/KEY: MOD_RES
<222> LOCATION: (2378)..(2378)
<223> OTHER INFORMATION: Ile or Val
<220> FEATURE:
<221> NAME/KEY: MOD_RES
<222> LOCATION: (2383)..(2383)
<223> OTHER INFORMATION: Ile or Val
<220> FEATURE:
<221> NAME/KEY: MOD_RES
<222> LOCATION: (2388)..(2388)
<223> OTHER INFORMATION: Ile or Val
<220> FEATURE:
<221> NAME/KEY: MOD_RES
<222> LOCATION: (2393)..(2393)
<223> OTHER INFORMATION: Ile or Val
<220> FEATURE:
<221> NAME/KEY: MOD_RES
<222> LOCATION: (2398)..(2398)
<223> OTHER INFORMATION: Ile or Val
<220> FEATURE:
<221> NAME/KEY: MOD_RES
<222> LOCATION: (2403)..(2403)
<223> OTHER INFORMATION: Ile or Val
<220> FEATURE:
<221> NAME/KEY: MOD_RES
<222> LOCATION: (2408)..(2408)
<223> OTHER INFORMATION: Ile or Val
<220> FEATURE:
<221> NAME/KEY: MOD_RES
<222> LOCATION: (2413)..(2413)
<223> OTHER INFORMATION: Ile or Val
<220> FEATURE:
<221> NAME/KEY: MOD_RES
<222> LOCATION: (2418)..(2418)
<223> OTHER INFORMATION: Ile or Val
<220> FEATURE:
<221> NAME/KEY: MOD_RES
<222> LOCATION: (2423)..(2423)
<223> OTHER INFORMATION: Ile or Val
<220> FEATURE:
<221> NAME/KEY: MOD_RES
<222> LOCATION: (2428)..(2428)
<223> OTHER INFORMATION: Ile or Val
<220> FEATURE:
<221> NAME/KEY: MOD_RES
<222> LOCATION: (2433)..(2433)
<223> OTHER INFORMATION: Ile or Val
<220> FEATURE:
<221> NAME/KEY: MOD_RES
<222> LOCATION: (2438)..(2438)
<223> OTHER INFORMATION: Ile or Val
<220> FEATURE:
<221> NAME/KEY: MOD_RES
<222> LOCATION: (2443)..(2443)
<223> OTHER INFORMATION: Ile or Val
<220> FEATURE:
<221> NAME/KEY: MOD_RES
<222> LOCATION: (2448)..(2448)
<223> OTHER INFORMATION: Ile or Val
<220> FEATURE:
<221> NAME/KEY: MOD_RES
<222> LOCATION: (2453)..(2453)
<223> OTHER INFORMATION: Ile or Val
<220> FEATURE:
<221> NAME/KEY: MOD_RES
<222> LOCATION: (2458)..(2458)
<223> OTHER INFORMATION: Ile or Val
<220> FEATURE:
<221> NAME/KEY: MOD_RES
<222> LOCATION: (2463)..(2463)
<223> OTHER INFORMATION: Ile or Val
<220> FEATURE:
```

```
<221> NAME/KEY: MOD_RES
<222> LOCATION: (2468)..(2468)
<223> OTHER INFORMATION: Ile or Val
<220> FEATURE:
<221> NAME/KEY: MOD_RES
<222> LOCATION: (2473)..(2473)
<223> OTHER INFORMATION: Ile or Val
<220> FEATURE:
<221> NAME/KEY: MOD_RES
<222> LOCATION: (2478)..(2478)
<223> OTHER INFORMATION: Ile or Val
<220> FEATURE:
<221> NAME/KEY: MOD_RES
<222> LOCATION: (2483)..(2483)
<223> OTHER INFORMATION: Ile or Val
<220> FEATURE:
<221> NAME/KEY: MOD_RES
<222> LOCATION: (2488)..(2488)
<223> OTHER INFORMATION: Ile or Val
<220> FEATURE:
<221> NAME/KEY: MOD_RES
<222> LOCATION: (2493)..(2493)
<223> OTHER INFORMATION: Ile or Val
<220> FEATURE:
<221> NAME/KEY: MOD_RES
<222> LOCATION: (2498)..(2498)
<223> OTHER INFORMATION: Ile or Val
<220> FEATURE:
<221> NAME/KEY: MOD_RES
<222> LOCATION: (2503)..(2503)
<223> OTHER INFORMATION: Ile or Val
<220> FEATURE:
<221> NAME/KEY: MOD_RES
<222> LOCATION: (2508)..(2508)
<223> OTHER INFORMATION: Ile or Val
<220> FEATURE:
<221> NAME/KEY: MOD_RES
<222> LOCATION: (2513)..(2513)
<223> OTHER INFORMATION: Ile or Val
<220> FEATURE:
<221> NAME/KEY: MOD_RES
<222> LOCATION: (2518)..(2518)
<223> OTHER INFORMATION: Ile or Val
<220> FEATURE:
<221> NAME/KEY: MOD_RES
<222> LOCATION: (2523)..(2523)
<223> OTHER INFORMATION: Ile or Val
<220> FEATURE:
<221> NAME/KEY: MOD_RES
<222> LOCATION: (2528)..(2528)
<223> OTHER INFORMATION: Ile or Val
<220> FEATURE:
<221> NAME/KEY: MISC_FEATURE
<222> LOCATION: (2533)..(2558)
<223> OTHER INFORMATION: This region may encompass "ETTS", "CRGD",
      "RGDSAGAGAGPEGTSCK", "RGDSETTSRGDSAGAGAGPEGTSCKL", or
      "ETTSRGDSAGAGAGPEGTSCKL", wherein some positions may be absent
<220> FEATURE:
<221> NAME/KEY: MISC_FEATURE
<222> LOCATION: (33)..(2532)
<223> OTHER INFORMATION: This region may encompass 5-500 "XPAVG"
      repeating units, wherein X is Ile or Val and some
      positions may be absent

<400> SEQUENCE: 85

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Pro Ala Val Gly Xaa Pro Ala Val Gly Xaa Pro Ala Val Gly Xaa
                35                  40                  45

Pro Ala Val Gly Xaa Pro Ala Val Gly Xaa Pro Ala Val Gly Xaa Pro
                50                  55                  60

Ala Val Gly Xaa Pro Ala Val Gly Xaa Pro Ala Val Gly Xaa Pro Ala
```

```
                65                  70                  75                  80
Val Gly Xaa Pro Ala Val Gly Xaa Pro Ala Val Gly Xaa Pro Ala Val
                    85                  90                  95
Gly Xaa Pro Ala Val Gly Xaa Pro Ala Val Gly Xaa Pro Ala Val Gly
                100                 105                 110
Xaa Pro Ala Val Gly Xaa Pro Ala Val Gly Xaa Pro Ala Val Gly Xaa
                115                 120                 125
Pro Ala Val Gly Xaa Pro Ala Val Gly Xaa Pro Ala Val Gly Xaa Pro
                130                 135                 140
Ala Val Gly Xaa Pro Ala Val Gly Xaa Pro Ala Val Gly Xaa Pro Ala
145                 150                 155                 160
Val Gly Xaa Pro Ala Val Gly Xaa Pro Ala Val Gly Xaa Pro Ala Val
                165                 170                 175
Gly Xaa Pro Ala Val Gly Xaa Pro Ala Val Gly Xaa Pro Ala Val Gly
                180                 185                 190
Xaa Pro Ala Val Gly Xaa Pro Ala Val Gly Xaa Pro Ala Val Gly Xaa
                195                 200                 205
Pro Ala Val Gly Xaa Pro Ala Val Gly Xaa Pro Ala Val Gly Xaa Pro
                210                 215                 220
Ala Val Gly Xaa Pro Ala Val Gly Xaa Pro Ala Val Gly Xaa Pro Ala
225                 230                 235                 240
Val Gly Xaa Pro Ala Val Gly Xaa Pro Ala Val Gly Xaa Pro Ala Val
                245                 250                 255
Gly Xaa Pro Ala Val Gly Xaa Pro Ala Val Gly Xaa Pro Ala Val Gly
                260                 265                 270
Xaa Pro Ala Val Gly Xaa Pro Ala Val Gly Xaa Pro Ala Val Gly Xaa
                275                 280                 285
Pro Ala Val Gly Xaa Pro Ala Val Gly Xaa Pro Ala Val Gly Xaa Pro
                290                 295                 300
Ala Val Gly Xaa Pro Ala Val Gly Xaa Pro Ala Val Gly Xaa Pro Ala
305                 310                 315                 320
Val Gly Xaa Pro Ala Val Gly Xaa Pro Ala Val Gly Xaa Pro Ala Val
                325                 330                 335
Gly Xaa Pro Ala Val Gly Xaa Pro Ala Val Gly Xaa Pro Ala Val Gly
                340                 345                 350
Xaa Pro Ala Val Gly Xaa Pro Ala Val Gly Xaa Pro Ala Val Gly Xaa
                355                 360                 365
Pro Ala Val Gly Xaa Pro Ala Val Gly Xaa Pro Ala Val Gly Xaa Pro
                370                 375                 380
Ala Val Gly Xaa Pro Ala Val Gly Xaa Pro Ala Val Gly Xaa Pro Ala
385                 390                 395                 400
Val Gly Xaa Pro Ala Val Gly Xaa Pro Ala Val Gly Xaa Pro Ala Val
                405                 410                 415
Gly Xaa Pro Ala Val Gly Xaa Pro Ala Val Gly Xaa Pro Ala Val Gly
                420                 425                 430
Xaa Pro Ala Val Gly Xaa Pro Ala Val Gly Xaa Pro Ala Val Gly Xaa
                435                 440                 445
Pro Ala Val Gly Xaa Pro Ala Val Gly Xaa Pro Ala Val Gly Xaa Pro
                450                 455                 460
Ala Val Gly Xaa Pro Ala Val Gly Xaa Pro Ala Val Gly Xaa Pro Ala
465                 470                 475                 480
Val Gly Xaa Pro Ala Val Gly Xaa Pro Ala Val Gly Xaa Pro Ala Val
                485                 490                 495
```

-continued

Gly Xaa Pro Ala Val Gly Xaa Pro Ala Val Gly Xaa Pro Ala Val Gly
            500                 505                 510

Xaa Pro Ala Val Gly Xaa Pro Ala Val Gly Xaa Pro Ala Val Gly Xaa
        515                 520                 525

Pro Ala Val Gly Xaa Pro Ala Val Gly Xaa Pro Ala Val Gly Xaa Pro
    530                 535                 540

Ala Val Gly Xaa Pro Ala Val Gly Xaa Pro Ala Val Gly Xaa Pro Ala
545                 550                 555                 560

Val Gly Xaa Pro Ala Val Gly Xaa Pro Ala Val Gly Xaa Pro Ala Val
                565                 570                 575

Gly Xaa Pro Ala Val Gly Xaa Pro Ala Val Gly Xaa Pro Ala Val Gly
            580                 585                 590

Xaa Pro Ala Val Gly Xaa Pro Ala Val Gly Xaa Pro Ala Val Gly Xaa
        595                 600                 605

Pro Ala Val Gly Xaa Pro Ala Val Gly Xaa Pro Ala Val Gly Xaa Pro
    610                 615                 620

Ala Val Gly Xaa Pro Ala Val Gly Xaa Pro Ala Val Gly Xaa Pro Ala
625                 630                 635                 640

Val Gly Xaa Pro Ala Val Gly Xaa Pro Ala Val Gly Xaa Pro Ala Val
                645                 650                 655

Gly Xaa Pro Ala Val Gly Xaa Pro Ala Val Gly Xaa Pro Ala Val Gly
            660                 665                 670

Xaa Pro Ala Val Gly Xaa Pro Ala Val Gly Xaa Pro Ala Val Gly Xaa
        675                 680                 685

Pro Ala Val Gly Xaa Pro Ala Val Gly Xaa Pro Ala Val Gly Xaa Pro
    690                 695                 700

Ala Val Gly Xaa Pro Ala Val Gly Xaa Pro Ala Val Gly Xaa Pro Ala
705                 710                 715                 720

Val Gly Xaa Pro Ala Val Gly Xaa Pro Ala Val Gly Xaa Pro Ala Val
                725                 730                 735

Gly Xaa Pro Ala Val Gly Xaa Pro Ala Val Gly Xaa Pro Ala Val Gly
            740                 745                 750

Xaa Pro Ala Val Gly Xaa Pro Ala Val Gly Xaa Pro Ala Val Gly Xaa
        755                 760                 765

Pro Ala Val Gly Xaa Pro Ala Val Gly Xaa Pro Ala Val Gly Xaa Pro
    770                 775                 780

Ala Val Gly Xaa Pro Ala Val Gly Xaa Pro Ala Val Gly Xaa Pro Ala
785                 790                 795                 800

Val Gly Xaa Pro Ala Val Gly Xaa Pro Ala Val Gly Xaa Pro Ala Val
                805                 810                 815

Gly Xaa Pro Ala Val Gly Xaa Pro Ala Val Gly Xaa Pro Ala Val Gly
            820                 825                 830

Xaa Pro Ala Val Gly Xaa Pro Ala Val Gly Xaa Pro Ala Val Gly Xaa
        835                 840                 845

Pro Ala Val Gly Xaa Pro Ala Val Gly Xaa Pro Ala Val Gly Xaa Pro
    850                 855                 860

Ala Val Gly Xaa Pro Ala Val Gly Xaa Pro Ala Val Gly Xaa Pro Ala
865                 870                 875                 880

Val Gly Xaa Pro Ala Val Gly Xaa Pro Ala Val Gly Xaa Pro Ala Val
                885                 890                 895

Gly Xaa Pro Ala Val Gly Xaa Pro Ala Val Gly Xaa Pro Ala Val Gly
            900                 905                 910

```
Xaa Pro Ala Val Gly Xaa Pro Ala Val Gly Xaa Pro Ala Val Gly Xaa
        915                 920                 925

Pro Ala Val Gly Xaa Pro Ala Val Gly Xaa Pro Ala Val Gly Xaa Pro
    930                 935                 940

Ala Val Gly Xaa Pro Ala Val Gly Xaa Pro Ala Val Gly Xaa Pro Ala
945                 950                 955                 960

Val Gly Xaa Pro Ala Val Gly Xaa Pro Ala Val Gly Xaa Pro Ala Val
            965                 970                 975

Gly Xaa Pro Ala Val Gly Xaa Pro Ala Val Gly Xaa Pro Ala Val Gly
        980                 985                 990

Xaa Pro Ala Val Gly Xaa Pro Ala  Val Gly Xaa Pro Ala  Val Gly Xaa
        995                 1000                1005

Pro Ala  Val Gly Xaa Pro Ala  Val Gly Xaa Pro Ala  Val Gly Xaa
    1010                 1015                1020

Pro Ala  Val Gly Xaa Pro Ala  Val Gly Xaa Pro Ala  Val Gly Xaa
    1025                 1030                1035

Pro Ala  Val Gly Xaa Pro Ala  Val Gly Xaa Pro Ala  Val Gly Xaa
    1040                 1045                1050

Pro Ala  Val Gly Xaa Pro Ala  Val Gly Xaa Pro Ala  Val Gly Xaa
    1055                 1060                1065

Pro Ala  Val Gly Xaa Pro Ala  Val Gly Xaa Pro Ala  Val Gly Xaa
    1070                 1075                1080

Pro Ala  Val Gly Xaa Pro Ala  Val Gly Xaa Pro Ala  Val Gly Xaa
    1085                 1090                1095

Pro Ala  Val Gly Xaa Pro Ala  Val Gly Xaa Pro Ala  Val Gly Xaa
    1100                 1105                1110

Pro Ala  Val Gly Xaa Pro Ala  Val Gly Xaa Pro Ala  Val Gly Xaa
    1115                 1120                1125

Pro Ala  Val Gly Xaa Pro Ala  Val Gly Xaa Pro Ala  Val Gly Xaa
    1130                 1135                1140

Pro Ala  Val Gly Xaa Pro Ala  Val Gly Xaa Pro Ala  Val Gly Xaa
    1145                 1150                1155

Pro Ala  Val Gly Xaa Pro Ala  Val Gly Xaa Pro Ala  Val Gly Xaa
    1160                 1165                1170

Pro Ala  Val Gly Xaa Pro Ala  Val Gly Xaa Pro Ala  Val Gly Xaa
    1175                 1180                1185

Pro Ala  Val Gly Xaa Pro Ala  Val Gly Xaa Pro Ala  Val Gly Xaa
    1190                 1195                1200

Pro Ala  Val Gly Xaa Pro Ala  Val Gly Xaa Pro Ala  Val Gly Xaa
    1205                 1210                1215

Pro Ala  Val Gly Xaa Pro Ala  Val Gly Xaa Pro Ala  Val Gly Xaa
    1220                 1225                1230

Pro Ala  Val Gly Xaa Pro Ala  Val Gly Xaa Pro Ala  Val Gly Xaa
    1235                 1240                1245

Pro Ala  Val Gly Xaa Pro Ala  Val Gly Xaa Pro Ala  Val Gly Xaa
    1250                 1255                1260

Pro Ala  Val Gly Xaa Pro Ala  Val Gly Xaa Pro Ala  Val Gly Xaa
    1265                 1270                1275

Pro Ala  Val Gly Xaa Pro Ala  Val Gly Xaa Pro Ala  Val Gly Xaa
    1280                 1285                1290

Pro Ala  Val Gly Xaa Pro Ala  Val Gly Xaa Pro Ala  Val Gly Xaa
    1295                 1300                1305

Pro Ala  Val Gly Xaa Pro Ala  Val Gly Xaa Pro Ala  Val Gly Xaa
```

-continued

```
            1310                1315                1320

Pro Ala Val Gly Xaa Pro Ala Val Gly Xaa Pro Ala Val Gly Xaa
    1325                1330                1335

Pro Ala Val Gly Xaa Pro Ala Val Gly Xaa Pro Ala Val Gly Xaa
    1340                1345                1350

Pro Ala Val Gly Xaa Pro Ala Val Gly Xaa Pro Ala Val Gly Xaa
    1355                1360                1365

Pro Ala Val Gly Xaa Pro Ala Val Gly Xaa Pro Ala Val Gly Xaa
    1370                1375                1380

Pro Ala Val Gly Xaa Pro Ala Val Gly Xaa Pro Ala Val Gly Xaa
    1385                1390                1395

Pro Ala Val Gly Xaa Pro Ala Val Gly Xaa Pro Ala Val Gly Xaa
    1400                1405                1410

Pro Ala Val Gly Xaa Pro Ala Val Gly Xaa Pro Ala Val Gly Xaa
    1415                1420                1425

Pro Ala Val Gly Xaa Pro Ala Val Gly Xaa Pro Ala Val Gly Xaa
    1430                1435                1440

Pro Ala Val Gly Xaa Pro Ala Val Gly Xaa Pro Ala Val Gly Xaa
    1445                1450                1455

Pro Ala Val Gly Xaa Pro Ala Val Gly Xaa Pro Ala Val Gly Xaa
    1460                1465                1470

Pro Ala Val Gly Xaa Pro Ala Val Gly Xaa Pro Ala Val Gly Xaa
    1475                1480                1485

Pro Ala Val Gly Xaa Pro Ala Val Gly Xaa Pro Ala Val Gly Xaa
    1490                1495                1500

Pro Ala Val Gly Xaa Pro Ala Val Gly Xaa Pro Ala Val Gly Xaa
    1505                1510                1515

Pro Ala Val Gly Xaa Pro Ala Val Gly Xaa Pro Ala Val Gly Xaa
    1520                1525                1530

Pro Ala Val Gly Xaa Pro Ala Val Gly Xaa Pro Ala Val Gly Xaa
    1535                1540                1545

Pro Ala Val Gly Xaa Pro Ala Val Gly Xaa Pro Ala Val Gly Xaa
    1550                1555                1560

Pro Ala Val Gly Xaa Pro Ala Val Gly Xaa Pro Ala Val Gly Xaa
    1565                1570                1575

Pro Ala Val Gly Xaa Pro Ala Val Gly Xaa Pro Ala Val Gly Xaa
    1580                1585                1590

Pro Ala Val Gly Xaa Pro Ala Val Gly Xaa Pro Ala Val Gly Xaa
    1595                1600                1605

Pro Ala Val Gly Xaa Pro Ala Val Gly Xaa Pro Ala Val Gly Xaa
    1610                1615                1620

Pro Ala Val Gly Xaa Pro Ala Val Gly Xaa Pro Ala Val Gly Xaa
    1625                1630                1635

Pro Ala Val Gly Xaa Pro Ala Val Gly Xaa Pro Ala Val Gly Xaa
    1640                1645                1650

Pro Ala Val Gly Xaa Pro Ala Val Gly Xaa Pro Ala Val Gly Xaa
    1655                1660                1665

Pro Ala Val Gly Xaa Pro Ala Val Gly Xaa Pro Ala Val Gly Xaa
    1670                1675                1680

Pro Ala Val Gly Xaa Pro Ala Val Gly Xaa Pro Ala Val Gly Xaa
    1685                1690                1695

Pro Ala Val Gly Xaa Pro Ala Val Gly Xaa Pro Ala Val Gly Xaa
    1700                1705                1710
```

```
Pro Ala Val Gly Xaa Pro Ala Val Gly Xaa Pro Ala Val Gly Xaa
    1715                1720                1725

Pro Ala Val Gly Xaa Pro Ala Val Gly Xaa Pro Ala Val Gly Xaa
    1730                1735                1740

Pro Ala Val Gly Xaa Pro Ala Val Gly Xaa Pro Ala Val Gly Xaa
    1745                1750                1755

Pro Ala Val Gly Xaa Pro Ala Val Gly Xaa Pro Ala Val Gly Xaa
    1760                1765                1770

Pro Ala Val Gly Xaa Pro Ala Val Gly Xaa Pro Ala Val Gly Xaa
    1775                1780                1785

Pro Ala Val Gly Xaa Pro Ala Val Gly Xaa Pro Ala Val Gly Xaa
    1790                1795                1800

Pro Ala Val Gly Xaa Pro Ala Val Gly Xaa Pro Ala Val Gly Xaa
    1805                1810                1815

Pro Ala Val Gly Xaa Pro Ala Val Gly Xaa Pro Ala Val Gly Xaa
    1820                1825                1830

Pro Ala Val Gly Xaa Pro Ala Val Gly Xaa Pro Ala Val Gly Xaa
    1835                1840                1845

Pro Ala Val Gly Xaa Pro Ala Val Gly Xaa Pro Ala Val Gly Xaa
    1850                1855                1860

Pro Ala Val Gly Xaa Pro Ala Val Gly Xaa Pro Ala Val Gly Xaa
    1865                1870                1875

Pro Ala Val Gly Xaa Pro Ala Val Gly Xaa Pro Ala Val Gly Xaa
    1880                1885                1890

Pro Ala Val Gly Xaa Pro Ala Val Gly Xaa Pro Ala Val Gly Xaa
    1895                1900                1905

Pro Ala Val Gly Xaa Pro Ala Val Gly Xaa Pro Ala Val Gly Xaa
    1910                1915                1920

Pro Ala Val Gly Xaa Pro Ala Val Gly Xaa Pro Ala Val Gly Xaa
    1925                1930                1935

Pro Ala Val Gly Xaa Pro Ala Val Gly Xaa Pro Ala Val Gly Xaa
    1940                1945                1950

Pro Ala Val Gly Xaa Pro Ala Val Gly Xaa Pro Ala Val Gly Xaa
    1955                1960                1965

Pro Ala Val Gly Xaa Pro Ala Val Gly Xaa Pro Ala Val Gly Xaa
    1970                1975                1980

Pro Ala Val Gly Xaa Pro Ala Val Gly Xaa Pro Ala Val Gly Xaa
    1985                1990                1995

Pro Ala Val Gly Xaa Pro Ala Val Gly Xaa Pro Ala Val Gly Xaa
    2000                2005                2010

Pro Ala Val Gly Xaa Pro Ala Val Gly Xaa Pro Ala Val Gly Xaa
    2015                2020                2025

Pro Ala Val Gly Xaa Pro Ala Val Gly Xaa Pro Ala Val Gly Xaa
    2030                2035                2040

Pro Ala Val Gly Xaa Pro Ala Val Gly Xaa Pro Ala Val Gly Xaa
    2045                2050                2055

Pro Ala Val Gly Xaa Pro Ala Val Gly Xaa Pro Ala Val Gly Xaa
    2060                2065                2070

Pro Ala Val Gly Xaa Pro Ala Val Gly Xaa Pro Ala Val Gly Xaa
    2075                2080                2085

Pro Ala Val Gly Xaa Pro Ala Val Gly Xaa Pro Ala Val Gly Xaa
    2090                2095                2100
```

```
Pro Ala  Val Gly Xaa Pro Ala  Val Gly Xaa Pro Ala  Val Gly Xaa
    2105                2110                2115

Pro Ala  Val Gly Xaa Pro Ala  Val Gly Xaa Pro Ala  Val Gly Xaa
    2120                2125                2130

Pro Ala  Val Gly Xaa Pro Ala  Val Gly Xaa Pro Ala  Val Gly Xaa
    2135                2140                2145

Pro Ala  Val Gly Xaa Pro Ala  Val Gly Xaa Pro Ala  Val Gly Xaa
    2150                2155                2160

Pro Ala  Val Gly Xaa Pro Ala  Val Gly Xaa Pro Ala  Val Gly Xaa
    2165                2170                2175

Pro Ala  Val Gly Xaa Pro Ala  Val Gly Xaa Pro Ala  Val Gly Xaa
    2180                2185                2190

Pro Ala  Val Gly Xaa Pro Ala  Val Gly Xaa Pro Ala  Val Gly Xaa
    2195                2200                2205

Pro Ala  Val Gly Xaa Pro Ala  Val Gly Xaa Pro Ala  Val Gly Xaa
    2210                2215                2220

Pro Ala  Val Gly Xaa Pro Ala  Val Gly Xaa Pro Ala  Val Gly Xaa
    2225                2230                2235

Pro Ala  Val Gly Xaa Pro Ala  Val Gly Xaa Pro Ala  Val Gly Xaa
    2240                2245                2250

Pro Ala  Val Gly Xaa Pro Ala  Val Gly Xaa Pro Ala  Val Gly Xaa
    2255                2260                2265

Pro Ala  Val Gly Xaa Pro Ala  Val Gly Xaa Pro Ala  Val Gly Xaa
    2270                2275                2280

Pro Ala  Val Gly Xaa Pro Ala  Val Gly Xaa Pro Ala  Val Gly Xaa
    2285                2290                2295

Pro Ala  Val Gly Xaa Pro Ala  Val Gly Xaa Pro Ala  Val Gly Xaa
    2300                2305                2310

Pro Ala  Val Gly Xaa Pro Ala  Val Gly Xaa Pro Ala  Val Gly Xaa
    2315                2320                2325

Pro Ala  Val Gly Xaa Pro Ala  Val Gly Xaa Pro Ala  Val Gly Xaa
    2330                2335                2340

Pro Ala  Val Gly Xaa Pro Ala  Val Gly Xaa Pro Ala  Val Gly Xaa
    2345                2350                2355

Pro Ala  Val Gly Xaa Pro Ala  Val Gly Xaa Pro Ala  Val Gly Xaa
    2360                2365                2370

Pro Ala  Val Gly Xaa Pro Ala  Val Gly Xaa Pro Ala  Val Gly Xaa
    2375                2380                2385

Pro Ala  Val Gly Xaa Pro Ala  Val Gly Xaa Pro Ala  Val Gly Xaa
    2390                2395                2400

Pro Ala  Val Gly Xaa Pro Ala  Val Gly Xaa Pro Ala  Val Gly Xaa
    2405                2410                2415

Pro Ala  Val Gly Xaa Pro Ala  Val Gly Xaa Pro Ala  Val Gly Xaa
    2420                2425                2430

Pro Ala  Val Gly Xaa Pro Ala  Val Gly Xaa Pro Ala  Val Gly Xaa
    2435                2440                2445

Pro Ala  Val Gly Xaa Pro Ala  Val Gly Xaa Pro Ala  Val Gly Xaa
    2450                2455                2460

Pro Ala  Val Gly Xaa Pro Ala  Val Gly Xaa Pro Ala  Val Gly Xaa
    2465                2470                2475

Pro Ala  Val Gly Xaa Pro Ala  Val Gly Xaa Pro Ala  Val Gly Xaa
    2480                2485                2490

Pro Ala  Val Gly Xaa Pro Ala  Val Gly Xaa Pro Ala  Val Gly Xaa
```

```
              2495                2500                2505

Pro Ala  Val Gly Xaa Pro Ala  Val Gly Xaa Pro Ala  Val Gly Xaa
    2510                2515                2520

Pro Ala  Val Gly Xaa Pro Ala  Val Gly Xaa Xaa Xaa  Xaa Xaa Xaa
    2525                2530                2535

Xaa Xaa  Xaa Xaa Xaa Xaa Xaa  Xaa Xaa Xaa Xaa Xaa  Xaa Xaa Xaa
    2540                2545                2550

Xaa Xaa  Xaa Xaa Xaa
    2555

<210> SEQ ID NO 86
<211> LENGTH: 308
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(32)
<223> OTHER INFORMATION: This region may encompass "MGWGSASGLVG",
      "KCTSAGAGAGPEGRGDS", "MGWGSKCTSAGAGAGPEGRGDSTSGLVG",
      "MGWGSKCTSAGAGAGPEGRGDS TSGLVGRGD", or
      "MGWGSKCTSAGAGAGPEGRGDSTSGLVGRGDS", wherein some positions may be
      absent
<220> FEATURE:
<221> NAME/KEY: MISC_FEATURE
<222> LOCATION: (283)..(308)
<223> OTHER INFORMATION: This region may encompass "ETTS", "CRGD",
      "RGDSAGAGAGPEGTSCK", "RGDSETTSRGDSAGAGAGPEGTSCKL", or
      "ETTSRGDSAGAGAGPEGTSCKL", wherein some positions may be absent

<400> SEQUENCE: 86

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Ile Pro Ala Val Gly Val Pro Ala Val Gly Ile Pro Ala Val Gly Val
                35                  40                  45

Pro Ala Val Gly Ile Pro Ala Val Gly Ile Pro Ala Val Gly Val Pro
        50                  55                  60

Ala Val Gly Ile Pro Ala Val Gly Val Pro Ala Val Gly Ile Pro Ala
65                  70                  75                  80

Val Gly Ile Pro Ala Val Gly Val Pro Ala Val Gly Ile Pro Ala Val
                85                  90                  95

Gly Val Pro Ala Val Gly Ile Pro Ala Val Gly Ile Pro Ala Val Gly
            100                 105                 110

Val Pro Ala Val Gly Ile Pro Ala Val Gly Val Pro Ala Val Gly Ile
        115                 120                 125

Pro Ala Val Gly Ile Pro Ala Val Gly Val Pro Ala Val Gly Ile Pro
    130                 135                 140

Ala Val Gly Val Pro Ala Val Gly Ile Pro Ala Val Gly Ile Pro Ala
145                 150                 155                 160

Val Gly Val Pro Ala Val Gly Ile Pro Ala Val Gly Val Pro Ala Val
                165                 170                 175

Gly Ile Pro Ala Val Gly Ile Pro Ala Val Gly Val Pro Ala Val Gly
            180                 185                 190

Ile Pro Ala Val Gly Val Pro Ala Val Gly Ile Pro Ala Val Gly Ile
        195                 200                 205

Pro Ala Val Gly Val Pro Ala Val Gly Ile Pro Ala Val Gly Val Pro
```

-continued

```
                210                 215                 220
Ala Val Gly Ile Pro Ala Val Gly Ile Pro Ala Val Gly Val Pro Ala
225                 230                 235                 240

Val Gly Ile Pro Ala Val Gly Val Pro Ala Val Gly Ile Pro Ala Val
                245                 250                 255

Gly Ile Pro Ala Val Gly Val Pro Ala Val Gly Ile Pro Ala Val Gly
                260                 265                 270

Val Pro Ala Val Gly Ile Pro Ala Val Gly Xaa Xaa Xaa Xaa Xaa
                275                 280                 285

Xaa Xaa Xaa Xaa Xaa Xaa Xaa Xaa Xaa Xaa Xaa Xaa Xaa Xaa Xaa
                290                 295                 300

Xaa Xaa Xaa Xaa
305

<210> SEQ ID NO 87
<211> LENGTH: 308
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(32)
<223> OTHER INFORMATION: This region may encompass "MGWGSASGLVG",
      "KCTSAGAGAGPEGRGDS", "MGWGSKCTSAGAGAGPEGRGDSTSGLVG",
      "MGWGSKCTSAGAGAGPEGRGDS TSGLVGRGD", or
      "MGWGSKCTSAGAGAGPEGRGDSTSGLVGRGDS", wherein some positions may be
      absent
<220> FEATURE:
<221> NAME/KEY: MISC_FEATURE
<222> LOCATION: (283)..(308)
<223> OTHER INFORMATION: This region may encompass "ETTS", "CRGD",
      "RGDSAGAGAGPEGTSCK", "RGDSETTSRGDSAGAGAGPEGTSCKL", or
      "ETTSRGDSAGAGAGPEGTSCKL", wherein some positions may be absent

<400> SEQUENCE: 87

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Val Pro Ala Val Gly Val Pro Ala Val Gly Ile Pro Ala Val Gly Val
                35                  40                  45

Pro Ala Val Gly Val Pro Ala Val Gly Val Pro Ala Val Gly Val Pro
                50                  55                  60

Ala Val Gly Ile Pro Ala Val Gly Val Pro Ala Val Gly Val Pro Ala
65                  70                  75                  80

Val Gly Val Pro Ala Val Gly Val Pro Ala Val Gly Ile Pro Ala Val
                85                  90                  95

Gly Val Pro Ala Val Gly Val Pro Ala Val Gly Val Pro Ala Val Gly
                100                 105                 110

Val Pro Ala Val Gly Ile Pro Ala Val Gly Val Pro Ala Val Gly Val
                115                 120                 125

Pro Ala Val Gly Val Pro Ala Val Gly Val Pro Ala Val Gly Ile Pro
                130                 135                 140

Ala Val Gly Val Pro Ala Val Gly Val Pro Ala Val Gly Val Pro Ala
145                 150                 155                 160

Val Gly Val Pro Ala Val Gly Ile Pro Ala Val Gly Val Pro Ala Val
                165                 170                 175

Gly Val Pro Ala Val Gly Val Pro Ala Val Gly Val Pro Ala Val Gly
```

```
                    180                 185                 190
Ile Pro Ala Val Gly Val Pro Ala Val Gly Val Pro Ala Val Gly Val
            195                 200                 205
Pro Ala Val Gly Val Pro Ala Val Gly Ile Pro Ala Val Gly Val Pro
            210                 215                 220
Ala Val Gly Val Pro Ala Val Gly Val Pro Ala Val Gly Val Pro Ala
225                 230                 235                 240
Val Gly Ile Pro Ala Val Gly Val Pro Ala Val Gly Val Pro Ala Val
                245                 250                 255
Gly Val Pro Ala Val Gly Val Pro Ala Val Gly Ile Pro Ala Val Gly
            260                 265                 270
Val Pro Ala Val Gly Val Pro Ala Val Gly Xaa Xaa Xaa Xaa Xaa Xaa
            275                 280                 285
Xaa Xaa Xaa Xaa Xaa Xaa Xaa Xaa Xaa Xaa Xaa Xaa Xaa Xaa Xaa
            290                 295                 300
Xaa Xaa Xaa Xaa
305

<210> SEQ ID NO 88
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(32)
<223> OTHER INFORMATION: This region may encompass "MGWGSASGLVG",
      "KCTSAGAGAGPEGRGDS", "MGWGSKCTSAGAGAGPEGRGDSTSGLVG",
      "MGWGSKCTSAGAGAGPEGRGDS TSGLVGRGD", or
      "MGWGSKCTSAGAGAGPEGRGDSTSGLVGRGDS", wherein some positions may be
      absent
<220> FEATURE:
<221> NAME/KEY: MISC_FEATURE
<222> LOCATION: (317)..(342)
<223> OTHER INFORMATION: This region may encompass "ETTS", "CRGD",
      "RGDSAGAGAGPEGTSCK", "RGDSETTSRGDSAGAGAGPEGTSCKL", or
      "ETTSRGDSAGAGAGPEGTSCKL", wherein some positions may be absent

<400> SEQUENCE: 88

Xaa Xaa Xaa Xaa Xaa Xaa Xaa Xaa Xaa Xaa Xaa Xaa Xaa Xaa Xaa Xaa
1               5                   10                  15
Xaa Xaa Xaa Xaa Xaa Xaa Xaa Xaa Xaa Xaa Xaa Xaa Xaa Xaa Xaa Xaa
                20                  25                  30
Lys Cys Thr Ser Ala Gly Ala Gly Ala Gly Pro Glu Gly Arg Gly Asp
            35                  40                  45
Ser Ile Pro Ala Val Gly Val Pro Ala Val Gly Ile Pro Ala Val Gly
        50                  55                  60
Val Pro Ala Val Gly Ile Pro Ala Val Gly Ile Pro Ala Val Gly Val
65                  70                  75                  80
Pro Ala Val Gly Ile Pro Ala Val Gly Val Pro Ala Val Gly Ile Pro
                85                  90                  95
Ala Val Gly Ile Pro Ala Val Gly Val Pro Ala Val Gly Ile Pro Ala
            100                 105                 110
Val Gly Val Pro Ala Val Gly Ile Pro Ala Val Gly Ile Pro Ala Val
        115                 120                 125
Gly Val Pro Ala Val Gly Ile Pro Ala Val Gly Val Pro Ala Val Gly
    130                 135                 140
Ile Pro Ala Val Gly Ile Pro Ala Val Gly Val Pro Ala Val Gly Ile
```

-continued

```
            145                 150                 155                 160
Pro Ala Val Gly Val Pro Ala Val Gly Ile Pro Ala Val Gly Ile Pro
                        165                 170                 175

Ala Val Gly Val Pro Ala Val Gly Ile Pro Ala Val Gly Val Pro Ala
                180                 185                 190

Val Gly Ile Pro Ala Val Gly Ile Pro Ala Val Gly Val Pro Ala Val
            195                 200                 205

Gly Ile Pro Ala Val Gly Val Pro Ala Val Gly Ile Pro Ala Val Gly
        210                 215                 220

Ile Pro Ala Val Gly Val Pro Ala Val Gly Ile Pro Ala Val Gly Val
225                 230                 235                 240

Pro Ala Val Gly Ile Pro Ala Val Gly Ile Pro Ala Val Gly Val Pro
                245                 250                 255

Ala Val Gly Ile Pro Ala Val Gly Val Pro Ala Val Gly Ile Pro Ala
                260                 265                 270

Val Gly Ile Pro Ala Val Gly Val Pro Ala Val Gly Ile Pro Ala Val
            275                 280                 285

Gly Val Pro Ala Val Gly Ile Pro Ala Val Gly Arg Gly Asp Ser Ala
        290                 295                 300

Gly Ala Gly Ala Gly Pro Glu Gly Thr Ser Cys Lys Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa
            340
```

US 10,517,990 B2

THERMOREVERSIBLE HYDROGELS FROM THE ARRESTED PHASE SEPARATION OF ELASTIN-LIKE POLYPEPTIDES

RELATED APPLICATIONS

This application claims the benefit of priority to U.S. Provisional Patent Application Ser. No. 62/086,496, filed Dec. 2, 2014, the contents of which are hereby incorporated by reference.

GOVERNMENT SUPPORT

This invention was made with Government support under Contract Nos. W911NF-07-D-0004 and W911NF-13-D-0001 awarded by the Army Research Office. The government has certain rights in the invention.

SEQUENCE LISTING

The instant application contains a Sequence Listing which has been submitted electronically in ASCII format and is hereby incorporated by reference in its entirety. Said ASCII copy, created on Jul. 17, 2018, is named MTV-15201 SL.txt and is 316,295 bytes in size.

BACKGROUND

Hydrogels are an important platform technology for biomedical applications in many areas, including managing chronic ailments, such as rheumatoid arthritis and osteoporosis, and treating acute conditions, such as hemorrhaging and cancer. Their utility is due in part to their high water content and tunable mechanical properties, which makes them inherently similar to living tissue. Hydrogels have been widely investigated for contact lenses, as materials for controlled drug release, and as scaffolds for load-bearing connective tissue.

The engineering or regeneration of load-bearing tissues is critically important for the repair of a broad range of defects with diverse causes, such as acute injuries or chronic tissue degradation. Artificial tissue matrices formed from polymeric materials are an essential component in the "toolbox" of tissue engineers, offering several important advantages over hard materials, such as ceramic and metallic implants, including: biodegradability, remoldability, injectability, and viscoelastic behavior programmable to match the response of the target tissue. Hydrogels are particularly promising biomaterials because their high water content, high porosity, modular synthesis, and ease of processing are suitable for a number of high value tasks, such as the encapsulation and injectable delivery of viable cells. Nevertheless, hydrogels often suffer from poor mechanical properties (e.g., low stiffness and toughness) that limit their application to the engineering of soft tissues, such as nerve tissue, or for use as substrates for the maintenance and study of laboratory cell strains in vitro. If used to regenerate connective tissues, these materials typically require mechanical isolation of the defect site, and are subject to degradation and clearance faster than replacement tissue can be formed. Hydrogels able to serve as robust, load-bearing materials, support the growth of encapsulated or invading cells, and ultimately lead to the regeneration of mature connective tissues (such as bone or cartilage) remain elusive. Thus, there is an unmet need for a simple hydrogel formulation capable of yielding tough biomaterials for the engineering of load-bearing tissues.

SUMMARY

In certain embodiments, the invention relates to a composition, comprising a polypeptide; and a solvent; wherein the polypeptide has the following sequence (SEQ ID NO: 1):

$y^1$-(XPAVG)$_n$-$y^2$ wherein, independently for each occurrence,
X is I or V;
n is an integer from 5-500; and
$y^1$ is hydrogen, an amine protecting group, a natural amino acid or unnatural amino acid, a plurality of natural amino acids or unnatural amino acids, a peptide, an oligopeptide, a polypeptide, a protein, a synthetic oligomer, a synthetic polymer, or a combination thereof; and
$y^2$ is hydrogen, a carboxylate protecting group, a natural or unnatural amino acid, a plurality of natural amino acids or unnatural amino acids, a peptide, an oligopeptide, a polypeptide, a protein, a synthetic oligomer, a synthetic polymer, or a combination thereof.

In certain embodiments, the invention relates to a biomedical material, consisting essentially of any one of the compositions described herein.

In certain embodiments, the invention relates to a cell culture medium, consisting essentially of any one of the compositions described herein.

In certain embodiments, the invention relates to a method, comprising the step of:
injecting into a subject in need thereof an effective amount of any one of the compositions described herein.

In certain embodiments, the invention relates to any one of the methods described herein, wherein the method is a method of replacing, reinforcing, or regenerating a load-bearing tissue in the subject.

BRIEF DESCRIPTION OF THE FIGURES

FIG. 7 discloses "C-RGD-P$_{10}$-RGD-C" as SEQ ID NO: 72.

FIG. 8A discloses "(X$^{0.6}$PAVG)$_{10}$" as SEQ ID NO: 27 and "C-(X$^{0.6}$PAVG)$_{10}$-C" as SEQ ID NO: 74.

FIG. 11 discloses "P$_{10}$-cys-RGD" as SEQ ID NO: 55.

FIG. 13 discloses SEQ ID NOS 52, 51, 54, 50 and 53, respectively, in order of appearance.

FIG. 17 discloses SEQ ID NOS 50, 54, 51 and 53, respectively, in order of appearance.

FIG. 21 discloses SEQ ID NOS 54, 50 and 53, respectively, in order of appearance.

FIG. 22(a) discloses SEQ ID NOS 51, 54, 50 and 53, respectively, in order of appearance. (b) Elastic moduli and (c) tan($\delta$) as a function of angular frequency in the linear regime ($\gamma_o$=0.01) for characteristic samples at 20 wt % in water. FIGS. 22(b) and (c) disclose SEQ ID NOS 51, 54, 50 and 53, respectively, in order of appearance. (d) Comparison of temperature ramps for 23 kDa ELPs at 1° C./min to equivalent distances from their DSC-determined transition temperature (T$_t$), where the real maximum temperature (i.e., right side of the plot) was 46° C. for (X$^1$PAVG)$_{50}$ (SEQ ID NO: 51) and 37° C. for (X$^2$PAVG)$_{50}$ (SEQ ID NO: 53). Note that in order to simplify the thermal history, the moduli here are measured during the heating step at a constant ramp rate, rather than following equilibration at each temperature.

FIGS. 25(a) and (b) disclose SEQ ID NOS 51, 54, 50 and 53, respectively, in order of appearance.

FIGS. 26(a) and (b) disclose SEQ ID NOS 51, 54, 50 and 53, respectively, in order of appearance.

FIGS. 28(a)-(d) disclose SEQ ID NOS 51, 54, 50 and 53, respectively, in order of appearance.

FIGS. 29(a)-(h) disclose SEQ ID NOS 51, 51, 54, 54, 50, 50, 53 and 53, respectively, in order of appearance.

FIGS. 33(a) disclose SEQ ID NOS 51, 54, 50 and 53, respectively, in order of appearance.

FIGS. 34(a)-(c) disclose SEQ ID NOS 57, 58, 57 and 58, respectively, in order of appearance.

FIG. 36(c) discloses SEQ ID NOS 57 and 58, respectively, in order of appearance.

FIGS. 37(c)-(d) disclose SEQ ID NOS 57, 58, 57 and 58, respectively, in order of appearance.

FIG. 44 discloses SEQ ID NOS 57 and 58, respectively, in order of appearance.

DETAILED DESCRIPTION

Overview

Figure 1A:
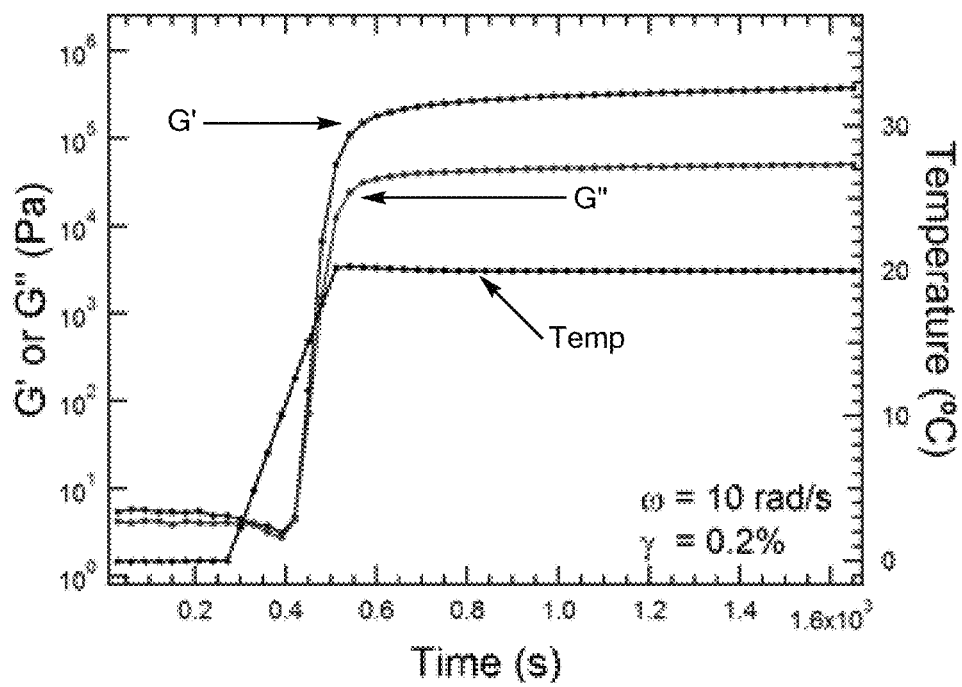
FIG. 1A depicts selected temperature ramps (reflecting rapid heating from 0° C. to 20° C.) during linear rheology using the sandblasted 25-mm cone-plate geometry. Note that this measurement was performed at $\omega=10$ rad/s.
Figure 1B:
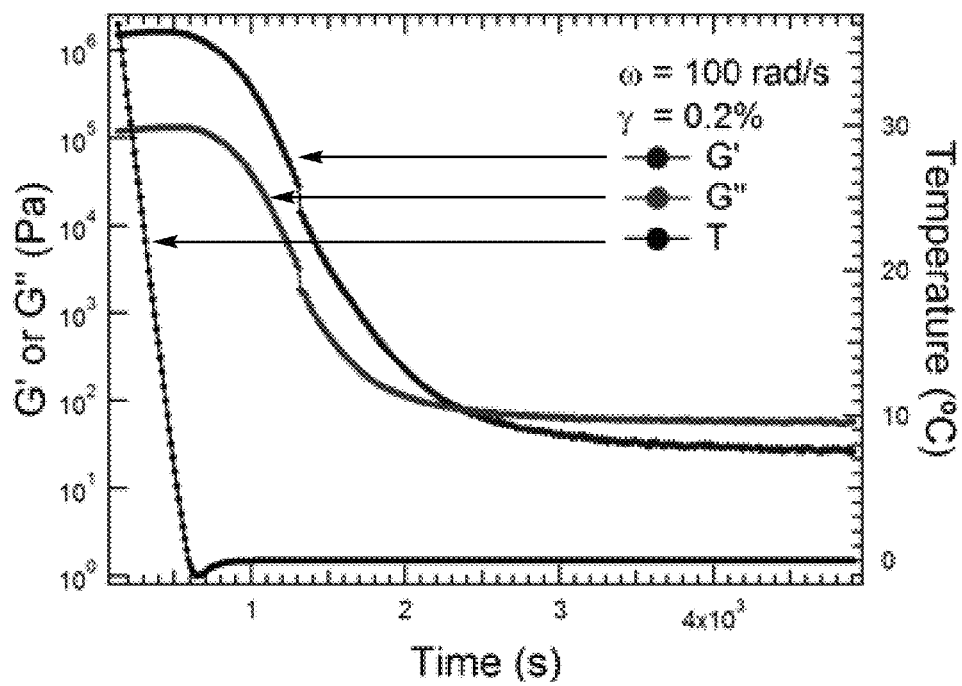
FIG. 1B depicts selected temperature ramps (upon cooling to 0° C. after several hours of experimentation at 37° C.) during linear rheology using the sandblasted 25-mm cone-plate geometry. Note that this measurement was performed at $\omega=100$ rad/s. The gap present in the data is due to a pause in data collection.
Figure 2A:
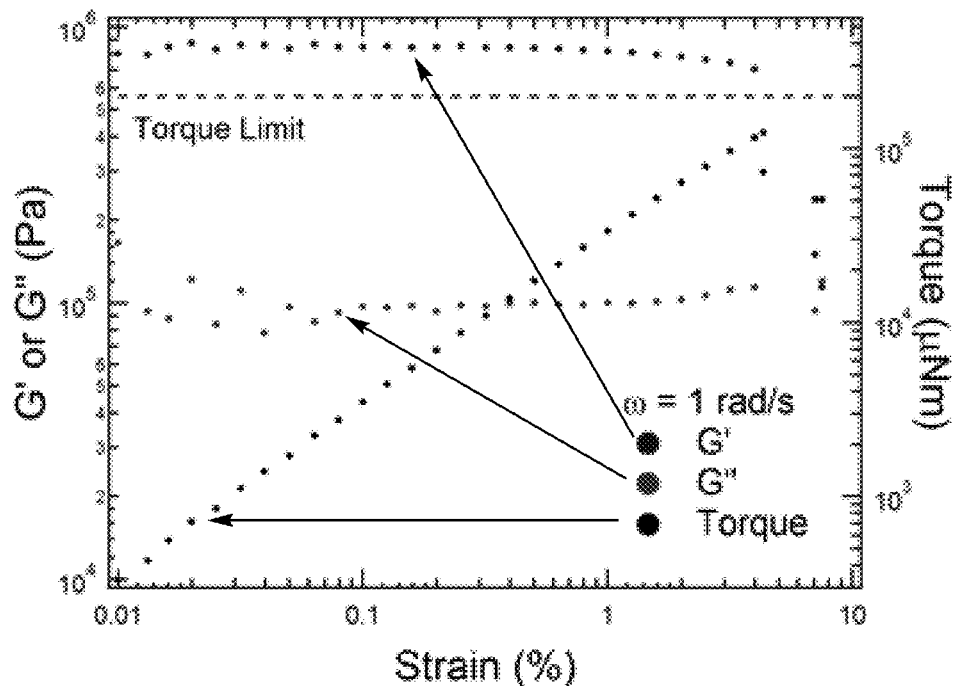
FIG. 2A depicts a strain sweep at 1 rad/s. The torque limit of the instrument was reached prior to yielding.
Figure 2B:
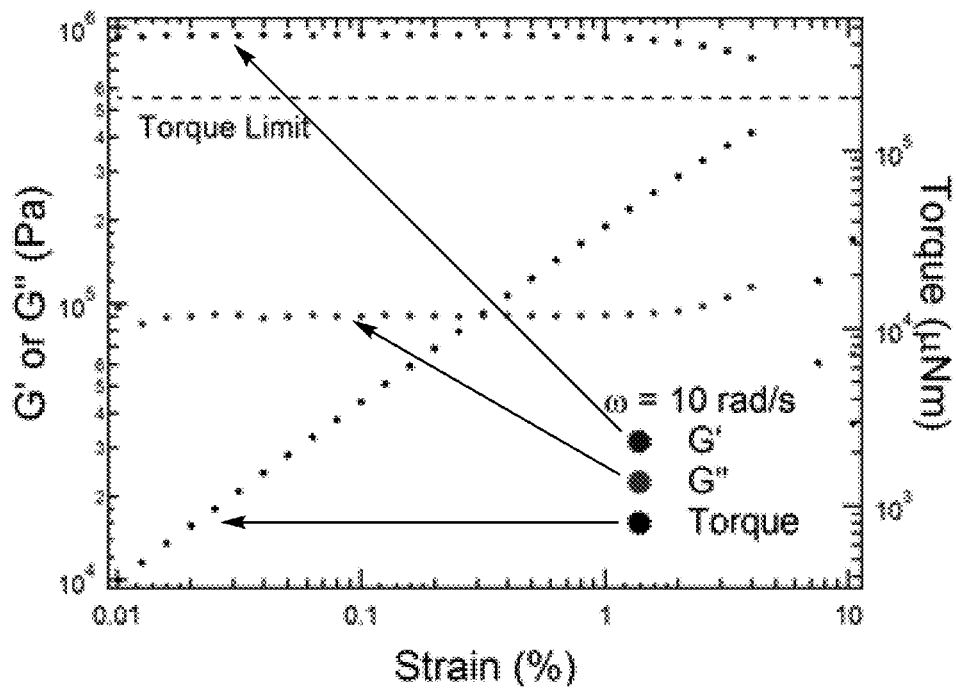
FIG. 2B depicts a strain sweep at 10 rad/s. The torque limit of the instrument was reached prior to yielding.
Figure 3:
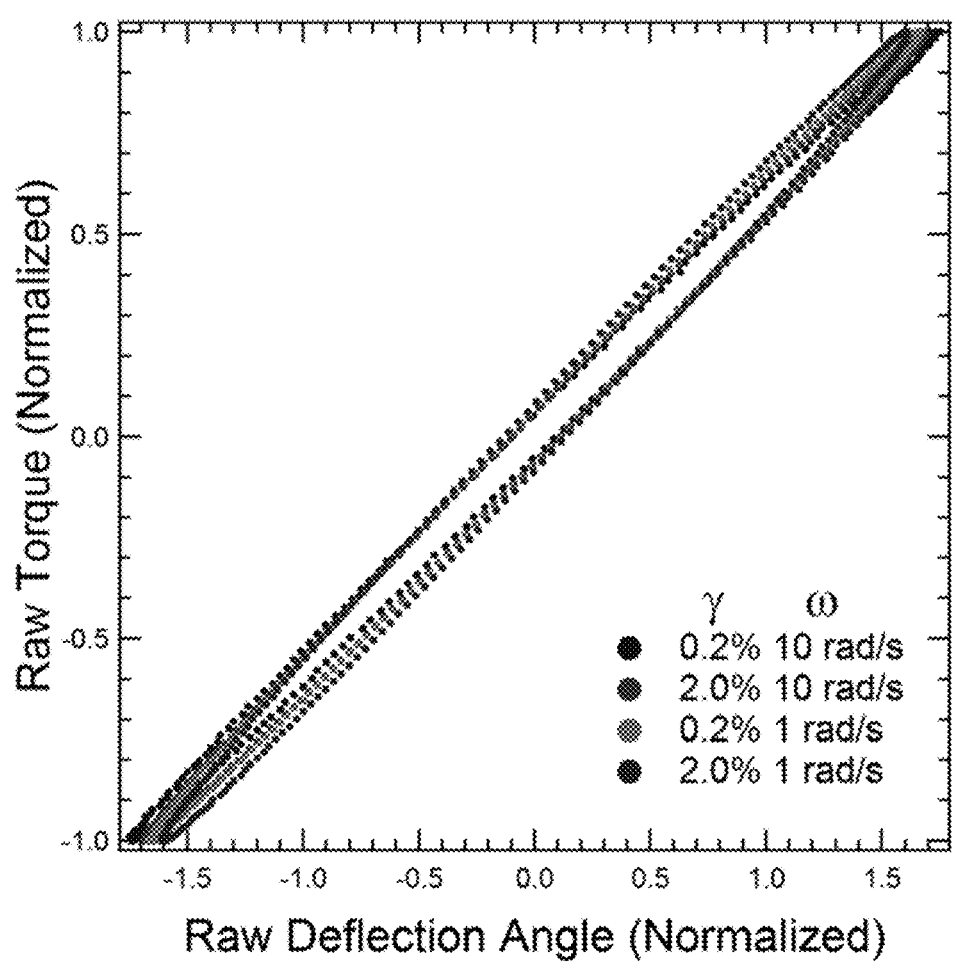
FIG. 3 depicts normalized Lissajous plots at the indicated strain/frequency combinations within the linear regime.
Figure 4:
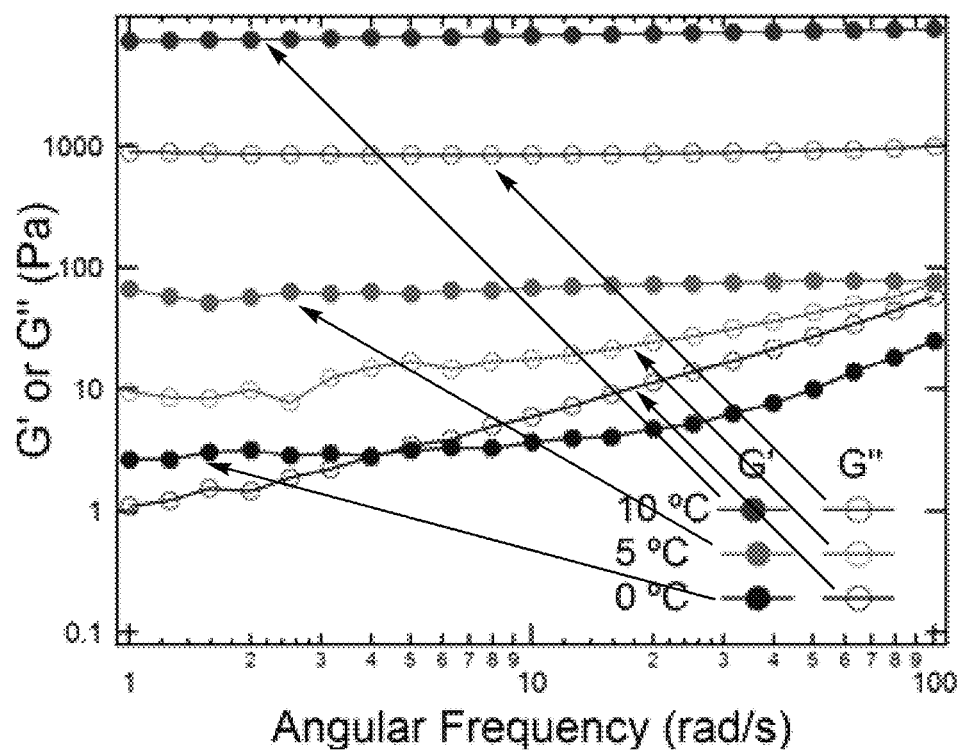
FIG. 4 depicts frequency sweeps ($\gamma=0.2\%$) showing the transition across the gel point.
Figure 5:
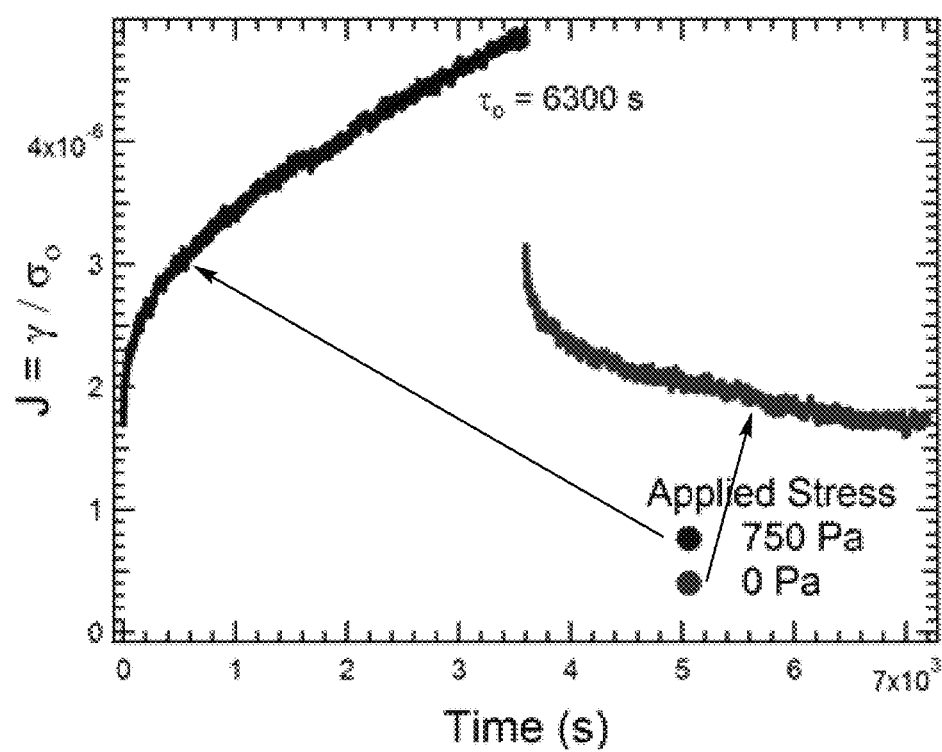
FIG. 5 depicts the results of a creep experiment to determine the longest stress relaxation time, $\tau_o$, which is comparable to the relaxation times of the thermoresponsive triblock gels. $G_o = j_\infty / \tau_o = 3.2 \times 10^5$ Pa, is at least 5-fold larger than typically seen in the stiffest 30% triblock gels.

In certain embodiments, the invention relates to a gel, for example a hydrogel, formed from the arrested macrophase separation of an elastin-like polypeptide (ELP).

ELPs are artificially-engineered repetitive proteins that typically comprise the sequence: (VPGVG)$_n$. (SEQ ID NO: 3) ELPs exhibit lower critical solution behavior in water, such that the proteins are soluble when cold, but collapse into a globule when warmed, e.g., to body temperature. When warmed, typical ELP solutions will form a coacervate phase, and generally exhibit poor mechanical properties. Thus, prior to this invention efforts to form hydrogels from ELPs focused on synthesis of more complex polymer architectures (typically, block copolymers), or chemically cross-linked ELPs. In the case of chemical crosslinking, the resulting hydrogels could no longer be injected, and heating resulted in gel shrinking and expulsion of water, resulting in materials that were unsuitable for many biomedical applications.

Surprisingly, ELPs designed with a particular composition and arrangement of amino acids, such as the polypeptides described herein, assemble into nanostructured hydrogels due to arrested macrophase separation in response to heating to body temperature.

In certain embodiments, the invention relates to a polypeptide with the generic sequence (XPAVG)$_n$ (SEQ ID NO: 4), wherein independently for each occurrence X can be any one of a number of different natural or unnatural amino acids, and n is chosen to determine the size of the protein. In certain embodiments, the polypeptide is artificially engineered and the invention relates to a method of engineering the polypeptide, for example, via biosynthesis. In certain embodiments, the sequence is modified at the N- or C-terminus or both. In certain embodiments, the sequence may be modified within the ELP sequence. In certain embodiments, the sequence is modified with cell-instructive peptide domains, such as cell adhesion ligands (for example, RGD or RGDS (SEQ ID NO: 5)), matrix metalloprotease (MMP) sites, and growth factor-mimetic peptides (for example, bone morphogenic protein (BMP)-mimetic peptides). Furthermore, in certain embodiments, the polypeptides are chain extended, for example, by using methods such as the oxidative coupling of thiol-containing cysteine residues. In certain embodiments, the polypeptide further comprises flexible linker groups. In certain embodiments, the flexible linker groups are soluble in the solvent that is to be gelled.

In certain embodiments, the invention relates to a composition, comprising a solvent; and any one of the polypeptides described herein, wherein the composition is a liquid at low temperatures; and the composition is a gel at higher temperatures. For example, in certain embodiments, the composition is a liquid at about 5° C., about 10° C., about 15° C., or about 20° C.; and the composition is a gel at about 25° C., about 30° C., about 35° C., or about 40° C., or at a higher temperature.

In certain embodiments, the invention relates to any one of the compositions described herein in the form of a gel, wherein the gel is stiff and extensible. In certain embodiments, the compositions comprise moderate concentrations of the polypeptide (e.g., about 20% w/w), and form a gel with a shear modulus of about 1 MPa or more at about 37° C.

In certain embodiments, the invention relates to any one of the compositions described herein for use as an injectable biomedical material, such as a reinforcing tissue filler for cosmetic surgery, or a matrix for the support of craniofacial bone tissue regeneration. In certain embodiments, the compositions direct the differentiation of mesenchymal stem cells (MSCs) into osteoblasts in 2D for bone formation. In certain embodiments, the compositions encapsulate chondrocytes for cartilage regeneration.

Exemplary Polypeptides

In certain embodiments, the invention relates to a polypeptide having the following sequence (SEQ ID NO: 1):

$$y^1\text{-}(XPAVG)_n\text{-}y^2$$

wherein, independently for each occurrence,
X is I or V;
n is an integer from 5-500; and
y$^1$ is hydrogen, an amine protecting group, a natural amino acid or unnatural amino acid, a plurality of natural amino acids or unnatural amino acids, a peptide, an oligopeptide, a polypeptide, a protein, a synthetic oligomer, a synthetic polymer, or a combination thereof; and
y$^2$ is hydrogen, a carboxylate protecting group, a natural or unnatural amino acid, a plurality of natural amino acids or unnatural amino acids, a peptide, an oligopeptide, a polypeptide, a protein, a synthetic oligomer, a synthetic polymer, or a combination thereof.

In certain embodiments, the invention relates to any one of the polypeptides described herein, wherein X has a ratio r; r is defined as (#I)/(#I+#V) for X; and r is about 0.1 to about 0.7. In certain embodiments, r is about 0.1, about 0.2, about 0.3, about 0.4, about 0.5, about 0.6, or about 0.7. In certain embodiments, r is from about 0.3 to about 0.5. In certain embodiments, r is about 0.4. In certain embodiments, r is from about 0.7 to about 0.9. In certain embodiments, r is from about 0.8.

In certain embodiments, the invention relates to any one of the polypeptides described herein, wherein n is an integer from 25-180. In certain embodiments, the invention relates to any one of the polypeptides described herein, wherein n is 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, or 180. In certain embodiments, the invention relates to any one of the polypeptides described herein, wherein n is from about 40 to about 60. In certain embodiments, the invention relates to any one of the polypeptides described herein, wherein n is about 50. In certain embodiments, the invention relates to any one of the polypeptides described herein, wherein n is from about 60 to about 80. In certain embodiments, the invention relates to any one of the polypeptides described herein, wherein n is about 70. In certain embodiments, the invention relates to any one of the polypeptides described herein, wherein n is from about 110 to about 130. In certain embodiments, the invention relates to any one of the polypeptides described herein, wherein n is about 120.

In certain embodiments, the invention relates to any one of the polypeptides described herein, wherein $y^1$ is hydrogen.

In certain embodiments, the invention relates to any one of the polypeptides described herein, wherein $y^2$ is hydrogen.

In certain embodiments, the invention relates to any one of the polypeptides described herein, wherein $y^1$ or $y^2$ comprises RGD. In certain embodiments, the invention relates to any one of the polypeptides described herein, wherein $y^1$ or $y^2$ comprises RGDS (SEQ ID NO: 5).

In certain embodiments, the invention relates to any one of the polypeptides described herein, wherein $y^1$ or $y^2$ comprises a cysteine residue.

In certain embodiments, the invention relates to any one of the polypeptides described herein, wherein $y^1$ or $y^2$ comprises a protein. In certain embodiments, the invention relates to any one of the polypeptides described herein, wherein $y^1$ or $y^2$ comprises an engineered protein.

In certain embodiments, the invention relates to any one of the polypeptides described herein, wherein $y^1$ or $y^2$ comprises a histidine tag.

In certain embodiments, the invention relates to any one of the polypeptides described herein, wherein $y^1$ or $y^2$ comprises five, six, seven, eight, nine, ten, eleven, or twelve histidine residues.

In certain embodiments, the invention relates to any one of the polypeptides described herein, wherein $y^1$ or $y^2$ comprises six histidine residues.

In certain embodiments, the invention relates to any one of the polypeptides described herein, wherein $y^1$ or $y^2$ comprises ten histidine residues.

In certain embodiments, the invention relates to any one of the polypeptides described herein, wherein $y^1$ or $y^2$ comprises a synthetic polymer.

In certain embodiments, the invention relates to any one of the polypeptides described herein, wherein the polypeptide has the following sequence (SEQ ID NO: 6):

$y^1$-[(IPAVGVPAVG)$_2$(IPAVG)]$_{10}$-$y^2$.

In certain embodiments, the invention relates to any one of the polypeptides described herein, wherein the polypeptide has the following sequence (SEQ ID NO: 7):

MGWGSASGLVGIPAVGVPAVGIPAVGVPAVGIPAVGIPAVGVPAVGIPAV

GVPAVGIPAVGIPAVGVPAVGIPAVGVPAVGIPAVGIPAVGVPAVGIPAV

GVPAVGIPAVGIPAVGVPAVGIPAVGVPAVGIPAVGIPAVGVPAVGIPAV

GVPAVGIPAVGIPAVGVPAVGIPAVGVPAVGIPAVGIPAVGVPAVGIPAV

GVPAVGIPAVGIPAVGVPAVGIPAVGVPAVGIPAVGIPAVGVPAVGIPAV

GVPAVGIPAVGETTS.

In certain embodiments, the invention relates to any one of the polypeptides described herein, wherein the polypeptide has the following sequence (SEQ ID NO: 8):

$y^1$-[(VPAVG)$_2$(IPAVG)(VPAVG)$_2$]$_{10}$-$y^2$.

In certain embodiments, the invention relates to any one of the polypeptides described herein, wherein the polypeptide has the following sequence (SEQ ID NO: 9):

MGWGSASGLVGVPAVGVPAVGIPAVGVPAVGVPAVGVPAVGVPAVGIPAV

GVPAVGVPAVGVPAVGIPAVGVPAVGVPAVGVPAVGVPAVGIPAV

GVPAVGVPAVGVPAVGIPAVGVPAVGVPAVGVPAVGVPAVGIPAV

GVPAVGVPAVGVPAVGIPAVGVPAVGVPAVGVPAVGVPAVGIPAV

GVPAVGVPAVGVPAVGIPAVGVPAVGVPAVGVPAVGVPAVGIPAV

GVPAVGVPAVGETTS.

In certain embodiments, the invention relates to any one of the polypeptides described herein, wherein the polypeptide has the following sequence (SEQ ID NO: 10):

$y^1$-KCTS-C$_1$-RGDS-[(IPAVGVPAVG)$_2$(IPAVG)]$_{10}$-RGDS-C$_1$-TSCK-$y^2$;

wherein C$_1$ is AGAGAGPEG (SEQ ID NO: 11).

In certain embodiments, the invention relates to any one of the polypeptides described herein, wherein the polypeptide has the following sequence (SEQ ID NO: 12):

MGWGSKCTSAGAGAGPEGRGDSTSGLVGIPAVGVPAVGIPAVGVPAVGIP

AVGIPAVGVPAVGIPAVGVPAVGIPAVGIPAVGVPAVGIPAVGVPAVGIP

AVGIPAVGVPAVGIPAVGVPAVGIPAVGIPAVGVPAVGIPAVGVPAVGIP

AVGIPAVGVPAVGIPAVGVPAVGIPAVGIPAVGVPAVGIPAVGVPAVGIP

AVGIPAVGVPAVGIPAVGVPAVGIPAVGIPAVGVPAVGIPAVGVPAVGIP

AVGIPAVGVPAVGIPAVGVPAVGIPAVGETTSRGDSAGAGAGPEGTSCK

L.

In certain embodiments, the invention relates to any one of the polypeptides described herein, wherein the polypeptide has the following sequence (SEQ ID NO: 13):

$y^1$-[(VPAVG)$_2$(IPAVG)(VPAVG)$_2$]$_{14}$-$y^2$.

In certain embodiments, the invention relates to any one of the polypeptides described herein, wherein the polypeptide has the following sequence (SEQ ID NO: 14):

```
MGWGSASGLVGVPAVGVPAVGIPAVGVPAVGVPAVGVPAVGVPAVGIPAV

GVPAVGVPAVGVPAVGVPAVGIPAVGVPAVGVPAVGVPAVGVPAVGIPAV

GVPAVGVPAVGVPAVGVPAVGIPAVGVPAVGVPAVGVPAVGVPAVGIPAV

GVPAVGVPAVGVPAVGVPAVGIPAVGVPAVGVPAVGVPAVGVPAVGIPAV

GVPAVGVPAVGVPAVGVPAVGIPAVGVPAVGVPAVGVPAVGVPAVGIPAV

GVPAVGVPAVGVPAVGVPAVGIPAVGVPAVGVPAVGVPAVGVPAVGIPAV

GVPAVGVPAVGVPAVGVPAVGIPAVGVPAVGVPAVGVPAVGVPAVGIPAV

GVPAVGVPAVGETTS.
```

In certain embodiments, the invention relates to any one of the polypeptides described herein, wherein the polypeptide has the following sequence (SEQ ID NO: 15):

$$y^1\text{-}[(VPAVG)_2(IPAVG)(VPAVG)_2]_{24}\text{-}y^2.$$

In certain embodiments, the invention relates to any one of the polypeptides described herein, wherein the polypeptide has the following sequence (SEQ ID NO: 16):

```
MGWGSASGLVGVPAVGVPAVGIPAVGVPAVGVPAVGVPAVGVPAVGIP

AVGVPAVGVPAVGVPAVGVPAVGIPAVGVPAVGVPAVGVPAVGVPAVG

IPAVGVPAVGVPAVGVPAVGVPAVGIPAVGVPAVGVPAVGVPAVGVPA

VGIPAVGVPAVGVPAVGVPAVGVPAVGIPAVGVPAVGVPAVGVPAVGV

PAVGIPAVGVPAVGVPAVGVPAVGVPAVGIPAVGVPAVGVPAVGVPAV

GVPAVGIPAVGVPAVGVPAVGVPAVGVPAVGIPAVGVPAVGVPAVGVP

AVGVPAVGIPAVGVPAVGVPAVGVPAVGVPAVGIPAVGVPAVGVPAVG

VPAVGVPAVGIPAVGVPAVGVPAVGVPAVGVPAVGIPAVGVPAVGVPA

VGVPAVGVPAVGIPAVGVPAVGVPAVGVPAVGVPAVGIPAVGVPAVGV

PAVGVPAVGVPAVGIPAVGVPAVGVPAVGVPAVGVPAVGIPAVGVPAV

GVPAVGVPAVGVPAVGIPAVGVPAVGVPAVGVPAVGVPAVGIPAVGVP

AVGVPAVGVPAVGVPAVGIPAVGVPAVGVPAVGVPAVGVPAVGIPAVG

VPAVGVPAVGVPAVGVPAVGIPAVGVPAVGVPAVGETTS.
```

In certain embodiments, the invention relates to any one of the polypeptides described herein, wherein the polypeptide has any of the sequences described herein.

There is a known and definite correspondence between the amino acid sequence of a particular polypeptide and the nucleotide sequences that can code for the polypeptide, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAG, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make polypeptides, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, in certain embodiments, the invention also relates to a nucleotide sequence of a DNA or RNA encoding any of the polypeptides described herein. Thus, description and/or disclosure of a polypeptide amino acid sequence herein should be considered to also include description and/or disclosure of all possible nucleotide sequences that can encode the amino acid sequence. An isolated nucleic acid molecule encoding a variant polypeptide can be created by introducing one or more nucleotide substitutions, additions or deletions into the nucleotide sequence of nucleic acids of the invention, such that one or more amino acid residue substitutions, additions, or deletions are introduced into the encoded polypeptide. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded polypeptide can be expressed recombinantly and the activity of the polypeptide can be determined.

In certain embodiments, the invention also relates to a polypeptide having an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the sequence of any one of the polypeptides described herein.

An "isolated" or "purified" polypeptide is substantially free of cellular material or other contaminating proteins from cells or tissue, or substantially free of chemical precursors or other chemicals when chemically synthesized. The language "substantially free of cellular material" includes preparations of polypeptides in which the polypeptide is separated from cellular components of the cells from which it is isolated or recombinantly produced. Thus, polypeptides that are substantially free of cellular material includes preparations of polypeptides having less than about 30%, 20%, 10%, or 5% (by dry weight) of heterologous proteins (also referred to herein as a "contaminating proteins"). When the polypeptide is recombinantly produced, it is also preferably substantially free of culture medium, i.e., culture medium represents less than about 20%, 10%, or 5% of the volume of the protein preparation. When the polypeptide is produced by chemical synthesis, it is preferably substantially free of chemical precursors or other chemicals, i.e., it is separated from chemical precursors or other chemicals which are involved in the synthesis of the polypeptide. Accordingly such preparations of the polypeptide have less than about 30%, 20%, 10%, 5% (by dry weight) of chemical precursors or compounds other than the polypeptide of interest.

Exemplary Compositions

In certain embodiments, the invention relates to a composition comprising, consisting essentially of, or consisting of any one of the aforementioned polypeptides; and a solvent.

In certain embodiments, the invention relates to any one of the compositions described herein, wherein the polypeptide is present in an amount from about 1% to about 50% by weight of the composition. In certain embodiments, the invention relates to any one of the compositions described herein, wherein the polypeptide is present in an amount from about 1% to about 40% by weight of the composition. In certain embodiments, the invention relates to any one of the compositions described herein, wherein the polypeptide is present in an amount from about 1% to about 30% by weight of the composition. In certain embodiments, the invention relates to any one of the compositions described herein, wherein the polypeptide is present in an amount from about 1% to about 25% by weight of the composition. In certain embodiments, the invention relates to any one of the compositions described herein, wherein the polypeptide is present in an amount from about 1% to about 20% by weight of the composition. In certain embodiments, the invention relates to any one of the compositions described herein, wherein the polypeptide is present in an amount of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25% by weight of the composition.

In certain embodiments, the invention relates to any one of the compositions described herein, wherein the solvent comprises water (i.e., is an aqueous solvent). In certain embodiments, the invention relates to any one of the compositions described herein, wherein the solvent is water.

In certain embodiments, the invention relates to any one of the compositions described herein, wherein the solvent comprises water; and the solvent is buffered (i.e., is a buffered aqueous solvent). In certain embodiments, the invention relates to any one of the compositions described herein, wherein the solvent is a buffered aqueous solvent having a pH from about 5.0 to about 9.0. In certain embodiments, the invention relates to any one of the compositions described herein, wherein the solvent is a buffered aqueous solvent having a pH from about 7.2 to about 8.0. In certain embodiments, the invention relates to any one of the compositions described herein, wherein the solvent is a buffered aqueous solvent having a pH of about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0. about 8.1, about 8.2, about 8.3, about 8.4, about 8.5, about 8.6, about 8.7, about 8.8, about 8.9, or about 9.0. In certain embodiments, the invention relates to any one of the compositions described herein, wherein the solvent is a buffered aqueous solvent having a pH of about 7.3, about 7.4, about 7.5, about 7.6, about 7.7, about 7.8, or about 7.9.

In certain embodiments, the invention relates to any one of the compositions described herein, wherein the solvent is a buffered aqueous solvent, comprising a buffer selected from the group consisting of: N-(2-acetamido)-2-aminoethanesulfonic acid (aces), N-(2-acetamido)iminodiacetic acid (ADA), acetate, 2-amino-2-methyl-1,3-propanediol (AMPD), 2-amino-2-methyl-1-propanol (AMP), N,N-bis(2-hydroxyethyl)-2-aminoethanesulfonic acid (BES), 3-(N,N-bis[2-hydroxyethyl]amino)-2-hydroxypropanesulfonic acid (DIPSO), N,N-bis(2-hydroxyethyl)glycine (Bicine), bis(2-hydroxyethyl)iminotris(hydroxymethyl)methane (Bis-Tris), 1,3-bis[tris(hydroxymethyl)methylamino]propane (Bis-Tris propane), borate, citrate, 4-(cyclohexylamino)-1-butanesulfonic acid (CABS), 2-(cyclohexylamino)ethanesulfonic acid (CHES), 3-(cyclohexylamino)-2-hydroxy-1-propanesulfonic acid (CAPSO), 3-(cyclohexylamino)-1-propanesulfonic acid (CAPS), diglycine (Gly-Gly), 3-([1,1-dimethyl-2-hydroxyethyl]amino)-2-hydroxypropanesulfonic acid (AMPSO), glycine, 2-[(2-hydroxy-1,1-bis[hydroxymethyl]ethyl)amino]ethanesulfonic acid (TES), N-(2-hydroxyethyl)piperazine-N'-(4-butanesulfonic acid) (HEPBS), N-(2-hydroxyethyl)-piperazine-N'-ethanesulfonic acid (HEPES), 4-(2-hydroxyethyl)-1-piperazinepropanesulfonic acid (EPPS), 4-(N-morpholino)butanesulfonic acid (MOBS), 2-(N-morpholino)ethanesulfonic acid (MES), 3-(N-morpholino)propanesulfonic acid (MOPS), 3-(N-morpholinyl)-2-hydroxypropanesulfonic acid (MOPSO), phosphate, piperazine-N,N'-bis(2-hydroxypropanesulfonic acid) (POPSO), 1,4-piperazinediethanesulfonic acid (PIPES), tris(hydroxymethyl)aminomethane (Tris), 3-(N-tris[hydroxymethyl]methylamino)-2-hydroxypropanesulfonic acid (TAPSO), N-tris(hydroxymethyl)methyl-3-aminopropanesulfonic acid (TAPS), and N-[tris(hydroxymethyl)methyl] glycine (Tricine).

In certain embodiments, the invention relates to any one of the compositions described herein, wherein the solvent is a buffered aqueous solvent comprising a buffer at a concentration from about 25 mM to about 500 mM. In certain embodiments, the invention relates to any one of the compositions described herein, wherein the solvent is a buffered aqueous solvent comprising a buffer at a concentration of about 50 mM, about 75 mM, about 100 mM, about 125 mM, about 150 mM, about 175 mM, about 200 mM, about 225 mM, about 250 mM, about 275 mM, about 300 mM, about 325 mM, about 350 mM, about 375 mM, about 400 mM, about 425 mM, about 450 mM, about 475 mM, or about 500 mM.

In certain embodiments, the invention relates to any one of the compositions described herein, wherein the composition further comprises a cell culture medium.

In certain embodiments, the invention relates to any one of the compositions described herein, wherein the composition is a liquid at a temperature less than 30° C. In certain embodiments, the invention relates to any one of the compositions described herein, wherein the composition is a liquid at a temperature less than 25° C. In certain embodiments, the invention relates to any one of the compositions described herein, wherein the composition is a liquid at a temperature less than 20° C. In certain embodiments, the invention relates to any one of the compositions described herein, wherein the composition is a liquid at a temperature less than about 15° C. In certain embodiments, the invention relates to any one of the compositions described herein, wherein the composition is a liquid at a temperature less than about 10° C. In certain embodiments, the invention relates to any one of the compositions described herein, wherein the composition is a liquid at a temperature less than about 5° C. In certain embodiments, the invention relates to any one of the compositions described herein, wherein the composition is a liquid at a temperature less than about 0° C.

In certain embodiments, the invention relates to any one of the compositions described herein, wherein the composition is a gel at a temperature greater than 20° C. In certain embodiments, the invention relates to any one of the compositions described herein, wherein the composition is a gel at a temperature greater than about 25° C. In certain embodiments, the invention relates to any one of the compositions described herein, wherein the composition is a gel at a temperature greater than about 30° C. In certain embodiments, the invention relates to any one of the compositions described herein, wherein the composition is a gel at a temperature greater than about 40° C.

In certain embodiments, the invention relates to any one of the compositions described herein, wherein the shear modulus (G) of the composition at about 37° C. is about 100 kPa to about 10 MPa. In certain embodiments, the invention relates to any one of the compositions described herein, wherein the shear modulus (G) of the composition at about 37° C. is about 100 kPa, about 200 kPa, about 300 kPa, about 400 kPa, about 500 kPa, about 600 kPa, about 700 kPa, about 800 kPa, about 900 kPa, about 1.0 MPa, about 1.1 MPa, about 1.2 MPa, about 1.3 MPa, about 1.4 MPa, about 1.5 MPa, about 1.6 MPa, about 1.7 MPa, about 1.8 MPa, about 1.9 MPa, about 2 MPa, about 2.5 MPa, about 3 MPa, about 3.5 MPa, about 4 MPa, about 4.5 MPa, about 5 MPa, about 5.5 MPa, about 6 MPa, about 6.5 MPa, about 7 MPa, about 7.5 MPa, about 8 MPa, about 8.5 MPa, about 9 MPa, about 9.5 MPa, or about 10 MPa.

In certain embodiments, the invention relates to any one of the compositions described herein, wherein the composition is substantially optically clear.

In certain embodiments, the invention relates to any one of the compositions described herein, wherein the composition forms a gel within a first amount of time after heating the composition to a first temperature; and the first temperature is greater than the transition temperature. In certain embodiments, the first amount of time is from about 30 seconds to about 5 minutes. In certain embodiments, the first amount of time is from about 1 minute to about 3 minutes. In certain embodiments, the first amount of time is about 1 minute, about 2 minutes, or about 3 minutes.

In certain embodiments, the invention relates to any one of the compositions described herein, wherein the composition substantially resolubilizes within a second amount of time after cooling the composition to a second temperature; and the second temperature is less than the transition temperature. In certain embodiments, the second amount of time is from about 10 minutes to about 90 minutes. In certain embodiments, the second amount of time is from about 20 minutes to about 60 minutes. In certain embodiments, the second amount of time is about 20 minutes, about 30 minutes, about 40 minutes, about 50 minutes, or about 60 minutes. In certain embodiments, the second temperature is about 0° C.

In certain embodiments, the invention relates to any one of the compositions described herein, wherein the yield stress of the composition is from about 5 kPa to about 150 kPa. In certain embodiments, the invention relates to any one of the compositions described herein, wherein the yield stress of the composition is from about 10 kPa to about 100 kPa. In certain embodiments, the invention relates to any one of the compositions described herein, wherein the yield stress of the composition is about 10 kPa, about 20 kPa, about 30 kPa, about 40 kPa, about 50 kPa, about 60 kPa, about 70 kPa, about 80 kPa, about 90 kPa, or about 100 kPa.

In certain embodiments, the invention relates to any one of the compositions described herein, wherein the yield strain of the composition is from about 5% to about 150%. In certain embodiments, the invention relates to any one of the compositions described herein, wherein the yield strain of the composition is from about 10% to about 100%. In certain embodiments, the invention relates to any one of the compositions described herein, wherein the yield strain of the composition is about 10%, about 20%, about 30%, about 40%, about 50%, about 60%, about 70%, about 80%, about 90%, or about 100%

In certain embodiments, the invention relates to any one of the compositions described herein, wherein the composition is nanostructured. In certain embodiments, the invention relates to any one of the compositions described herein, wherein the composition is nanostructured at about 37° C. In certain embodiments, the invention relates to any one of the compositions described herein, wherein the nanostructure of the composition has a length scale from about 15 nm to about 100 nm at about 37° C. In certain embodiments, the invention relates to any one of the compositions described herein, wherein the nanostructure of the composition has a length scale from about 30 nm to about 70 nm at about 37° C. In certain embodiments, the invention relates to any one of the compositions described herein, wherein the nanostructure of the composition has a length scale at about 37° C. of about 30 nm, about 40 nm, about 50 nm, about 60 nm, or about 70 nm.

Exemplary Materials

In certain embodiments, the invention relates to a biomedical material comprising, consisting essentially of, or consisting of any one of the polypeptides described herein or any one of the compositions described herein.

In certain embodiments, the invention relates to any one of the biomedical materials described herein for use in the replacement, reinforcement, or regeneration of load-bearing tissues.

In certain embodiments, the invention relates to any one of the compositions described herein for use as an injectable biomedical material.

In certain embodiments, the invention relates to any one of the compositions described herein for use in cosmetic surgery. In certain embodiments, the invention relates to any one of the compositions described herein for use as a tissue filler.

In certain embodiments, the invention relates to any one of the compositions described herein for use in bone formation. In certain embodiments, the invention relates to any one of the compositions described herein for use as a matrix for the support of craniofacial bone tissue regeneration.

In certain embodiments, the invention relates to any one of the compositions described herein for use in cartilage regeneration.

In certain embodiments, the invention relates to a cell culture medium comprising, consisting essentially of, or consisting of any one of the polypeptides described herein or any one of the compositions described herein.

In certain embodiments, the invention relates to any one of the cell culture media described herein, wherein the cell culture medium further comprises a cell. In certain embodiments, the invention relates to any one of the cell culture media described herein, wherein the cell culture medium further comprises a plurality of cells.

In certain embodiments, the invention relates to any one of the compositions described herein for use in growing or encapsulating a cell or a plurality of cells.

Exemplary Methods

In certain embodiments, the invention relates to a method, comprising the step of:

injecting into a subject in need thereof an effective amount of any one of the polypeptides described herein, any one of the compositions described herein, or any one of the biomedical materials described herein.

In certain embodiments, the invention relates to any one of the methods described herein, wherein the method is a method of replacing, reinforcing, or regenerating a load-bearing tissue in the subject.

In certain embodiments, the invention relates to any one of the methods described herein, wherein the method is a cosmetic surgical method. In certain embodiments, the invention relates to any one of the methods described herein, wherein the method is a method of replacing, reinforcing, or regenerating facial tissue in the subject.

In certain embodiments, the invention relates to any one of the methods described herein, wherein the method is a method of replacing, reinforcing, or regenerating bone in the subject. In certain embodiments, the invention relates to any one of the methods described herein, wherein the method is a method of replacing, reinforcing, or regenerating craniofacial bone tissue in the subject. In certain embodiments, the invention relates to any one of the methods described herein, wherein the method is a method of regenerating craniofacial bone tissue in the subject.

In certain embodiments, the invention relates to any one of the methods described herein, wherein the method is a method of replacing, reinforcing, or regenerating cartilage in the subject.

In certain embodiments, the invention relates to any one of the methods described herein, wherein the method is a method of regenerating cartilage in the subject.

EXEMPLIFICATION

The invention now being generally described, it will be more readily understood by reference to the following, which is included merely for purposes of illustration of certain aspects and embodiments of the present invention, and is not intended to limit the invention.

Example 1

Protein Sequences $P_{10}$: I/V=3/2
[(IPAVGVPAVG)$_2$(IPAVG)]$_{10}$ (SEQ ID NO: 60) (23.0 kDa)
Complete sequence (SEQ ID NO: 17):

MGWGSASGLVGIPAVGVPAVGIPAVGVPAVGIPAVGIPAVGVPAVGIP
AVGVPAVGIPAVGIPAVGVPAVGIPAVGVPAVGIPAVGIPAVGVPAVG
IPAVGVPAVGIPAVGIPAVGVPAVGIPAVGVPAVGIPAVGIPAVGVPA
VGIPAVGVPAVGIPAVGIPAVGVPAVGIPAVGVPAVGIPAVGIPAVGV
PAVGIPAVGVPAVGIPAVGIPAVGVPAVGIPAVGVPAVGIPAVGIPAV
GVPAVGIPAVGVPAVGIPAVGETTS $P'_{10}$: I/V=1/4
[(VPAVG)$_2$(IPAVG)(VPAVG)$_2$]$_{10}$ (SEQ ID NO: 61) (22.8 kDa)
Complete sequence (SEQ ID NO: 18):

MGWGSASGLVGVPAVGVPAVGIPAVGVPAVGVPAVGVPAVGVPAVGIP
AVGVPAVGVPAVGVPAVGVPAVGIPAVGVPAVGVPAVGVPAVGVPAVG
IPAVGVPAVGVPAVGVPAVGVPAVGIPAVGVPAVGVPAVGVPAVGVPA
VGIPAVGVPAVGVPAVGVPAVGVPAVGIPAVGVPAVGVPAVGVPAVGV
PAVGIPAVGVPAVGVPAVGVPAVGVPAVGIPAVGVPAVGVPAVGVPAV
GVPAVGIPAVGVPAVGVPAVGETTS

C-RGDS-$P_{10}$-RGDS-C (SEQ ID NO: 62)
KCTS-$C_1$-RGDS-$P_{10}$-RGDS-$C_1$-TSCK (SEQ ID NO: 63)
Complete sequence (SEQ ID NO: 19):

MGWGSKCTSAGAGAGPEGRGDSTSGLVGIPAVGVPAVGIPAVGVPAVG
IPAVGIPAVGVPAVGIPAVGVPAVGIPAVGIPAVGVPAVGIPAVGVPA
VGIPAVGIPAVGVPAVGIPAVGVPAVGIPAVGIPAVGVPAVGIPAVGV
PAVGIPAVGIPAVGVPAVGIPAVGVPAVGIPAVGIPAVGVPAVGIPAV
GVPAVGIPAVGIPAVGVPAVGIPAVGVPAVGIPAVGIPAVGVPAVGIP
AVGVPAVGIPAVGIPAVGVPAVGIPAVGVPAVGIPAVGETTSRGDSAG
AGAGPEGTSCKL

Synthesis by Cloning

Genes for various ELP sequences were concatamerized starting from double-stranded DNA 'monomers' (each encoding five pentapeptide repeats) that were digested with a type IIS restriction enzyme (such as BsaI). The digest pattern was designed to allow for seamless cloning of the concatamers in a robust, head-to-tail addition fashion. Multiple rounds of concatamerization were performed to yield genes that encoded proteins from 10 to 100 kDa in molar mass. The concatamerization reactions were re-ligated into a pET-22b vector with a modified multiple cloning site (MCS) (abbreviated: pETA) containing the following pattern of restriction sites: BamHI-NheI-ELP gene-SpeI-HindIII. Facile end-biofunctionalization of these genes could be performed from 4-component ligations made of: (1) BamHI/HindIII double-digested PETA vectors, (2) the BamHI/SpeI digested 5'-gene-prefix sequence, (3) the NheI/SpeI double digested ELP gene insert, and (4) the NheI/HindIII digested 3'-gene-suffix sequence. Proper insertion of the elements in the correct order can be confirmed by BamHI/SpeI or NheI/HindIII double digests, either of which would yield near full-length genes.

$P_{10}$ and $P'_{10}$ genes were concatamerized using Type IIS restriction enzymes for seamless cloning. Modified pET vectors (pETA) were prepared containing momeric subunits by inserting the following cassette between the BamHI/HindIII sites of pET-28b:

a. pETA-P$_1$ (SEQ ID NO: 20):
GGATCCGCTAGC<u>GGTCTC</u>GTTGGTATTCCTGCTGTTGGTGTGCCGGCT

GTTGGTATCCCAGCTGTTGGCGTTCCGGCTGTAGGTATTCCGGCTGTT

GGT<u>GAGACC</u>ACTAGTTAAATGAATAAGCTT b. pETA-P'$_1$ (SEQ ID NO: 21):
GGATCCGCTAGC<u>GGTCTC</u>GTTGGTGTTCCTGCTGTCGGTGTGCCGGCT

GTTGGTATTCCAGCTGTTGGCGTGCCGGCTGTAGGTGTCCCGGCTGTT

GGC<u>GAGACC</u>ACTAGTTAAATGAATAAGCTT

Genes containing 10 repeats were assembled starting from BsaI-digested momeric subunits. C-RGDS-$P_{10}$-RGDS-C (SEQ ID NO: 62) was cloned from a 4-component ligation reaction consisting of BamHI/HindIII digested pETA, NheI/SpeI digested Pro, and two annealed pairs of non-phosphorylated oligonucleotides with the following sequences:

a. 5' flanking pair (SEQ ID NOS 22 and 23):
i.
GATCCAAATGTACCTCTGCCGGCGCTGGTGCGGGCCCGGAAGGTCGTG
GTGATTCTA ii.
CAAATGTACCTCTGCCGGCGCTGGTGCGGGCCCGGAAGGTCGTGGTGA
TTCTACTAG b. 3' flanking pair (SEQ ID NOS 24 and 25):
i.
CTAGTCGTGGTGATTCTGCCGGCGCTGGTGCGGGCCCGGAAGGTACAA
GCTGTA ii.
TCGTGGTGATTCTGCCGGCGCTGGTGCGGGCCCGGAAGGTACAAGCTG
TAAGCT Expression and Purification Proteins were expressed in Tuner(DE3) cells without induction, typically in 5 L fermentations at 30° C. for 16 hours. Cell pellets were resuspended in 20 mM Tris, 100 mM NaCl, 1 mM EDTA, 5 mM MgCl$_2$ (pH=7.5) at 30 g WCM per 100 mL buffer. After clarification, RNAse A and DNAse I were added to the supernatant (2-4 mg per 100 mL cell suspension), and incubated at 37° C. for at least 2 hours. Then, the proteins were isolated by three rounds of thermal precipitation in buffer, cycling between 4° C. and 37° C. The proteins were finally passed over an ion exchange resin (HiTrap Q, GE Healthcare) under denaturing conditions (6 M urea, 20 mM Tris, pH=8.0), dialyzed against water, and lyophilized.

Preparation of Hydrogels

Thermoresponsive ELP hydrogels were prepared first by dissolving the lyophilized powder in water or buffer on ice for several hours. Oscillatory shear rheology (described below) demonstrated that these solutions gel over a narrow temperature range and stiffen dramatically to exhibit elastic moduli on the order of 1 MPa just above room temperature. These gels are physical and reversible in nature, although they exhibit extremely long stress relaxation times ($>>10^3$ seconds). While gelation is rapid over a narrow temperature window, the timescale of resolubilization of the individual ELP proteins will depend on the length of time the gel is held in the warmed state: disruption of the gel network occurs only after extended incubation at 0° C. for tens of minutes.

Rheology

Qualitative examination of 20% gels made from cysteine-flanked $P_{10}$ suggests that thiol oxidation and chain-extension improve the extensibility of the hydrogels. The proteins solubilized slowly even at 0° C. in 100 mM phosphate buffer, pH=7.6, but could be solubilized faster in pure water. These materials were more viscous at low temperatures, and when warmed appeared more adhesive and were also more difficult to cut with a spatula. See FIGS. 1-5.

Birefringence and Turbidimetry

Figure 6A:
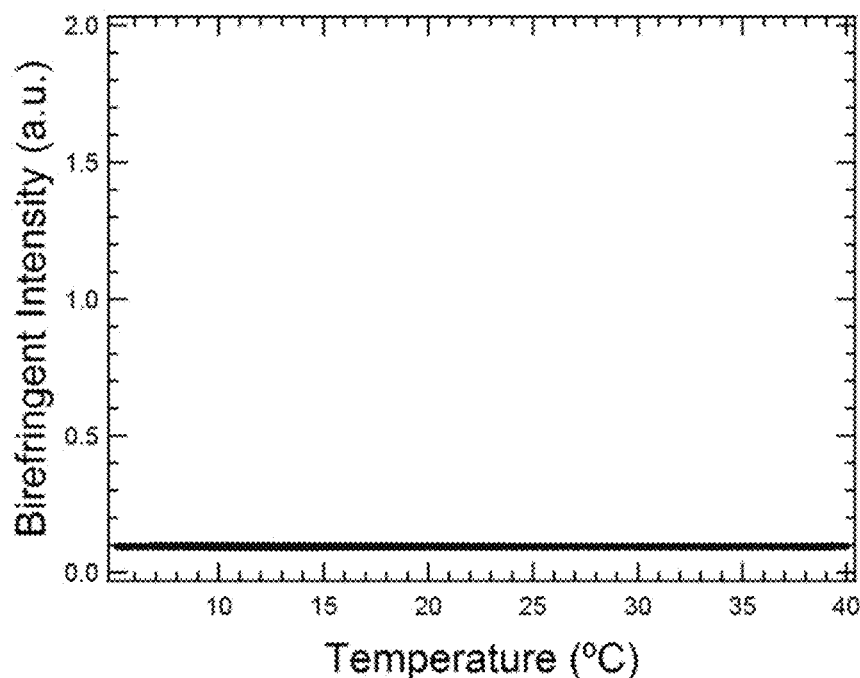
FIG. 6A depicts birefringence data for a 20% $P_{10}$ gel in phosphate buffer.
Figure 6B:
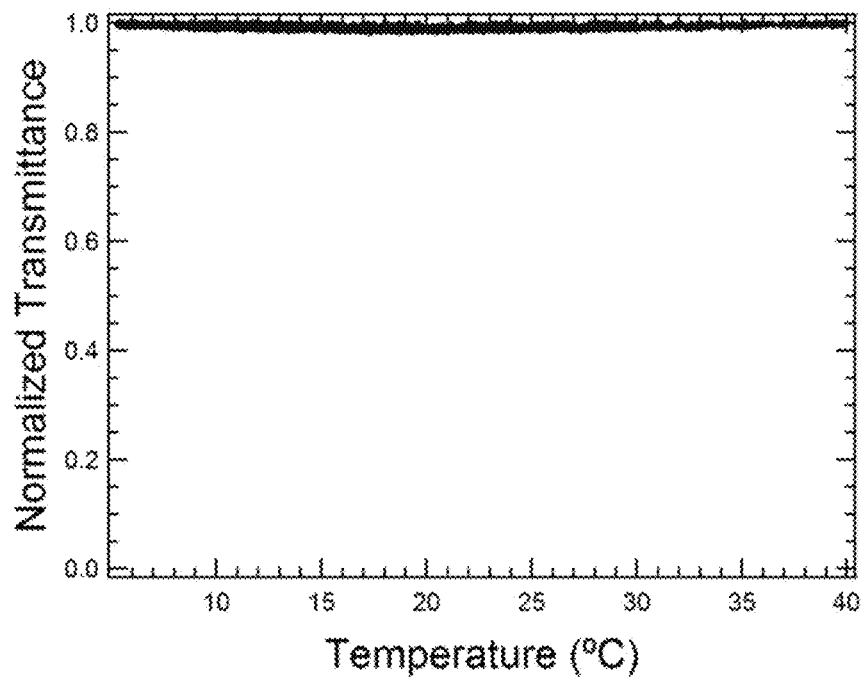
FIG. 6B depicts transmittance data for a 20% $P_{10}$ gel in phosphate buffer.

A $P_{10}$ gel at 20% did not appear birefringent or turbid over the range from 5-40° C. Slightly turbid gels squeezed into quartz DPLS cells can become clear; this is consistent with what is seen when triggering gelation for low concentration solutions (5-10%): a milky two-phase solution is formed when warmed, and the mixture can be separated by centrifugation into a translucent gel phase and a clear sol phase. See FIG. 6.

Differential Scanning Calorimetry

Figure 7:
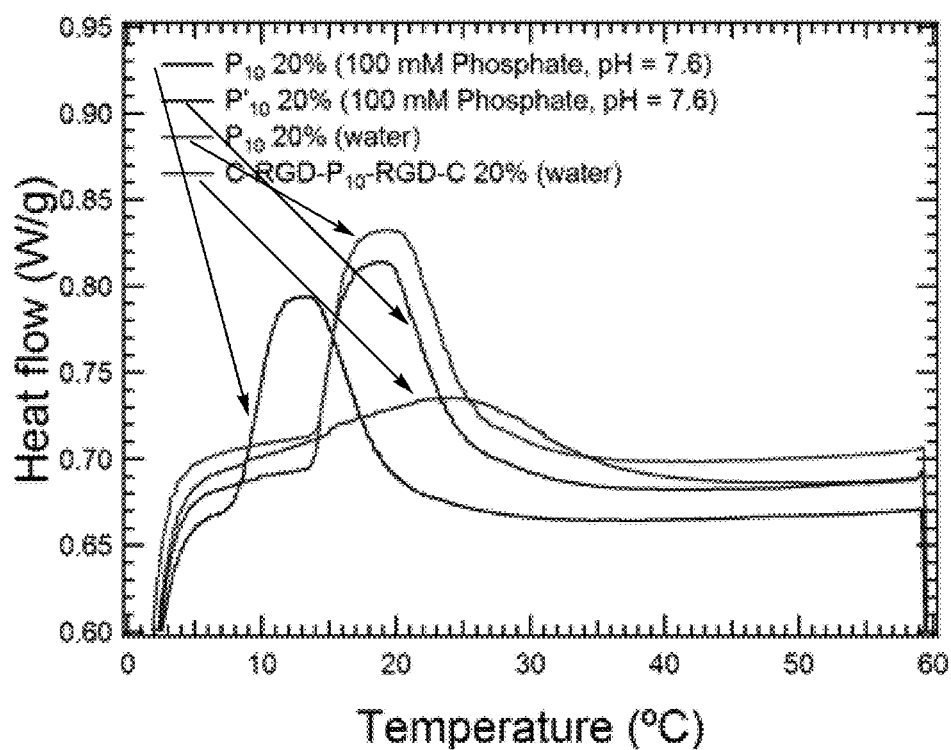
FIG. 7 depicts example DSC traces (endotherm up) for 20% $P_{10}$ and $P'_{10}$ gels, demonstrating the large asymmetric endothermic peak seen upon heating, while no features are discernible on the cooling cycle at this ramp rate (10° C./min).

Two ramps were run at 10° C./min from 0-60° C. with a 20 minute wait time between cycles. Analysis was performed on the second cycle, although the cycles were essentially indistinguishable. See Table 1 and FIG. 7.

TABLE 1

DSC data for 20% gels in the indicated solvent.

| Protein | Solvent | Onset Temperature | Temperature at Max |
|---|---|---|---|
| $P_{10}$ | 100 mM Phosphate, pH = 7.6 | 8.5 | 13.0 |
| $P'_{10}$ | 100 mM Phosphate, pH = 7.6 | 13.9 | 19.1 |
| $P_{10}$ | Water | 14.1 | 19.5 |
| C-RGDS-$P_{10}$-RGDS-C (SEQ ID NO: 62) | Water | — | 23.7 |

Example 2

Effect of Substitution of Valine for Isoleucine

Polypeptides were made according to the following formula (SEQ ID NO: 26):

(X'PAVG)$_n$ where $X^r$ is I or V $(r=(\#I)/(\#I+\#V))$.

Their physical properties were studied. See Table 2.

TABLE 2

Physical properties of various polypeptides

| Sequence | State at >20° C. |
|---|---|
| $(X^{0.6}PAVG)_{10}$ (SEQ ID NO: 27) | Stiff Gel |
| $(X^{0.2}PAVG)_{10}$ (SEQ ID NO: 28) | Stiff Gel |

Figure 10:
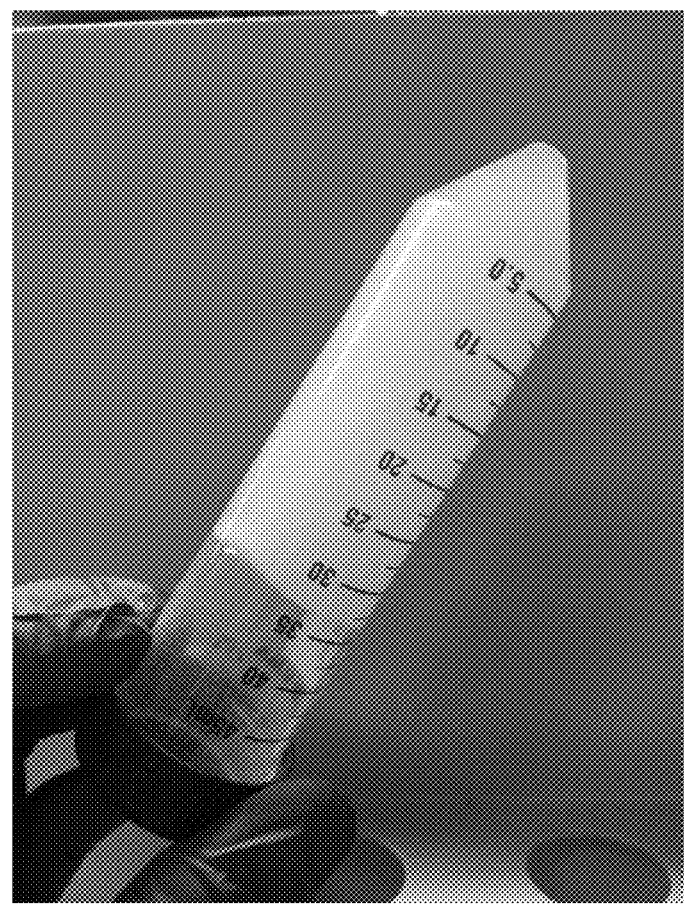
FIG. 10 depicts a photograph of a KCTS-C$_1$-RGDS-(X$^{0.6}$PAVG)$_{10}$-RGDS-C$_1$-TSCK (SEQ ID NO: 2) gel.

A photograph of a $(X^{0.6}PAVG)_{10}$ (SEQ ID NO: 27) gel is depicted in FIG. 10.

Effect of Substitution of Glycine for Alanine

Polypeptides were made according to the following formula (SEQ ID NO: 29):

$(X^r PYVG)_n$ 

where $X_r$ is I or V $(r=(\#I)/(\#I+\#V))$, and

Y is A or G.

The presence of alanine relates to gelation versus precipitation. See Table 3.

TABLE 3

Physical properties of various polypeptides

| Sequence | State at >20° C. |
|---|---|
| $(X^{0.2}PAVG)_{10}$ (SEQ ID NO: 28) | Stiff Gel |
| $(X^{0.2}PGVG)_{10}$ (SEQ ID NO: 31) | Turbid liquid |

Effect of Peptide Length

Polypeptides were made according to the following formula (SEQ ID NO: 30):

$(X^r PAVG)_n$ 

where $X^r$ is I or V $(r=(\#I)/(\#I+\#V))$.

Gels were formed for peptides with n=10, 14, 24. See Table 4.

TABLE 4

Physical properties of various polypeptides

| Sequence | State at >20° C. |
|---|---|
| $(X^{0.2}PAVG)_{10}$ (SEQ ID NO: 28) | Stiff Gel |
| $(X^{0.2}PAVG)_{14}$ (SEQ ID NO: 32) | Stiff Gel |
| $(X^{0.2}PAVG)_{24}$ (SEQ ID NO: 33) | Stiff Gel |

Example 3

Chain Extension Leads to Stiff Extensible Gels

The following polypeptide was synthesized by cloning (SEQ ID NO: 64):

C-RGD-$(X^{0.6}PAVG)_{10}$-RGD-C 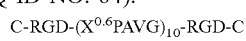

The properties of the gels were compared to those of gels formed by the unextended polypeptide. See FIG. 8A, FIG. 8B, and FIG. 11.

Figure 8A:
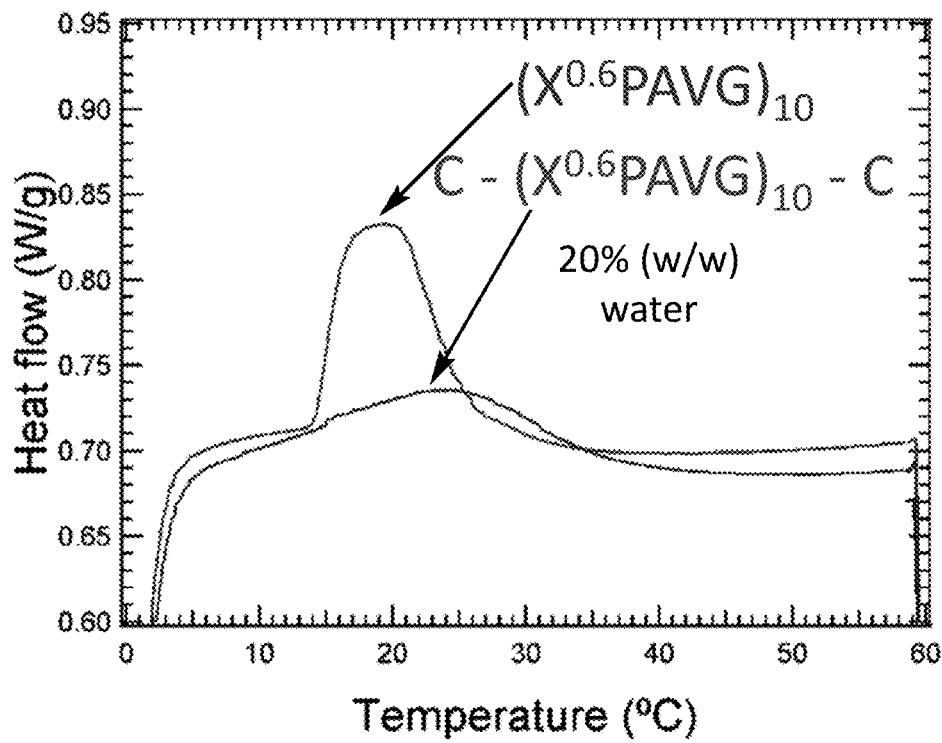
FIG. 8A depicts example DSC traces (endotherm up) showing the effect of oxidative chain extension on the thermal transition of the P$_{10}$ gels.
Figure 8B:
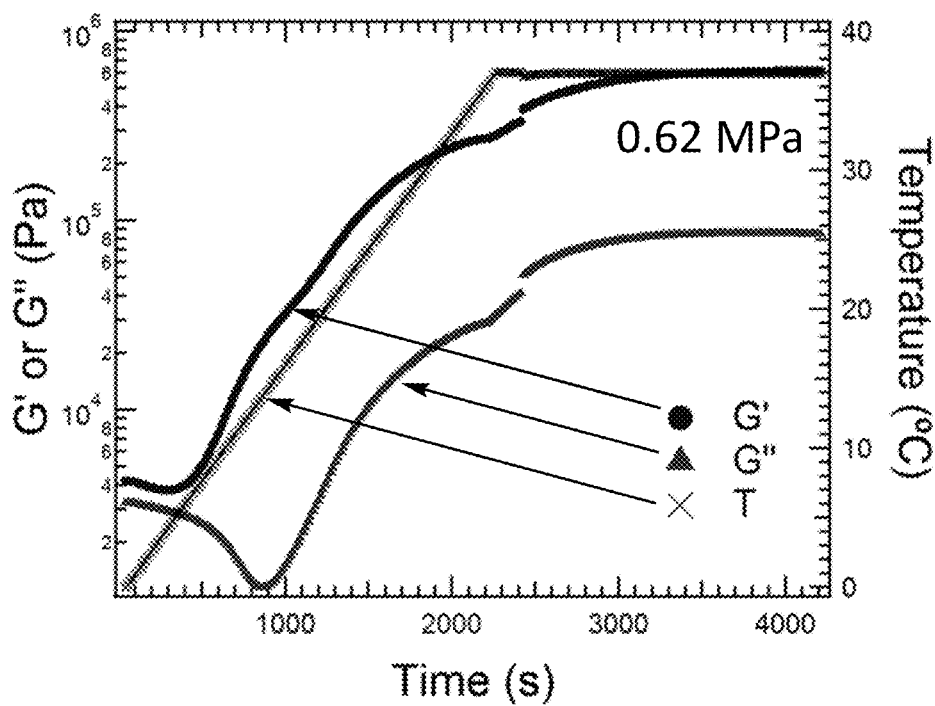
FIG. 8B depicts linear oscillatory shear rheology of oxidatively chain-extended P$_{10}$ gels, heated at 1° C./min. Measurements were performed at w=100 rad/s.
Figure 11:
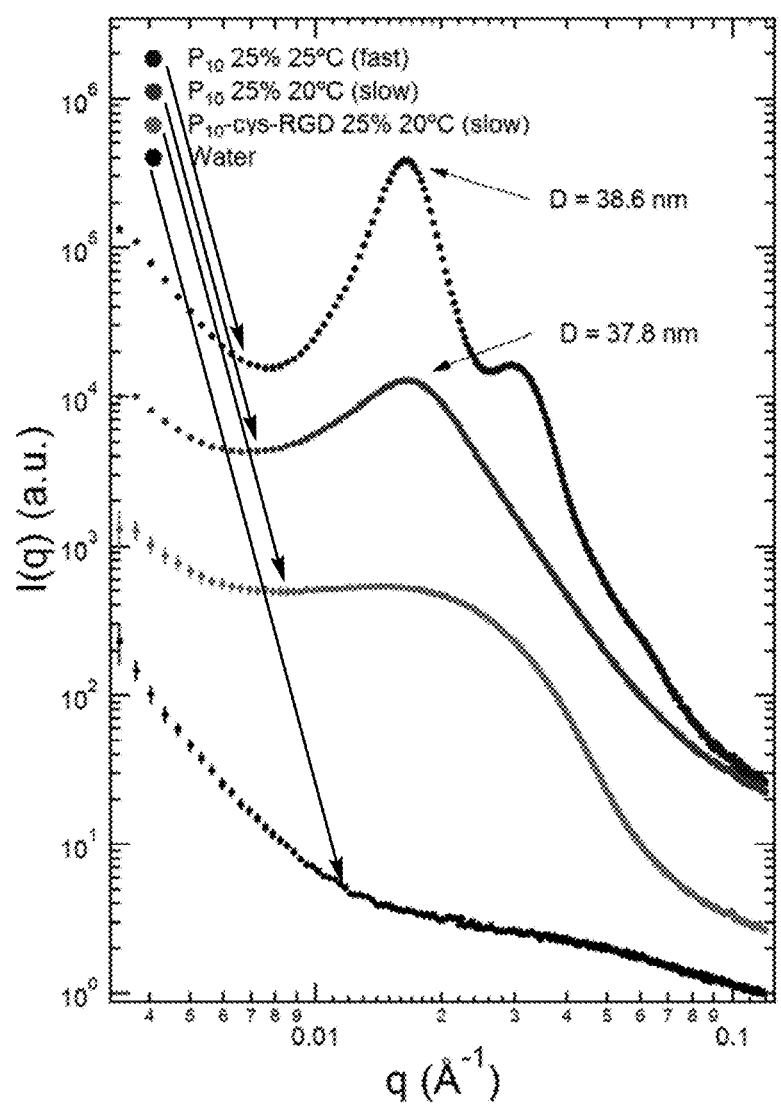
FIG. 11 depicts SAXS data relating to the gel structure of various polypeptides.
Figure 12A:
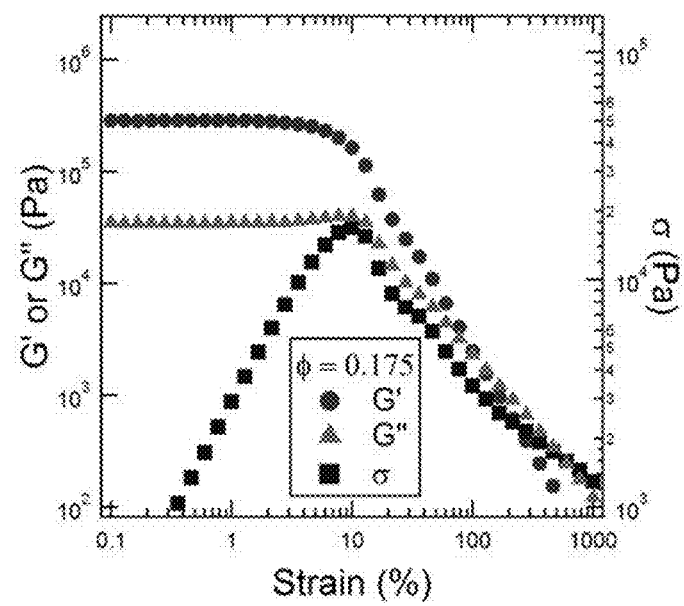
FIG. 12A depicts large amplitude oscillatory shear rheology of a P$_{10}$ gel at a concentration of 17.5% w/w through the yield point.
Figure 12B:
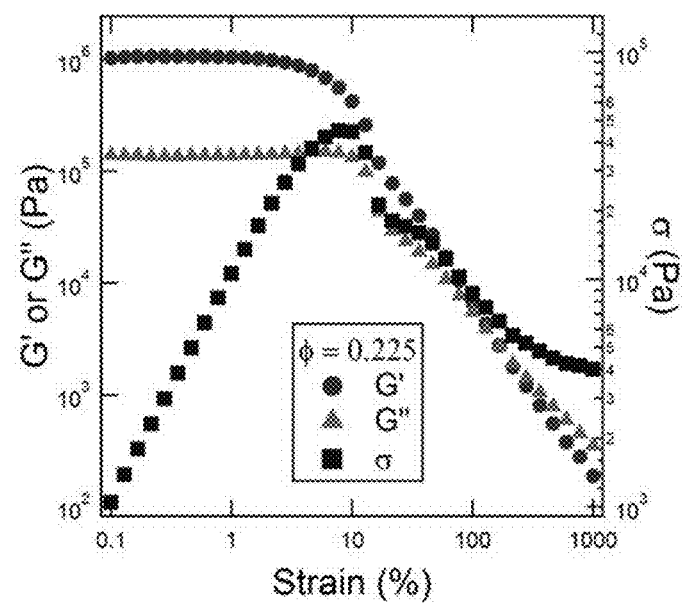
FIG. 12B depicts large amplitude oscillatory shear rheology of a P$_{10}$ gel at a concentration of 22.5% w/w through the yield point.
Figure 12C:
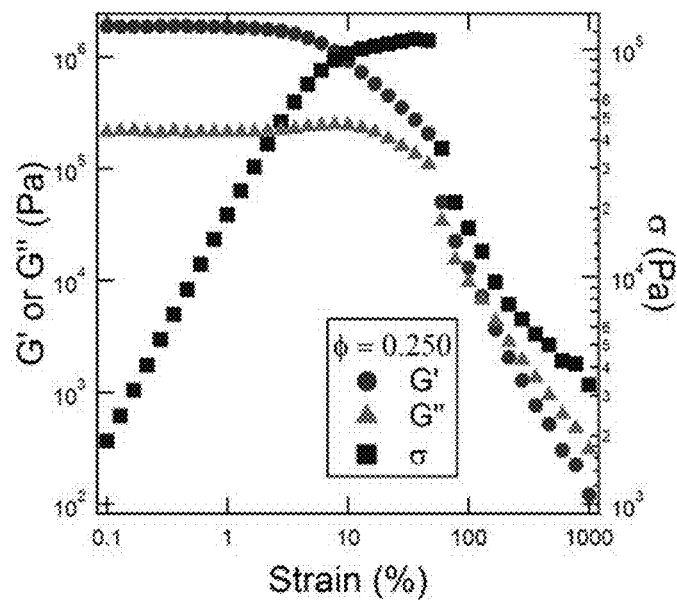
FIG. 12C depicts large amplitude oscillatory shear rheology of a Pro gel at a concentration of 25.0% w/w through the yield point.

DSC data indicate that chain extension leads to a broadened thermal transition, compared to the polypeptides without near-terminal cysteine residues ($P_{10}$; FIG. 8A). Gels prepared from chain-extended polypeptides are over an order of magnitude stiffer at 0° C. than gels prepared from unextended polypeptides, although are nearly as stiff (G'~1 MPa) at 37° C. (FIG. 8B). An unextended polypeptide typically forms brittle gels, but the chain-extended polypeptide forms gels that are qualitatively tough and extensible upon manual manipulation. The nanostructure of these gels changes upon chain-extension, exhibiting greater disorder in SAXS, as judged by the broadened scattering intensity in the q-range 0.01-0.04 Å$^{-1}$ (FIG. 11).

Biofunctionalized Gels are Biocompatible

Figure 9:
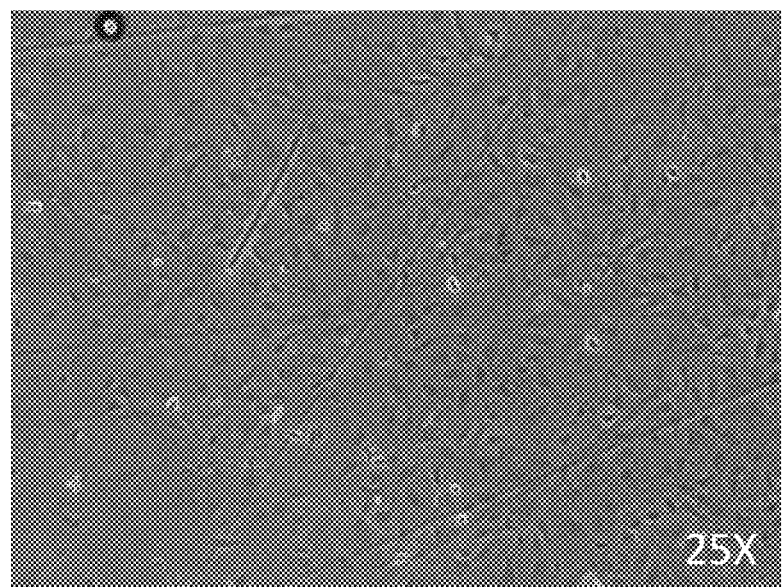
FIG. 9 depicts 2D seeding of mouse cardiac fibroblasts on 20% oxidatively chain-extended P$_{10}$ gels biofunctionalized with RGD.

The biocompability and bioactivity of gels formed from chain-extended $P_{10}$ proteins containing RGD peptides (C-RGD-$(X^{0.6}PAVG)_{10}$-RGD-C (SEQ ID NO: 64), 20% w/w) were assessed for a variety of cell types, including mouse cardiac fibroblasts, human mesenchymal stem cells (hMSCs), and bovine cartilage-derived chondrocytes. Cardiac fibroblasts (FIG. 9) and hMSCs (data not shown) attached to the surface of the gels in 2D experiments, and live/dead assays on MSCs confirmed cell survival out to at least 23 days. Immunostaining for osteocalcin at 23 days (data not shown) suggests that these substrates are promoting expression of osteoblast markers without the use of osteoinductive media. Live/dead assays in Transwell® permeable culture plate inserts (data not shown) also confirm that no toxic degradation products were released from the biosynthetic protein gels. Chondrocytes were also successfully encapsulated and survived through 5 days in 3D culture (data not shown).

Figure 13:
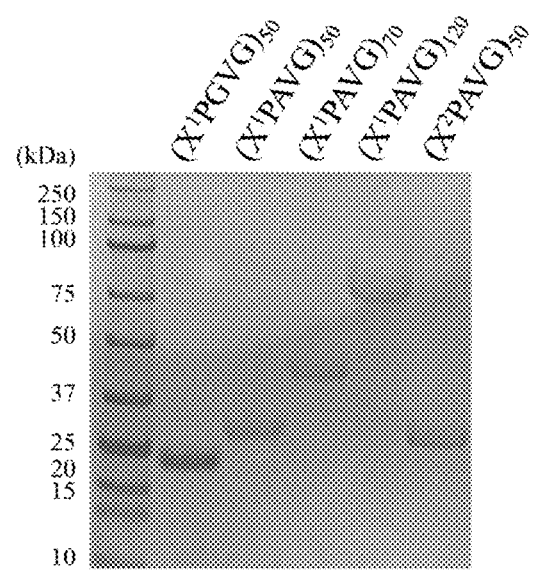
FIG. 13 depicts SDS-PAGE of certain elastin-like polypeptides.

Example 4—Arrested Phase Separation of Elastin-Like Polypeptide Solutions Yields Stiff, Thermoresponsive Gels Experimental Methods Genetic Engineering and Biosynthesis Concatemerization of ELPs with the general sequence $(XPZVG)_n$ was performed following literature procedures (see below). Genes in pETA plasmids were transformed into the E. coli strain Tuner (DE3). Expressions were performed in Terrific Broth (1 L), induced with 0.5 mM IPTG at an $OD_{600}$=0.9-1.1, and harvested by centrifugation 6 hours post-induction. ELPs were purified by thermal cycling from cell lysate and ion exchange chromatography, similar to previous protocols (see below). Purified proteins were confirmed by SDS-PAGE and MALDI-TOF (FIG. 13). Gels were prepared in 100 mM sodium phosphate buffer, pH=7.6, or in MilliQ water, where the final pH of the gel was 5.6.

Oligonucleotides 75 nt in length coding for the desired repetitive polypeptides were designed containing flanking recognition sequences for a Type IIS restriction enzyme, BsaI (NEB). The directionality of the asymmetric recognition sequences was chosen so that digestion produced fragments were flanked with TTGG overhangs, which are non-palindromic to ensure robust head-to-tail ligation, and so that the enzyme releases fragments that do not contain BsaI sites. More specifically, the following cassette was inserted between the NcoI and XhoI sites in pET-28b:

A₁ insert (SEQ ID NO: 34):
CCATGGGCGGATCCGCTAGC<u>GGTCTC</u>GTTGGTATTCCTGCTGTTGGTG

TGCCGGCTGTTGGTATCCCAGCTGTTGGCGTTCCGGCTGTAGGTATTC

CGGCTGTTGGT<u>GAGACC</u>ACTAGTTAAATGAATAAGCTTTAACTCGAG

A₁' (SEQ ID NO: 35):
CCATGGGCGGATCCGCTAGC<u>GGTCTC</u>GTTGGTGTTCCTGCTGTCGGTG

TGCCGGCTGTTGGTATTCCAGCTGTTGGCGTGCCGGCTGTAGGTGTCC

CGGCTGTTGGC<u>GAGACC</u>ACTAGTTAAATGAATAAGCTTTAACTCGAG

G₁ (SEQ ID NO: 36):
CCATGGGCGGATCCGCTAGC<u>GGTCTC</u>GTTGGTGTACCTGGTGTTGGCG

TCCCGGGTGTAGGTATCCCAGGCGTTGGTGTACCGGGTGTAGGCGTTC

CAGGCGTTGGC<u>GAGACC</u>ACTAGTTAAATGAATAAGCTTTAACTCGAG

The 75 nt sequences that code a set of five pentapeptide repeats for each ELP are highlighted in bold, and the asymmetric BsaI recognition sequences are underlined.

These fragments were ligated at 100-fold molar excess into modified pET-28b vectors (pETA) with the same arrangement of BsaI recognition sequences in the multiple cloning site (MCS). Because concatemerized genes did not have internal BsaI sites, multiple rounds of digestion and concatemerization were possible. Up to three rounds were typically required to produce the gene sizes used in this study, coding for up to 120 pentapeptide repeats.

Following expression and harvesting, cell pellets were resuspended in non-denaturing lysis buffer (MENT buffer: 10 mM Tris, 1 mM EDTA, 100 mM NaCl, 5 mM MgCl₂, pH=7.5) at a concentration of approximately 30 g wet cell mass (WCM) per 100 mL buffer. Resuspensions were frozen at −20° C. After thawing on ice, lysozyme (100 mg per 100 mL resuspension) was added, and after approximately 1 hour the suspension was sonicated. Cell debris was removed by centrifugation, and DNAse I and RNAse A (2 mg each) were added to the clarified supernatant and incubated for 2-3 hours at 37° C. The turbid lysates were then centrifuged at 37° C., and the pellets were redissolved in MENT buffer at 5° C., typically overnight. The protein solutions were thermally cycled between 5° C. and 37° C. in MENT buffer for two additional cycles. The solutions were then dialyzed against MilliQ water and purified in a final step by passing over anion exchange resin in 6 M urea, 20 mM Tris, pH=8.0, using HiTrap Q pre-packed columns (GE Healthcare) by automated chromatography. Bound contaminants were discarded, and the target proteins were collected in the flow-through step, dialyzed against MilliQ water, and lyophilized.

Protein Sequences:

$(X^1PGVG)_{50}$ (SEQ ID NO: 52):

(SEQ ID NO: 65)

[(VPGVG)₂(IPGVG)(VPGVG)₂]₁₀

(SEQ ID NO: 37)

MGWGSASGLVGVPGVGVPGVGIPGVGVPGVGVPGVGVPGVGVPGVGIP

GVGVPGVGVPGVGVPGVGVPGVGIPGVGVPGVGVPGVGVPGVGVPGVG

IPGVGVPGVGVPGVGVPGVGVPGVGIPGVGVPGVGVPGVGVPGVGVPG

VGIPGVGVPGVGVPGVGVPGVGVPGVGIPGVGVPGVGVPGVGVPGVGV

PGVGIPGVGVPGVGVPGVGVPGVGVPGVGIPGVGVPGVGVPGVGVPGV

GVPGVGIPGVGVPGVGVPGVGVPGVGVPGVGIPGVGVPGVGVPGVGVPGVGVPGVGVPGVGIPGVGVPGVGVPGVGVPGVGVPGVGVPGVGIPGVGVPGVGVPGVGVPGVGVPGVGVPGVGVPGVGIPGVGVPGVGVPGVGVPGVGVPGVGVPGVGVPGVGVPGVGIPGVGVPGVGVPGVGVPGVGVPGVGVPGVGIPGVGVPGVGVPGVGVPGVGVPGVGVPGVGVPGVGVPGVGIPGVGVPGVGVPGVGVPGVGVPGVGVPGVGVPGVGVPGVGVPGVGIPGVGVPGVGVPGVGVPGVGVPGVGVPGVGVPGVGVPGVGVPGVGIPGVGVPGVGVPGVGVPGVGVPGVGVPGVGVPGVGVPGVGVPGVGIPGVGVPGVGVPGVGVPGVGVPGVGVPGVGVPGVGVPGVGVPGVGVPGVGIPGVGVPGVGVPGVGVPGVGVPGVGVPGVGVPGVGVPGVGVPGVGVPGVGIPGVGVPGVGVPGVGVPGVGVPGVGVPGVGVPGVGVPGVGVPGVGVPGVGVPGVGIPGVGVPGVGVPGVGVPGVGVPGVGVPGVGVPGVGVPGVGVPGVGVPGVGVPGVGIPGVGVPGVGVPGVGVPGVGVPGVGVPGVGVPGVGVPGVGVPGVGVPGVGVPGVGIPGVGVPGVGVPGVGVPGVGVPGVGVPGVGVPGVGVPGVGVPGVGVPGVGVPGVGVPGVGIPGVGVPGVGVPGVGVPGVGVPGVGVPGVGVPGVGVPGVGVPGVGVPGVGVPGVGVPGVGV

GVPGVGIPGVGVPGVGVPGVGETTS*

$(X^1PAVG)_{50}$ (SEQ ID NO: 53):

(SEQ ID NO: 66)

[(VPAVG)₂(IPAVG)(VPAVG)₂]₁₀

(SEQ ID NO: 38)

MGWGSASGLVGVPAVGVPAVGIPAVGVPAVGVPAVGVPAVGVPAVGIP

AVGVPAVGVPAVGVPAVGVPAVGIPAVGVPAVGVPAVGVPAVGVPAVG

IPAVGVPAVGVPAVGVPAVGVPAVGIPAVGVPAVGVPAVGVPAVGVPA

VGIPAVGVPAVGVPAVGVPAVGVPAVGIPAVGVPAVGVPAVGVPAVGV

PAVGIPAVGVPAVGVPAVGVPAVGVPAVGIPAVGVPAVGVPAVGVPAV

GVPAVGIPAVGVPAVGVPAVGETTS*

$(X^1PAVG)_{70}$ (SEQ ID NO: 54):

(SEQ ID NO: 67)

[(VPAVG)₂(IPAVG)(VPAVG)₂]₁₄

(SEQ ID NO: 39)

MGWGSASGLVGVPAVGVPAVGIPAVGVPAVGVPAVGVPAVGVPAVGIP

AVGVPAVGVPAVGVPAVGVPAVGIPAVGVPAVGVPAVGVPAVGVPAVG

IPAVGVPAVGVPAVGVPAVGVPAVGIPAVGVPAVGVPAVGVPAVGVPA

VGIPAVGVPAVGVPAVGVPAVGVPAVGIPAVGVPAVGVPAVGVPAVGV

PAVGIPAVGVPAVGVPAVGVPAVGVPAVGIPAVGVPAVGVPAVGVPAV

GVPAVGIPAVGVPAVGVPAVGVPAVGVPAVGIPAVGVPAVGVPAVGVP

AVGVPAVGIPAVGVPAVGVPAVGVPAVGVPAVGIPAVGVPAVGVPAVG

VPAVGVPAVGIPAVGVPAVGVPAVGETTS*

$(X^1PAVG)_{120}$ (SEQ ID NO: 50):

(SEQ ID NO: 68)

[(VPAVG)₂(IPAVG)(VPAVG)₂]₂₄

(SEQ ID NO: 40)

MGWGSASGLVGVPAVGVPAVGIPAVGVPAVGVPAVGVPAVGVPAVGIP

AVGVPAVGVPAVGVPAVGVPAVGIPAVGVPAVGVPAVGVPAVGVPAVG

IPAVGVPAVGVPAVGVPAVGVPAVGIPAVGVPAVGVPAVGVPAVGVPA

VGIPAVGVPAVGVPAVGVPAVGVPAVGIPAVGVPAVGVPAVGVPAVGV

PAVGIPAVGVPAVGVPAVGVPAVGVPAVGIPAVGVPAVGVPAVGVPAV

GVPAVGIPAVGVPAVGVPAVGVPAVGVPAVGIPAVGVPAVGVPAVGVP

AVGVPAVGIPAVGVPAVGVPAVGVPAVGVPAVGIPAVGVPAVGVPAVG

VPAVGVPAVGIPAVGVPAVGVPAVGVPAVGVPAVGIPAVGVPAVGVPA

VGVPAVGVPAVGIPAVGVPAVGVPAVGVPAVGVPAVGIPAVGVPAVGV

PAVGVPAVGVPAVGIPAVGVPAVGVPAVGVPAVGVPAVGIPAVGVPAV

GVPAVGVPAVGVPAVGIPAVGVPAVGVPAVGVPAVGVPAVGIPAVGVP

AVGVPAVGVPAVGVPAVGIPAVGVPAVGVPAVGVPAVGVPAVGIPAVG

VPAVGVPAVGVPAVGVPAVGIPAVGVPAVGVPAVGETTS*

$(X^2PAVG)_{50}$ (SEQ ID NO: 53):

(SEQ ID NO: 69)

[(IPAVGVPAVG)₂(IPAVG)]₁₀

(SEQ ID NO: 41)

MGWGSASGLVGIPAVGVPAVGIPAVGVPAVGIPAVGIPAVGVPAVGIP

AVGVPAVGIPAVGIPAVGVPAVGIPAVGVPAVGIPAVGIPAVGVPAVG

IPAVGVPAVGIPAVGIPAVGVPAVGIPAVGVPAVGIPAVGIPAVGVPA

-continued
VGIPAVGVPAVGIPAVGIPAVGVPAVGIPAVGVPAVGIPAVGV

PAVGIPAVGVPAVGIPAVGIPAVGVPAVGIPAVGVPAVGIPAV

GVPAVGIPAVGVPAVGIPAVGETTS*

TABLE 5

MALDI-TOF of elastin-like polypeptides investigated in this study.

| Identifier | MALDI-TOF (kDa) | Theoretical (kDa) |
|---|---|---|
| $(X^1PGVG)_{50}$ (SEQ ID NO: 52) | 21.8 | 22.1 |
| $(X^1PAVG)_{50}$ (SEQ ID NO: 51) | 22.6 | 22.8 |
| $(X^1PAVG)_{70}$ (SEQ ID NO: 54) | 31.2 | 31.3 |
| $(X^1PAVG)_{120}$ (SEQ ID NO: 50) | 54.1 | 52.6 |
| $(X^2PAVG)_{50}$ (SEQ ID NO: 53) | 22.9 | 23.0 |

Figure 14:
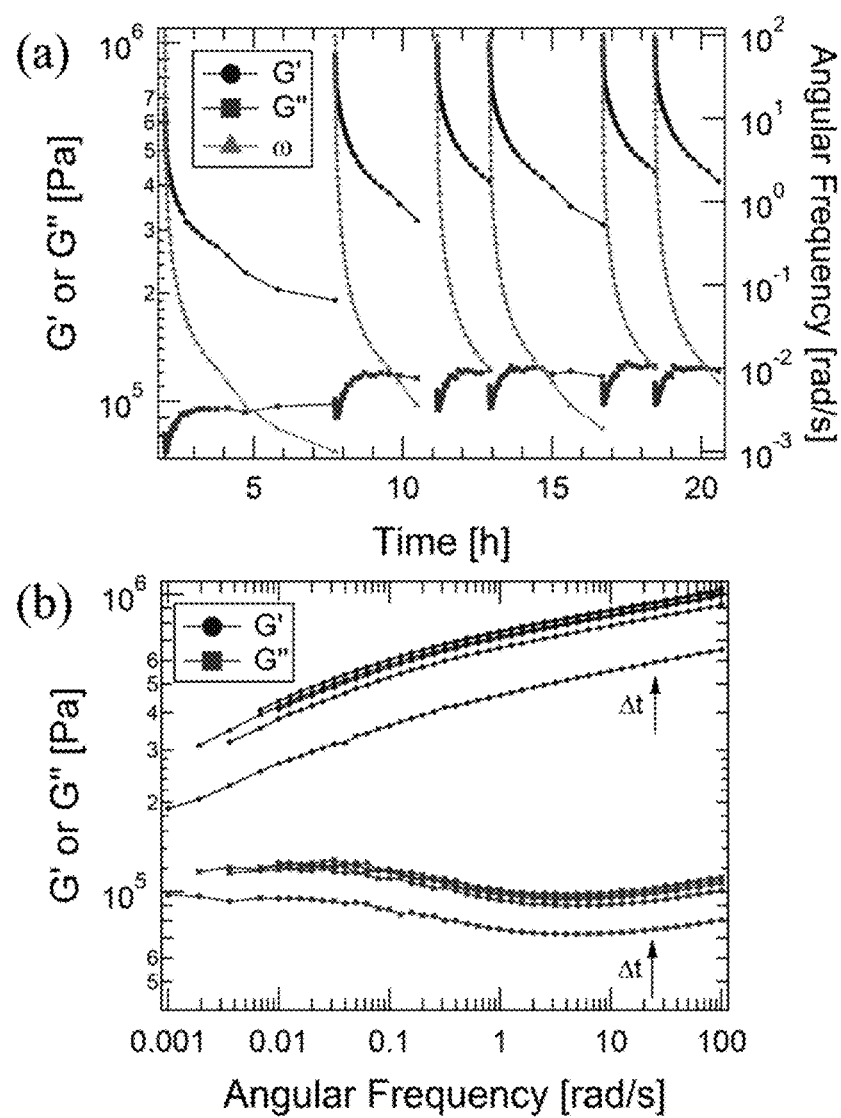
FIG. 14 has two panels (a and b) depicting frequency sweep linear viscoelasticity data for (X$^1$PAVG)$_{120}$ (SEQ ID NO: 50) at 20 wt % in water plotted as a function of (panel a) equilibration time at 37° C., and (panel b) frequency.

Shear Rheology Small amplitude oscillatory shear (SAOS) rheology experiments were performed on an Anton-Paar MCR-702 rheometer operating in a single-motor configuration in pseudo-strain control (Direct Strain Oscillation) mode. Temperature was controlled using a Peltier heating element below the lower geometry and a circulating-air environmental enclosure to minimize thermal gradients across the sample. A 10 mm diameter, 2° cone-and-plate sample geometry with sandblasted surfaces was used, where the gap was zeroed at the target temperature. Moduli were reported at 100 rad/s following a 30 minute equilibration. Each sample was thermally cycled 3 times, and each gel condition was repeated in triplicate. For frequency-sweep experiments, measurements were performed using a 25 mm diameter, 10 cone-and-plate TruGap-compatible sample geometry for active gap compensation. To minimize any evolution of mechanical properties that occurs over the course of the frequency-sweep, samples were held at the target temperature for 15 hours prior to the start of the measurement. This equilibration time was selected because after this amount of time, minimal sample aging over the course of a single long frequency-sweep was observed (i.e., repeated frequency sweeps were overlapping; FIG. 14).

For large amplitude oscillatory shear (LAOS) measurements, the instrument was configured to operate in dual-motor (TwinDrive™) mode for strain-controlled experiments. Temperature was controlled using a circulating-air environmental chamber. A 10 mm diameter, 2° cone-and-plate sample geometry with sandblasted surfaces was used for all nonlinear measurements. Samples were loaded at 0° C. and equilibrated for 30 minutes. The temperature was ramped up to 37° C. at 1° C./min and samples were equilibrated at 37° C. for 2 hours prior to the start of the experiments, beyond which time the gels' nonlinear response was not observed to change significantly. Waveforms were processed using MITlaos v2.2 beta.

State Diagram Construction

ELP solutions were prepared in MilliQ water and dissolved completely on ice.

Turbidimetry was performed using a 662 nm 20 mW laser, on samples sealed in quartz with a 1 mm thick Teflon spacer and 2 mm bore. Samples were heated on a water-chilled brass stage at a heating rate of 1° C./min. The transition temperature was determined as the point at which the transmittance dropped by 10%. A TA Instruments Discovery Differential Scanning Calorimeter was used to perform DSC measurements. Samples were loaded into hermetically sealed aluminum pans and scanned from 0-60° C. at 10° C./min for two cycles, followed by a 1° C./min ramp. The transition temperature was determined from the onset point of the 1° C./min ramp. Rheological transitions were determined by oscillatory shear rheology based on the temperature at which G' became greater than G" upon heating at 1° C./min. All transition temperatures determined in triplicate.

Small Angle Neutron Scattering

Figure 15:
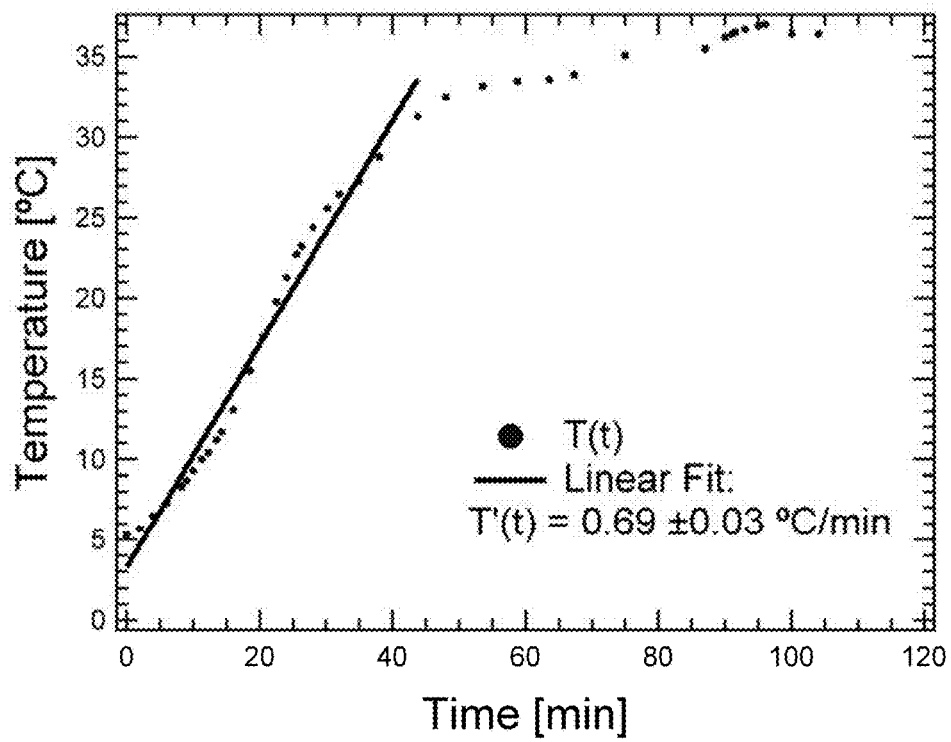
FIG. 15 depicts the temperature profile of the SANS sample holder during the heating step (heat source was a circulating water bath). The heating rate was approximately 0.7° C./min through 30° C. Measurements for the data analyzed in the body of the manuscript were taken at t=150 min, an effective equilibration of 60 min at T=37° C.±0.5° C.

Experiments were performed at the NGB 30 m SANS instrument at the NIST Center for Neutron Research. Samples were prepared at molar concentrations matching the rheology experiments by dissolving lyophilized proteins directly into either $D_2O$ or $D_2O$ supplemented with 100 mM sodium phosphate, using the same ratio of monosodium phosphate to disodium phosphate as in water to target pH=7.6. Swollen samples were loaded into cells and then equilibrated at 0° C. for several hours. All sample cells were loaded into the holder and subjected to the same temperature ramp at roughly 0.7° C./min (FIG. 15). The samples were equilibrated for at least 60 minutes at 37° C. This equilibration time was chosen because SANS curves no longer changed with time (i.e., they were overlapping) after this length of equilibration.

Data were corrected for the incoherent scattering background by fitting the high q region to a linear relation of the form:

$$I(q)q^4 \to A+Bq^4$$

The value B was computed for each acquisition and subtracted.

Large Amplitude Oscillatory Shear Rheology

The range of valid strain amplitudes for the LAOS measurements was assessed by examining the spectral purity of the input waveforms by Fourier transform analysis. While the third and fifth harmonic ratios of the strain waveform are less than 3%, a window considered valid for LAOStress, apparent high frequency stress oscillations occur in elastic Lissajous-Bowditch plots at high strain amplitude and suggest poor control. Because these oscillations were observed to occur where the strain is small and shear rate is high, the spectral purity of the shear rate waveform $$\left(\frac{d}{dt}\gamma(t) = \gamma_o\omega\,\cos(\omega t)\right)$$

was investigated for each sample.

Note that for each sample, there is typically an intermediate region of target strain amplitudes where the quality of the strain and shear rate waveforms deteriorate, as judged by the non-monotonic increase in the harmonic ratios. This non-ideality in the strain control does not increase significantly beyond 1% for any sample, but can peak sharply (i.e., in $(X^1PAVG)_{50}$ (SEQ ID NO: 51) and $(X^2PAVG)_{50}$ (SEQ ID NO: 53)) above $\gamma_o=0.1$. While in a strict sense the shear rate is not the control parameter in LAOS measurements, an ideal sinusoidal shear rate waveform is assumed when computing the first order measures of nonlinearity according to the Ewoldt/McKinley framework. In particular, the computation of $G_M'$ and $\eta_L'$ from the experimental data are assumed to be performed when the shear rate is maximized (and strain minimized), otherwise these measures do not represent elastic or viscous-like measurements, respectively. Based on the analysis of the spectral purity of the input stress waveforms for LAOStress provided in Dimitriou, et al, a conservative cutoff of 1% in the first harmonic ratio of the shear rate waveform was applied to determine data suitable for further analysis.

Results and Discussion

Formation of Arrested Networks from Solutions of ELPs

The gelation of uncrosslinked ELP homopolymers was investigated here using proteins that were designed based on the repeat unit XPZVG, where the amino acids in the first (X) and third (Z) position were mutated. The choice of G or A in position Z was investigated while holding the ratio of I:V in position X fixed at 1:4 (i.e., $X^1 \equiv I^{0.2} V^{0.8}$, Table 6) to compare 'elastic' and 'plastic' sequences, while the changing composition in position X enables the hydrophobicity to be varied. Note that $(XPGVG)_n$ (SEQ ID NO: 42) and $(XPAVG)_n$ (SEQ ID NO: 4) have been identified previously in the literature as 'elastic' and 'plastic' ELPs, based on the difference in apparent mechanical response in the bulk state. These ELPs have been utilized to engineer triblock artificial proteins, containing 'plastic' ELP endblocks and 'elastic' ELP midblocks, to form thermoresponsive stiff hydrogels due to micellization above the endblock transition temperature, and also as bulk microphase-separated plastic. Classical studies on materials made from individual 'plastic' ELPs in the form of γ-crosslinked gels and bulk materials demonstrated in that the alanine mutation in the third position lead to stiffer solids when incorporated into a network. Thermoresponsive phase separation of 'plastic' ELPs was also utilized to form drug delivery microparticles by heating low concentration ELP solutions and isolating the spherical aggregates. These 'plastic' ELPs also show non-negligible thermal hysteresis in resolution from the aggregated state, requiring substantial undercooling to completely redissolve in solution unlike for 'elastic' ELPs, differences which have been related to the dynamics of the folded state in the coacervate.

Figure 16:
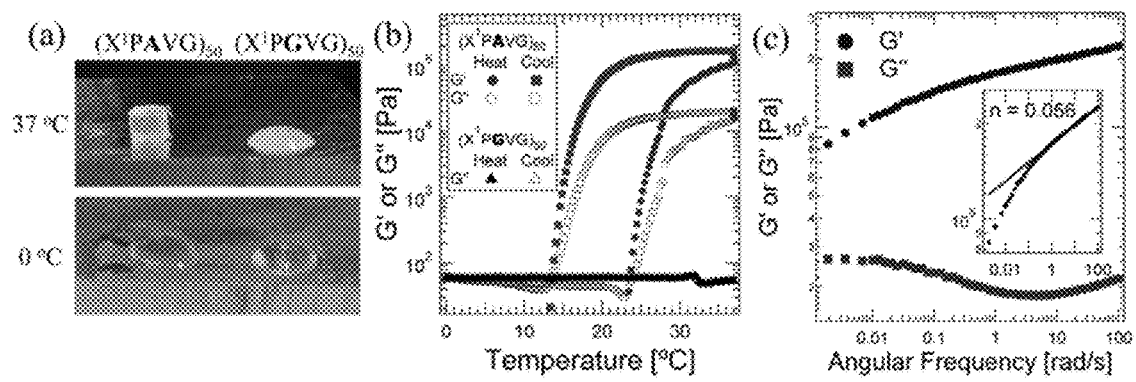
FIG. 16 has three panels (a-c) depicting the gelation of concentrated ELP solutions. (a) Images and (b) temperature-dependent SAOS ($\omega$=100 rad/s, $\gamma_0$=1%) of 20% (w/w) solutions of (X$^1$PAVG)$_{50}$ (SEQ ID NO: 51) and (X$^1$PGVG)$_{50}$ (SEQ ID NO: 52). (c) Frequency-dependent SAOS of (X$^1$PAVG)$_{50}$ (SEQ ID NO: 51) at 20% (w/w) at 37° C., $\gamma_0$=0.01. Inset shows power-law fit to G' over the range $\omega$=1-100 rad/s.

Given that previous gels from ELPs have been formed with chemical crosslinking or block copolymer structures, it is surprising to observe that concentrated aqueous solutions of 'plastic' ELP homopolymers can gel upon heating. The differences in the behavior of concentrated aqueous solutions of $(X^1PGVG)_{50}$ (SEQ ID NO: 52) and $(X^1PAVG)_{50}$ (SEQ ID NO: 51) can be confirmed easily by visual inspection upon heating from 0° C. to 37° C. (FIG. 16, panel a). At a concentration of 20 wt % in water, both ELP solutions are clear liquids at 0° C., but $(X^1PGVG)_{50}$ (SEQ ID NO: 52) will start to form a turbid liquid when warmed to 37° C., and an ELP-rich coacervate phase will separate over time. However, under the same conditions $(X^1PAVG)_{50}$ (SEQ ID NO: 51) forms a slightly translucent (>95% clarity for 1 mm), surprisingly stiff hydrogel. As with ELP coacervation, the gelation mechanism was thermoreversible: upon returning to ice, the $(X^1PAVG)_{50}$ (SEQ ID NO: 51) gel liquefied.

Figure 17:
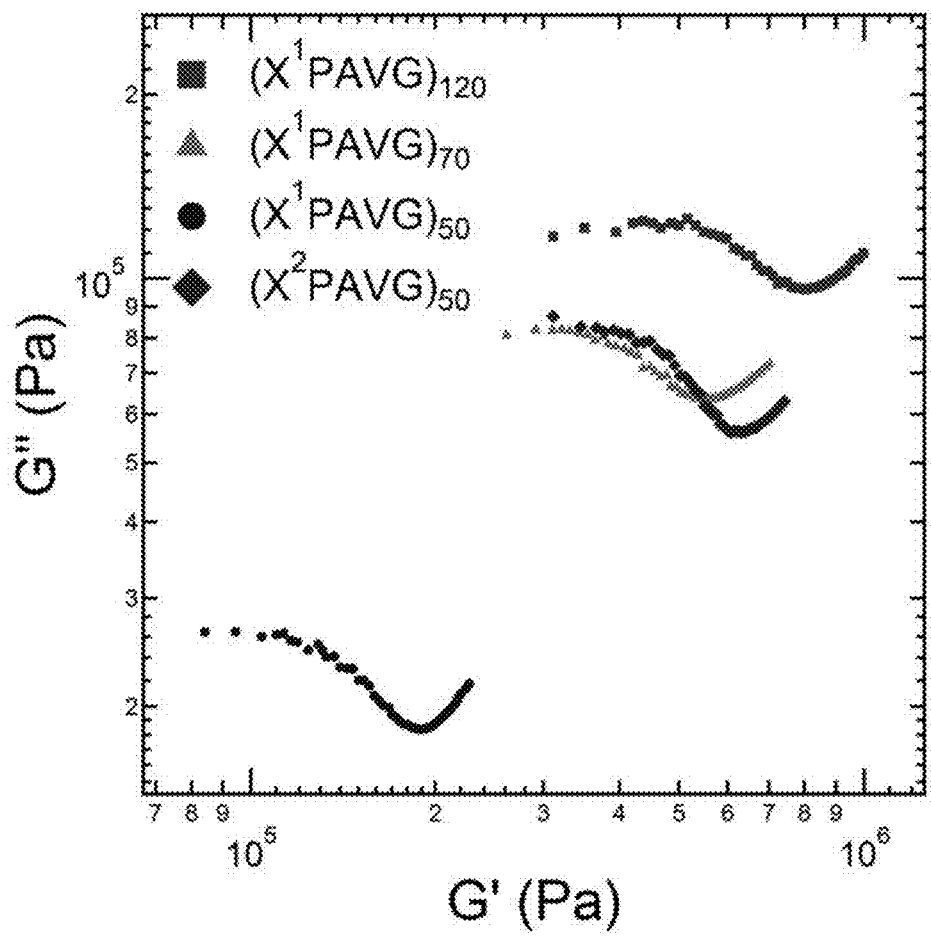
FIG. 17 depicts cole-cole plots of linear viscoelasticity data for gels at 20 wt %. A simple Maxwell model, which would be represented by a semicircle on this plot, fails to describe the relaxation time distribution for these networks.

The linear viscoelasticity of these ELP hydrogels shows that these physical interactions led to stiff networks with a broad relaxation spectrum (FIG. 16, panels b and c). Upon heating, the solution transitions to the gel state over a narrow temperature range, and the network continues to stiffen slowly even when held isothermally, stabilizing after roughly 15 hours. The hysteresis in network disassembly upon cooling is consistent with solvation hysteresis typically observed in dilute solution (FIG. 16, panel b). Frequency sweep rheology shows no high frequency plateau; instead, a power law region is observed over the range ω=1-100 rad/s. The longest stress relaxation time is longer than the lowest measured frequency, corresponding to a time greater than $3.3 \times 10^3$ s. This broad relaxation spectrum clearly cannot be described by a simple Maxwell model (FIG. 17), and also fails to satisfactorily fit the fractional Maxwell model (FMM) for power law fluids. Nevertheless, the shallow decay in this spectrum indicates that the physical interactions relax by processes occurring over a broad range of timescales, as is observed in many complex fluids lacking well-defined characteristic relaxation processes.

TABLE 6

Elastin-like polypeptides investigated in this study.

| Identifier | Sequence | I:V Ratio in X | MW (kDa) |
|---|---|---|---|
| $(X^1PGVG)_{50}$ (SEQ ID NO: 52) | MGWGSASGLVG [(VPGVG)$_2$(IPGVG) (VPGVG)$_2$]$_{10}$ ETTS (SEQ ID NO: 37) | 1:4 | 22.1 |
| $(X^1PAVG)_{50}$ (SEQ ID NO: 51) | MGWGSASGLVG [(VPAVG)$_2$(IPAVG) (VPAVG)$_2$]$_{10}$ ETTS (SEQ ID NO: 38) | 1:4 | 22.8 |
| $(X^1PAVG)_{70}$ (SEQ ID NO: 54) | MGWGSASGLVG [(VPAVG)$_2$(IPAVG) (VPAVG)$_2$]$_{14}$ ETTS (SEQ ID NO: 39) | 1:4 | 31.3 |
| $(X^1PAVG)_{120}$ (SEQ ID NO: 50) | MGWGSASGLVG [(VPAVG)$_2$(IPAVG) (VPAVG)$_2$]$_{24}$ ETTS (SEQ ID NO: 40) | 1:4 | 52.6 |
| $(X^2PAVG)_{50}$ (SEQ ID NO: 53) | MGWGSASGLVG [(IPAVGVPAVG)$_2$ (IPAVG)]$_{10}$ ETTS (SEQ ID NO: 41) | 3:2 | 23.0 |

Figure 18:
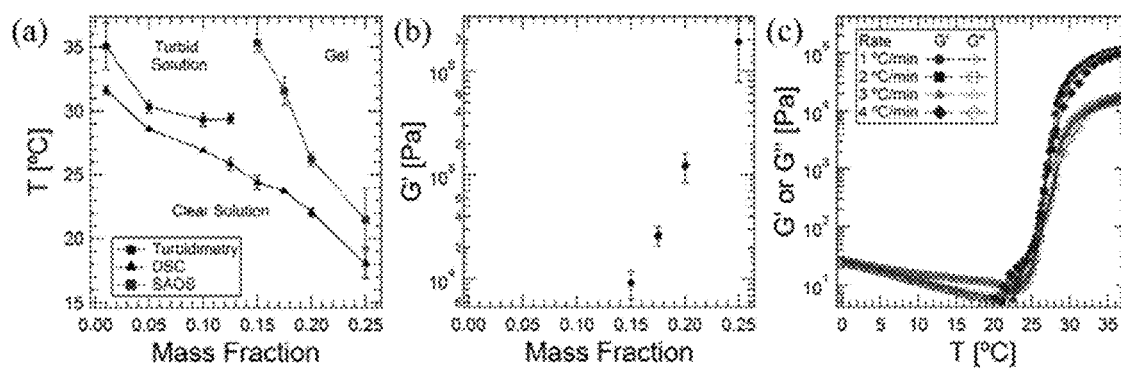
FIG. 18 has three panels (a-c) depicting (a) T-c state diagram for (X$^1$PAVG)$_{50}$ (SEQ ID NO: 51) from a combination of turbidimetry, rheology, and DSC measurements for experiments performed at a heating rate of 1° C./min. Lines connecting data points are intended solely as guides for the eye. All measurements performed in triplicate. (b) Storage moduli ($\omega$=100 rad/s, $\gamma_0$=0.01) for (X$^1$PAVG)$_{50}$ (SEQ ID NO: 51) gels as a function of concentration. (c) Effect of heating rate on the transition of (X$^1$PAVG)$_{50}$ (SEQ ID NO: 51) at 20 wt %.
Figure 19A:
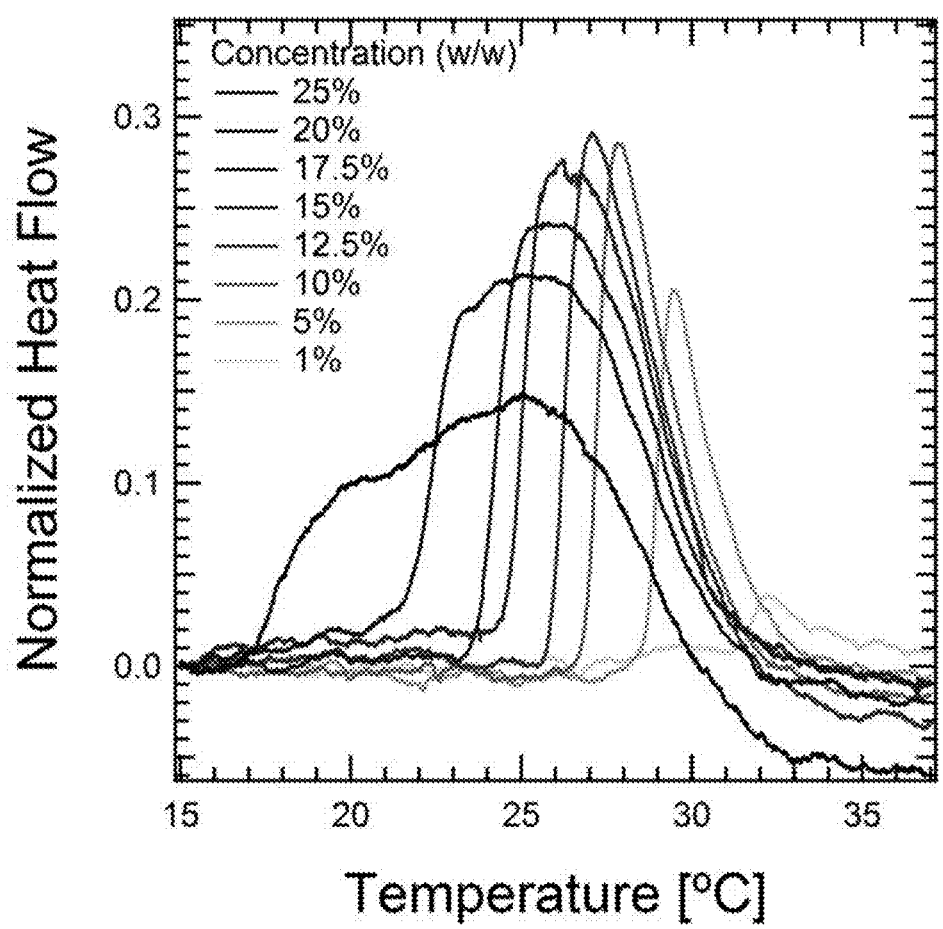
FIG. 19A depicts DSC traces of solutions of (X$^1$PAVG)$_{50}$ (SEQ ID NO: 51) on heating (dT/dt=1° C./min) showing the effect of concentration on the onset and peak temperatures of the transition.
Figure 19B:
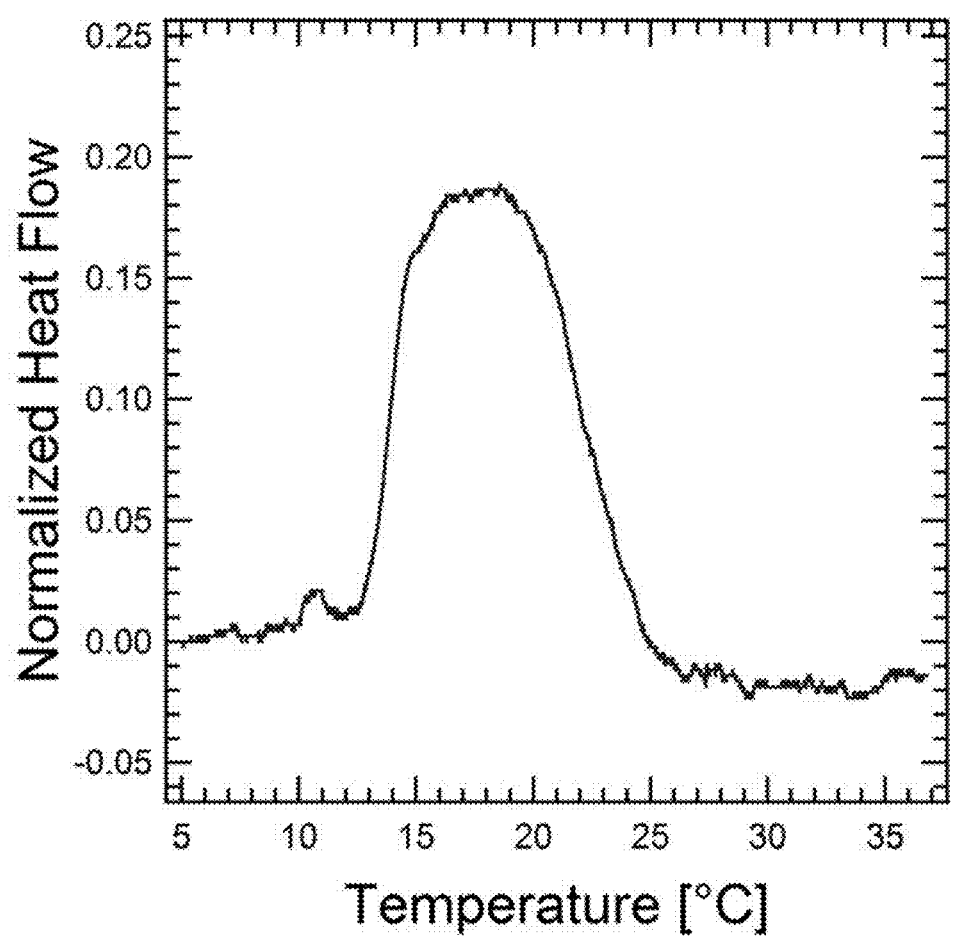
FIG. 19B depicts DSC trace of a 20 wt % solution of (X$^1$PAVG)$_{50}$ (SEQ ID NO: 51) on heating (dT/dt=1° C./min).

Using a combination of temperature-dependent turbidimetry, rheology, and DSC measurements, the behavior of $(X^1PAVG)_{50}$ (SEQ ID NO: 51) solutions was mapped in a T-c state diagram, demonstrating that gelation occurred due to hydrophobic chain collapse above the transition temperature only above a critical concentration ca. 15 wt % (FIG. 18, panel a). This gelation concentration is much higher than the typical polymer overlap concentration (1-2 wt %), and higher than is seen in other thermoreversible polypeptide systems such as amphiphilic β-hairpin peptides (ca. 1 wt %) which assemble into entangled fibrils, diblock copolypeptide hydrogels (ca. 3 wt %), or methylcellulose hydrogels (ca. 0.1 wt %), which are formed by hydrophobic association and arrested phase separation process that leads to the formation of a fibrillar network. The onset temperature of the transition measured by calorimetry is monotonically decreasing over the concentration range investigated, as is typical even in the dilute regime. However, the breadth of the transition also increases substantially above the observed gelation concentration, occurring over approximately a 15° C. temperature range for gels formed from 25.0 wt % solutions (FIG. 19). Note that at high concentrations, the canonical logarithmic relationship between ELP solution concentration and the calorimetric transition is not strictly followed, potentially related to the differences in molecular interactions related to the arresting mechanism.

Figure 20A:
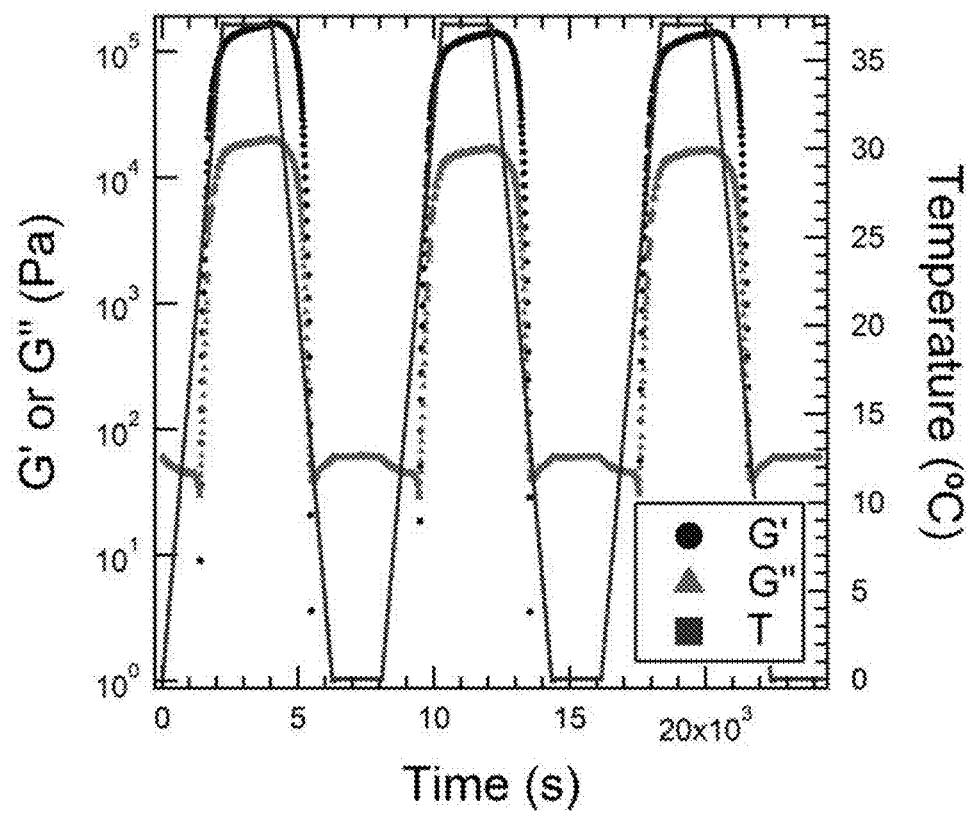
FIG. 20A depicts thermal cycling of (X$^1$PAVG)$_{50}$ (SEQ ID NO: 51) at c=20% (w/w) at a heating rate of 1° C./min. Measurements were taken at $\omega$=100 rad/s, $\gamma$=0.01. Below the transition temperature in this sample (c.a. 20° C.), tan($\delta$)>10$^4$, and the G' data are out of range of the plot.
Figure 20B:
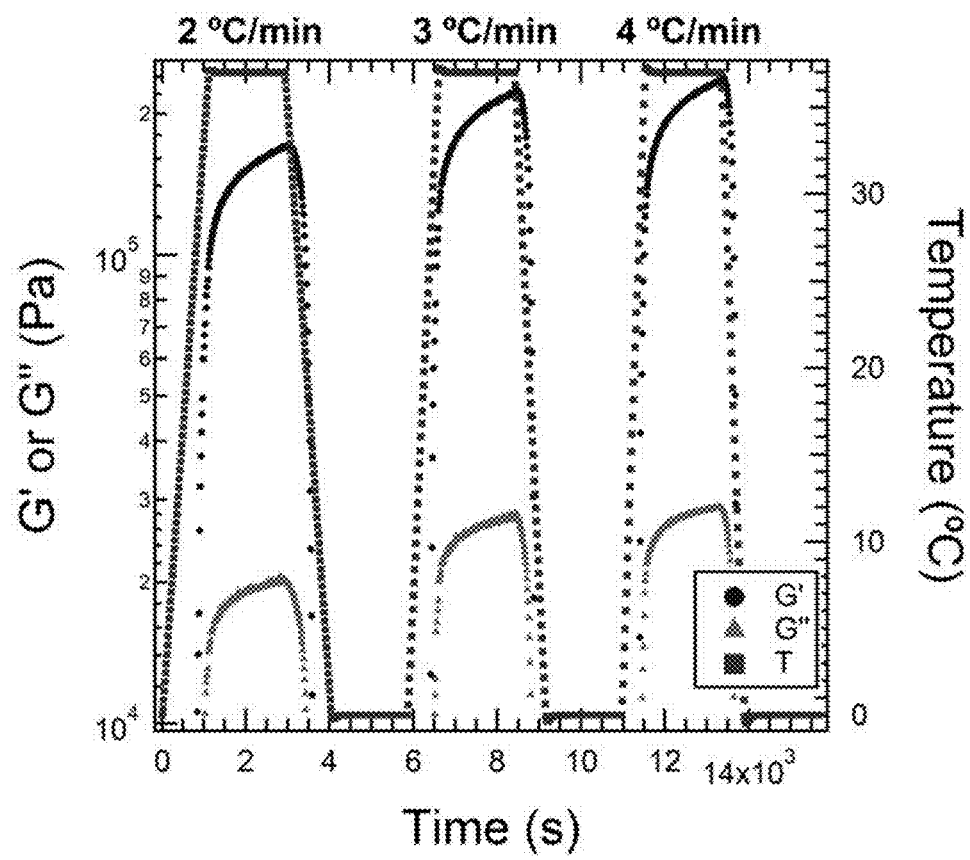
FIG. 20B depicts the effect of heating rate on the gelation of (X$^1$PAVG)$_{50}$ (SEQ ID NO: 51) at 20 wt %. Moduli at the end of the heating step are 0.17, 0.22, 0.24 MPa for ramp rates of 2, 3, and 4° C./min, versus 0.15±0.01 MPa at a heating rate of 1° C./min. Note that these data are generated with a different sample from that used to collect the data shown in FIG. 18, panel c.

An interesting region in the state diagram occurs between ca. 15.0 and 17.5 wt %, where the onset of the calorimetric transition is below the rheological transition by roughly 10° C. (or 10 minutes at the experimental heating rates). The existence of these states suggests that the tendency for hydrophobic ELPs to form physical networks is a process that occurs en route to coalescence, potentially due to increasingly slow molecular rearrangements within domains that inhibit further phase separation. While the DSC measurement monitors the transition to desolvated chains, a rheological transition to the gel state requires the formation of the interconnected ELP-rich phase and solidification of that phase. Therefore, the peak in the desolvation transition may be observed at a lower temperature than gelation. These gels are greater than 90% transparent (at l=1 mm) and do not undergo a sharp decrease in transparency up to 37° C., suggesting that density fluctuations on the optical length scales do not grow significantly in this concentration range. Heating a 20.0 wt % solution of $(X^1PAVG)_{50}$ (SEQ ID NO: 51) at rates ranging from 1-4° C./min (as fast as the heating stage can perform) has a minor influence on the rheological transition (FIG. 18, panel c), consistent with a spinodal decomposition mechanism. However, faster heating rates lead to nearly a 2-fold difference in gel modulus following the 30 minute equilibration (FIG. 20) suggesting that the underlying relaxation spectrum of the network will depend on the processing history, consistent with a kinetically-arrested gelation process.

Figure 21:
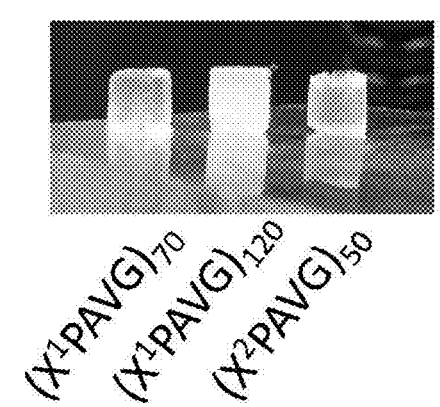
FIG. 21 depicts additional images of 20 wt % gels.

Increasing the number of repeat units in the polypeptide leads to stiffer networks. To demonstrate this dependence, two additional ELPs were prepared with the sequence $(X^1PAVG)_n$, where n=70 (SEQ ID NO: 54) or 120 (SEQ ID NO: 50), demonstrating a 5-fold increase in the high frequency modulus to above 0.5 MPa as the ELP molecular weight grows by 2.4. Changing protein molecular weight results in gels with more broadly-varying optical clarity at 20.0 wt % (FIG. 21). In addition, buffer choice had a strong effect on the mechanical response of these networks, with high frequency moduli nearly 2-7 fold higher in 100 mM sodium phosphate buffer, pH=7.6, compared to gels formed in water. As an example, at 20.0 wt %, $(X^1PAVG)_{120}$ (SEQ ID NO: 50) gels had a remarkably high modulus of over 1 MPa (FIG. 22, panel a).

ELPs that vary slightly in hydrophobicity (by changing the I:V ratio in position X) will responsively solidify by the same mechanism, but the changes in polypeptide sequence influence the ultimate gel stiffness. A more hydrophobic ELP was synthesized where I:V was 3:2 (i.e., $X^2 \equiv I^{0.6}V^{0.4}$, Table 6), resulting in roughly a 5-fold increase in the high frequency modulus (FIG. 22, panel a). Increasing overall hydrophobicity results in a decrease of the DSC-determined transition temperature by 9.1° C., as well as an increase in the high frequency modulus at 37° C. This shift to lower $T_t$ means that by 37° C., $(X^2PAVG)_{50}$ (SEQ ID NO: 53) gels have been heated farther above their transition temperature than $(X^1PAVG)_{50}$ (SEQ ID NO: 51) gels. Nevertheless, gels made from $(X^2PAVG)_{50}$ (SEQ ID NO: 53) form stiffer networks than $(X^1PAVG)_{50}$ (SEQ ID NO: 51), even when the gels are heated by the same ΔT above their calorimetric transition (FIG. 22, panel d). The ability to make some substitutions to the first position, as well as the disruptive effect of a glycine substitution in the third position, suggests that the alanine immediately following the proline is an important determinant for the formation of an arrested network in these solutions when heated. While hydrophobicity certainly plays a role in the observed behavior, ELPs without the alanine substitution may also be strongly hydrophobic, so while hydrophobicity is required, it is not the key parameter. During the gelation process, the polypeptide must phase separate, but then the structure has to become arrested before it can coarsen into a macrophase separated structure, requiring dramatic slowing in chain dynamics, and ultimately preserving the optical clarity and mechanical interconnectivity of the gels.

Figure 22:
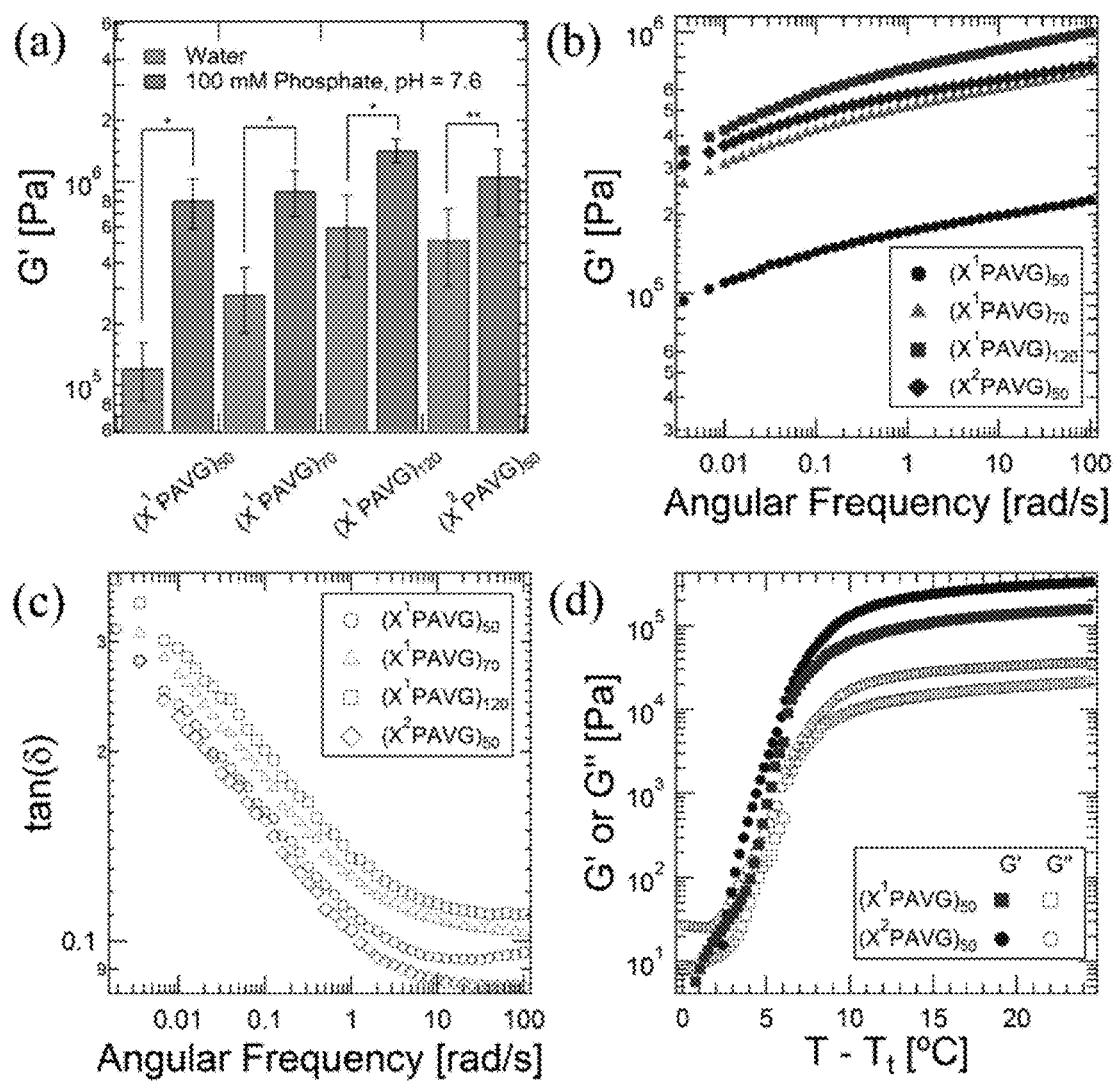
FIG. 22 has four panels (a-d) depicting the effect of ELP sequence linear viscoelasticity. (a) Storage modulus ($\omega$=100 rad/s, $\gamma_0$=0.01) after 30 min equilibration at 37° C. for 20 wt % gels prepared in either water or phosphate buffer (*: p<0.02; **: p<0.1).
Figure 23A:
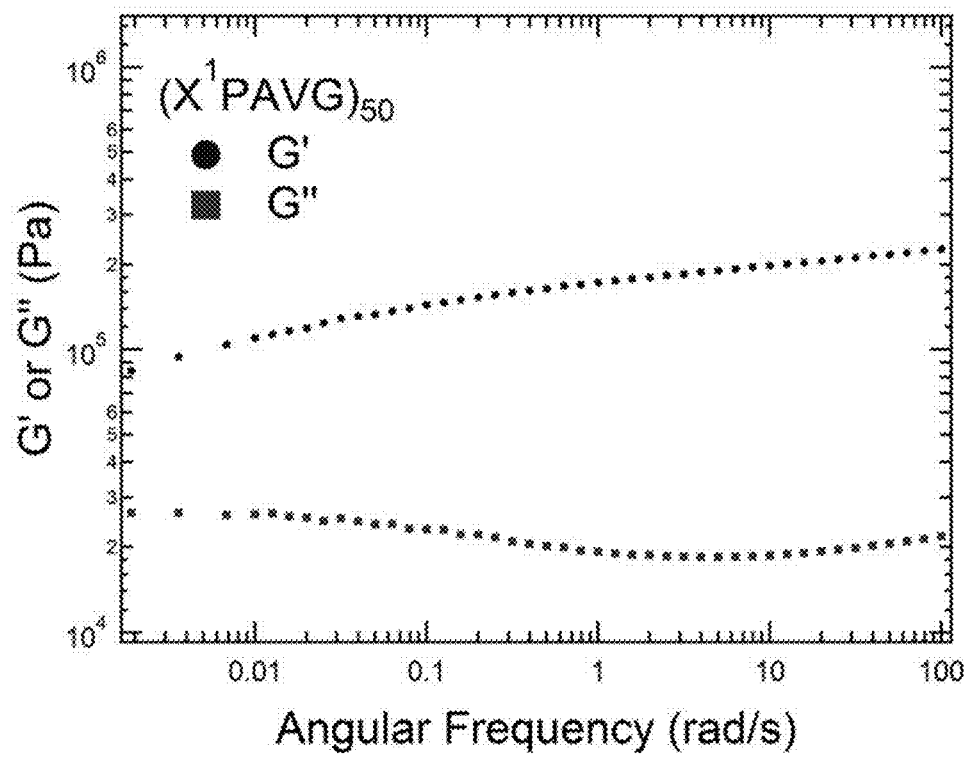
FIG. 23A depicts frequency sweeps for 20 wt % gels ((X$^1$PAVG)$_{50}$ (SEQ ID NO: 51)) at T=37° C., $\gamma_o$=0.01.
Figure 23B:
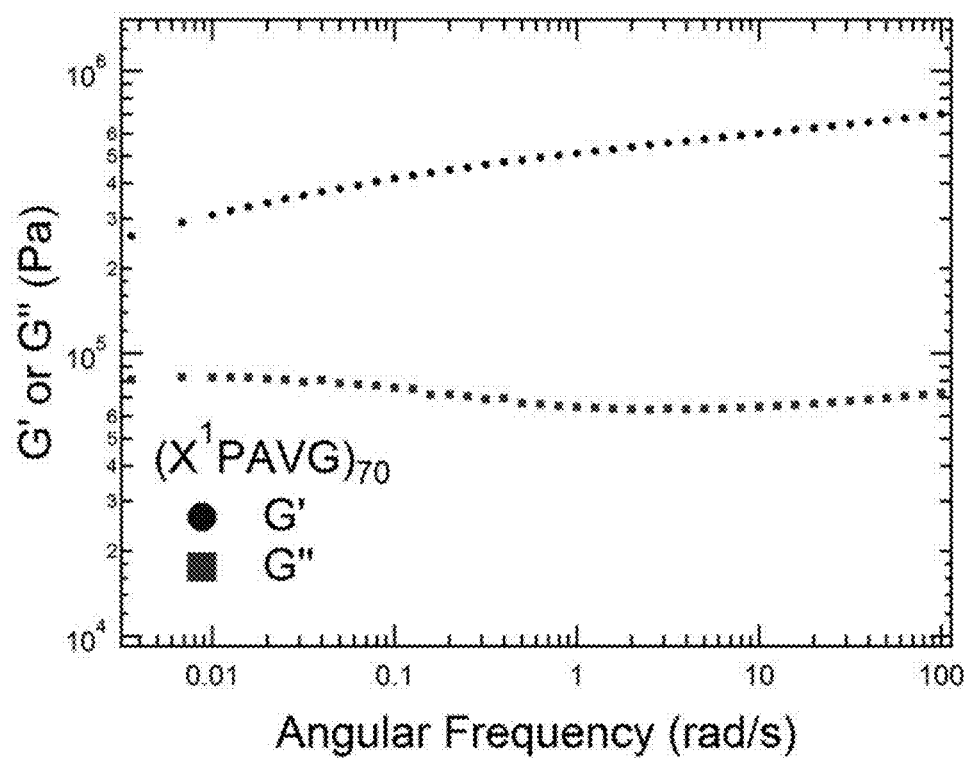
FIG. 23B depicts frequency sweeps for 20 wt % gels ((X$^1$PAVG)$_{70}$ (SEQ ID NO: 54)) at T=37° C., $\gamma_o$=0.01.
Figure 23C:
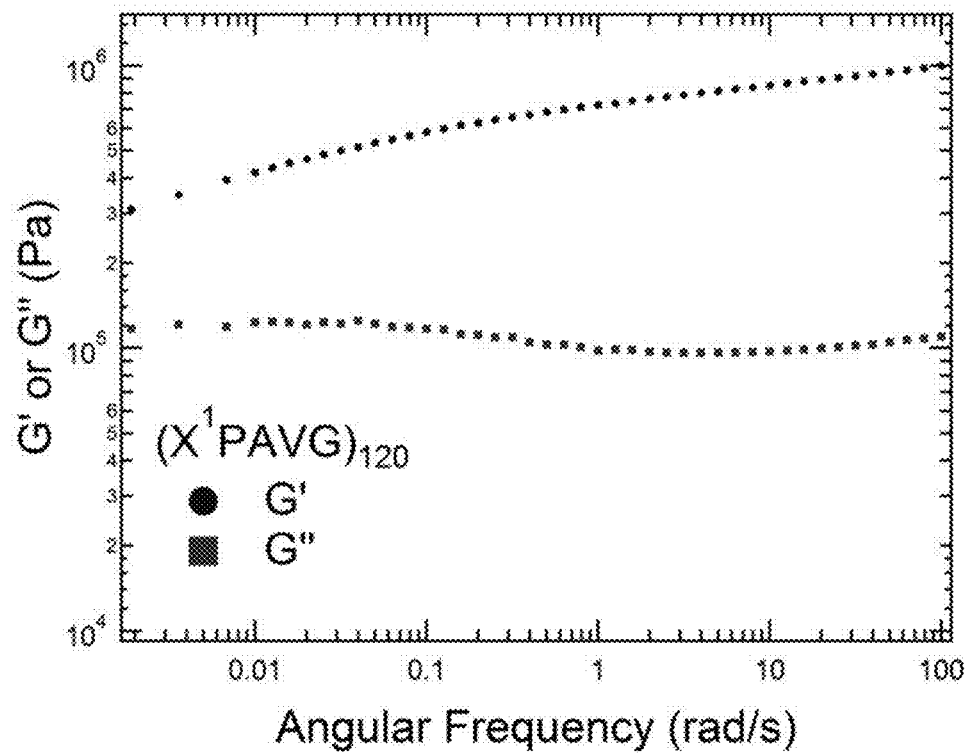
FIG. 23C depicts frequency sweeps for 20 wt % gels ((X$^1$PAVG)$_{120}$ (SEQ ID NO: 50)) at T=37° C., $\gamma_o$=0.01.
Figure 23D:
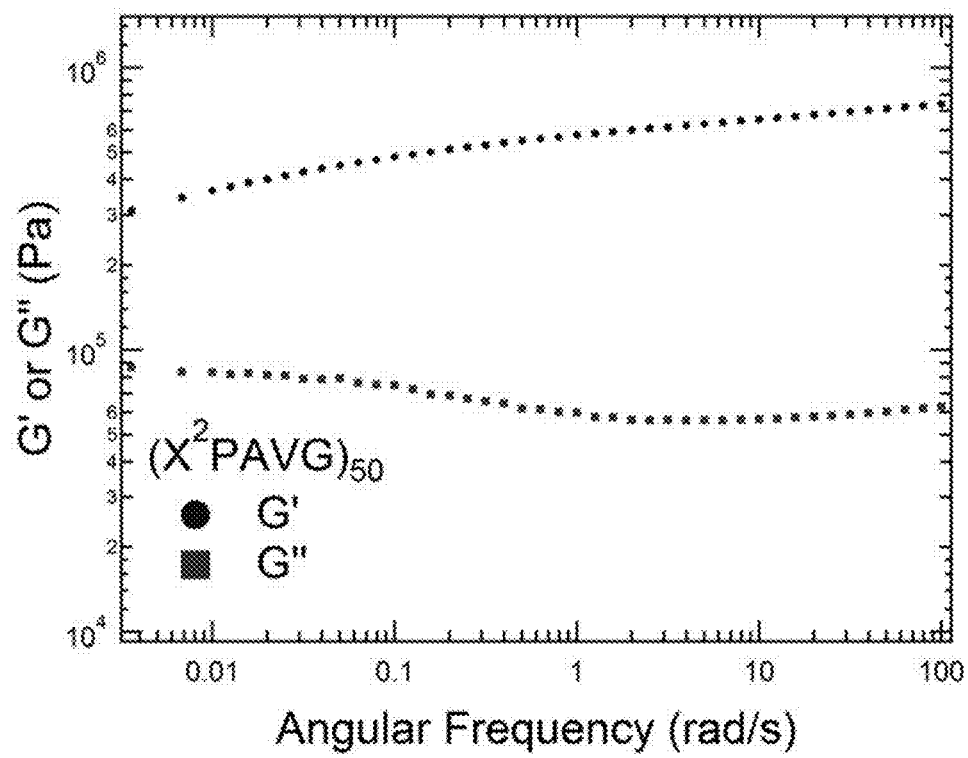
FIG. 23D depicts frequency sweeps for 20 wt % gels ((X$^2$PAVG)$_{50}$ (SEQ ID NO: 53)) at T=37° C., $\gamma_o$=0.01.

While sequence design can influence gel stiffness, the time-dependent viscoelastic responses of all gels exhibit important similarities. For gels with constant overall hydrophobicity but increasing molecular weight, i.e., $(X^1PAVG)_n$, where n=50 (SEQ ID NO: 51), 70 (SEQ ID NO: 54), or 120 (SEQ ID NO: 50), increasing chain length results in an increase in the modulus of the gels across the entire frequency spectrum. In general, all gels exhibit qualitatively similar relaxation spectra (FIG. 22, FIG. 17, and FIG. 23), although a slight decrease in the slope of G' in the high frequency regime can be seen for the more hydrophobic sequence, $(X^2PAVG)_{50}$ (SEQ ID NO: 53), suggesting potentially a small difference in the distribution of relaxation times. Nevertheless, the samples show $$\tan(\delta) = \frac{G''(\omega)}{G''(\omega)}$$

nearly approaching frequency independence above ω=10 rad/s, and all spectra transition to a regime where $\tan(\delta) \sim \alpha$ (α~0.1-0.2) at nearly the same characteristic timescale (FIG. 22, panel c). As suggested by the insensitivity of the shape of the viscoelastic spectra to changes to polypeptide molecular weight and hydrophobicity, these parameters do not significantly perturb the spacing of modes in the underlying relaxation distribution of the networks. However, the magnitude of these modes is strongly dependent on both the polypeptide's molecular design and the assembly conditions, as judged by the vertical shift of these spectra by roughly half an order of magnitude.

Nanostructure of the Arrested Networks

Figure 24:
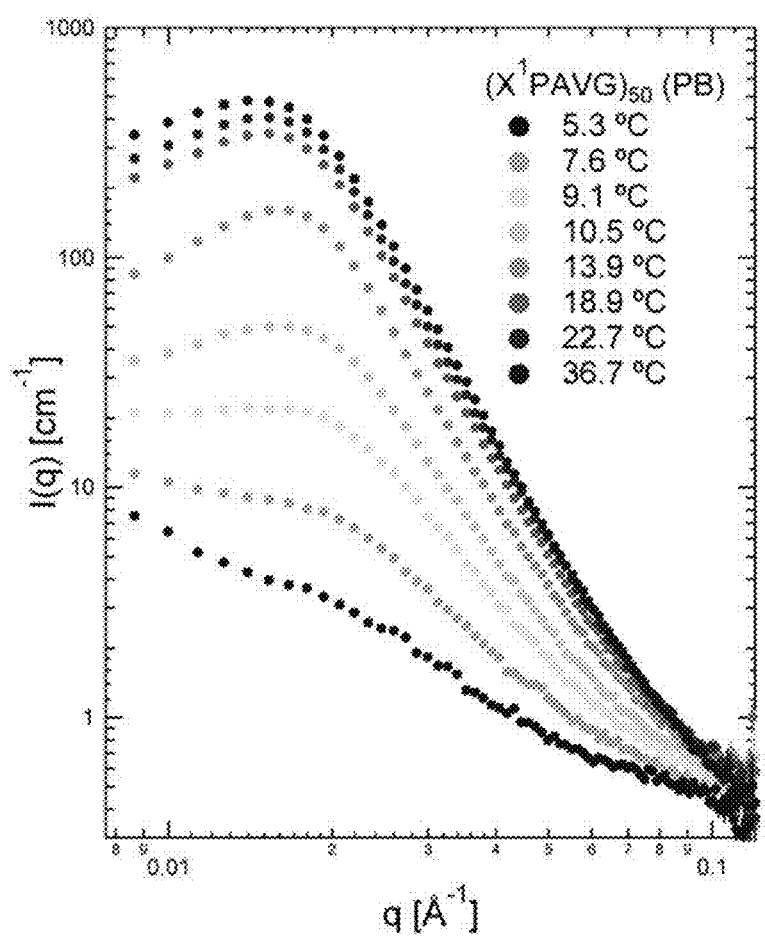
FIG. 24 depicts small angle neutron scattering showing the thermal evolution of the scattering pattern on one (X$^1$PAVG)$_{50}$ (SEQ ID NO: 51) in 100 mM sodium phosphate, pH=7.6, at 20% (w/v). Data collected at the temperature extremes (T=5.3° C. and 36.7° C.) were from samples equilibrated for at least 60 minutes. Data at intermediate temperatures were collected over 2 min during the temperature ramp step without equilibration, with acquisitions starting at the temperature indicated in the legend.

These gels exhibit weak order on the nanoscale, and the correlation length scales can be controlled by protein molecular weight and buffer conditions, as is evident in SANS measurements performed at 37° C. Under all conditions, the scattered intensity increases significantly upon warming above the transition temperature, resulting in the growth of a single shoulder or peak. This result is consistent with an arrested phase separation process that occurs by spinodal decomposition, where the typical process of coalescence ceases upon densification of one of the domains. No major changes in the scattering patterns were observed after equilibrating beyond one hour (FIG. 24), which is interesting given that the gels will continue to stiffen for roughly 15 hours after heating. This difference suggests that gel stiffness is influenced not only by the nanostructure but also by sub-nanoscale changes that occur slowly as the arrested state ages. All gels exhibit Porod law decay above ca. q=0.02 Å$^{-1}$, with a power law exponent of essentially −4, consistent with scattering from domains with smooth interfaces and constant subdomain density (Table 7). This general result suggests that local scattering from the interface of the nanodomains is not substantially perturbed by the protein sequence or buffer conditions. Furthermore, the correlation peak that develops in many samples at low q (<0.02 Å$^{-1}$) indicates that the domains form on a characteristic length scale of 40-60 nm. The combination of features observed in SANS experiments suggests that the nanostructure can be approximated by a correlation function with at least two distinct length scales: one accounting for Porod law scattering from the interface and another for periodicity resulting from longer-range density correlations between domains.

Given the inference of sharp domain interfaces, analysis of the SANS intensity distributions allows an estimation of the total volume fraction of the dense phase. As suggested in the definition of the Porod invariant, $Q=V<p^2>$, a relationship between the total scattered intensity and the volume fraction of the two phases can be established. Such an analysis assumes that the scattering contrast fluctuates between two constant values in each phase. The $q^{-4}$ behavior at high wavevectors is consistent with this behavior, so the volume fraction of the polypeptide-rich phase, $\phi_1$, can be estimated by:

$$Q=(\rho_1-\rho_2)^2\phi_1(1-\phi_1) \quad (4.1)$$

where $\rho_1$ and $\rho_2$ are the scattering length density in the dense and dilute phase, respectively. Assuming further that all the protein accumulates in the dense phase of the gel, the scattering length density in the two phases becomes a function of only the volume fraction of the dense phase and several constants:

$$\rho_1 = \rho_{Protein}\frac{\phi_{Protein,gel}}{\phi_1} + \rho_{D2O}\left(1 - \frac{\phi_{Protein,gel}}{\phi_1}\right) \quad (4.2)$$

$$\rho_1 = \rho_{D2O} \quad (4.3)$$

$\phi_{Protein,\,gel}$ is computed from the mass fraction of the gels (20 wt %), and the values for $\rho_{Protein}$ and $\rho_{D2O}$ can be estimated from NIST's online scattering length density calculator for thermal neutrons, which can be used to approximate the experimental results obtained using NGB at the NCNR, operating with a source of cold neutrons. The protein density was estimated to be 1.3 g/cm³, and ideal mixing is assumed. Measurements of the invariant for all samples indicate that the networks arrest with $\phi_1=0.19$-$0.22$ (Table 7), indicating that the dense phase is the minority phase but is not completely dehydrated. This measurement corresponds to protein volume fractions in the dense phase of approximately $\phi_{1,protein}=0.70$-$0.84$ This composition is in contrast to ternary polymer blends that can adopt similar apparent structures, where the volume fraction of each phase is typically carefully matched to 0.5.

Modeling these scattered intensity distributions reveals that their nanostructure is consistent with that of random bicontinuous two-phase systems. While many SANS models require an assumption of domain morphology, the empirical Clipped Random Wave model (CRW) developed for non-isometric systems (i.e., where $\phi_1 \neq \phi_2$) can be applied for domains without regular structure. This model assumes that the density distribution randomly fluctuates between two states (dense and dilute phases) and is capable of describing the spacing and width of these phases as well as the curvature of the interface. The CRW model is closely related to the Teubner-Strey (TS) and Modified Berk (MB) models, which have been applied the study of thermodynamically-stable bicontinuous microemulsions as well as phase separating polymer blends. According to the CRW model, the scattered intensity distribution is described by the following key equations:

$$I(q) = 4\pi\langle\eta^2\rangle \int_0^\infty r^2 \frac{\sin(qr)}{qr}\Gamma(r)dr \quad (4.4)$$

$$\Gamma(r) = 1 - \frac{1}{2\pi\phi_1(1-\phi_2)}\int_0^{\cos^{-1}[g(r)]} \exp\left[-\frac{\beta^2}{1+\cos\theta}\right]d\theta \quad (4.5)$$

$$g(r) = K_1\frac{1}{r}[e^{-cr}(K_2 + K_3r) + e^{-br}(K_4\sin(ar) - K_5\cos(ar))] \quad (4.6)$$

where the $K_i$ are collections of the model parameters a, b, and c. The clipping level, $\beta$, used to convert the Gaussian random field into a two-state discrete process is related to the volume fraction of the dense phase, $\phi_1$ by:

$$\phi_1 = \frac{1}{2} + \frac{1}{\sqrt{2\pi}}\int_0^\beta \exp\left[\frac{-x^2}{2}\right]dx \quad (4.7)$$

Figure 25:
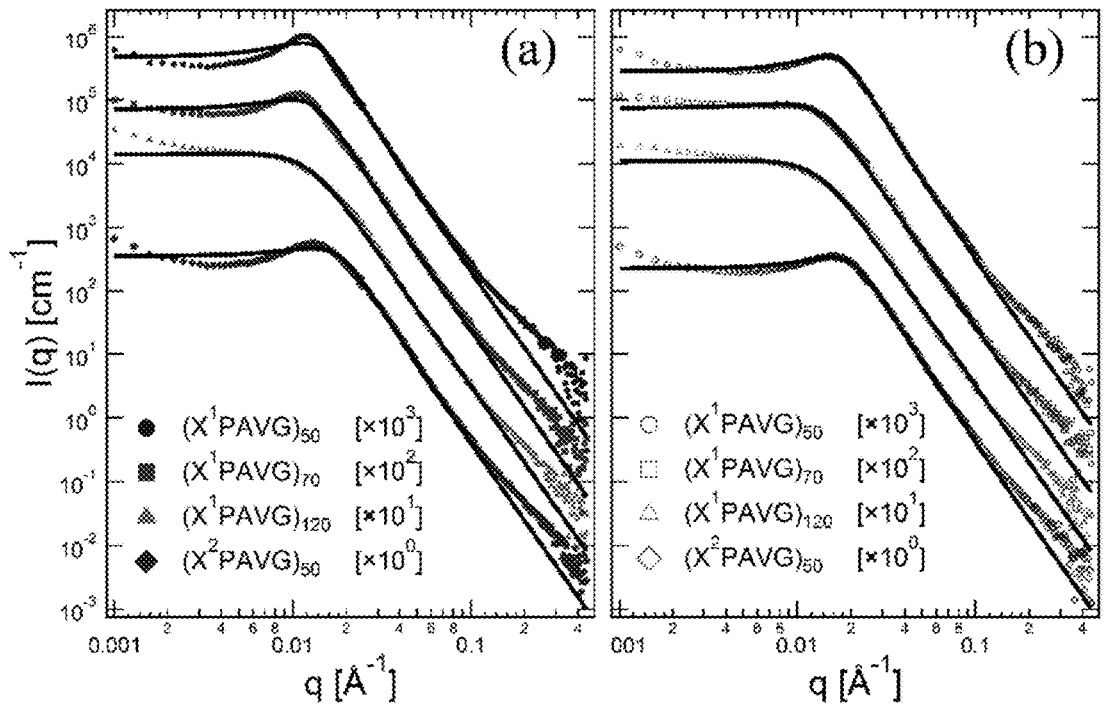
FIG. 25 has two panels (a and b) depicting SANS intensity distributions and fits to the Teubner-Strey model (solid black lines) for gels prepared in (a) D$_2$O or (b) 100 mM sodium phosphate buffer, pH=7.6. For clarity, the data are shifted by the multiplicative factor indicated in the figure legend.
Figure 26:
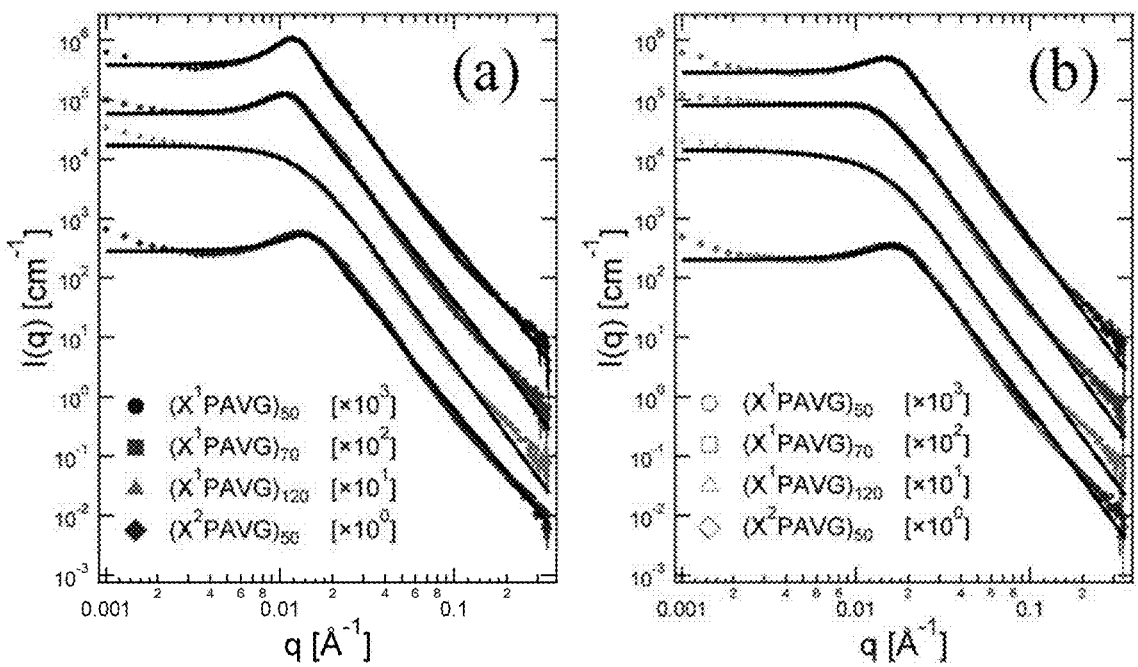
FIG. 26 has two panels (a and b) depicting SANS intensity distributions and fits to the CRW model (solid black lines) for gels prepared in (a) $D_2O$ or (b) 100 mM sodium phosphate buffer, pH=7.6. The incoherent background, B, has been subtracted from the experimental and modeled data. For clarity, the data are shifted by the multiplicative factor indicated in the figure legend.

The SANS data fit well to the CRW model for all four gel-forming ELPs in both solvent conditions, capturing both the shallow peak at low q and the Porod-like decay over 3 decades of intensity. The CRW model provides substantially improved fits compared with the simpler TS model (FIG. 25), which does not directly model the effects of interfacial curvature and fails to simultaneously capture the peak sharpness and $q^{-4}$ decay at high wavevetors for all gels. The CRW fits are consistent with the hypothesis that these networks share similar structural features with disordered systems undergoing phase separation, such as polymer blends in the immiscible regime, although in these ELP gels, network coarsening arrests while domains still have a nanoscale size. Deviation from the model occurs slightly at low wavevectors (q<0.002 Å⁻¹) potentially due to slight clustering typical in water-soluble systems or where larger structural features that also affect the gel's optical clarity may begin to contribute. In addition, the model deviates from the experimental data slightly at high wavevectors (q>0.2 Å⁻¹), potentially due to small features at the domain interface or monomer-level structure within domains.

The CRW fits reveal that the length scales in these arrested networks can be manipulated both on the molecular level and by the assembly conditions. In particular, it is interesting to note that any method of increasing the effective hydrophobicity of the polypeptide investigated here (increasing molecular weight, I:V ratio, or buffer strength) leads to a decrease in the intradomain correlation length scale (1/b) and an increase in the curvature length scale (1/c) for all arrested networks. Moreover, all of these measures of increasing hydrophobicity are also positively correlated with increasing gel stiffness (FIG. 22, panel a). While the normalized change for each construct is quite different with increasing ionic strength, the normalized change in elastic modulus is also quite different. (X¹PAVG)₅₀ (SEQ ID NO: 51) (which shows the greatest normalized change in the length scales) is roughly 8-fold stiffer upon increasing ionic strength, while (X¹PAVG)₁₂₀ (SEQ ID NO: 50) and (X²PAVG)₅₀ (SEQ ID NO: 53) (which show much smaller normalized changes in length scales) are roughly 2-fold stiffer upon increasing ionic strength. On the other hand, the dependence of the interdomain correlation length scale (2π/a) on polypeptide sequence or buffer conditions is less straightforward. For the sequence (X¹PAVG)ₙ (SEQ ID NO: 4) in D₂O, increasing molecular weight leads to an increase in the interdomain length scale, but the trend is not monotonic in phosphate buffer. Furthermore, increasing sequence hydrophobicity, from (X¹PAVG)₅₀ (SEQ ID NO: 51) to (X²PAVG)₅₀ (SEQ ID NO: 53), or switching from D₂O to phosphate buffer leads to a decrease in the interdomain length scale. Taken together, these observations suggest that controlling intradomain and interfacial structure by manipulating polypeptide hydrophobicity provides a route to engineer the linear mechanics of these networks.

TABLE 7

Porod law analysis and structural parameters from the CRW model fits of the scattered intensity from SANS experiments.

| Identifier | Solvent* | $n^\dagger$ | $2\pi/a$ [nm] | $1/b$ [nm] | $1/c$ [nm] | $\phi_2^\ddagger$ [—] | $\langle\eta^2\rangle^\ddagger$ [×10$^{-20}$ cm$^{-4}$] | $B^\ddagger$ [cm$^{-1}$] |
|---|---|---|---|---|---|---|---|---|
| (X$^1$PGVG)$_{50}$ | D$_2$O | −4.18 ± 0.03 | 50.6 ± 0.2 | 33.3 ± 0.6 | 0.21 ± 0.07 | 0.22 | 1.42 | 0.225 |
| (SEQ ID NO: 52) | PB | −4.11 ± 0.06 | 37.8 ± 0.2 | 18.3 ± 0.2 | 1.69 ± 0.06 | 0.20 | 1.67 | 0.227 |
| (X$^1$PGVG)$_{70}$ | D$_2$O | −4.17 ± 0.08 | 54.9 ± 0.2 | 28.5 ± 0.3 | 0.66 ± 0.07 | 0.21 | 1.54 | 0.192 |
| (SEQ ID NO: 50) | PB | −4.02 ± 0.09 | 51.9 ± 0.6 | 12.8 ± 0.2 | 2.58 ± 0.01 | 0.22 | 1.46 | 0.207 |
| (X$^1$PGVG)$_{120}$ | D$_2$O | −4.18 ± 0.06 | 63.9 ± 2.7 | 8.71 ± 0.45 | 3.68 ± 0.30 | 0.19 | 1.72 | 0.218 |
| (SEQ ID NO: 70) | PB | −4.00 ± 0.08 | 38.1 ± 2.2 | 6.82 ± 0.33 | 5.87 ± 0.03 | 0.21 | 1.57 | 0.221 |
| (X$^2$PGVG)$_{50}$ | D$_2$O | −3.83 ± 0.06 | 41.9 ± 0.3 | 19.2 ± 0.5 | 0.18 ± 0.07 | 0.19 | 1.81 | 0.220 |
| (SEQ ID NO: 71) | PB | −3.82 ± 0.09 | 34.9 ± 0.2 | 15.0 ± 0.2 | 0.90 ± 0.05 | 0.19 | 1.80 | 0.241 |

*PB = 100 mM sodium phosphate in D$_2$O, pH = 7.6.
$^\dagger$Porod-law exponent fit directly to the high-q region of the experimental data.
$^\ddagger$Parameters determined directly from experimental data and fixed as constants during the fitting procedure.

The CRW model allows for analysis of interfacial properties of the nanostructured gels, revealing that the scattering from these ELP gels is consistent with a bicontinuous network. From the CRW fit parameters, various measures of the domain curvature can be estimated (Table 8). Mean curvature, <H>, is non-zero as expected for a non-isometric case, and the Gaussian curvature, <K>, is negative, consistent with a bicontinuous structure. Furthermore, the gels are seen to have a range of S/V typical for bicontinuous microemulsions and ternary polymer blends. The greatest interfacial area is observed in D$_2$O for (X$^1$PAVG)$_{50}$ (SEQ ID NO: 51) and (X$^2$PAVG)$_{50}$ (SEQ ID NO: 53), ELPs with the lowest molecular weight. The mean curvature decreases as polypeptide molar mass increases and the total interfacial area decreases, consistent with a smoother interface at nearly constant volume fraction. Furthermore, for every sample, the mean curvature is smaller in buffer than in D$_2$O. These results suggest that the density of polypeptide chain ends, which are charged, may play a role in structural details at the domain interface.

TABLE 8

Curvature, interface, and order quality parameters for (X$^2$PAVG)$_{50}$ (SEQ ID NO: 53) gels computed from the fit parameters to the CRW model.

| Identifier | Solvent* | $\langle H \rangle$ [×10$^{-2}$ nm$^{-1}$] | $\langle K \rangle$ [×10$^{-3}$ nm$^{-2}$] | $\langle H^2 \rangle$ [×10$^{-2}$ nm$^{-2}$] | S/V [nm$^{-1}$] | $\frac{2\pi b}{a}$ |
|---|---|---|---|---|---|---|
| (X$^1$PGVG)$_{50}$ | D$_2$O | 11.1 | −10.5 | 40.8 | 0.108 | 0.658 |
| (SEQ ID NO: 52) | PB | 7.3 | −2.80 | 6.23 | 0.062 | 0.483 |
| (X$^1$PGVG)$_{70}$ | D$_2$O | 7.5 | −3.83 | 39.9 | 0.068 | 0.517 |
| (SEQ ID NO: 50) | PB | 5.8 | −2.85 | 4.08 | 0.056 | 0.247 |
| (X$^1$PGVG)$_{120}$ | D$_2$O | 6.2 | −1.46 | 3.40 | 0.049 | 0.136 |
| (SEQ ID NO: 70) | PB | 5.8 | −2.31 | 2.61 | 0.053 | 0.179 |
| (X$^2$PGVG)$_{50}$ | D$_2$O | 17.6 | −11.8 | 57.2 | 0.139 | 0.457 |
| (SEQ ID NO: 71) | PB | 10.3 | −3.99 | 22.2 | 0.081 | 0.431 |

*PB = 100 mM sodium phosphate in D$_2$O, pH = 7.6.

Figure 27:
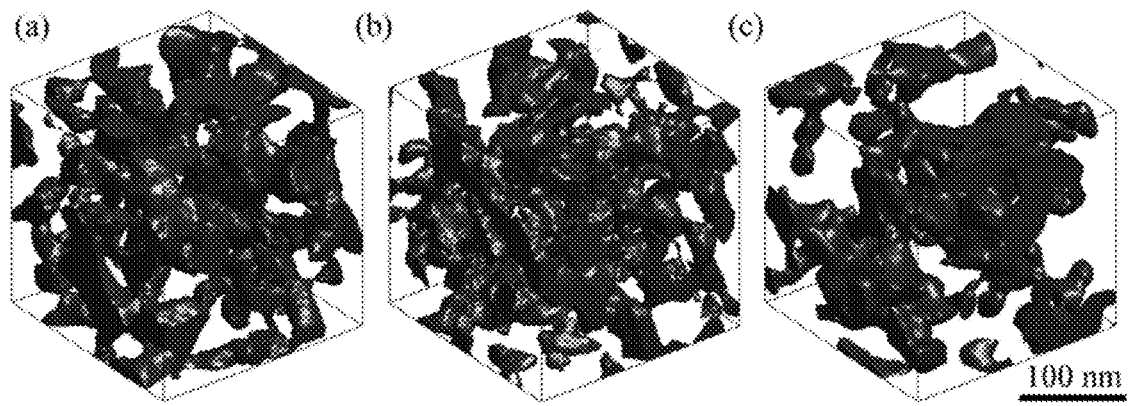
FIG. 27 has three panels (a-c) depicting 3D plots of the real-space distribution of the protein dense phase from simulations of the nanostructure for a 200×200×200 nm simulation (1 nm resolution) of (a) $(X^1PAVG)_{50}$ (SEQ ID NO: 51) and (b) $(X^2PAVG)_{50}$ (SEQ ID NO: 53), and (c) $(X^1PAVG)_{120}$ (SEQ ID NO: 50). Note that the interface is drawn where the value of $\psi(r)$ crosses the clipping parameter, $\beta$, consistent with $\phi_1$ measured for each gel.

The Gaussian random process at the core of the CRW model allows for real-space simulations of the density distribution in these arrested ELP networks, providing a 3D picture that summarizes the interpretations of the gel nanostructure. This visualization method has been used in the context of bicontinuous microemulsions and anisometric systems with various spectral distribution functions. The order parameter field of the random process is given by:

$$\psi(r) = \sqrt{\frac{2}{N}} \sum_{1}^{N} \cos(k_n \cdot r + \phi_n) \quad (4.8)$$

where N=10,000 is the number of cosine waves in the simulation, r is the real space vector, and $k_n$ and $\phi_n$ describe the random wavevector, which is sampled according to the spectral distribution function. Based on the assumption of an isotropic system, each wavevector is assigned a random phase and random orientation, and the wavevector magnitude is described by a function, $f(k)$, which for the CRW model is given by:

$$f(k) = \frac{bc(a^2 + (b+c)^2)^2/(b+c)\pi^2}{(k^2+c^2)^4(k^4 + 2(b^2 - a^2)k^2 + (a^2+b^2)^2)} \quad (4.9)$$

where k is the wavevector magnitude and a, b, c are model parameters. A Monte Carlo sampling procedure is implemented to identify the N wavevector magnitudes used in the analysis. The interface between the phases is given by the level set $\psi(r)=\beta$, where $\beta$ is the clipping parameter defined above. Visualizations of the CRW fits are consistent with a disordered but highly connected network of the dense protein phase (FIG. 27). In particular, these simulations present a clear picture of the influence of increased interfacial persistence length (1/c) on gel nanostructure, as can be seen in the rougher interfaces in (X$^1$PAVG)$_{50}$ (SEQ ID NO: 51) gels compared with (X$^1$PAVG)$_{120}$ (SEQ ID NO: 50). These effects are consistent with the higher curvature and S/V seen in the lower molecular weight ELPs, as derived directly from the CRW fit parameters. Studies on drug delivery microparticles formed from the macrophase separation of 'plastic' ELP coacervates suggests that, when heated at low concentrations, coalescence leads to the formation of spherical, micron-scale aggregates. In contrast, the large interfacial area evident from 3D reconstructions suggests that arrest occurs well before molecular rearrangements allow the interface to evolve substantially. Ultimately, these arrested networks exhibit structural features that closely resemble bicontinuous microemulsions, although no interface-stabilizing component is required.

Figure 28:
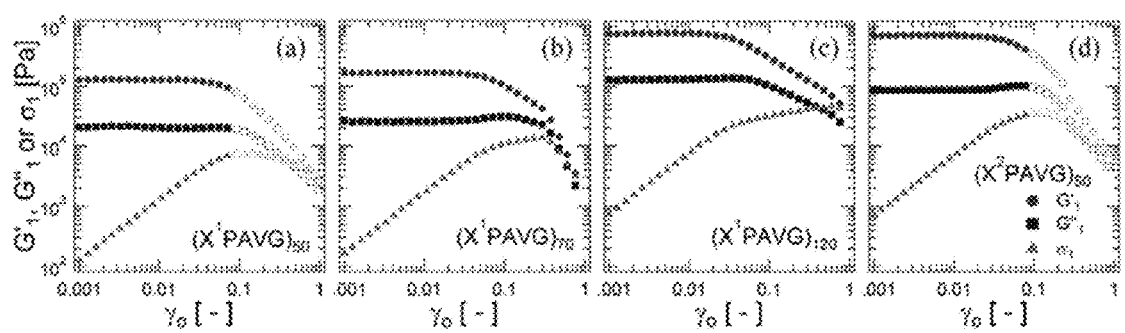
FIG. 28 has four panels (a-d) depicting the behavior of the first harmonic of the stress waveform in large amplitude oscillatory shear rheology for 20 wt % gels at 37° C. ($\omega$=1 rad/s). Data in open circles indicate where the spectral purity of the shear rate waveform is poor, as judged by the third harmonic ratio growing beyond 1% (FIG. 29).
Figure 29:
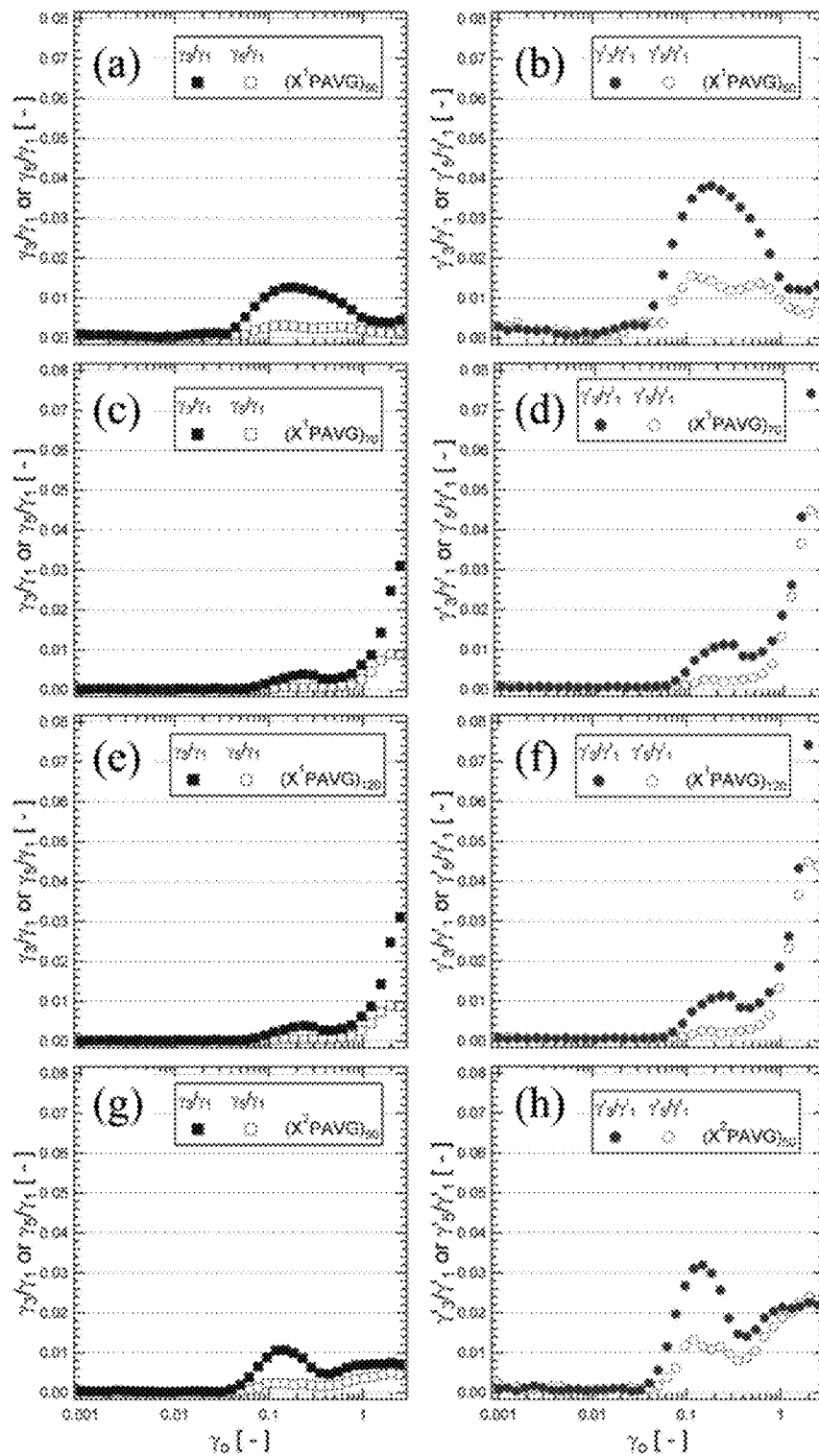
FIG. 29 has eight panels (a-h) depicting spectral purity analysis of the strain and shear rate waveforms during LAOS.
Figure 30:
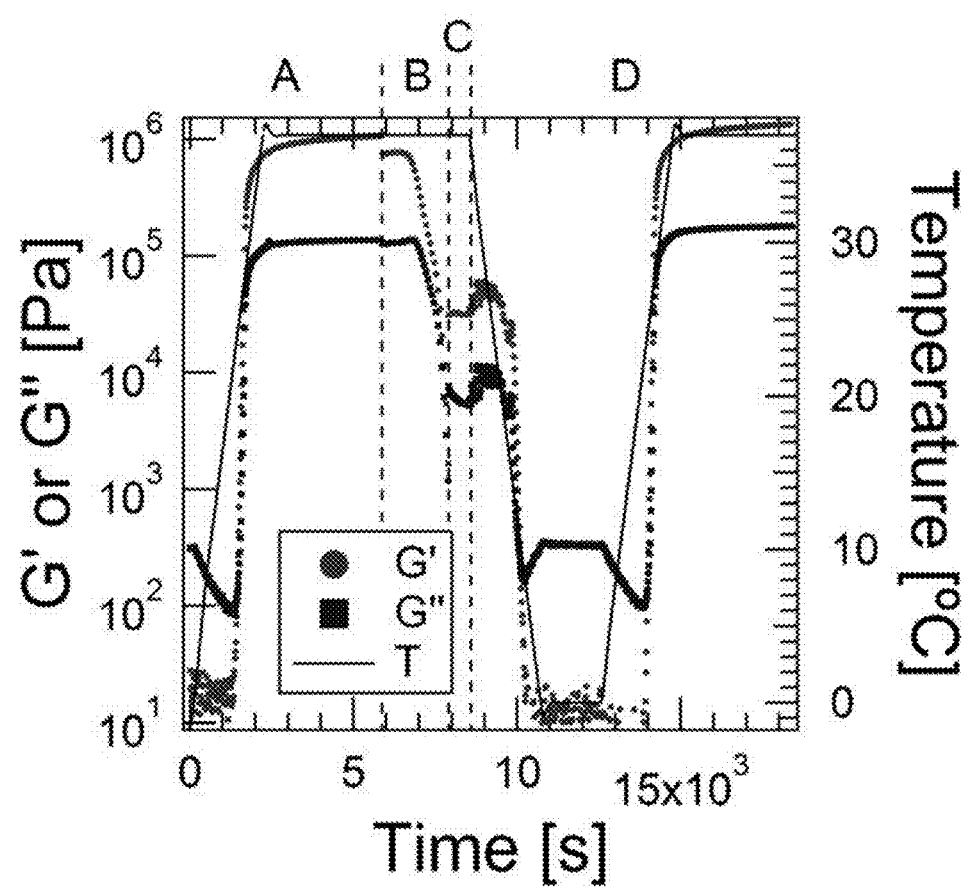
FIG. 30 depicts recovery following large amplitude oscillatory shear rheology of $(X^1PAVG)_{120}$ (SEQ ID NO: 50) at a concentration of 20 wt % in water. Region A: The sample is heated to 37° C. and equilibrated, and SAOS is applied at $\omega$=100 rad/s and $\gamma_o$=0.01. Region B: LAOS is applied at $\omega$=1 rad/s over a series of strain amplitudes from $\gamma_o$=0.001 to $\gamma_o$=2.5. Region C: SAOS is applied at $\omega$=100 rad/s and $\gamma_o$=0.01 immediately, demonstrating the gel does not recover to the state prior to LAOS. Region D: After cooling, equilibrating at 0° C., then reheating and equilibrating at 37° C., stiff gels are reformed.

Yielding and Recovery in Nonlinear Shear Differences in polypeptide design influence the yielding and recovery of these hydrogels, as measured by large amplitude oscillatory shear (LAOS) rheology. As indicated in the behavior of the first harmonic of the stress response as a function of strain amplitude (FIG. 28), the linear viscoelastic range ends around approximately $\gamma_o$=0.05-0.1, followed by a region where both viscoelastic moduli decrease slowly while the stress continues to rise with a decreased slope. This nonlinear region is clear in the higher molecular weight samples, while for $(X^1PAVG)_{50}$ (SEQ ID NO: 51) and $(X^2PAVG)_{50}$ (SEQ ID NO: 53) the quality of the strain control becomes too poor for detailed analysis just at the end of the linear viscoelastic range. Nevertheless, both the peak in the shear stress and the corresponding strain amplitude are greatest for the gel with the highest molecular weight, $(X^1PAVG)_{120}$ (SEQ ID NO: 50). Qualitatively, gels made with this polypeptide appear much less brittle, consistent with these quantitative differences in the nonlinear behavior judged by the dependence of the first harmonic of the stress. Following sweeps to $\gamma_o$=5.0, none of the gels recover, indicating that these networks are irreversibly damaged during high strain perturbations and cannot heal when held in the warm state. This observation indicates that while these gels are formed from physical interactions alone, the associations are not reversible in the traditional sense of transient networks, as is consistent with noncovalent interactions formed due to a non-equilibrium process. However, after being liquefied by cooling below the $T_t$ and reheated, the gels recover their linear and nonlinear mechanical properties (FIG. 30).

Figure 31:
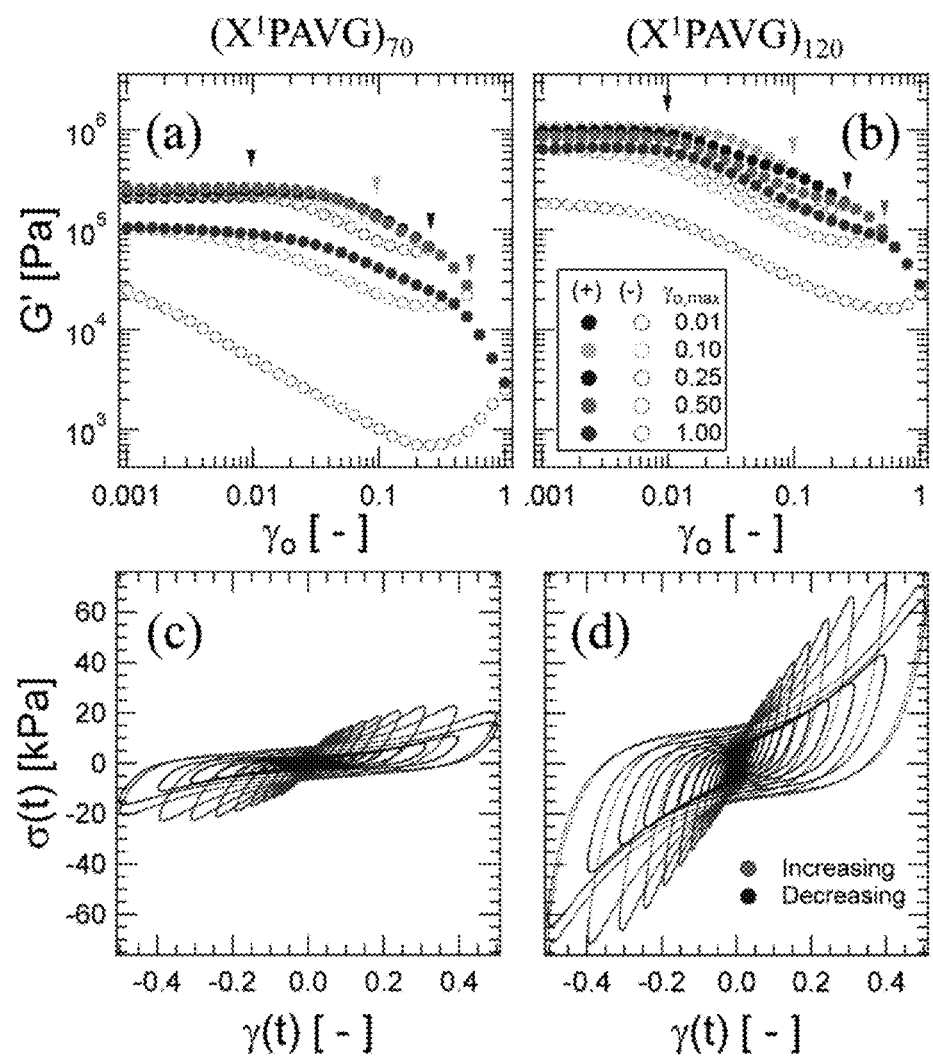
FIG. 31 has four panels (a-d) depicting yielding and recovery in large amplitude oscillatory shear sweeps, cycling up to an increasing maximum strain amplitude, $\gamma_{o, max}$. The behavior of the first harmonic of the elastic modulus (G') for (a) $(X^1PAVG)_{70}$ (SEQ ID NO: 54) and (b) $(X^1PAVG)_{120}$ (SEQ ID NO: 50). Arrowheads highlight the point of maximum strain amplitude for intermediate cycles. Elastic Lissajous-Bowditch curves shown for the increasing and decreasing sweeps during cycles up to $\gamma_{o, max}$ of 0.5 for (c) $(X^1PAVG)_{70}$ (SEQ ID NO: 54) and (d) $(X^1PAVG)_{120}$ (SEQ ID NO: 50) (20 wt %, $\omega$=1 rad/s).

While sufficiently large oscillatory shear irreversibly degrades the networks, cyclic strain sweeps performed to increasing maximum strain amplitudes ($\gamma_{o,max}$) reveal that the gels can exhibit some recovery (FIG. 31). For $(X^1PAVG)_{70}$ (SEQ ID NO: 54) in particular, strain sweep cycles up through $\gamma_{o,max}$=0.25 allow for recovery of the mechanical response at small perturbations, as seen in the superimposable behavior upon returning to lower strain amplitudes. Minor hysteresis can be observed in $G_1'$ between the increasing and decreasing strain sweeps for this gel, but subsequent increasing sweeps overlap with that of the previous cycle. The behavior of the gel made from $(X^1PAVG)_{120}$ (SEQ ID NO: 50) is similar, although increasing strain sweeps are clearly not exactly superimposable due to a decrease in the end of the linear viscoelastic range from roughly $\gamma_o$=0.03 to 0.01. This observation suggests that although the behavior of the gel recovers well (through $\gamma_{o,max}$=0.25), the network retains some memory of the nonlinear perturbations. Interestingly, the increasing strain sweep of one cycle passes through exactly the same point as the maximum strain amplitude of the previous cycle (FIG. 31, panels a,b). As a result, a curve that follows the boundary states swept out on increasing strain overlaps well with a single sweep to increasing strain. In both gels, a large increase in hysteresis in $G_1'$ and $G_1''$ appears to indicate substantial network disruption, occurring just above the point at which the $\sigma_1$ is maximized in the single sweep experiments. After this point, the moduli following decreasing strain sweeps are at least a factor of 2 lower than the previous cycle.

Parametric Lissajous-Bowditch curves made from the raw waveforms during the cyclic strain sweeps reveal important features of the stress response in the nonlinear regime for $(X^1PAVG)_{70}$ (SEQ ID NO: 54) and $(X^1PAVG)_{120}$ (SEQ ID NO: 50) (FIG. 31, panels c, d). For both gels, upon increasing strain sweeps to $\gamma_{o,max}$=0.5, within the nonlinear regime, intracycle dissipation increases significantly as the curves rotate and broaden. At high enough strains, the curves also begin to flatten at small strains. While there is a difference in the scale of the response between the two gels, the parametric stress increases near the maximum strain (minimum shear rate). This type of response indicates that the networks behave substantially softer at small strains than at high strains, indicative of complex intracycle strain stiffening that is not captured by the behavior of $G_1'$ alone. Furthermore, that the curves trace out a substantial area at sufficiently high strains indicates that the nonlinear mechanical response is dissipative in nature.

Figure 32:
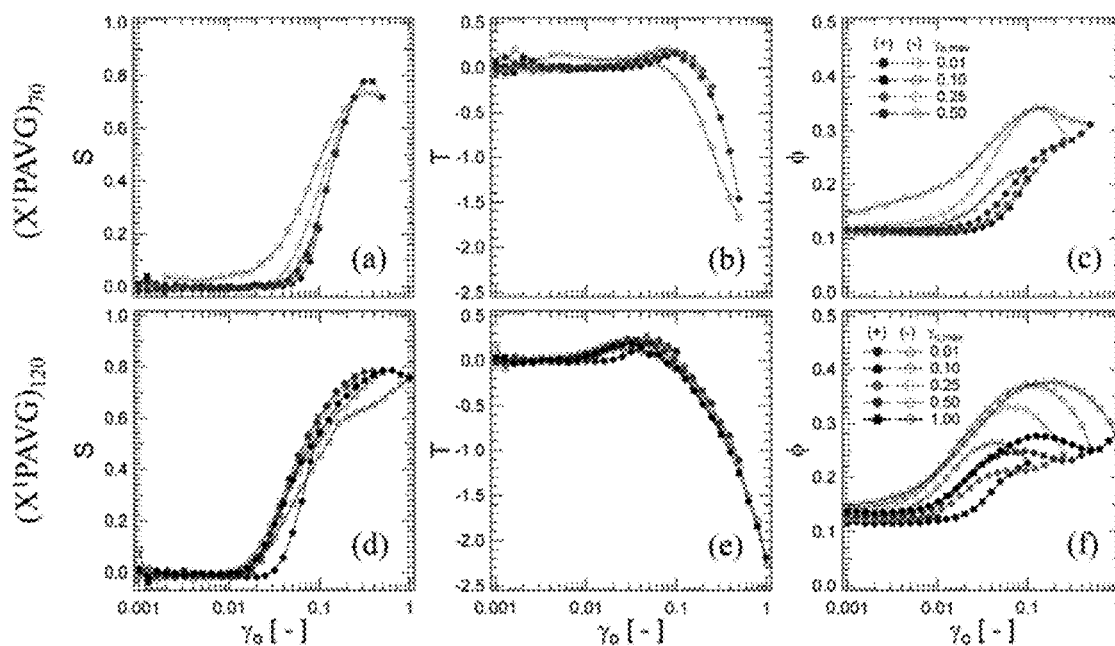
FIG. 32 has six panels (a-f) depicting the stiffening ratio, S, thickening ratio, T, and perfect plastic dissipation ratio, $\phi$, for: (a-c) $(X^1PAVG)_{70}$ (SEQ ID NO: 54) and (d-f) $(X^1PAVG)_{120}$ (SEQ ID NO: 50) during strain cycling.

To quantify these important intracycle responses and understand the yielding behavior of these gels, the tangent moduli ($G_M'$) and secant moduli ($G_L'$) and the tangent viscosities ($\eta_M'$) and secant viscosities ($\eta_L'$) were extracted from the elastic and viscous Lissajous-Bowditch curves as a function of strain amplitude and strain history. The ratios of these moduli and viscosities are a first order representation of the intracycle nonlinearities, and they provide a more detailed quantitative description of the shape of the steady-state waveforms as a function of maximum strain amplitude (FIG. 32). Three important derived properties that can summarize these complex effects are the thickening ratio, $$T = \frac{\eta_L - \eta_M}{\eta_L},$$

the stiffening ratio, $$S = \frac{G_L' - G_M'}{G_L'},$$

and the perfect plastic dissipation ratio, $$\phi = \frac{\pi \gamma_o G_1''}{4\sigma_{max}}.$$

The sign of T indicates intracycle shear thickening/thinning (positive/negative values, respectively), while the sign of S indicates strain stiffening/softening. $\phi$ represents the area swept out on the elastic Lissajous-Bowditch curves as a fraction of a perfect plastic with a yield stress equal to the maximum in the parametric stress.

Figure 33:
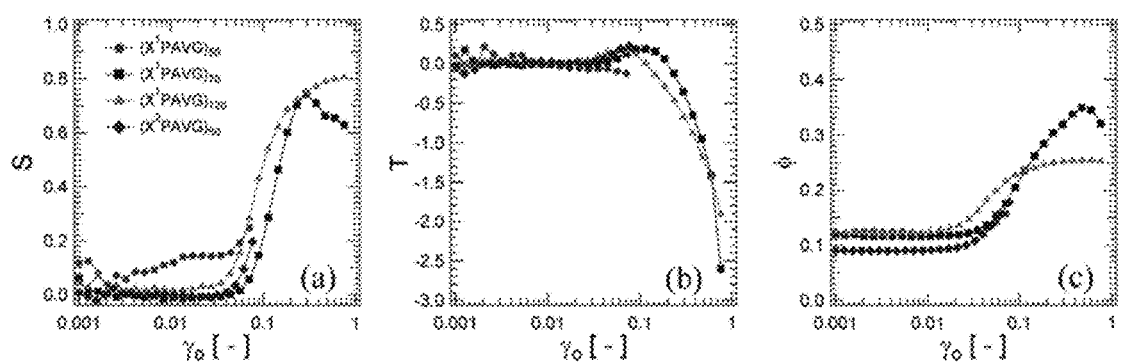
FIG. 33 has three panels (a-c) depicting the (a) stiffening ratio, S, (b) thickening ratio, T, and (c) perfect plastic dissipation ratio, $\phi$, for all gels during a single strain sweep out to failure.

Examining the behavior of these parameters for the gels reveals that the initial transition to the nonlinear regime is characterized by a sharp increase in dissipation, slight intracycle shear thickening, and increased intracycle strain stiffening, although well into the nonlinear regime the gels exhibit shear thinning behavior (FIG. 32, FIG. 33). For $(X^1PAVG)_{70}$ (SEQ ID NO: 54), the peak in the first harmonic of the stress (FIG. 28, panel b) coincides with the drop in the magnitude of the intracycle strain stiffening (FIG. 32, panel a) as well as the transition to intracycle shear thinning (FIG. 32, panel b). The dependence of these nonlinearity parameters during cyclic strain sweeps reveals important differences in how these two networks are disrupted in nonlinear shear. In the case of (X$^1$PAVG)$_{70}$ (SEQ ID NO: 54), the cyclic dependence of T and S are nearly superimposable through $\gamma_{o,max}$=0.25 (FIG. 32, panels a, b), with the development of hysteresis at larger $\gamma_{o,max}$ where the gel experiences irreversible changes in the first harmonic stress response (FIG. 31, panel a). However, hysteresis in $\theta$ clearly occurs even during a cycle to $\gamma_{o,max}$=0.25, indicating that these nonlinear deformations do lead to a plastic-like response of the network, but that the effects are partially reversible (FIG. 32, panel c).

In the case of (X$^1$PAVG)$_{120}$ (SEQ ID NO: 50), S shows slight hysteresis for $\gamma_{o,max}$=0.1 as the gel is initially cycled into the nonlinear regime, and again after network disruption to $\gamma_{o,max}$=1.0 (FIG. 32, panel d). However the behavior of T for this gel remarkably shows negligible hysteresis through all cycles, even out to $\gamma_{o,max}$=1.0 (FIG. 32, panel e), suggesting that the molecular mechanisms responsible for this measure of dissipation are independent of the history of nonlinear structural deformations. This result is surprising, as other measures of increased dissipation, such as the cyclic dependence φ (FIG. 32, panel f), clearly exhibit hysteresis. The dependence of φ highlights that while progressive cycles within the nonlinear regime do not show significant changes in the dependence of either T or S, nonlinear perturbations do have an irreversible effect on the network and lead to enhanced plastic-like responses (i.e., flattening of the elastic Lissajous-Bowditch plots) in all subsequent sweeps. Interestingly, while the behavior of the first harmonic G$_1$' for (X$^1$PAVG)$_{120}$ (SEQ ID NO: 50) is non-superimposable during increasing cyclic sweeps (unlike in the case of (X$^1$PAVG)$_{70}$ (SEQ ID NO: 54)), the cyclic behavior of 4 shows that increasing sweeps do exhibit some overlap with previous cycles in the nonlinear regime, although they follow a different curve than when a particular deformation cycle is being applied for the first time (FIG. 32, panel f). This new curve has a similar slope but is shifted to a lower initial strain amplitude, suggesting that the network has transitioned to a new state with a shorter linear viscoelastic range but otherwise very similar dissipative nature in its nonlinear response.

Overall, analysis of intracycle nonlinearities during cyclic strain sweeps provides crucial evidence of the reversible and irreversible effects of nonlinear oscillatory perturbations on the network viscoelasticity, with polypeptide molecular weight playing an important role in controlling the gel's response. More specifically, the (X$^1$PAVG)$_{70}$ (SEQ ID NO: 54) gel is able to recover its linear and nonlinear responses after the oscillatory deformations return to sufficiently small amplitudes, while the (X$^1$PAVG)$_{120}$ (SEQ ID NO: 50) gel irreversibly transitions to a state characterized by a shorter linear viscoelastic range. Nevertheless, the (X$^1$PAVG)$_{120}$ (SEQ ID NO: 50) gel exhibits important similarities in S, T, and φ in subsequent nonlinear deformations that are not evident in analysis of the behavior of the first harmonic of the stress response alone. Ultimately, large amplitude oscillatory shear rheology reveals that increasing ELP molecular weight improves the peak stress sustained, which corresponds to an increase in the perceptible toughness of these gels. While gels from both short ELPs ((X$^1$PAVG)$_{50}$ (SEQ ID NO: 51) and (X$^2$PAVG)$_{50}$ (SEQ ID NO: 53)) were quite brittle, changing polypeptide sequence length provides a straightforward approach to manipulating the nonlinear mechanics of the gels.

Example 5—Toughening of Thermoresponsive Arrested Networks of Elastin-Like Polypeptides to Engineer Biocompatible Tissue Scaffolds Experimental Methods
Genetic Engineering and Biosynthesis To leverage the arrested phase separation of ELPs to engineer tough biomaterials, the tolerance of this gelation mechanism to telechelic modifications of the polypeptide and chain extension polymerization was explored by the addition of sequences encoding biofunctional (i.e., containing RGDS (SEQ ID NO: 5)) and toughening moieties (i.e., containing cysteine residues for oxidative chain extension). These modifications were introduced onto the N- and C-termini of the ELP ([I$^{0.6}$V$^{0.4}$]PAVG)$_{50}$ (SEQ ID NO: 57) using a one-step ligation strategy (Table 9). Telechelic ELPs with flanking sequences containing cysteine and cell adhesive sites were produced in a 4-component ligation reaction: (1) an adapted pET-28b vector (pETA), with a modified MCS containing a BamHI and NheI site on the 5' end, and a SpeI and HindIII site on the 3' end; (2) an ELP gene flanked by NheI and SpeI sites encoding 50 repeats of the XPAVG pentapeptide, where X consists of isoleucine or valine in a 3:2 ratio (SEQ ID NO: 43); (3) an annealed pair of oligonucleotides for the 5' modifications; and (4) an annealed pair of oligonucleotides for the 3' modifications. Annealed oligonucleotide pairs were designed to have the appropriate overhangs for programmed assembly of the N- and C-terminal modifications.

The following unphosphorylated oligonucleotides were annealed to form the 5' pair:
N_for (SEQ ID NO: 44):
GATCCAAATGTACCTCTGCCGGCGCTGGTGCGGGCCCGGAAGGTCGTG
GTGATTCTA N_rev (SEQ ID NO: 45):
CTAGTAGAATCACCACGACCTTCCGGGCCCGCACCAGCGCCGGCAGAG
GTACATTTG The following unphosphorylated oligonucleotides were annealed to form the 3' pair:
C_for (SEQ ID NO: 46):
CTAGTCGTGGTGATTCTGCCGGCGCTGGTGCGGGCCCGGAAGGTACAA
GCTGTA C_rev (SEQ ID NO: 47):
AGCTTACAGCTTGTACCTTCCGGGCCCGCACCAGCGCCGGCAGAATCA
CCACGA pETA was double-digested with BamHI and HindIII, and the ELP insert was double-digested with NheI and SpeI. Along with the 2 oligonucleotide pairs, these 4 components were ligated in a 1:6:6:6 molar ratio.

Genes in pETA plasmids were transformed into the *E. coli* strain Tuner (DE3). Overnight cultures (5 mL) were used to inoculate expressions in Terrific Broth (1 L) under Kanamycin selection. Expression was induced with 0.5 mM IPTG at an OD$_{600}$=0.9-1.1, and cells were harvested by centrifugation 6 hours post-induction. Cell pellets were suspended in non-denaturing lysis buffer (MENT buffer: 10 mM Tris, 1 mM EDTA, 100 mM NaCl, pH=7.5, 5 mM MgCl$_2$) at a concentration of approximately 30 g wet cell mass (WCM) per 100 mL buffer. Resuspensions were stored at −20° C.

After thawing on ice, lysozyme (100 mg per 100 mL resuspension) was added, then after approximately 1 hour the suspension was sonicated. Cell debris was removed by centrifugation, and DNAse I and RNAse A (2 mg each) were added to the clarified supernatant and incubated for 2-3 hours at 37° C. The turbid lysates were then centrifuged at 37° C., and the pellets were redissolved in MENT buffer at 5° C., typically overnight. The protein solutions were thermally cycled between 5° C. and 37° C. in MENT buffer for two additional cycles. The solutions were then dialyzed against ultrapure water and purified in a final step by passing over anion exchange resin in 6 M urea, 20 mM Tris, pH=8.0, using HiTrap Q pre-packed columns (GE Healthcare) by automated chromatography. Bound contaminants were discarded, and the target proteins were collected in the flow-through step, dialyzed against ultrapure water, and lyophilized.

Genes and Protein Sequences $([I^{0.6}V^{0.4}]PAVG)_{50}$ (SEQ ID NO: 57)

(SEQ ID NO: 48)
MGWGSASGLVGIPAVGVPAVGIPAVGVPAVGIPAVGIPAVGVPAVGIP
AVGVPAVGIPAVGIPAVGVPAVGIPAVGVPAVGIPAVGIPAVGVPAVG
IPAVGVPAVGIPAVGIPAVGVPAVGIPAVGVPAVGIPAVGIPAVGVPA
VGIPAVGVPAVGIPAVGIPAVGVPAVGIPAVGVPAVGIPAVGIPAVGV
PAVGIPAVGVPAVGIPAVGIPAVGVPAVGIPAVGVPAVGIPAVGIPAV
GVPAVGIPAVGVPAVGIPAVGETTS*

$C-([I^{0.6}V^{0.4}]PAVG)_{50}-C$ (SEQ ID NO: 58)

(SEQ ID NO: 49)
MGWGSKCTSAGAGAGPEGRGDSTSGLVGIPAVGVPAVGIPAVGVPAVG
IPAVGIPAVGVPAVGIPAVGVPAVGIPAVGIPAVGVPAVGIPAVGVPA
VGIPAVGIPAVGVPAVGIPAVGVPAVGIPAVGIPAVGVPAVGIPAVGV
PAVGIPAVGIPAVGVPAVGIPAVGVPAVGIPAVGIPAVGVPAVGIPAV
GVPAVGIPAVGIPAVGVPAVGIPAVGVPAVGIPAVGIPAVGVPAVGIP
AVGVPAVGIPAVGIPAVGVPAVGIPAVGVPAVGIPAVGETTSRGDSAG
AGAGPEGTSCKL*

Temperature-concentration (T-c) State Diagram Construction

Hydrogel samples were prepared in ultrapure water. Turbidimetry was performed using a 662 nm 20 mW laser, on samples sealed in quartz with a 1 mm thick Teflon spacer and 2 mm bore. Samples were heated on a water-chilled brass stage at a heating rate of 1° C./min. A TA Instruments Discovery Differential Scanning Calorimeter was used to perform DSC measurements. Samples were swollen in buffer and loaded into hermetically sealed aluminum pans, and measurements were performed over 0-60° C. at 10° C./min for two cycles followed by one cycle at 1° C./min. The heat flow signal for the chain-extended ELP gels was insufficient to determine the onset of the transition at 1° C./min, so $T_t$ are reported from the second heating ramp at 10° C./min. DSC measurements at 1° C./min on unextended ELP gel samples resulted in transition temperatures ($T_t$) that deviated by less than 1° C. from the 10° C./min ramp. Rheological $T_t$ were determined as the point when G'>G" at $\omega=100$ rad/s.

Oscillatory Shear Rheology

Linear oscillatory shear rheology experiments were performed on an Anton-Paar MCR-702 rheometer operating in single-motor configuration in pseudo-strain control (Direct Strain Oscillation) mode. Sample temperature was controlled using a Peltier heating element below the lower geometry and a circulating air environmental enclosure to minimize thermal gradients across the sample. Measurements were performed with a 10 mm diameter, 20 cone-and-plate sample geometry, where the gap was zeroed at 37° C. and corrected for thermal expansion. Moduli were reported following a 30 minute equilibration, at $\omega=100$ rad/s and $\gamma_o=0.01$ unless otherwise noted.

Large amplitude oscillatory shear (LAOS) measurements were performed on the MCR-702 operating in dual-motor (TwinDrive™) mode for true strain-control. Temperature was controlled using a circulating-air chamber. A 10 mm diameter, 20 cone-and-plate sample geometry with sand-blasted surfaces was used. The gap was zeroed at 37° C. and corrected for thermal expansion. Samples were loaded at 0° C. and equilibrated for 20 minutes, then ramped up to 37° C. and equilibrated for 1 hour prior to the start of the experiments. Strain sweeps were performed at $\omega=1$ rad/s, and cyclic sweeps were performed to increasing maximum strain amplitudes with no waiting between cycles. The quality of the strain control was verified by evaluating the harmonic ratios of both the input strain and shear rate waveforms (Supporting Information). A cutoff of 1% in the fifth harmonic ratio ($\gamma_5'/\gamma_1'$) was used to determine the range of valid strain amplitudes for LAOS analysis. Waveforms were analyzed with MITlaos v2.2 beta.

Small Angle Scattering

Small angle X-ray scattering (SAXS) measurements were performed at the 12-ID-B beamline at the Advanced Photon Source at Argonne National Lab, with an X-ray wavelength of 13.998 Å and acquisition time of 0.02 s. ID reductions were performed using beamline software and corrected for empty cell and solvent backgrounds. Samples were swollen in $H_2O$ or 100 mM sodium phosphate, pH=7.6. Measurements were performed on samples that had been equilibrated for at least 2 hours on ice, then transferred to a pre-warmed brass sample holder at 37° C. Following the loading procedure, multiple measurements were taken at 10 minute intervals, and no changes in nanostructure could be resolved. Fitting of the chain-extended scattering data was performed using software written in IGOR Pro made available by NIST.

Tensile Testing

Samples were directly shaped into dogbones using a split Teflon mold 1 mm thick with a 3 mm gauge length machined with a water jet. The split mold was coated in a thin layer of mineral oil, was held together with a rigid aluminum centering plate, and chilled on ice. Liquefied samples were loaded and then clamped between two Teflon sheets supported on brass plates. Samples were chilled on ice for at least 30 minutes, and then transferred to a forced air incubator at 37° C. and equilibrated for at least 8 hours. Tensile measurements were performed at room temperature (22±1° C.) on a Zwick Z2.5 linear mechanical tester with a 20 N load cell, at an engineering strain rate of 0.033 $s^{-1}$.

Erosion Tests

Samples were loaded into plastic molds with a laser-engraved cylindrical well 5 mm in diameter and 1 mm deep. Hydrogels were prepared at 20 wt % in ultrapure water and completely dissolved on ice. Approximately 30 µL of gel was scooped into a well, incubated on an aluminum plate held at 0° C. to liquefy, and then warmed to room temperature to solidify. Samples were transferred to scintillation vials, 10 mL of water pre-warmed to 37° C. was added, and the vials sealed with Parafilm to prevent evaporation. Vials were transferred to a 37° C. forced air incubator for the duration of the experiment. Gel erosion was measured gravimetrically to the nearest 10 µg, with measurements performed in triplicate (i.e., dry off the mold, weigh, return to water, and then repeat twice more) for each sample replicate (N=4) at each time point.

Release Tests

Hydrogels were prepared at 20 wt. % in solutions of ultrapure water containing FITC-dextran particles (Sigma) at 1 mg/mL. Samples were loaded into plastic molds as described in the erosion experiment, and 4 mL of pre-warmed water was added to each vial at the start of the experiment. Measurements of released dextran molecules were performed by extracting 100 μL at each timepoint, buffering the samples to 50 mM sodium phosphate, pH=7.6, and measuring the fluorescence at excitation/emission wavelengths of 470/530 nm. Measurements were performed on three independent samples.

2D Biocompatibility Testing with Human Mesenchymal Stem Cells (hMSCs)

Human bone marrow-derived mesenchymal stem cells (hMSCs) were purchased from Lonza (PT-2501). Cells were thawed and expanded according to recommendations from Lonza (6,000 cells/cm$^2$; 0.2 mL media/cm$^2$). MSC media (MSCGM BulletKit™ media; PT-3238 and PT-4105, Lonza) was used for culturing MSCs in an undifferentiated state prior to seeding. Subculturing was performed according to Lonza protocols with media being replaced every 3-4 days. Cells for seeding were used prior to the 5$^{th}$ passage.

Lyophilized ELP was hydrated at 20 wt % in sterile Dulbecco's Phosphate-Buffered Saline (PBS; Cat. No: 14190, Life Technologies) at 4° C. until the ELP solid was completely dissolved, fully hydrated, and transparent. Hydrated ELP samples in sterile Eppendorf tubes (VWR) were then transferred into an ice bath within a cell culture hood for seeding or encapsulation.

Untreated glass slides (48300-025, VWR) were cut into ~12.5×12.5 mm squares and a 5 mm diameter circle was etched on the surface of the glass slide (depth ~100 μm) with a laser cutter (Universal Laser System, VLS2.30) to roughen the surface and improve hydrogel adhesion. The glass was washed with ethanol and exposed to cell culture UV for 20 minutes. Etched glass slides were placed on a metal substrate on the surface of the ice bath. Chilled 20 wt % ELP hydrogel was added to the center of the etched glass slide and flattened by adding the weight of another cut glass slide (~12.5×12.5 mm) on top of the ELP hydrogel. The system was allowed 1 minute to flatten. The sample was then removed from the ice bath and warmed to room temperature, at which point the glass slides were pulled apart, leaving the ELP on the etched glass slide. The ELP-coated etched glass slide was then placed in a 12 well plate containing PBS with 1% penicillin/streptomycin (Life Technologies, Cat. No: 15140-122). All samples were incubated overnight (37° C., 5% CO$_2$). PBS was then removed and the samples were incubated for 30 minutes in the respective media prior to seeding hMSCs. hMSC cultures were trypsinized with 1% trypsin (0.5% EDTA, 10×, 15400-054, Life Technologies). Cell pellets were suspended in MSC media at a concentration of 1×10$^6$ cells/mL. 20,000 cells/well were added to 12 well plate wells containing either ELP-coated etched glass slides or similarly sized cut glass slides. Samples were incubated for 24 hours with MSC media. After 1 day, the MSC media was replaced with either standard media (10% fetal bovine serum (FBS) (10437-028, Life Technologies) in DMEM media (Life Technologies), 1% penicillin streptomycin (15140-122, Life Technologies)) or osteoinductive media (PT-3924 & PT-4120, Lonza). Additional details on reagents and cells are provided in the Supporting Information.

Bovine Chondrocyte Encapsulation

Bovine chondrocytes were isolated from bovine joints (Research 87, Inc.). Excess tissue was removed from the femur to expose the upper neck of the knee joint. The ball joint was sawed off and fixed into a holder. The joint was cleaned with 70% ethanol and placed into a cell culture hood. The femoral condyle was exposed by removing the outer fascia and cutting the medial and lateral collateral ligaments. Additionally, the anterior and posterior cruciate ligaments were cut and the rest of the tissue that connects the tibia and femur was removed. Using sterile aluminum foil to collect the tissue, cartilage was removed from the femoral condyle at shallow angles to prevent removing any bone or blood vessels. The cartilage shavings were placed in a petri dish filled with sterile PBS.

Shavings were then transferred into a beaker containing pronase (0.1 g solid pronase per 50 mL media) in isolation medium ((5% FBS-add later), 47.5 mL DMEM (low glucose+Sodium pyruvate), 0.5 mL HEPES, 0.5 mL NEAA, 0.5 mL Penstrep, 200 uL L-proline; sterile filtered). The cartilage was digested for 1 h in a 37° C. incubator. The pronase solution was removed and the cartilage was rinsed with warm sterile PBS and pipetted thoroughly to mix the cartilage. The PBS was aspirated and the cartilage washed again. Collagenase solution was added to the cartilage (0.0125 g collagenase P to isolation medium). The cartilage was then digested stirring overnight at 37° C. The digested solution was filtered into Falcon tubes using a 70 m cell strainer followed by a 40 μm cell strainer. The suspension was centrifuged for 8 min at 1900×g. Media was aspirated and the pellet suspended in sterile PBS. The pellet was suspended and centrifuged for 8 min at 1900×g twice. The cells were suspend in culture media (86 or 95 mL Hi-glucose DMEM containing NaPyr, 1 mL NEAA, 1 mL HEPES, 0.4 mL L-proline, 0.1 mL Ascorbate, 1 mL P/S/A, 1 mL ITS (insulin/transferrin/selenium) if only using a little FBS, otherwise 10 mL FBS (Grodzinsky lab usually uses less, 2.5 mL depending on lot)) that has been warmed to 37° C. in a water bath. Samples were cryopreserved at a concentration of 1.4×10$^7$ cells/mL. Cells were not cultured prior to encapsulation. 28 wt. % ELP hydrogels were fully hydrated in sterile Eppendorf tubes (VWR) with sterile PBS at 4° C. After hydration, the tube was transferred into an ice bath within a cell culture hood. Bovine chondrocytes were rapidly thawed from cryopreserved ampules (14 million cells/mL) in a 37° C. water bath. The cells were pipetted into 4 mL warm chondrocyte media (Hi-glucose DMEM (11965-092, Life Technologies), 1% sodium pyruvate (100 mM, 11360-070, Life Technologies), 1% non-essential amino acids (100×, 11140-050, Life Technologies), 1% HEPES buffer (1 M, pH 7.2, sterile filtered), 1% penicillin/streptomycin, at the time of seeding add proline (400 μM in DMEM, Sigma-Aldrich), ascorbate (20 μg/mL in water, Sigma-Aldrich), 10% FBS). 20 μL of the cell suspension was used for cell counting by trypan blue staining. The cells were centrifuged (200×g, 4° C., 5 minutes) and suspended in chondrocyte media. The cell suspension was added to the ELP hydrogel at a concentration to yield a cell concentration of 1×10$^7$ chondrocytes/mL ELP hydrogel and an ELP solid concentration of 20 wt %. The chondrocyte ELP gel mixture was placed on a glass slide on a chilled metal substrate to liquefy and flatten. Another glass slide was placed on top of the ELP hydrogel with 150 μm spacers (No. 1.5 coverslip, VWR) separating the glass slides to generate a uniform thickness hydrogel. After the hydrogel was flattened, the hydrogel was placed in the incubator for 5 minutes to solidify. It was then removed and cut into ~3×3 mm squares with a surgical blade and placed in 12 well plate wells containing chondrocyte media. Media was replaced after 24 hours and then replaced every 3-4 days. Chondrocytes that were not mixed into the gels were seeded into 6 well plate wells at 100,000 cells/well and cultured overnight in chondrocyte media to characterize the cell population prior to encapsulation.

MSC Immunostaining

Media was aspirated from the sample wells and samples were washed with warm PBS. Samples were then fixed with 4% paraformaldehyde for 10 minutes at room temperature. Two PBS rinses were performed for 5 minutes each followed by storage in PBS at 4° C. until further processing is completed. When immunostaining was performed, samples were permeabilized with 0.1% Triton (X100, Sigma-Aldrich) in PBS for 2 minutes. Samples were washed 4 times with PBS for 5 minutes each. Samples were blocked with 1% bovine serum albumin in PBS for 30 minutes. A primary antibody diluted 1:100 in 1% BSA solution was incubated on the samples for 1 hour. Three PBS washes were then performed for 5 minutes each. Secondary antibodies diluted 1:100 in 1% BSA were then incubated on the samples for 30 minutes, followed by 3 PBS washes for 5 minutes each.

Samples were blocked with 1% BSA prior to additional primary and secondary staining. After all antibodies are stained, samples were counterstained with DAPI (1 μg/mL PBS, 62248, Life Technologies). Samples were incubated for 5 minutes and rinsed 3 times with PBS. A final washing in distilled water was performed and samples were mounted onto glass slides using Permount (Sigma) and the coverslip sealed with nail polish (72180, Electron Microscopy Sciences). Samples were stored at −20° C. until imaged.

Confocal Microscopy 3D encapsulated chondrocytes in ELP gels were stained as described above. Samples were then imaged using an Olympus FV1200 Laser Scanning Confocal Microscope. Stacking and z-projections were performed using ImageJ.

Hematoxylin and Eosin Staining

6-μm thick cryomicrotomed chondrocyte encapsulated ELP gels were stained with hematoxylin and eosin according to methods known in the art.

Results and Discussion

Toughening of Gel-Forming ELPs by Oxidative Chain Extension

TABLE 9

ELP sequences.

| Notation | Amino Acid Sequence | MW (kDa) |
|---|---|---|
| ([$I^{0.6}V^{0.4}$]PAVG)$_{50}$ (SEQ ID NO: 57) | MGWGSASGLVG [(IPAVGVPAVG)$_2$ (IPAVG)]$_{10}$ ETTS (SEQ ID NO: 72) | 23.0 |
| C-([$I^{0.6}V^{0.4}$]PAVG)$_{50}$-C (SEQ ID NO: 58) | MGWGSKCTSAGAGAG PEGRGDSTSGLVG [(IPAVGVPAVG)$_2$ (IPAVG)]$_{10}$ ETTSR GDSAGAGAGPEGTSCKL (SEQ ID NO: 73) | 26.2 |

Figure 34:
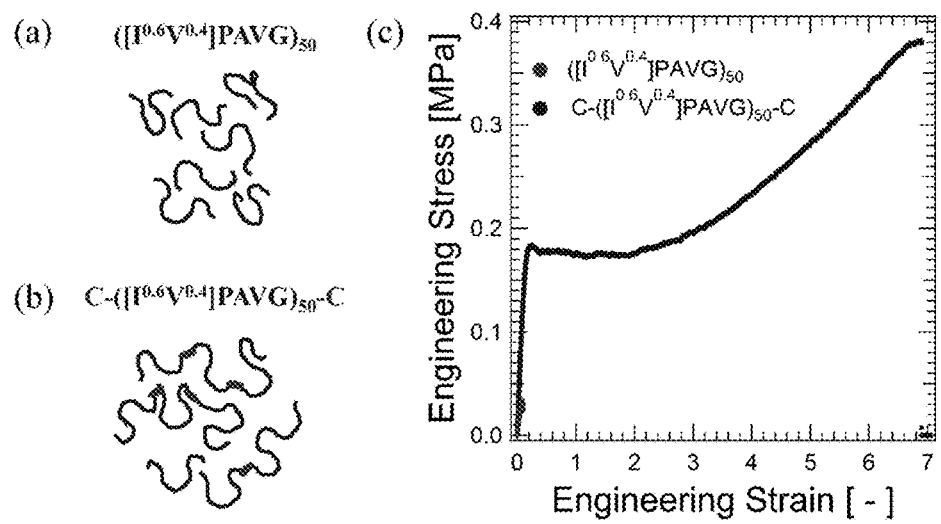
FIG. 34 has three panels (a-c) depicting a schematic of solutions of the (a) unextended ELP and (b) oxidatively chain-extended ELP. (c) Uniaxial tension on gels prepared at 20 wt. % in water. Samples were equilibrated at 37° C. prior to experimentation at room temperature at 0.1 mm/s (engineering strain rate of 0.033 s$^{-1}$).
Figure 35:
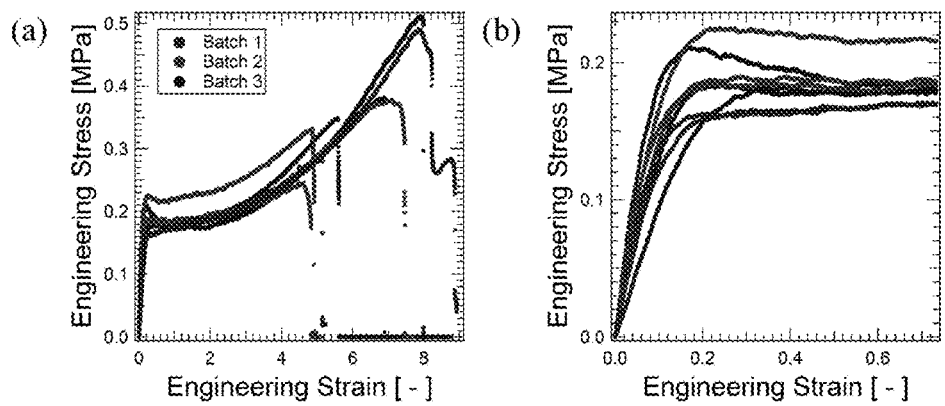
FIG. 35 has two panels (a and b) depicting replicates of tensile testing performed in separate batches of 20% C-([I$^{0.6}$V$^{0.4}$]PAVG)-C (SEQ ID NO: 56) gels prepared on 3 separate occasions: (a) extension to failure, and (b) highlight of the low extension regime.

Gelation of the modified ELP sequence, denoted C-([$I^{0.6}V^{0.4}$]PAVG)$_{50}$-C (SEQ ID NO: 58), was found to proceed in a similar manner to the unmodified polypeptide: at sufficiently high concentrations, stiff gels were formed upon heating. While the gels without chain extension were brittle, the gels with chain extension were observed to be extensible and exhibit rapid recovery to their molded shapes. These improvements in gel toughness due to chain-extension are clear in tension, resulting in significant improvements in gel extensibility (FIG. 34). While gels made from ([$I^{0.6}V^{0.4}$]PAVG)$_{50}$ (SEQ ID NO: 57) are too brittle to be extended, C-([$I^{0.6}V^{0.4}$]PAVG)$_{50}$-C (SEQ ID NO: 58) gels equilibrated at 37° C. for 8 hours can be extended to engineering strains greater than 620%±140%. The Young's modulus estimated from the initial slope is 1.6±0.4 MPa (FIG. 35). The linear range extends to less than 20% engineering strain, which is followed by a necking regime, and finally strain-stiffening prior to failure.

Figure 36:
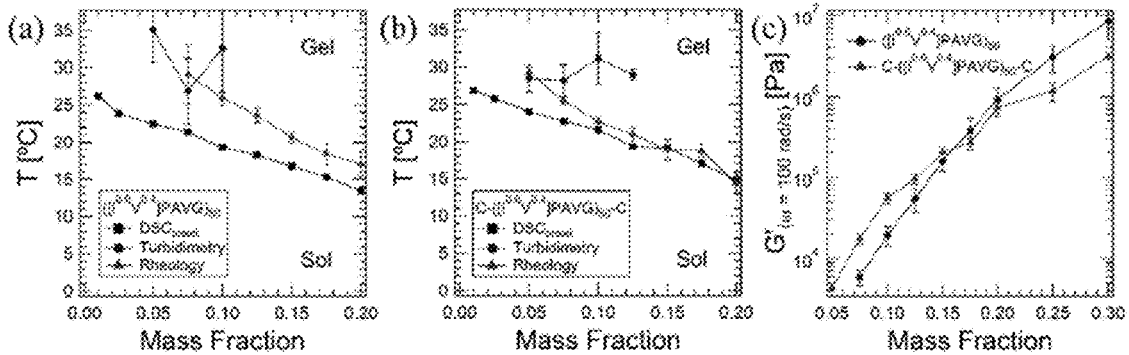
FIG. 36 has three panels (a-c) depicting T-c state diagrams for (a) ([I$^{0.6}$V$^{0.4}$]PAVG)$_{50}$ (SEQ ID NO: 57) and (b) chain-extended C-([I$^{0.6}$V$^{0.4}$]PAVG)$_{50}$-C (SEQ ID NO: 58). (c) Comparison of the high frequency elastic modulus (G' (w=100 rad/s)) for gels under various conditions to examine the effect of telechelic modifications on the linear viscoelastic properties. Measurements were taken at T=37° C. after 30 minute equilibration following a 1° C./min heating ramp, at $\gamma_o$=0.01.

To quantify the gelation conditions for both sequences, T-c state diagrams were constructed from a combination of DSC, turbidimetry, and rheological measurements, revealing that the chain-extended ELP forms gels as low as 5 wt %, roughly similar to the unmodified sequences (FIG. 36, panels a,b). This gelation concentration, $c_{min}$, is half of that previously reported for a related but less hydrophobic sequence ([$I^{0.2}V^{0.8}$]PAVG)$_{50}$ (SEQ ID NO: 57) where $c_{min}$ was 15 wt %. The shear moduli of these gels at ω=100 rad/s was found to range from 5 kPa at $c_{min}$ to over 1 MPa at 30 wt %, with no substantial difference in the high frequency mechanics observed at high temperature due to chain-extension (FIG. 36, panel c). Solutions of ([$I^{0.6}V^{0.4}$]PAVG)$_{50}$ (SEQ ID NO: 57) at 30 wt. % transition from thin liquids to 7 MPa gels by from 0° C. to 37° C., while chain-extension results in viscoelastic liquids (presumably due to chain entanglement at low temperature) that become 3 MPa gels over the temperature range.

Figure 37:
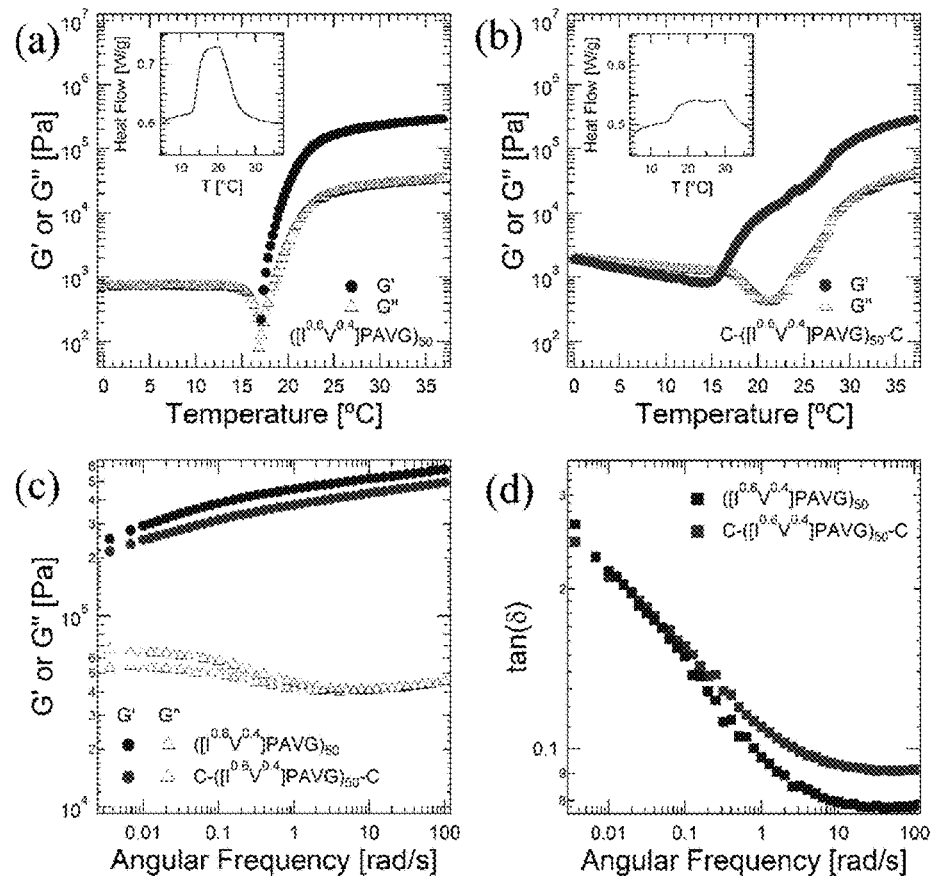
FIG. 37 has four panels (a-d) depicting the effect of chain extension on the linear viscoelasticity of 20 wt % gels. Temperature ramp experiment ($\omega$=100 rad/s, $\gamma_o$=0.01, dT/dt=1° C./min) on (a) ([I$^{0.6}$V$^{0.4}$]PAVG)$_{50}$ (SEQ ID NO: 57) and (b) C-([I$^{0.6}$V$^{0.4}$]PAVG)$_{50}$-C (SEQ ID NO: 58) gels. Insets show DSC heating ramps at 10° C./min. Comparison of the frequency dependence of (c) the viscoelastic moduli and (d) tan($\delta$) at 37° C.

Despite these similarities, the temperature- and frequency-dependence of the viscoelastic moduli suggest that network formation in chain-extended ELPs is modified as compared to the unextended sequences (FIG. 37). Solutions of C-([$I^{0.6}V^{0.4}$]PAVG)$_{50}$-C (SEQ ID NO: 58) are more viscous than those of ([$I^{0.6}V^{0.4}$]PAVG)$_{50}$ (SEQ ID NO: 57) at low temperatures, exhibiting a crossover at high frequency (near ω=100 rad/s) for concentrations around 20 wt %. For ([$I^{0.6}V^{0.4}$]PAVG)$_{50}$ (SEQ ID NO: 57) gels, a narrow stiffening transition is observed upon heating above the DSC-determined $T_t$, with a slower evolution of modulus nearer to 37° C. Upon heating, C-([$I^{0.6}V^{0.4}$]PAVG)$_{50}$-C (SEQ ID NO: 58) exhibits a significantly broader transition, characterized by a 5° C. difference between where G' becomes greater than G" and where G" begins to increase (FIG. 37, panel b). This broad, apparent two-step transition spanning nearly 10° C. is potentially related to the broad molecular weight distribution in the population of chain-extended species in C-([$I^{0.6}V^{0.4}$]PAVG)$_{50}$-C (SEQ ID NO: 58) gels, as ELPs are generally known to exhibit a molecular weight dependence of the apparent $T_t$. This result is consistent with the broader transition observed by DSC (FIG. 37, panel b insets). Frequency sweeps at the 37° C. reveal the distribution of relaxation times in the chain-extended ELP gels is very similar to the unextended ELP gels (FIG. 37, panels c, d). This result is reasonable because the longest experimentally-accessible relaxation time is governed by the kinetic arrest of the network, obscuring the effect of entanglements on the linear viscoelastic properties of the gels.

Effect of Chain-Extension on Gel Nanostructure

Figure 38:
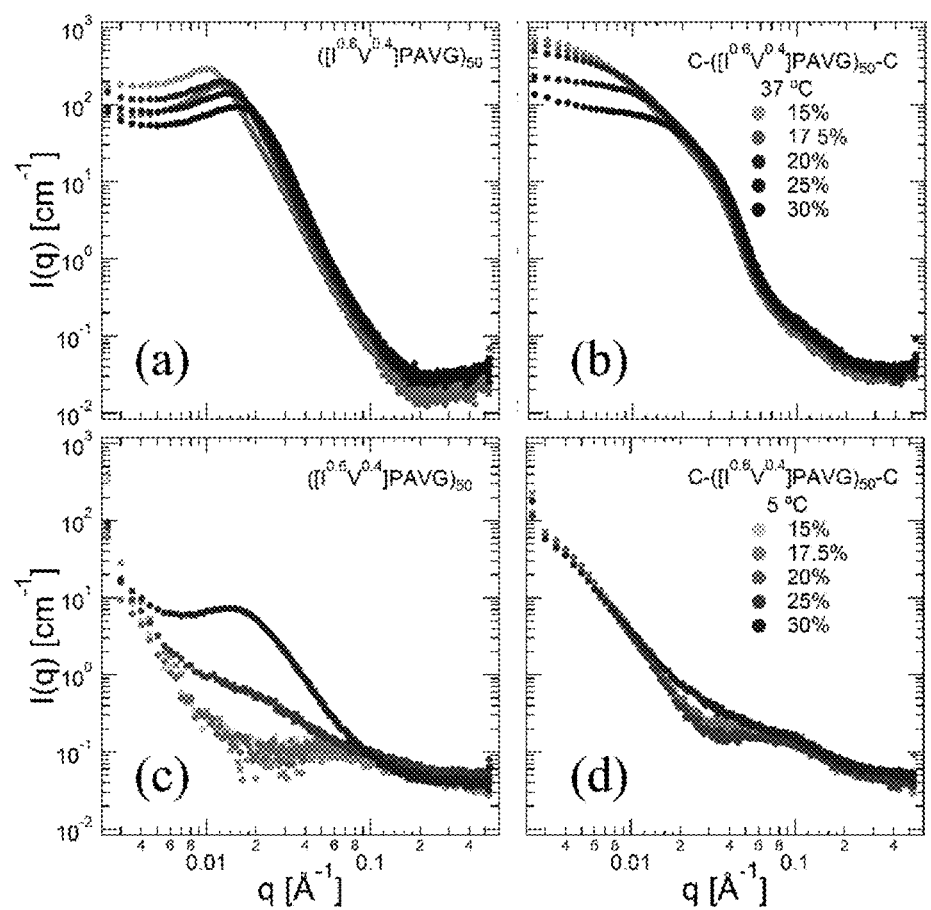
FIG. 38 has four panels (a-d) depicting SAXS intensity distributions for (a,c) ([I$^{0.6}$V$^{0.4}$]PAVG)$_{50}$ (SEQ ID NO: 57) and (b,d)C-([I$^{0.6}$V$^{0.4}$]PAVG)$_{50}$-C (SEQ ID NO: 58) at 5° C. and 37° C., respectively.

SAXS measurements reveal that arrested phase separation in gels prepared from chain-extended ELPs leads to a distinct nanostructure compared with gels formed from the unextended polypeptides alone, however gelation of both polypeptides resulted in bicontinuous networks. Gels from concentrated solutions of ($[I^{0.6}V^{0.4}]PAVG)_{50}$ (SEQ ID NO: 57) at 37° C. exhibit scattering characteristic of a random two-phase system with sharp domain interfaces, evidenced by a broad peak at low wavevectors followed by power law decay with an exponent of −4 (FIG. 38, panel a). The interdomain correlation length scale decreases with increasing gel concentration, as indicated by the peak shifting to lower wavevectors, without perturbing the Porod law scattering at high wavevectors. The qualitative picture is substantially different for gels from concentrated solutions of C-($[I^{0.6}V^{0.4}]PAVG)_{50}$-C (SEQ ID NO: 58), which exhibit no peak over the observed q-range, no clear Porod regime, and exhibit a shoulder at high wavevectors (i.e., over the range $0.08 \text{ Å}^{-1} < q < 0.2 \text{ Å}^{-1}$) The concentration dependence of the scattered intensity distributions for the ($[I^{0.6}V^{0.4}]PAVG)_{50}$ (SEQ ID NO: 57) gels is consistent with a phase separation process that arrests when a critical local polypeptide concentration is reached (FIG. 38, panel b). To estimate this concentration, the volume fraction of the dense polypeptide phase can be estimated from the invariant, Q, based on evidence of sharp domain interfaces in the Porod regime, according to:

$$Q = (\rho_1 - \rho_2)^2 \phi_1 (1 - \phi_1) \quad (5.1)$$

where $\rho_i$ is the X-ray scattering length density in phase i, and $\phi_1$ is the volume fraction of the dense phase. Assuming that the ELP accumulates entirely in the dense phase, the scattering length density in each phase can be reasonably approximated by:

$$\rho_1 = \rho_{ELP} \frac{\phi_{ELP,gel}}{\phi_1} + \rho_{H2O}\left(1 - \frac{\phi_{ELP,gel}}{\phi_1}\right) \quad (5.2)$$

$$\rho_2 = \rho_{H2O} \quad (5.3)$$

where $\phi_{ELP,gel}$ is the overall gel concentration and $\rho_{H2O}$ and $\rho_{ELP}$ are the X-ray scattering length densities of the pure components. This calculation reveals a nearly linear dependence of $\phi_1$ on the overall mass fraction of the gel. The origin of this can be seen by calculating the concentration of polypeptide in the dense phase, $\phi_{ELP,1} = \phi_{ELP}/\phi_1$, which is nearly constant with an average value of 0.45. This result suggests that polypeptide densification during phase separation arrests when a critical concentration is reached. This concentration is likely related to protein sequence and thermal processing history, but that it remains constant is consistent with phase separation arresting due to slowing of chain reorganization that is necessary for further coalescence of the nanoscale domains above a critical concentration.

Figure 39:
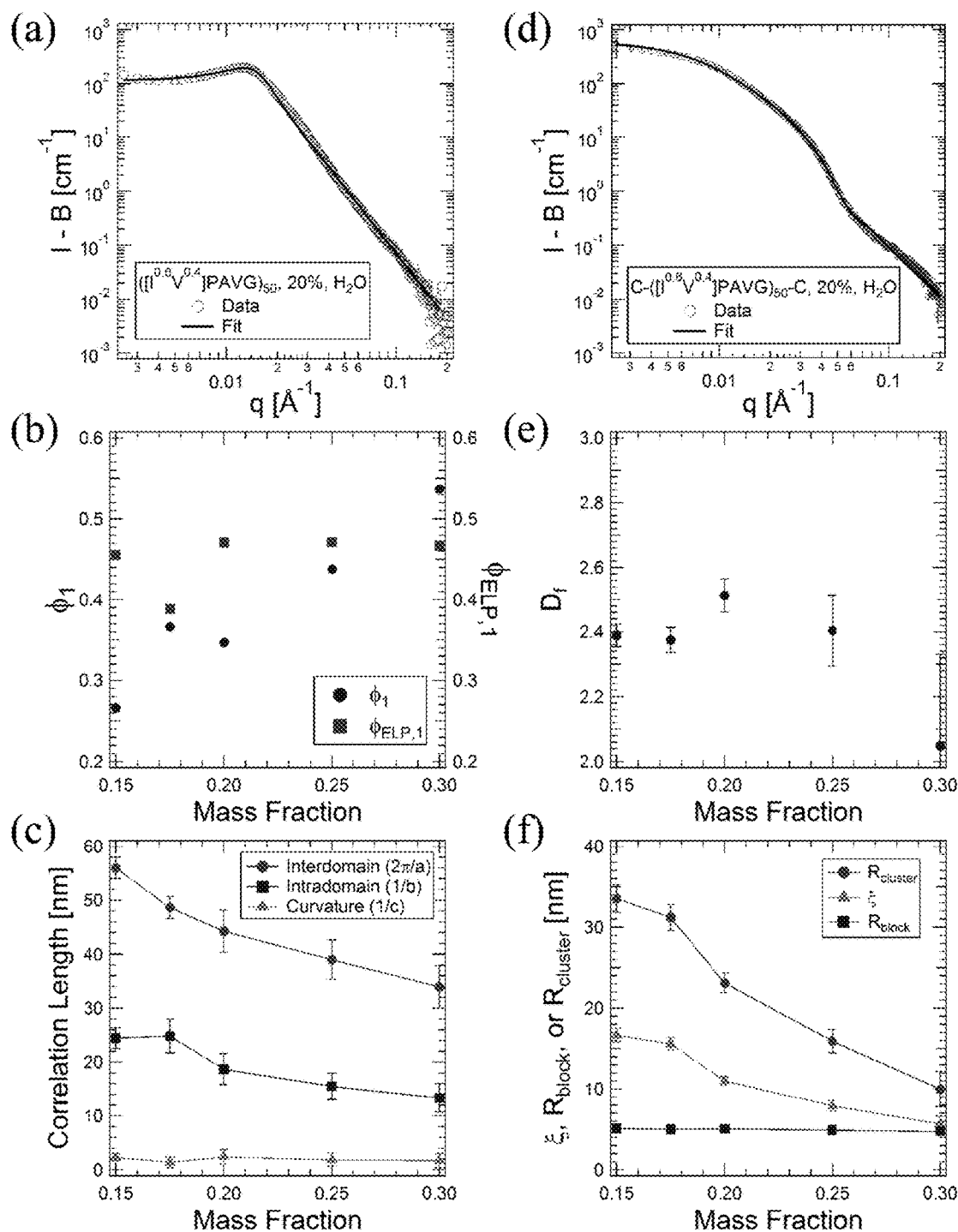
FIG. 39 has six panels (a-f) depicting modeling of the SAXS intensity distributions for (a-c) ([I$^{0.6}$V$^{0.4}$]PAVG)$_{50}$ (SEQ ID NO: 57) and (d-f)C-([I$^{0.6}$V$^{0.4}$]PAVG)$_{50}$-C (SEQ ID NO: 58). (a) Example of Vonk-corrected data for 20 wt % ([I$^{0.6}$V$^{0.4}$]PAVG)$_{50}$ (SEQ ID NO: 57) gels fit to the Clipped Random Wave model. (b) Porod analysis of the ELP concentration in the dense phase. (c) Correlation length scales fit to the CRW model. (d) Example of Vonk-corrected data for 20 wt % C-([I$^{0.6}$V$^{0.4}$]PAVG)$_{50}$-C (SEQ ID NO: 58) gels fit to the model for fractal aggregation of polydisperse core shell spheres. (e) Fractal dimension of chain-extended gels from the model fits. (f) Gel correlation length scales from the model fits.
Figure 40A:
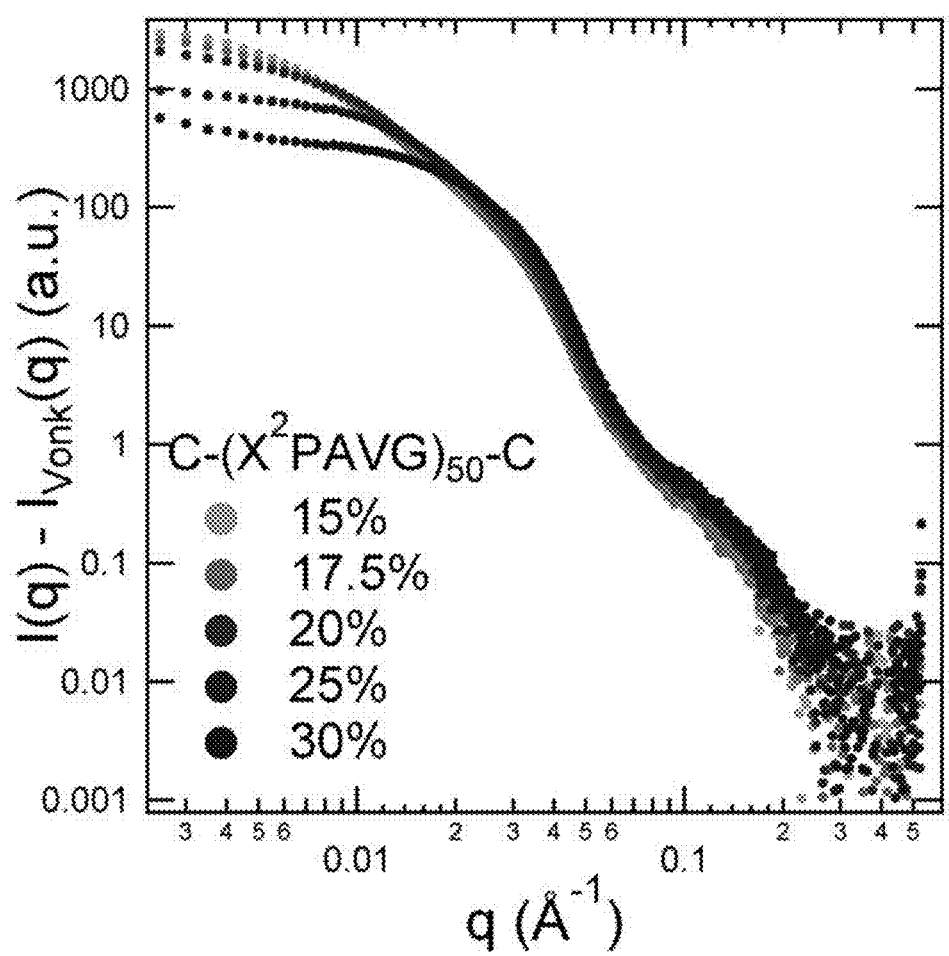
FIG. 40A depicts SAXS intensity distributions for C—(X$^2$PAVG)$_{50}$-C (SEQ ID NO: 59) at 37° C. corrected for the scattering due to background thermal density fluctuations at high wavevectors.
Figure 40B:
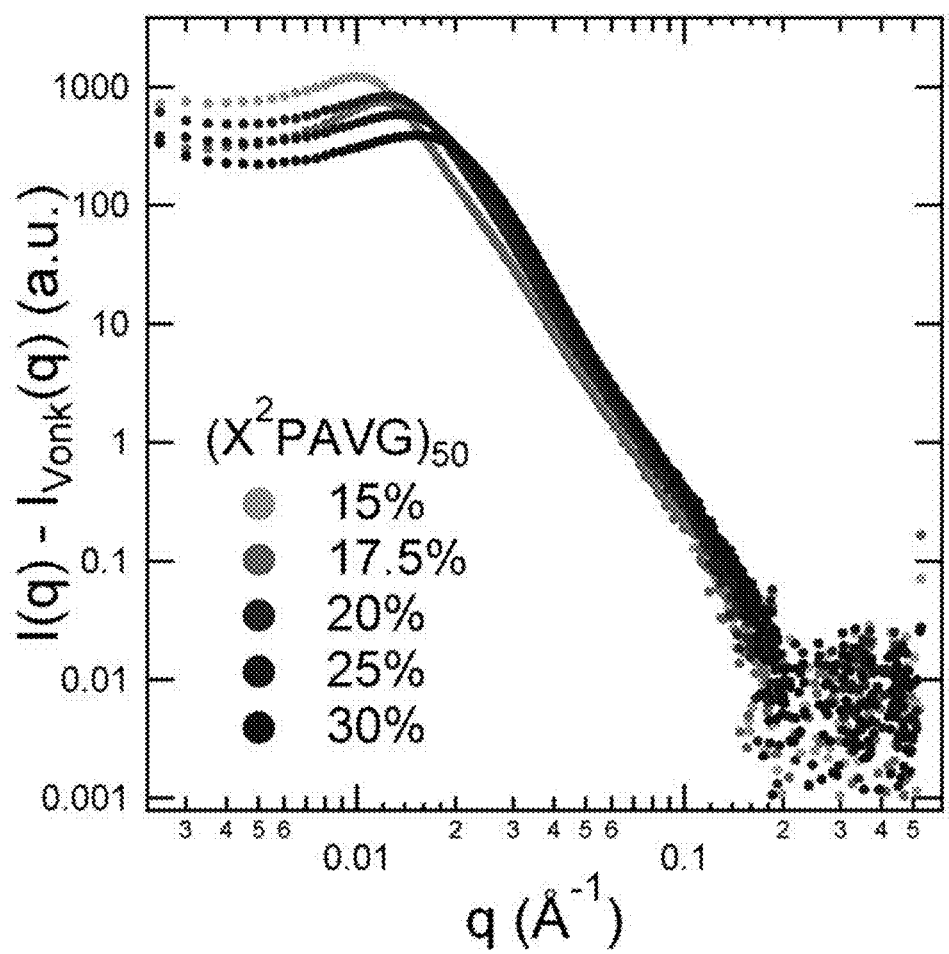
FIG. 40B depicts SAXS intensity distributions for (X$^2$PAVG)$_{50}$ (SEQ ID NO: 53) at 37° C. corrected for the scattering due to background thermal density fluctuations at high wavevectors.

For unextended ELP gels from ($[I^{0.6}V^{0.4}]PAVG)_{50}$ (SEQ ID NO: 57) at 37° C., the data were fit to the Clipped Random Wave (CRW) model, which offers a simplified description of random inhomogeneous two-phase media. This model has been successfully applied to investigate the arrested phase separation of these ELPs, in addition to bicontinuous microemulsions and phase separating polymer blends (FIG. 39, panels a,c, Table 10). The CRW model is parameterized by three length scales that describe interdomain and intradomain correlations as well as interfacial curvature for random two-phase media with arbitrary composition. The power law slope, n, is fit directly to the experimental data, while the curvatures are computed from the parameters a, b, and c from the CRW model fits (Table 11). Prior to fitting, the absolute intensity distributions were corrected to account for thermal density fluctuations in random two-phase inhomogeneous systems, which manifest as a slight positive deviation in the background-corrected scattering curves above ca. $q \approx 0.3 \text{ Å}^{-1}$ (FIG. 38, panel a). An empirical procedure for fitting an even power-law to the high q region according to the Vonk method accounts for this scattering well, leading to the expected pure monotonic decay in all scattered intensity distributions down to the level of experimental noise (FIG. 40). This scattering feature is not present in the scattered intensity for solutions at 5° C., consistent with the origin of this positive deviation being in phase separated systems as opposed to polymer solutions.

Modeling of the scattering from ($[I^{0.6}V^{0.4}]PAVG)_{50}$ (SEQ ID NO: 57) gels indicates that their structure is consistent with bicontinuous, nanoscale networks with porosity that depends on gel concentration. Increasing overall gel concentration results in a more compact network, as indicated by a decrease in the interdomain correlation length (FIG. 39, panel c), consistent with the increased volume fraction of the polypeptide-rich phase from the Porod analysis. While the intradomain correlation length also decreases, the ratio $2\pi b/a$ is roughly constant, suggesting that the relative order quality of the domains does not change with concentration. However, the interfacial curvature remains essentially constant with concentration, and in all cases the Gaussian curvature, $\langle K \rangle$, is negative, consistent with a bicontinuous structure. The total interfacial area, related to S/V, is positively correlated with concentration across the studied range, indicating that high curvature is maintained even when arrest occurs at higher dense-phase volume fractions.

TABLE 10

Curvature, interface, and order quality parameters for ($[I^{0.6}V^{0.4}]PAVG)_{50}$ (SEQ ID NO: 57) gels.

| Mass Fraction | n | $\langle H \rangle$ [×10$^{-2}$ nm$^{-1}$] | $\langle K \rangle$ [×10$^{-3}$ nm$^{-2}$] | $\langle H^2 \rangle$ [×10$^{-2}$ nm$^{-2}$] | S/V [×10$^{-2}$ nm$^{-1}$] | $\frac{2\pi b}{a}$ |
|---|---|---|---|---|---|---|
| 0.15 | −3.81 ± 0.08 | 3.80 | −3.05 | 3.36 | 5.22 | 0.437 |
| 0.175 | −3.85 ± 0.08 | 2.53 | −6.59 | 7.95 | 7.33 | 0.511 |
| 0.20 | −3.91 ± 0.05 | 2.78 | −5.66 | 3.10 | 6.81 | 0.423 |
| 0.25 | −3.89 ± 0.05 | 1.31 | −9.41 | 5.19 | 8.73 | 0.397 |
| 0.30 | −3.93 ± 0.04 | −0.987 | −12.2 | 6.16 | 9.93 | 0.394 |

TABLE 11

Fit parameters for ($[I^{0.6}V^{0.4}]PAVG)_{50}$ (SEQ ID NO: 57) to the CRW model. Note that the volume fraction of the dense phase, $\varphi_1$, is computed from the Porod invariant.

| Conc. [wt %] | a [×10$^{-2}$ nm$^{-1}$] | b [×10$^{-3}$ nm$^{-1}$] | c [×10$^{-2}$ nm$^{-1}$] | $\varphi_1$ |
|---|---|---|---|---|
| 15 | 1.12 ± 0.004 | 4.09 ± 0.033 | 4.36 ± 0.14 | 0.27 |
| 17.5 | 1.29 ± 0.005 | 4.02 ± 0.051 | 7.12 ± 0.49 | 0.37 |
| 20 | 1.42 ± 0.012 | 5.34 ± 0.082 | 4.13 ± 0.23 | 0.35 |

TABLE 11-continued

Fit parameters for ($[I^{0.6}V^{0.4}]PAVG)_{50}$ (SEQ ID NO: 57) to the CRW model. Note that the volume fraction of the dense phase, $\varphi_1$, is computed from the Porod invariant.

| Conc. [wt %] | a [×10$^{-2}$ nm$^{-1}$] | b [×10$^{-3}$ nm$^{-1}$] | c [×10$^{-2}$ nm$^{-1}$] | $\varphi_1$ |
|---|---|---|---|---|
| 25 | 1.61 ± 0.015 | 6.46 ± 0.105 | 5.36 ± 0.34 | 0.44 |
| 30 | 1.85 ± 0.022 | 7.48 ± 0.149 | 5.81 ± 0.43 | 0.54 |

For the chain-extended gels, the CRW model fails to describe the scattered intensity distributions, but analysis of the general scattering features reveals evidence of fractal aggregation. Instead of a broad peak, the intermediate-q region (q~0.01-0.04 Å$^{-1}$) in chain-extended gels appears to exhibit a decay characterized by an exponent between −2 and −3, which suggests scattering from a mass fractal. On the length scales suggested by this q-range, this type of behavior might be expected from the fractal aggregation of nanoscale building blocks, where the form factor of these building blocks is potentially evident at high q. The scattered intensity distributions for the chain-extended gels across all concentrations are nearly superimposable above q>0.02 Å$^{-1}$, suggesting that the structure of these building blocks is very similar under the conditions investigated.

Given this combination of structural features, the scattered intensity distributions for C-($[I^{0.6}V^{0.4}]PAVG)_{50}$-C (SEQ ID NO: 58) gels were fit to a fractal model with a form factor for nanoscale building blocks of polydisperse core-shell spheres. This structure is envisioned as a dense core of ELP surrounded by a lower density layer. This model consists of parameters describing the volume fraction, $\phi$, sphere core radius, $R_{block}$, sphere core polydispersity, $\sigma_{block}$, shell thickness, $T_{shell}$, fractal dimension, $D_f$, and network correlation length, $\xi$. This model was found to describe the scattering well across all concentrations (FIG. 39, panels d-e). The model predictions support the observation that changing gel concentration does not strongly perturb the structure of the building blocks of the network and instead influences the effective density of these blocks as they form a percolating network. Crucially, the model predicts that the fractal dimension of the gel does not exhibit significant differences for the samples investigated, suggesting that the self-similar arrangement of building blocks is not significantly changed as a function of concentration.

This modeling provides an important description of the structure of these chain-extended gels and how it differs from the unextended sequences. Specifically, chain-extension changes both the form of the gel building blocks as well as their arrangement into a fractal percolating network, contrasting the two-phase network with sharp interfaces that forms from the assembly of the unextended sequences. Neither the form factor of the building blocks nor the fractal dimension of the aggregating network is perturbed significantly by the overall gel concentration (FIG. 38). Instead, the average cluster size in the arrested state is larger at lower gel concentrations, indicative of a more porous gel.

Figure 41:
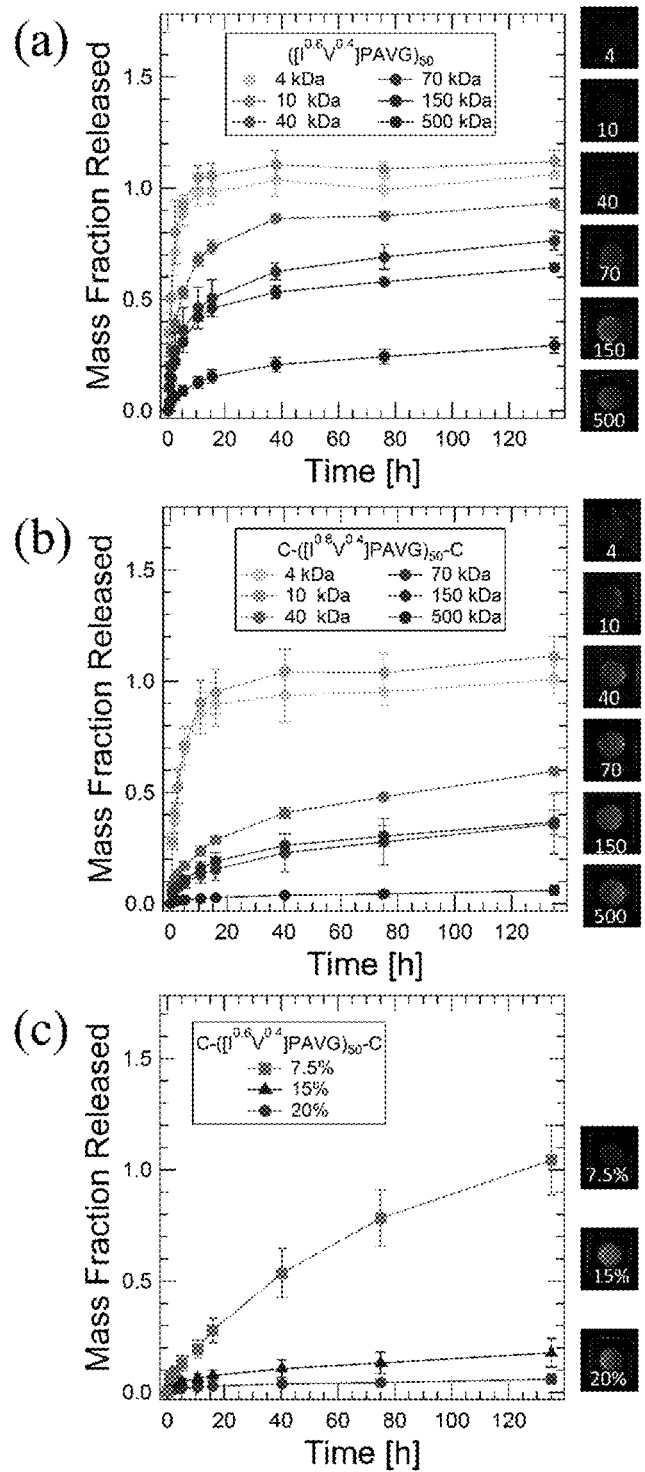
FIG. 41 has three panels (a-c) depicting the release studied from gels at 20 wt % with 0.1% Dextran from 4 kDa to 500 kDa in (a) ([I$^{0.6}$V$^{0.4}$]PAVG)$_{50}$ (SEQ ID NO: 57) and (b) C-([I$^{0.6}$V$^{0.4}$]PAVG)$_{50}$-C (SEQ ID NO: 58) gels. (c) Release of 500 kDa Dextran from C-([I$^{0.6}$V$^{0.4}$]PAVG)$_{50}$-C (SEQ ID NO: 58) as a function of concentration from 7.5 to 20 wt %. Images show residual Dextran in the gels at the final time point.

Diffusion of labeled biomolecules through the hydrogels supports the conclusion that they form bicontinuous networks with nanoscale pores. FITC-labelled Dextran molecules were encapsulated in both ($[I^{0.6}V^{0.4}]PAVG)_{50}$ (SEQ ID NO: 57) and C-($[I^{0.6}V^{0.4}]PAVG)_{50}$-C (SEQ ID NO: 58) gels and their release rates were measured fluorometrically (FIG. 41). A clear size dependence of release was observed, with rapid and statistically similar release occurring for molar masses below 10 kDa within the first 20 hours, and substantially slower release rates for larger Dextran. For both gels, these release rates suggest a broad distribution of pore sizes; however, in the case of the chain-extended ELP gels, there is a much greater size dependence in release rate, especially for Dextran greater than 10 kDa. In particular, 500 kDa Dextran exhibits negligible release over the course of the experiment, indicating that rearrangements of the physical network structure occur on extremely slow timescales consistent with rheological measurements. However, decreasing overall gel concentration to 7.5% improves the release rate of 500 kDa Dextran significantly due to increasing pore size, consistent with SAXS modeling of the chain-extended gels (FIG. 39).

Figure 42:
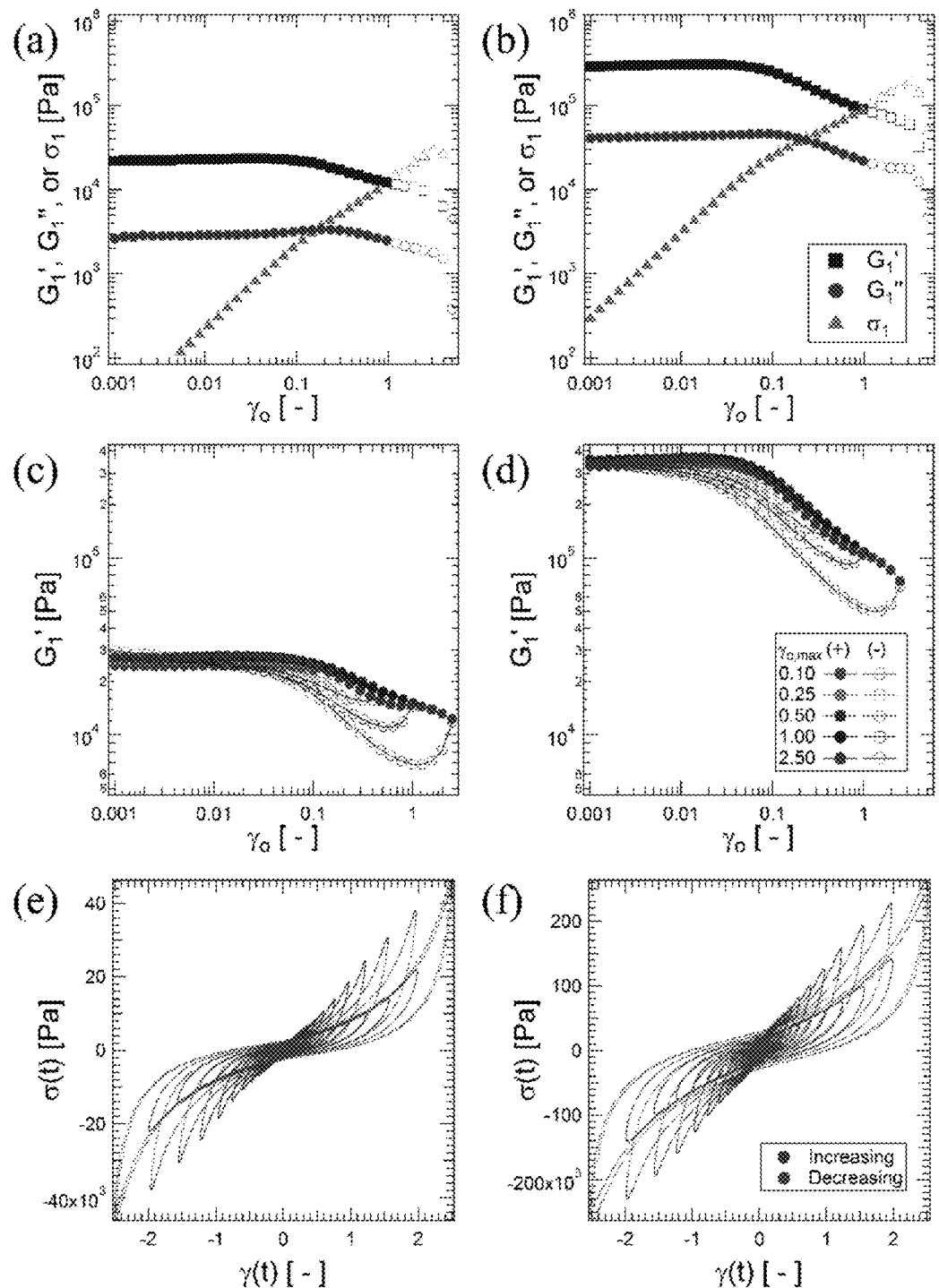
FIG. 42 has six panels (a-f) depicting the behavior of the first harmonic of the stress response as a function of increasing maximum strain amplitude into the nonlinear regime for C-([I$^{0.6}$V$^{0.4}$]PAVG)$_{50}$-C (SEQ ID NO: 58) at (a) 10 wt % and (b) 20 wt % in $H_2O$ at 37° C. Data where the spectral purity of the shear rate waveform is between 0.01 and 0.03 are plotted in open symbols. Cyclic strain sweeps to increasing maximum strain amplitudes for C-([I$^{0.6}$V$^{0.4}$]PAVG)$_{50}$-C (SEQ ID NO: 58) at (c) 10 wt % and (d) 20 wt %. Elastic Lissajous-Bowditch plots for (e) 10 wt % and (f) 20 wt % gels during cyclic strain sweeps to a maximum strain amplitude, $\gamma_{o,max}$=2.5.

Nonlinear Mechanics and Recovery in Oscillatory Shear C-($[I^{0.6}V^{0.4}]PAVG)_{50}$-C (SEQ ID NO: 58) gels are compressible and extensible, exhibiting rapid recovery to their original shapes after moderate deformation, while ($[I^{0.6}V^{0.4}]PAVG)_{50}$ (SEQ ID NO: 57) gels are extremely brittle. To characterize the effect of chain-extension on nonlinear mechanics, the gels were tested in large amplitude oscillatory shear (LAOS) rheology, which allows for interpretation of the viscous and elastic contributions during high strain perturbations. The behavior of the first harmonic of the stress response ($G_1'$, $G_1''$, and $\sigma_1'$; FIG. 42, panels a, b) reveals that the chain-extended ELP gels experience two nonlinear regimes. In the first regime, the gels appear to strain soften but the stress amplitude continues to increase with increasing strain amplitude. In the second regime, the stress amplitude drops significantly with increasing strain amplitude, and the gels do not recover to their original performance unless liquefied by cooling to 0° C. and then reheated. Compared with the previous studies on the brittle unextended gels, the chain-extended gels are clearly tougher in shear. In particular, the peak stress in the chain-extended gels occurs at approximately $\gamma_o$=3 at either concentration, which is over an order of magnitude greater than what is observed for the unextended networks. This result is similar to the effect of increasing ELP molecular weight in unextended gels, where strain at peak stress is seen to increase from roughly $\gamma_o$=0.1 to 1 when the molecular weight is increased from 23 kDa to 53 kDa, at constant amino acid composition and gel concentration.

While the gels fail irreversibly after strain amplitude sweeps to $\gamma_o$=5.0, cyclic strain amplitude sweeps indicate that the gels can recover following nonlinear oscillatory perturbations to intermediate strain amplitudes below $\gamma_{o,max}$=2.5. Elastic Lissajous-Bowditch plots of the LAOS waveforms at increasing and decreasing strain amplitudes in a cyclic sweep reveal complex intracycle nonlinearities that are not captured by the behavior of the first harmonic alone. Thus, to understand in more detail the nonlinear response and recovery, the LAOS waveforms at various strain amplitudes were processed to extract the first order measures of elastic ($G_M'$, $G_L'$) and viscous nonlinearities ($\eta_M'$ and $\eta_L'$) for each individual oscillation cycle. The ratios of these two parameters provide measures of the intracycle stiffening/softening $$\left(S = \frac{G_L' - G_M'}{G_L'}\right)$$

and thickening/thinning $$\left(T = \frac{\eta_L' - \eta_M'}{\eta_L'}\right).$$

Furthermore, the proximity to perfectly plastic behavior can be assessed by computing the ratio of energy dissipated in a LAOS cycle compared to that of a perfectly plastic yield stress material over the same range cycle $$\phi \equiv \frac{\pi \gamma_o G_1''}{4\sigma_{max}}.$$

Figure 43:
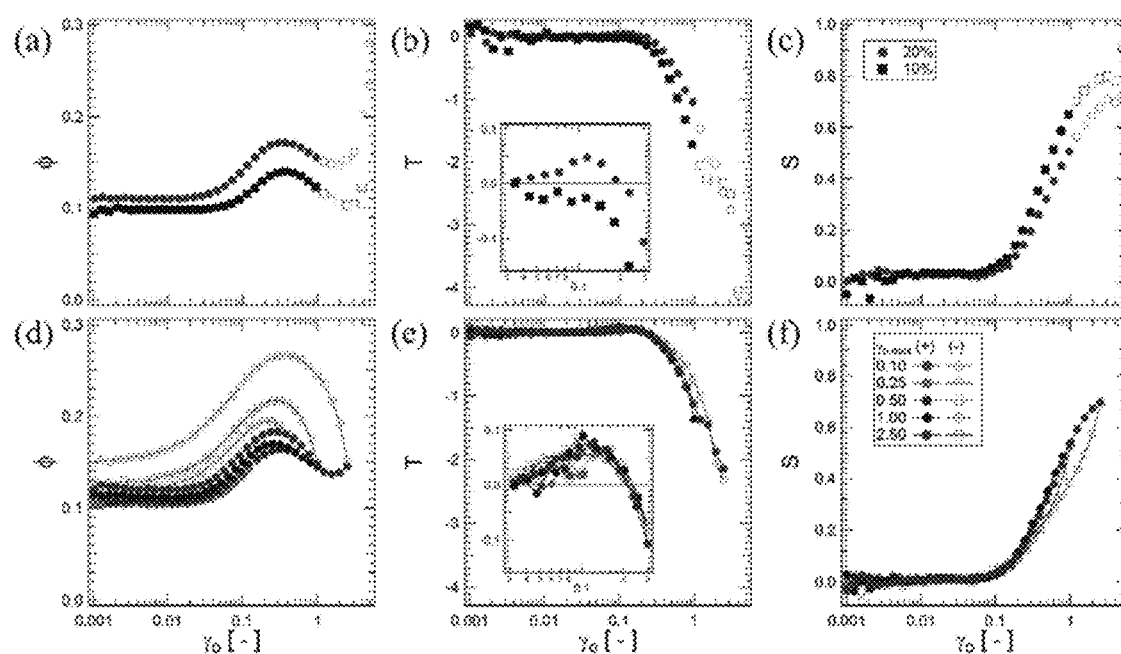
FIG. 43 has six panels (a-f) depicting intracycle nonlinearities during a single strain sweep out to the maximum strain amplitude comparing the effect of gel concentration for C-([I$^{0.6}$V$^{0.4}$]PAVG)$_{50}$-C (SEQ ID NO: 58) at 10 wt % and 20 wt %: (a) perfect plastic dissipation ratio, (b) thickening ratio, and (c) stiffening ratio. Data where the spectral purity of the shear rate waveform is between 0.01 and 0.03 are plotted in open symbols. Intracycle nonlinearities during cyclic strain sweeps for 20 wt % C-([I$^{0.6}$V$^{0.4}$]PAVG)$_{50}$-C (SEQ ID NO: 58): (d) perfect plastic dissipation ratio, (e) thickening ratio, and (f) stiffening ratio.

Examining the behavior of these parameters during a single sweep to failure reveals that chain-extension results in tough networks characterized by reduced dissipation at large strain amplitudes (FIG. 43). In general, the behavior of S and T in both chain-extended gels (at 10 wt % and 20 wt %) is similar to that of gels from unextended, high molecular weight ELPs. The transition to the first nonlinear regime is characterized by substantial strain stiffening (S>0) beyond $\gamma_{o,max}$=0.1, and shear thinning (T<0) is observed at large strain amplitudes for both gels. In addition, the chain-extended ELP gel exhibits a regime of slight shear thickening just at the transition point to the first nonlinear regime, although this is not observed at a concentration of 10 wt % (FIG. 43, panel b). However, at both concentrations, the chain-extended ELP gels exhibit relatively less dissipation than unextended ELPs when comparing the magnitude of $\phi$. Furthermore, for the chain-extended ELP gels, P actually decreases above $\gamma_o$=0.5, suggesting that the gels exhibit substantial elasticity well into the nonlinear regime.

Analysis of the strain amplitude dependence of the intra-cycle nonlinearities indicates that the chain-extended ELP gels recover well for perturbations less than $\gamma_{o,max}$=2.5. While the first harmonic G' and G" exhibit hysteresis between increasing and decreasing strain sweeps (FIG. 42, panels c, d), minimal hysteresis is observed in S and T (FIG. 43). While the hysteresis loop in Q is non-negligible, the increasing strain sweeps are essentially superimposable, indicating that the gel recovers after the oscillatory perturbations decrease to within the linear regime. This behavior is in contrast to the behavior of unextended, high molecular weight ELP gels, which have shortened linear viscoelastic ranges after oscillatory shear above $\gamma_{o,max}$=0.1, indicating the accumulation of irreversible damage to the network. Thus, chain-extension results in significantly improved gel recovery after nonlinear deformation as well as minimal hysteresis during cycling in shear.

Biomaterial Performance In Vitro

Figure 44:
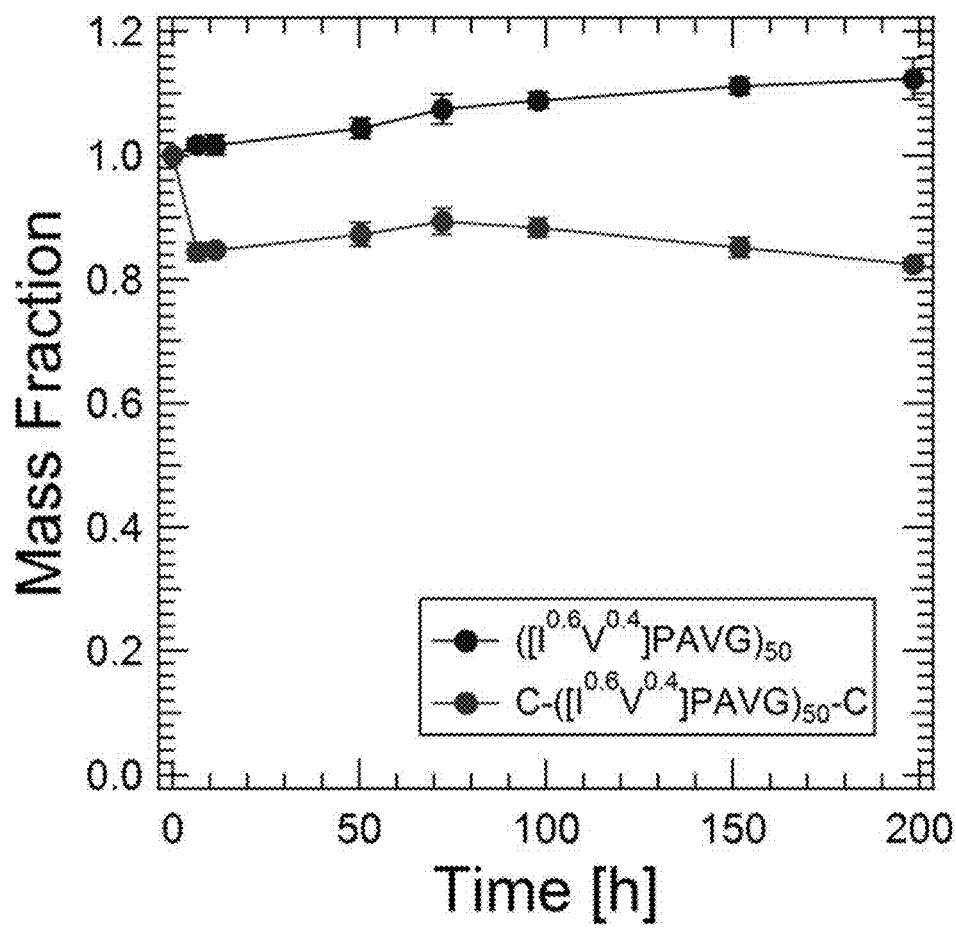
FIG. 44 depicts mass fraction remaining as a function of time measured gravimetrically from cylindrical wells (5 mm diameter, 1 mm deep, N=4) in water at 37° C.

In vitro assessment of these arrested physical networks reveals their long-term persistence in solution at 37° C. (FIG. 44), an important property for in vivo applications where early degradation of physical gels by erosion poses an important limitation. Gel erosion was evaluated in water for gels prepared at 20 wt %, and ([$I^{0.6}V^{0.4}$]PAVG)$_{50}$ (SEQ ID NO: 57) gels exhibited no measurable mass loss over the time periods investigated, appearing to slightly swell over the course of 1 week. While the chain-extended gels lost approximately 20% of their mass prior to the first measurement (at 6 hours), the gels were stable for longer time periods (FIG. 44). This rapid initial mass loss is likely due to the gel shrinking (deswelling) rather than erosion, given the long term stability of the stiff gel after extended equilibration in excess water at 37° C.

Figure 45:
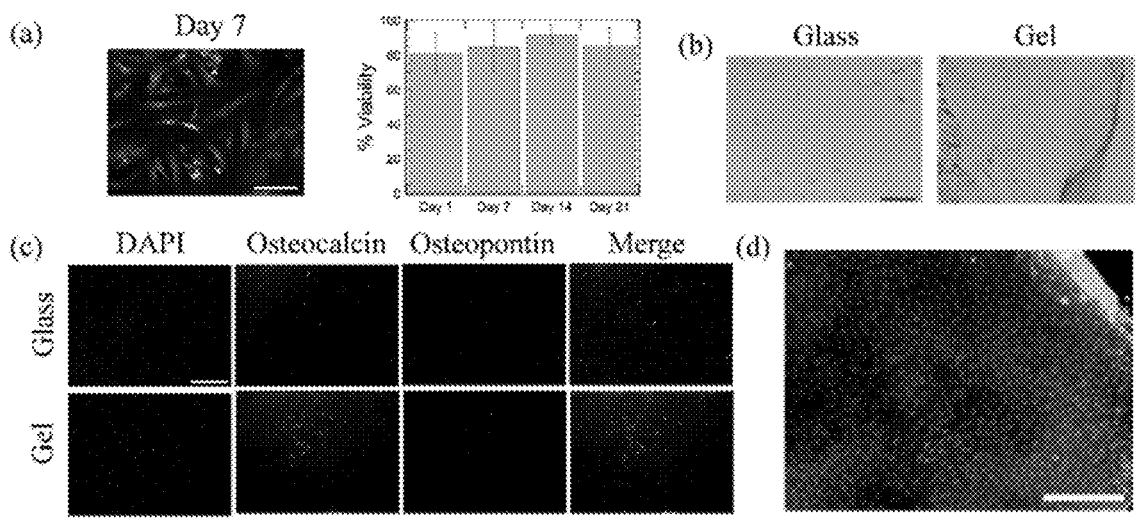
FIG. 45 has four panels (a-d) depicting hMSC viability and osteogenesis on C-([I$^{0.6}$V$^{0.4}$]PAVG)$_{50}$-C (SEQ ID NO: 58) gels. (a) Cell viability: image of LIVE/DEAD® staining on day 7 and quantified by cell counting in ImageJ. (b) Staining for alkaline phosphatase activity on day 21 for cells seeded directly on glass slides and onto the surface of the gel in standard cell media. (c) Immunohistochemical staining for osteocalcin and osteopontin expression. (d) Viability of bovine chondrocytes mixed with C-([I$^{0.6}$V$^{0.4}$]PAVG)$_{50}$-C (SEQ ID NO: 58) gels after 28 days incubation.

The high modulus, improved toughness, and easy preparation of the chain extended gels makes them attractive as tissue engineering matrices for relatively stiff tissues such as cartilage or bone. Matrix elasticity has been shown to control the phenotype of MSCs, with stiff substrates supporting osteogenic differentiation. To investigate the biocompatibility of the biofunctionalized, chain-extended gels and determine their potential to be used in the engineering of stiff tissues, 20 wt % gels of C-([$I^{0.6}V^{0.4}$]PAVG)$_{50}$-C (SEQ ID NO: 58) were initially explored as substrates for 2D seeding of hMSCs. These sequences contained two cell-adhesive RGDS (SEQ ID NO: 5) peptides genetically fused near the N- and C-termini of the ELP, one on each side. As the moduli of these networks are greater than 1 MPa, experiments were performed in media without osteogenic molecules to assess the ability of the substrates to support osteogenesis. The gels were prepared in water, washed in PBS, and soaked in media prior to seeding. They exhibited no significant decay throughout the experimentation, consistent with erosion measurements performed in pure water. Seeded cells demonstrated good attachment, remaining viable out to 21 days post-seeding (FIG. 45, panels a, b). Osteogenesis was inferred by examining the alkaline phosphatase activity of the gels at day 21 compared with cells seeded on the tissue culture plate in media without osteogenic molecules and osteoinductive media (FIG. 45, panel b). Alkaline phosphatase is a secreted enzyme whose activity is associated with bone formation and typically suggestive of osteogenesis. While alkaline phosphatase activity was less than that observed for hMSCs seeded on glass slides in osteoinductive media by day 21 (data not shown), the cells expressed greater alkaline phosphatase activity distributed throughout the gel compared with the control, consistent with weak osteogenesis. Image quantification indicates approximately a 2-fold increase in activity over the control, not as potent as the 9-fold increase in activity observed under osteoinductive conditions. Immunohistochemical staining for osteocalcin and osteopontin expression, non-collagenous proteins (NCPs) found in the extracellular matrix (ECM) of bone, supports this conclusion (FIG. 45, panel c). Similar to alkaline phosphatase expression, hMSCs seeded on top of the gels exhibit greater production of these markers of osteogenesis compared in the absence of the gel, although not as strong as in osteoinductive media. Image quantification indicates a 2-fold increase in osteopontin expression and a 30-fold increase in osteocalcin expression over the control in the gel, compared with a 20-fold and 6-fold increase in osteopontin and osteocalcin expression under osteoinductive conditions.

Because of the ability to rapidly transition from a viscoelastic liquid to an extremely stiff gel with a mild shift in temperature, primary cell isolates of bovine chondrocytes can also easily be mixed into these gels. To achieve a final concentration of 20 wt %, the gels were prepared at 28 wt % in PBS to minimize potential osmotic shock when the suspended chondrocytes were mixed with the viscoelastic fluid. Cells and the ELP were then mixed to a final ELP concentration of 20 wt % and a cell density of $1\times10^7$ chondrocytes/mL. The gels were prepared with a thickness of 0.4 mm, and seeded chondrocytes were viable and retained their rounded morphology throughout 28 days of incubation (FIG. 45, panel d).

INCORPORATION BY REFERENCE

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

EQUIVALENTS

The invention has been described broadly and generically herein. Those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention. Further, each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

We claim:

1. A composition comprising a polypeptide and a solvent; wherein the polypeptide has the following sequence (SEQ ID NO: 85):

$y^1$-(XPAVG)$_n$-$y^2$ wherein, independently for each occurrence,
X is I or V;
n is an integer from 5-500; and
$y^1$ is a polypeptide, wherein the polypeptide is selected from the group consisting of MGWGSASGLVG (SEQ ID NO: 75), KCTSAGAGAGPEGRGDS (SEQ ID NO: 76), MGWGSKCTSAGAGAGPEGRGDSTSGLVG (SEQ ID NO: 77), MGWGSKCTSAGAGAGPEGRGDSTSGLVGRGD (SEQ ID NO: 78), and MGWGSKCTSAGAGAGPEGRGDSTSGLVGRGDS (SEQ ID NO: 79); and
$y^2$ is a polypeptide, wherein the polypeptide is selected from the group consisting of ETTS (SEQ ID NO: 80), CRGD (SEQ ID NO: 81), RGDSAGAGAGPEGTSCK (SEQ ID NO: 82), RGDSETTSRGDSAGAGAGPEGTSCKL (SEQ ID NO: 83), and ETTSRGDSAGAGAGPEGTSCKL (SEQ ID NO: 84).

wherein
$y^1$ is a polypeptide, wherein the polypeptide is selected from the group consisting of MGWGSASGLVG (SEQ ID NO: 75), KCTSAGAGAGPEGRGDS (SEQ ID NO: 76), MGWGSKCTSAGAGAGPEGRGDSTSGLVG (SEQ ID NO: 77), MGWGSKCTSAGAGAGPEGRGDSTSGLVGRGD (SEQ ID NO: 78), and MGWGSKCTSAGAGAGPEGRGDSTSGLVGRGDS (SEQ ID NO: 79); and
$y^2$ is a polypeptide, wherein the polypeptide is selected from the group consisting of ETTS (SEQ ID NO: 80), CRGD (SEQ ID NO: 81), RGDSAGAGAGPEGTSCK (SEQ ID NO: 82), RGDSETTSRGDSAGAGAGPEGTSCKL (SEQ ID NO: 83), and ETTSRGDSAGAGAGPEGTSCKL (SEQ ID NO: 84).

2. The composition of claim 1, wherein X has a ratio r; r is defined as (#I)/(#I+#V) for X; and r is about 0.1 to about 0.7.

3. The composition of claim 1, wherein n is an integer from 25-180.

4. The composition of claim 1, wherein the polypeptide has the following sequence (SEQ ID NO: 86):

$y^1$-[(IPAVGVPAVG)$_2$(IPAVG)]$_{10}$-$y^2$

5. The composition of claim 1, wherein the polypeptide has the following sequence (SEQ ID NO: 7):

```
MGWGSASGLVGIPAVGVPAVGIPAVGVPAVGIPAVGIPAVGVPAVGIP
AVGVPAVGIPAVGIPAVGVPAVGIPAVGVPAVGIPAVGIPAVGVPAVG
IPAVGVPAVGIPAVGIPAVGVPAVGIPAVGVPAVGIPAVGIPAVGVPA
VGIPAVGVPAVGIPAVGIPAVGVPAVGIPAVGVPAVGIPAVGIPAVGV
PAVGIPAVGVPAVGIPAVGIPAVGVPAVGIPAVGVPAVGIPAVGIPAV
GVPAVGIPAVGVPAVGIPAVGETTS.
```

6. The composition of claim 1, wherein the polypeptide has the following sequence (SEQ ID NO: 87):

$y^1$-[(VPAVG)$_2$(IPAVG)(VPAVG)$_2$]$_{10}$-$y^2$ wherein
- y¹ is a polypeptide, wherein the polypeptide is selected from the group consisting of MGWGSASGLVG (SEQ ID NO: 75), KCTSAGAGAGPEGRGDS (SEQ ID NO: 76), MGWGSKCTSAGAGAGPEGRGDSTSGLVG (SEQ ID NO: 77), MGWGSKCTSAGAGAGPEGRGDSTSGLVGRGD (SEQ ID NO: 78), and MGWGSKCTSAGAGAGPEGRGDSTSGLVGRGDS (SEQ ID NO: 79); and
- y² is a polypeptide, wherein the polypeptide is selected from the group consisting of ETTS (SEQ ID NO: 80), CRGD (SEQ ID NO: 81), RGDSAGAGAGPEGTSCK (SEQ ID NO: 82), RGDSETTSRGDSAGAGAGPEGTSCKL (SEQ ID NO: 83), and ETTSRGDSAGAGAGPEGTSCKL (SEQ ID NO: 84).

7. The composition of claim 1, wherein the polypeptide has the following sequence (SEQ ID NO: 9):

```
MGWGSASGLVGVPAVGVPAVGIPAVGVPAVGVPAVGVPAVGVPAVGIP
AVGVPAVGVPAVGVPAVGVPAVGIPAVGVPAVGVPAVGVPAVGVPAVG
IPAVGVPAVGVPAVGVPAVGVPAVGIPAVGVPAVGVPAVGVPAVGVPA
VGIPAVGVPAVGVPAVGVPAVGVPAVGIPAVGVPAVGVPAVGVPAVGV
PAVGIPAVGVPAVGVPAVGVPAVGVPAVGIPAVGVPAVGVPAVGVPAV
GVPAVGIPAVGVPAVGVPAVGETTS.
```

8. The composition of claim 1, wherein the polypeptide has the following sequence (SEQ ID NO: 13 or 15):

[(VPAVG)₂(IPAVG)(VPAVG)₂]$_n$-y²;

wherein
- n is 14 or 24;
- y¹ is a polypeptide, wherein the polypeptide is selected from the group consisting of MGWGSASGLVG (SEQ ID NO: 75), KCTSAGAGAGPEGRGDS (SEQ ID NO: 76), MGWGSKCTSAGAGAGPEGRGDSTSGLVG (SEQ ID NO: 77), MGWGSKCTSAGAGAGPEGRGDSTSGLVGRGD (SEQ ID NO: 78), and MGWGSKCTSAGAGAGPEGRGDSTSGLVGRGDS (SEQ ID NO: 79); and
- y² is a polypeptide, wherein the polypeptide is selected from the group consisting of ETTS (SEQ ID NO: 80), CRGD (SEQ ID NO: 81), RGDSAGAGAGPEGTSCK (SEQ ID NO: 82), RGDSETTSRGDSAGAGAGPEGTSCKL (SEQ ID NO: 83), and ETTSRGDSAGAGAGPEGTSCKL (SEQ ID NO: 84).

9. The composition of claim 1, wherein the polypeptide has the following sequence (SEQ ID NO: 12):

```
MGWGSKCTSAGAGAGPEGRGDSTSGLVGIPAVGVPAVGIPAVGVPAVG
IPAVGIPAVGVPAVGIPAVGVPAVGIPAVGIPAVGVPAVGIPAVGVPA
VGIPAVGIPAVGVPAVGIPAVGVPAVGIPAVGIPAVGVPAVGIPAVGV
PAVGIPAVGIPAVGVPAVGIPAVGVPAVGIPAVGIPAVGVPAVGIPAV
GVPAVGIPAVGIPAVGVPAVGIPAVGVPAVGIPAVGIPAVGVPAVGIP
AVGVPAVGIPAVGIPAVGVPAVGIPAVGVPAVGIPAVGETTSRGDSAG
AGAGPEGTSCKL.
```

10. The composition of claim 1, wherein the polypeptide is present in an amount from about 1% to about 30% by weight of the composition.

11. The composition of claim 1, wherein the solvent comprises water.

12. The composition of claim 1, wherein the composition is a liquid at a temperature less than about 15° C.

13. The composition of claim 1, wherein the composition is a gel at a temperature greater than about 25° C.

14. The composition of claim 1, wherein the shear modulus (G) of the composition at about 37° C. is about 500 kPa to about 2 MPa.

15. The composition of claim 1, wherein y¹ is selected from the group consisting of KCTSAGAGAGPEGRGDS (SEQ ID NO: 76), MGWGSKCTSAGAGAGPEGRGDSTSGLVG (SEQ ID NO: 77), MGWGSKCTSAGAGAGPEGRGDSTSGLVGRGD (SEQ ID NO: 78), and MGWGSKCTSAGAGAGPEGRGDSTSGLVGRGDS (SEQ ID NO: 79).

16. The composition of claim 1, wherein y² is selected from the group consisting of CRGD (SEQ ID NO: 81), RGDSAGAGAGPEGTSCK (SEQ ID NO: 82), RGDSETTSRGDSAGAGAGPEGTSCKL (SEQ ID NO: 83), and ETTSRGDSAGAGAGPEGTSCKL (SEQ ID NO: 84).

* * * * *